(12) United States Patent
Tan et al.

(10) Patent No.: US 10,874,686 B2
(45) Date of Patent: Dec. 29, 2020

(54) ANTHRANILYL-ADENOSINEMONOSULFAMATE ANALOGS AND USES THEREOF

(71) Applicants: Memorial Sloan-Kettering Cancer Center, New York, NY (US); The General Hospital Corporation, Boston, MA (US); East Carolina University, Greenville, NC (US)

(72) Inventors: Derek Shieh Tan, New York, NY (US); Cheng Ji, Buffalo Grove, IL (US); Indrajeet Sharma, Norman, OK (US); Debarshi Pratihar, Kolkata (IN); James P. Coleman, Farmville, NC (US); Everett C. Pesci, Greenville, NC (US); Laurence G. Rahme, Brookline, MA (US)

(73) Assignees: Memorial Sloan-Kettering Cancer Center, New York, NY (US); The General Hospital Corporation, Boston, MA (US); East Carolina University, Greenville, NC (US)

( * ) Notice: Subject to any disclaimer, the term of this patent is extended or adjusted under 35 U.S.C. 154(b) by 0 days.

(21) Appl. No.: 15/765,004

(22) PCT Filed: Oct. 3, 2016

(86) PCT No.: PCT/US2016/055200
§ 371 (c)(1),
(2) Date: Mar. 30, 2018

(87) PCT Pub. No.: WO2017/059446
PCT Pub. Date: Apr. 6, 2017

(65) Prior Publication Data
US 2019/0038656 A1   Feb. 7, 2019

Related U.S. Application Data

(60) Provisional application No. 62/236,031, filed on Oct. 1, 2015.

(51) Int. Cl.
| | | |
|---|---|---|
| A01N 43/04 | (2006.01) | |
| A61K 31/70 | (2006.01) | |
| A61K 31/7076 | (2006.01) | |
| C07D 473/34 | (2006.01) | |
| A61P 31/04 | (2006.01) | |
| A61K 45/06 | (2006.01) | |

(52) U.S. Cl.
CPC .......... *A61K 31/7076* (2013.01); *A61P 31/04* (2018.01); *C07D 473/34* (2013.01); *A61K 45/06* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,730,767 B2 | 5/2004 | Salamone et al. | |
| 6,989,430 B2 | 1/2006 | Salamone et al. | |
| 7,816,326 B2 | 10/2010 | Velazquez et al. | |
| 7,989,430 B2 | 8/2011 | Aldrich et al. | |
| 8,067,379 B2 | 11/2011 | Bennett et al. | |
| 8,461,128 B2 | 6/2013 | Tan et al. | |
| 8,946,188 B2 | 2/2015 | Tan et al. | |
| 2007/0042968 A1 | 2/2007 | Bennett et al. | |
| 2018/0273573 A1 | 9/2018 | Tan et al. | |

FOREIGN PATENT DOCUMENTS

| | | |
|---|---|---|
| EP | 0433898 | 6/1991 |
| WO | WO 2006/113615 | 10/2006 |
| WO | WO 2007/067559 | 6/2007 |

OTHER PUBLICATIONS

Somu et al. J. Med. Chem. (2006), vol. 49, pp. 31-34.*
Kulka et al. (2012). Growth of Mycobacterium tuberculosis biofilms. JoVE (Journal of Visualized Experiments), (60), e3820.*
Qiao et al. JACS (2007), vol. 129, pp. 6350-6351.*
International Search Report and Written Opinion for PCT/US2016/055200.
International Preliminary Report on Patentability for PCT/US2016/055136 dated Apr. 12, 2018.
International Search Report and Written Opinion for PCT/US2016/055136.
International Preliminary Report on Patentability for PCT/US2016/055200 dated Apr. 12, 2018.
Ackerley et al., Substrate specificity of the nonribosomal peptide synthetase PvdD from Pseudomonas aeruginosa. J Bacteriol. May 2003;185(9):2848-55.

(Continued)

*Primary Examiner* — Patrick T Lewis
(74) *Attorney, Agent, or Firm* — Wolf, Greenfield & Sacks, P.C.

(57) ABSTRACT

Provided herein are compounds of Formula (I) and pharmaceuticals acceptable salts, solvates, hydrates, polymorphs, co-crystals, tautomers, stereoisomers, and prodrugs thereof. Also provided are pharmaceutical compositions, kits, and methods involving the inventive compounds for the treatment and/or of an infectious disease (e.g., bacterial infection (e.g., *P. aeruginosa* infection).

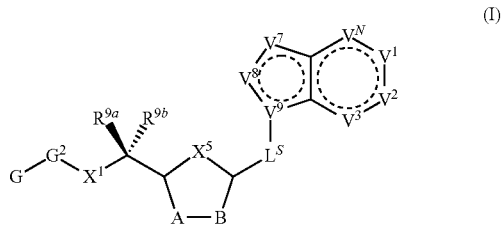

(I)

36 Claims, 13 Drawing Sheets
Specification includes a Sequence Listing.

(56) References Cited

OTHER PUBLICATIONS

Arora et al., Mechanistic and functional insights into fatty acid activation in Mycobacterium tuberculosis. Nat Chem Biol. Mar. 2009;5(3):166-73. doi: 10.1038/nchembio.143. Epub Feb. 1, 2009.

Bandarian et al., Domain alternation switches B(12)-dependent methionine synthase to the activation conformation. Nat Struct Biol. Jan. 2002;9(1):53-6.

Bardaweel et al., Synthesis and evaluation of potential inhibitors of human and *Escherichia coli* histidine triad nucleotide binding proteins. Bioorg Med Chem Lett. Jan. 1, 2012;22(1):558-60. doi:10.1016/j.bmcl.2011.10.082. Epub Oct. 31, 2011.

Branchini et al., Synthesis of an N-acyl sulfamate analog of luciferyl-AMP: a stable and potent inhibitor of firefly luciferase. Bioorg Med Chem Lett. Sep. 1, 2005;15(17):3860-4.

Calfee et al., Interference with Pseudomonas quinolone signal synthesis inhibits virulence factor expression by Pseudomonas aeruginosa. Proc Natl Acad Sci U S A. Sep. 25, 2001;98(20):11633-7.

Castro-Pichel et al., A facile synthesis of ascamycin and related analogues. Tetrahedron. 1987; 43(2);383-389.

Chen et al., Structural Basis for the ATP-dependent Configuration of Adenylation Active Site in Bacillus subtilis o-Succinylbenzoyl-CoA Synthetase. J Biol Chem. Sep. 25, 2015;290(39):23971-83. doi: 10.1074/jbc.M115.676304. Epub Aug. 14, 2015.

Ciulli et al., Inhibition of Mycobacterium tuberculosis pantothenate synthetase by analogues of the reaction intermediate. Chembiochem. Nov. 3, 2008;9(16):2606-11. doi: 10.1002/cbic.200800437.

Coleman et al., Pseudomonas aeruginosa PqsA is an anthranilate-coenzyme A ligase. J Bacteriol. Feb. 2008;190(4):1247-55. Epub Dec. 14, 2007.

Davis et al., General platform for systematic quantitative evaluation of small-molecule permeability in bacteria. ACS Chem Biol. Nov. 21, 2014;9(11):2535-44. doi: 10.1021/cb5003015. Epub Sep. 8, 2014.

Drake et al., Biochemical and structural characterization of bisubstrate inhibitors of BasE, the self-standing nonribosomal peptide synthetase adenylate-forming enzyme of acinetobactin synthesis. Biochemistry. Nov. 2, 2010;49(43):9292-305. doi: 10.1021/bi101226n.

Felczak et al., Cofactor-type inhibitors of inosine monophosphate dehydrogenase via modular approach: targeting the pyrophosphate binding sub-domain. Bioorg Med Chem. Mar. 1, 2011;19(5):1594-605. doi: 10.1016/j.bmc.2011.01.042. Epub Jan. 27, 2011.

Ferreras et al., Mycobacterial phenolic glycolipid virulence factor biosynthesis: mechanism and small-molecule inhibition of polyketide chain initiation. Chem Biol. Jan. 2008;15(1):51-61. Epub Dec. 27, 2007.

Ferreras et al., Small-molecule inhibition of siderophore biosynthesis in Mycobacterium tuberculosis and Yersinia pestis. Nat Chem Biol. Jun. 2005;1(1):29-32. Epub May 24, 2005.

Finking et al., Aminoacyl adenylate substrate analogues for the inhibition of adenylation domains of nonribosomal peptide synthetases. Chembiochem. Sep. 5, 2003;4(9):903-6.

Gulick, Conformational Dynamics in the Acyl-CoA Synthetases, Adenylation Domains of Non-ribosomal Peptide Synthetases, and Firefly Luciferase. ACS Chem Biol. Oct. 16, 2009;4(10):811-27. doi: 10.1021/cb900156h.

Ilangovan et al., Structural basis for native agonist and synthetic inhibitor recognition by the Pseudomonas aeruginosa quorum sensing regulator PqsR (MvfR). PLoS Pathog. 2013;9(7):e1003508. doi: 10.1371/journal.ppat.1003508. Epub Jul. 25, 2013.

Isono et al., Ascamycin and dealanylascamycin, nucleoside antibiotics from *Streptomyces* sp. J Antibiot (Tokyo). Jun. 1984;37(6):670-2.

Kasper et al., Chemical Inhibition of Kynureninase Reduces Pseudomonas aeruginosa Quorum Sensing and Virulence Factor Expression. ACS Chem Biol. Apr. 15, 2016;11(4):1106-17. doi: 10.1021/acschembio.5b01082. Epub Feb. 10, 2016.

Koroniak et al., Synthesis and characterization of an N-acylsulfonamide inhibitor of human asparagine synthetase. Org Lett. Jun. 12, 2003;5(12):2033-6.

Lu et al., Designed semisynthetic protein inhibitors of Ub/Ubl E1 activating enzymes.J Am Chem Soc. Feb. 17, 2010;132(6):1748-9. doi: 10.1021/ja9088549.

Lu et al., Mechanism-based inhibitors of MenE, an acyl-CoA synthetase involved in bacterial menaquinone biosynthesis. Bioorg Med Chem Lett. Nov. 15, 2008;18(22):5963-6. doi: 10.1016/j.bmcl.2008.07.130. Epub Aug. 12, 2008.

Lu et al., Stable analogues of OSB-AMP: potent inhibitors of MenE, the o-succinylbenzoate-CoA synthetase from bacterial menaquinone biosynthesis. Chembiochem. Jan. 2, 2012;13(1):129-36. doi: 10.1002/cbic.201100585. Epub Nov. 23, 2011.

Lun et al., Pharmacokinetic and in vivo efficacy studies of the mycobactin biosynthesis inhibitor salicyl-AMS in mice. Antimicrob Agents Chemother. Oct. 2013;57(10):5138-40. doi: 10.1128/AAC.00918-13. Epub Jul. 15, 2013.

Matarlo et al., Mechanism of MenE inhibition by acyl-adenylate analogues and discovery of novel antibacterial agents. Biochemistry. Oct. 27, 2015;54(42):6514-6524. doi: 10.1021/acs.biochem.5b00966. Epub Oct. 15, 2015.

Miethke et al., Inhibition of aryl acid adenylation domains involved in bacterial siderophore synthesis. FEBS J. Jan. 2006;273(2):409-19.

Migron et al., A facile synthesis of $\alpha,\alpha,\omega,\omega$-tetrahalo-$\alpha,\omega$-dicarboxylic esters. Tetrahedron. 1987;43(2):361-364.

Morton et al., The structure of nucleocidin. 3. (A new structure). J Am Chem Soc. Mar. 12, 1969;91(6):1535-7.

Qiao et al., 5'-O-[(N-acyl)sulfamoyl]adenosines as antitubercular agents that inhibit MbtA: an adenylation enzyme required for siderophore biosynthesis of the mycobactins. J Med Chem. Nov. 29, 2007;50(24):6080-94. Epub Oct. 30, 2007.

Qiao et al., A mechanism-based aryl carrier protein/thiolation domain affinity probe. J Am Chem Soc. May 23, 2007;129(20):6350-1. Epub May 1, 2007.

Sikora et al., Kinetic and inhibition studies of dihydroxybenzoate-AMP ligase from *Escherichia coli*. Biochemistry. May 4, 2010;49(17):3648-57. doi: 10.1021/bi100350c.

Somu et al., Rationally designed nucleoside antibiotics that inhibit siderophore biosynthesis of Mycobacterium tuberculosis. J Med Chem. Jan. 12, 2006;49(1):7623-7635.

Sundlov et al., Structural and functional investigation of the intermolecular interaction between NRPS adenylation and carrier protein domains. Chem Biol. Feb. 24, 2012;19(2):188-98. doi: 10.1016/j.chembiol.2011.11.013.

Tian et al., Bacillus anthracis o-succinylbenzoyl-CoA synthetase: reaction kinetics and a novel inhibitor mimicking its reaction intermediate Biochemistry. Nov. 25, 2008;47(47):12434-47. doi: 10.1021/bi801311d.

Ueda et al., X-ray crystallographic conformational study of 5'-O-[N-(L-alanyl)-sulfamoyl]adenosine, a substrate analogue for alanyl-tRNA synthetase. Biochim Biophys Acta. Oct. 25, 1991;1080(2):126-34.

Waller et al., The Structure of Nucleocidin. I. J. Am. Chem. Soc. 1957;79(4):1011-1012. DOI: 10.1021/ja01561a076.

Zhang et al., Engineering the substrate specificity of the DhbE adenylation domain by yeast cell surface display. Chem Biol. Jan. 24, 2013;20(1):92-101. doi:10.1016/j.chembiol.2012.10.020.

U.S. Appl. No. 15/764,613, filed Mar. 29, 2018, Tan et al.

EP 16852815.6, May 10, 2019, Extended European Search Report. Extended European Search Report dated May 10, 2019, in connection with Application No. EP 16852815.6.

Evans et al., Stereoselective Synthesis, Docking, and Biological Evaluation of Difluoroindanediol-Based MenE Inhibitors as Antibiotics. Org Lett. Dec. 16, 2016;18(24):6384-6387. Epub Dec. 1, 2016.

Evans et al., Structure-based Design, Synthesis, and Biological Evaluation of Non-Acyl Sulfamate Inhibitors of the Adenylate-Forming Enzyme MenE. Biochemistry. Mar. 26, 2019;58:1918-30. PCT/US2016/055136, dated Jan. 6, 2017, International Search Report and Written Opinion.

(56) References Cited

OTHER PUBLICATIONS

PCT/US2016/055136, dated Apr. 12, 2018, International Preliminary Report on Patentability.
PCT/US2016/055200, dated Feb. 17, 2017, International Search Report and Written Opinion.
PCT/US2016/055200, dated Apr. 12, 2018, International Preliminary Report on Patentability.

* cited by examiner

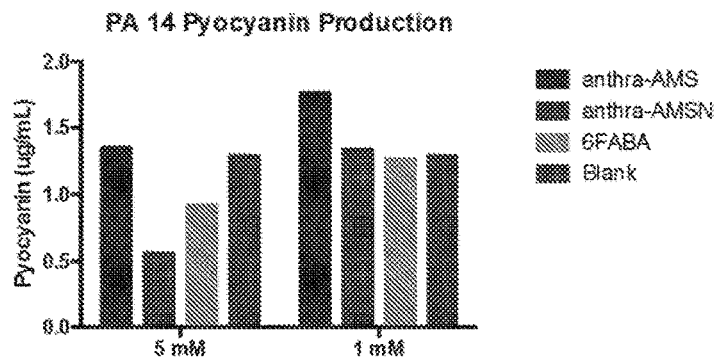
Figure 2B
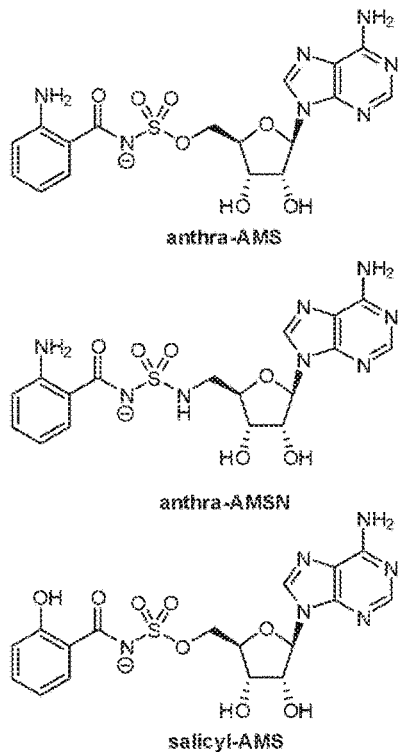
Figure 2C
Figure 2D

| inhibitor | R | X | $K_i^{app}$ (nM)[b] |
|---|---|---|---|
| anthranilyl-AMS (1) | NH$_2$ | O | 205 ± 4.0[c] |
| anthranilyl-AMSN (2) | NH$_2$ | NH | 170 ± 20[c] |
| salicyl-AMS (3) | OH | O | 88 ± 12 |
| salicyl-AMSN (4) | OH | NH | 109 ± 18 |
| benzoyl-AMS (5) | H | O | 420 ± 69 |
| anthranilyl-AVSN (6) | NH$_2$ | | 36300 ± 4300 |
| salicyl-AVSN (7) | OH | | 15400 ± 1700 |

ANTHRANILYL-ADENOSINEMONOSULFAMATE ANALOGS AND USES THEREOF

RELATED APPLICATIONS

This application is a national stage filing under 35 U.S.C. § 371 of international PCT application, PCT/US2016/055200, filed Oct. 3, 2016, which claims priority under 35 U.S.C. § 119(e) to U.S. provisional patent application, U.S. Ser. No. 62/236,031, filed Oct. 1, 2015, each of which is incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII co created on Aug. 3, 2020, is named S171570019US01-SEQ-PJH and is 4.82 kilobytes in size.

GOVERNMENT SUPPORT

This invention was made with Government support under AI098802, AI105902, AI076272, and CA008748 awarded by the National Institutes of Health. The Government has certain rights in the invention.

BACKGROUND

The bacteria *Pseudomonas aeruginosa* is a pathogen with natural resistance to a broad range of antibiotics. Infections with *P. aeruginosa* are common in hospitals and other health care settings, and *P. aeruginosa* is known to cause severe infections in immunocompromised patients. The bacteria has several intrinsic factors that lead to multi-drug resistance, including low cell permeability, multi-drug efflux pumps, and biofilm formation. See, e.g., Jimenez et al., *Microbiol. Mol. Biol. Rev.* (2012) 46-65. *P. aeruginosa* also displays a high degree of adaptability, due to complex sensing and signaling mechanisms that regulate genetic expression. These quorum sensing pathways promote the production of various virulence factors that enable full pathogenesis. See, e.g., Tashiro et al., *Microbes Environ.* (2013) 28:13-24; Dubern et al, *Mol. Biosyst.* (2008) 4:882-888; Williams et al., *Curr. Opin. Microbiol.* (2009) 12:182-191. Agents that target these sensing pathways may provide methods of treating and preventing *P. aeruginosa* infections or impairing its drug resistance.

SUMMARY

The *Pseudomonas* quinolone signal (PQS) refers to the compound 2-heptyl-3-hydroxy-4-quinolone. PQS is synthesized by a biosynthetic pathway (see FIG. 1) from anthranilic acid utilizing the enzymes encoded by the genes pqsABCD. Once present in sufficient concentration PQS binds to and activates the receptor PqsR, which subsequently up-regulates expression of pqsABCDE and phnAB. See, e.g., Jimenez et al., *Microbiol. Mol. Biol. Rev.* (2012) 46-65, which is incorporated herein by reference. The molecule is used as a signal in quorum sensing to regulate the production of virulence factors, formation of biofilms, and motility. PQS biosynthesis occurs in *P. aeruginosa* as well as other *Pseudomonas* species and subspecies. Quorum sensing is a method by which some bacteria control and regulate gene expression through a bacterial population. Quorum sensing is sensitive to changes in the cell density of a bacterial colony or infection, and can be used to coordinate changes in gene expression. Such regulation may, for example, allow the bacteria of a colony to all up-regulate biosynthesis of a virulence factor necessary for biofilm formation in response to the colony surpassing a certain population density.

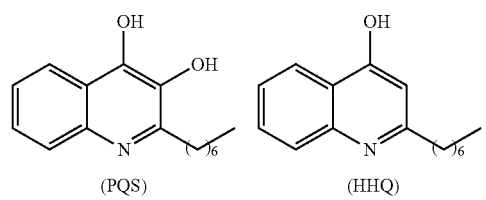

(PQS)    (HHQ)

The proteins PqsA-D catalyze steps in the transformation of anthranilic acid to 2-heptyl-4-hydroxyquinoline (HHQ). The last hydroxylation step converting HHQ to PQS is catalyzed by the protein PqsH. HHQ itself has also been shown to function in cell-to-cell signaling and activation of PqsR. The proteins encoded by phnAB catalyze the conversion of shikimic acid to anthranilic acid, through chorismic acid. And alternative biosynthesis of anthranilic acid begins with tryptophan, with formylkynurenine and kynurenine as intermediates.

Virulence factors regulated by PQS or HHQ binding to the PqsR receptor include PQS and HHQ themselves (via autoinduction), pyocyanin, and protein PqsE. PqsE is known to effect the production of other virulence factors, including pyocyanin, lectin, HCN, and rhamnolipids. Phenazines such as pyocyanin have been shown to be toxic to prokaryotic and eukaryotic cells, allowing *P. aeruginosa* to kill other competing bacteria and weaken the host by several mechanisms, including suppressing lymphocyte proliferation, damaging epithelial cells, and inactivating protease inhibitors. Disruption of quorum sensing mechanisms, such as the PQS pathway, can limit the virulence of *P. aeruginosa*. The effect has been demonstrated in strains with pqsA and pqsE mutation. See, e.g., Deziel et al., *Mol. Microbiol.* (2005) 55:998-1014; Rampioni et al., (2010) *Environ. Microbiol.* (2010) 12:1659-1673.

The protein anthranilate-CoA synthetase, or PqsA, catalyzes the first step in the synthesis of PQS from anthranilic acid (see FIG. 1). PqsA is an adenylate-forming acyl-CoA synthetase responsible for two steps: (1) the adenylation of anthranilic acid with ATP to form an anthranilyl-AMP intermediate; and (2) the coupling of the adenylated acyl group to coenzyme A with release of AMP.

Compounds of the present invention are capable of inhibiting anthranilate-CoA synthetase (PqsA). The compounds provided are analogs of the PqsA intermediate anthranilyl-adensosinemonophosphate (anthranilyl-AMP). The analogs comprise a linker, such as a sulfonyl moiety, that mimics the phosphate between the o-succinylbenzoate and adenosine moieties in anthranilyl-AMP.

Compounds of the present invention are of Formula (I):

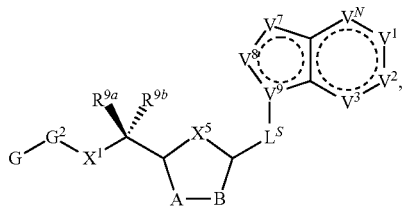

wherein, in certain embodiments, the anthranilyl moiety of anthranilyl-AMP is replaced with group G. Group G is of formula:

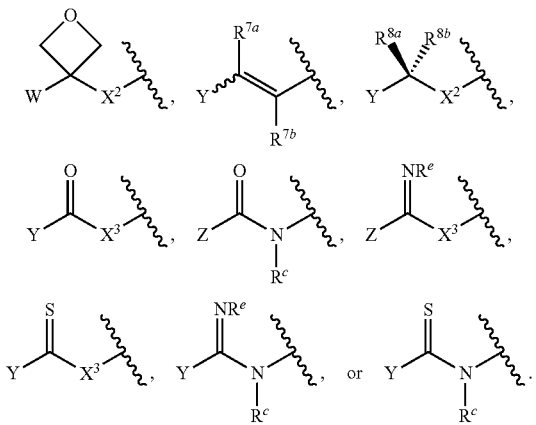

In certain embodiments, a provided compound is of Formula (III), (IV), or (V):

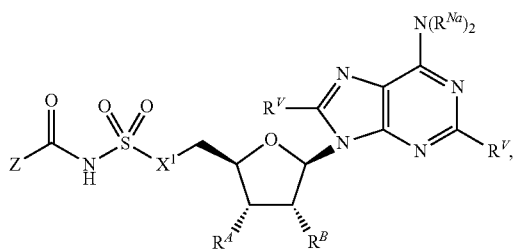

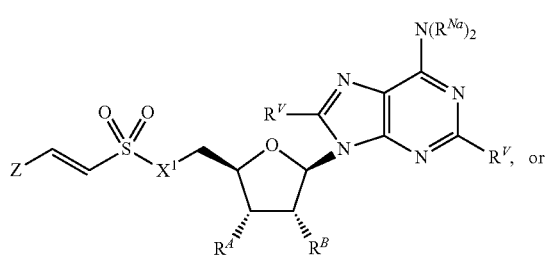

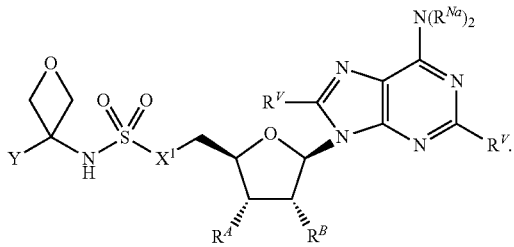

Pharmaceutical compositions of the compounds are also provided, in addition to methods of preventing and/or treating an infectious disease using the compound or compositions thereof. The infectious disease may be a bacterial infection. The compositions and methods provided may be useful in the treatment of an infection with a Gram-positive or Gram-negative bacteria. The methods may useful in the treatment of a *Pseudomonas* infection, such as a *P. aeruginosa* infection.

The invention also provides methods useful for inhibiting anthranilate-CoA synthetase (PqsA) or inhibiting PQS and/or HHQ biosynthesis in an infectious microorganism by contacting the microorganism with a compound or composition provided herein. Additionally provided are methods for inhibiting anthranilate-CoA synthetase (PqsA) or inhibiting PQS and/or HHQ biosynthesis in an infectious microorganism in a subject by administering to the subject a compound or composition provided herein.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

FIG. 2B shows $IC_{50}$ values for PQS (20 hours) and HHQ (8 hours) biosynthesis inhibition. FIG. 2C shows the pyocyanin concentration in *P. aeruginosa* PA14 cell cultures, measured in μg/mL, in the presence of 1 mM or 5 mM anthranilyl-AMS, anthranilyl-AMSN, and 6FABA. FIG. 2D shows the structure of compounds anthra-AMS, anthra-AMSN, and salicyl-AMS.

DETAILED DESCRIPTION OF CERTAIN EMBODIMENTS

Figure 1:
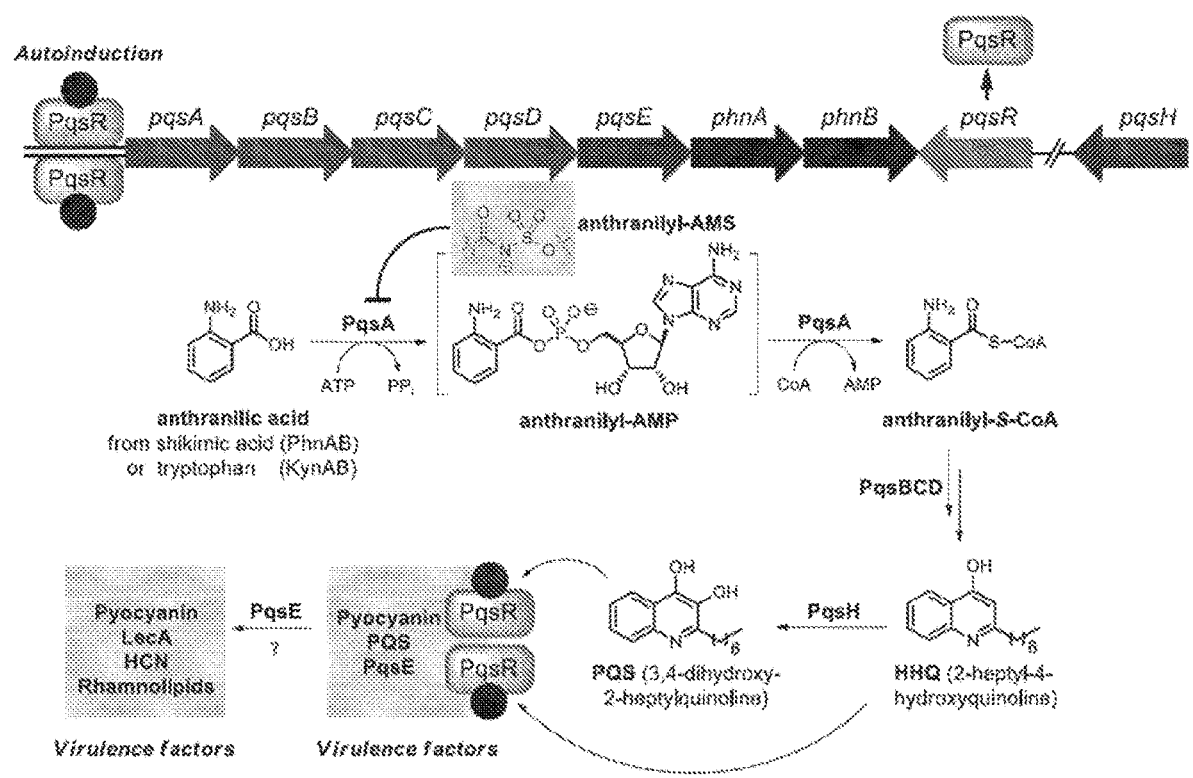
FIG. 1. Diagram depicting PQS biosynthesis in *P. aeruginosa*. PqsA converts anthranilic acid to anthranilyl-S-CoA, and may be inhibited by the anthranilyl-AMP analog, anthranilyl-AMS. Anthranilyl-S-CoA is converted to HHQ by other proteins encoded by pqsBCDE, and then to PQS by PqsH. PQS and HHQ bind to receptor PqsR leading to up-regulation of pqsABCDE and phnAB and promotion of the biosynthesis of virulence factors including pyocyanin. See also, e.g., Zender et al. *ACS Chem. Biol.* (2016) 11, 1755-1763.

Provided herein are compounds which may inhibit anthranilate-CoA synthetase (PqsA). The compounds may interact with PqsA so as to disrupt the activity of PqsA in converting anthranilic acid to anthranilyl-CoA. PqsA catalyzes two transformations in tandem (see FIG. 1). The first reaction combines anthranilic acid and ATP to form the intermediate anthranilyl-AMP and pyrophosphate as a by-product. In the second reaction, CoA is conjugated to anthranilate to form anthranilyl-CoA, and AMP is released. In some embodiments, a provided compound affects the ability of PqsA to form anthranilyl-AMP, i.e., inhibits the first transformation. In some embodiments, a provided compound affects the ability of PqsA to form anthranilyl-CoA, i.e., inhibits the second transformation. In some embodiments, the compound inhibits both the first and second transformation.

Anthranilyl-CoA is a precursor in the biosynthesis of 2-heptyl-3,4-dihydroxyquinoline (PQS) and 2-heptyl-4-hydroxyquinoline (HHQ). Thus, a compound of the invention may inhibit PQS and/or HHQ biosynthesis. In some embodiments, a compound provided herein inhibits PQS biosynthesis by inhibiting PqsA. In some embodiments, a compound provided herein inhibits HHQ biosynthesis by inhibiting PqsA. In some embodiments, a compound provided herein inhibits PQS and HHQ biosynthesis by inhibiting PqsA.

Without wishing to be bound by a particular theory, the compounds provided may inhibit PqsA based on its structural similarity to anthranilyl-AMP. The phosphate-carbonyl bond of anthranilyl-AMP is cleaved during the conversion of anthranilyl-AMP to anthranilyl-CoA. The compounds provided replace the phosphate linker with other linkers, e.g., a sulfonyl group, which are not readily cleaved or displaced by CoA. For example, the compound anthranilyl-AMS (anthranilyl-adenosinemonosulfamate) is a structural analog of anthranilyl-AMP (anthranilyl-adenosinemonophosphate), in which the phosphate group is replaced with a sulfamate moiety.

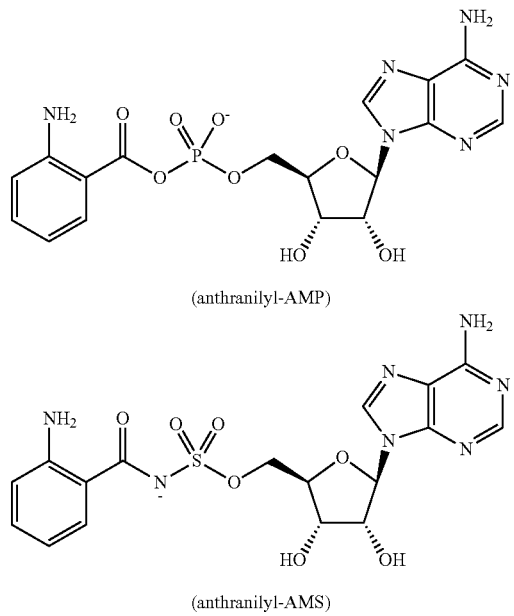

(anthranilyl-AMP)

(anthranilyl-AMS)

Many linker alternatives to phosphate are contemplated herein. In certain embodiments, the linker is a sulfamate or sulfamide linker. In certain embodiments, the linker is a vinylsulfonamide. In some embodiments, an inhibitor comprising a vinyl sulfonamide linker forms a covalent attachment with CoA in the presence of PqsA and CoA.

In certain embodiments, the compound is of Formula (Z):

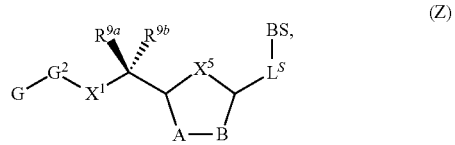

(Z)

or a pharmaceutically acceptable salt, solvate, hydrate, polymorph, co-crystal, tautomer, stereoisomer, prodrug, or isotopically labeled derivative thereof, wherein:

BS is optionally substituted heterocyclyl, or optionally substituted heteroaryl, or an optionally substituted nucleobase or nucleobase analog;

$G^2$ is $-S(=O)_2-$, $-P(=O)(R^e)-$, $-P(=O)(OR^e)-$, $-P(=O)(N(R^e)_2)-$, $-P(=S)(R^e)-$, $-P(=S)(OR^e)-$, $-P(=S)(N(R^e)_2)-$, $-Si(OR^e)_2-$, $-C(=O)-$, $-C(=S)-$, $-C(=NR^f)-$, $-(CH_2)_h-$,

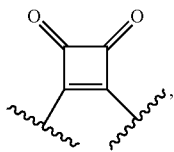 [SMILES: *c1c(*)c(=O)c1=O]

or optionally substituted monocyclic 5- or 6-membered heteroarylene, wherein 1, 2, 3, or 4 atoms in the heteroarylene ring system are independently oxygen, nitrogen, or sulfur;

G is of formula:

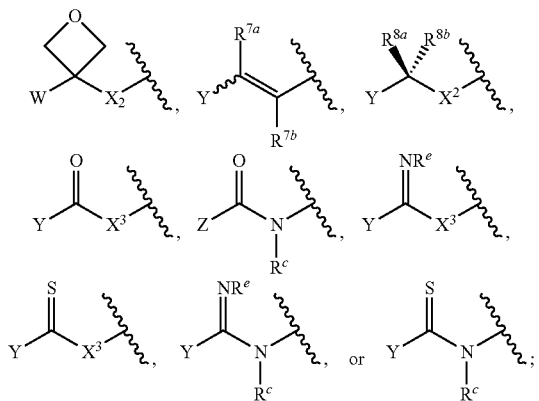

each of W, Y, and Z is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, $-OR^e$, $-N(R^e)_2$, substituted carbocyclyl, optionally substituted heterocyclyl, optionally substituted aryl, optionally substituted heteroaryl, or of formula:

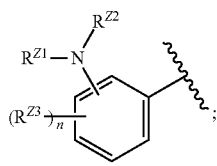

n is 0, 1, 2, 3, or 4;

each of $R^{Z1}$ and $R^{Z2}$ is independently hydrogen, optionally substituted alkyl, optionally, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form an optionally substituted heterocyclic or optionally substituted heteroaryl ring;

each occurrence of $R^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-NO_2$, $-CN$, $-OR^e$, or $-N(R^e)_2$, or two $R^{Z3}$ are joined to form an optionally substituted aryl or optionally substituted heteroaryl ring;

$X^1$ is a bond, $-O-$, $-C(R^d)_2-$, $-(CH_2)_q-$, or $-NR^f-$;

$X^2$ is a bond, $-O-$, $-C(R^d)_2-$, $-(CH_2)_t-$, or $-NR^f-$;

$X^3$ is a bond, $-O-$, $-C(R^d)_2-$, or $-(CH_2)_t-$;

A-B is $-(R^A)_2C-C(R^B)_2-$ or $-R^AC=CR^B-$, wherein each occurrence of $R^A$ is independently hydrogen, halogen, optionally substituted alkyl, optionally substituted acyl, $-OR^{S1}$, or $-N(R^e)_2$, and each occurrence of $R^B$ is independently hydrogen, halogen, optionally substituted alkyl, optionally substituted acyl, $-OR^{S2}$, or $-N(R^e)_2$;

$X^5$ is $-O-$, $-S-$, $-C(R^d)_2-$, or $-NR^c-$;

each of $R^{7a}$ and $R^{7b}$ is independently hydrogen, halogen, optionally substituted $C_{1-6}$ alkyl, $-OR^e$, or $-N(R^e)_2$;

each of $R^{8a}$ and $R^{8b}$ is independently hydrogen, halogen, optionally substituted $C_{1-6}$ alkyl, $-OR^e$, or $-N(R^e)_2$;

each of $R^{9a}$ and $R^{9b}$ is independently hydrogen, halogen, optionally substituted $C_{1-6}$ alkyl, $-OR^e$, or $-N(R^e)_2$;

each of $R^{S1}$ and $R^{S2}$ is independently hydrogen, optionally substituted $C_{1-6}$ alkyl, optionally substituted acyl, or an oxygen protecting group, or $R^{S1}$ and $R^{S2}$ are joined to form an optionally substituted heterocyclic ring;

$L^S$ is a bond, $-O-$, $-NR^c-$, optionally substituted alkylene, optionally substituted alkenylene, optionally substituted alkynylene, optionally substituted acylene, or optionally substituted arylene;

each occurrence of $R^d$ is independently hydrogen, halogen, optionally substituted $C_{1-6}$ alkyl, $-OR^e$, or $-N(R^e)_2$;

each occurrence of $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two $R^e$ are joined to form and optionally substituted heterocyclic or optionally substituted heteroaryl ring;

each occurrence of $R^c$ is independently hydrogen, optionally substituted $C_{1-6}$ alkyl, optionally substituted acyl, or a nitrogen protecting group; and each of h, q, and t is independently 1, 2, or 3.

In certain embodiments, the compound is of Formula (I):

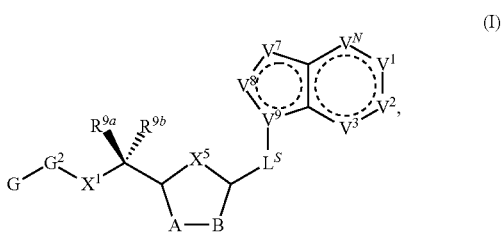

(I)

or a pharmaceutically acceptable salt, solvate, hydrate, polymorph, co-crystal, tautomer, stereoisomer, prodrug, or isotopically labeled derivative thereof, wherein:

G² is —S(=O)₂—, —P(=O)(Rᵉ)—, —P(=O)(ORᵉ)—, —P(=O)(N(Rᵉ)₂)—, —P(=S)(Rᵉ)—, —P(=S)(ORᵉ)—, —P(=S)(N(Rᵉ)₂)—, —Si(ORᵉ)₂—, —C(=O)—, —C(=S)—, —C(=NRᶠ)—, —(CH₂)ₕ—,

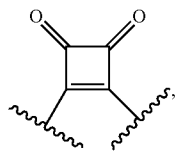 [SMILES: *c1c(*)c(=O)c1=O]

or optionally substituted monocyclic 5- or 6-membered heteroarylene, wherein 1, 2, 3, or 4 atoms in the heteroarylene ring system are independently oxygen, nitrogen, or sulfur;

G is of formula:

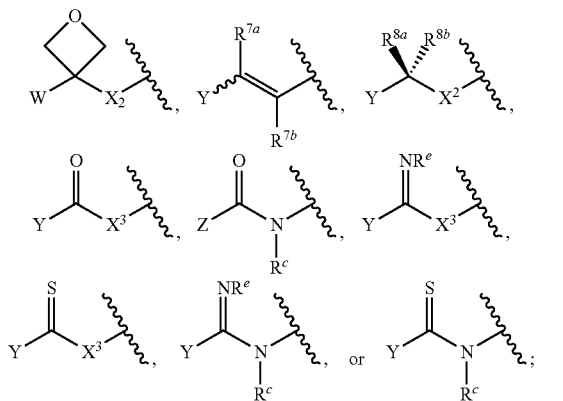

each of W, Y, and Z is independently optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —ORᵉ, —N(Rᵉ)₂, optionally substituted carbocyclyl, optionally substituted heterocyclyl, optionally substituted aryl, optionally substituted heteroaryl, or of formula:

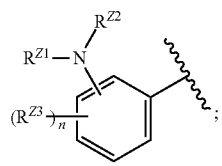

n is 0, 1, 2, 3, or 4;

each of $R^{Z1}$ and $R^{Z2}$ is independently hydrogen, optionally substituted alkyl, optionally, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form an optionally substituted heterocyclic or optionally substituted heteroaryl ring;

each occurrence of $R^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO₂, —CN, —ORᵉ, or —N(Rᵉ)₂, or two $R^{Z3}$ are joined to form an optionally substituted aryl or optionally substituted heteroaryl ring;

$X^1$ is a bond, —O—, —C(Rᵈ)₂—, —(CH₂)_q—, or —NRᶠ—;

$X^2$ is a bond, —O—, —C(Rᵈ)₂—, —(CH₂)_t—, or —NRᶠ—;

$X^3$ is a bond, —O—, —C(Rᵈ)₂—, or —(CH₂)_r—;

A-B is —(Rᴬ)₂C—C(Rᴮ)₂— or —RᴬC=CRᴮ—, wherein each occurrence of Rᴬ is independently hydrogen, halogen, optionally substituted alkyl, optionally substituted acyl, —OR^{S1}, or —N(Rᵉ)₂, and each occurrence of Rᴮ is independently hydrogen, halogen, optionally substituted alkyl, optionally substituted acyl, —OR^{S2}, or —N(Rᵉ)₂;

$X^5$ is —O—, —S—, —C(Rᵈ)₂—, or —NRᶜ—;

each of $R^{7a}$ and $R^{7b}$ is independently hydrogen, halogen, optionally substituted $C_{1-6}$ alkyl, —ORᵉ, or —N(Rᵉ)₂;

each of $R^{8a}$ and $R^{8b}$ is independently hydrogen, halogen, optionally substituted $C_{1-6}$ alkyl, —ORᵉ, or —N(Rᵉ)₂;

each of $R^{9a}$ and $R^{9b}$ is independently hydrogen, halogen, optionally substituted $C_{1-6}$ alkyl, —ORᵉ, or —N(Rᵉ)₂;

each of $R^{S1}$ and $R^{S2}$ is independently hydrogen, optionally substituted $C_{1-6}$ alkyl, optionally substituted acyl, or an oxygen protecting group, or $R^{S1}$ and $R^{S2}$ are joined to form an optionally substituted heterocyclic ring;

Lˢ is a bond, —O—, —NRᶜ—, optionally substituted alkylene, optionally substituted alkenylene, optionally substituted alkynylene, optionally substituted acylene, or optionally substituted arylene;

each of $V^1$, $V^2$, $V^3$, $V^7$, $V^8$, and $V^9$ is independently N, NRⱽ, or CRⱽ;

each occurrence of Rⱽ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO₂, —CN, —ORᵉ, or —N(Rᵉ)₂;

$V^N$ is N, $NR^N$, or $CR^N$;

$R^N$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO₂, —CN, —ORᵉ, or —N(R^{Na})₂;

each occurrence of $R^{Na}$ independently hydrogen, optionally substituted $C_{1-6}$ alkyl, optionally substituted acyl, or a nitrogen protecting group, or both $R^{Na}$ are joined to form and optionally substituted heterocyclic or optionally substituted heteroaryl ring;

each occurrence of Rᵈ is independently hydrogen, halogen, optionally substituted $C_{1-6}$ alkyl, —ORᵉ, or —N(Rᵉ)₂;

each occurrence of Rᵉ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two Rᵉ are joined to form and optionally substituted heterocyclic or optionally substituted heteroaryl ring;

each occurrence of $R^c$ is independently hydrogen, optionally substituted $C_{1-6}$ alkyl, optionally substituted acyl, or a nitrogen protecting group;

each of h, q, and t is independently 1, 2, or 3; and

⌬ indicates that each bond of the ring is a single or double bond.

In certain embodiments, the compound is not of formula:

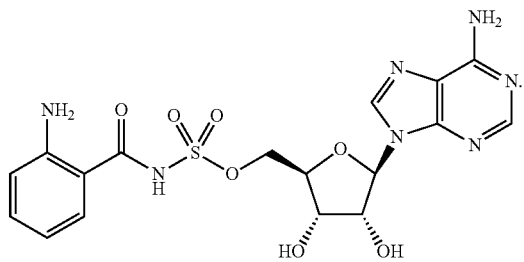 [SMILES: Nc1ccccc1C(=O)NS(=O)(=O)OC[C@H]1O[C@@H](n2cnc3c(N)ncnc32)[C@H](O)[C@@H]1O]

In certain embodiments, Z is not:

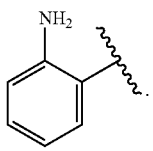 [SMILES: *c1ccccc1N]

In certain embodiments, G is not:

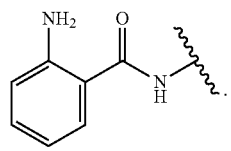 [SMILES: *NC(=O)c1ccccc1N]

In certain embodiments, the compounds is not a compound disclosed in: Davis et al., ACS Chem. Bio. (2014), 9, 2535-2544; U.S. Pat. Nos. 8,461,128; 8,946,188; U.S. patent application Ser. No. 11/911,525, filed Jul. 2, 2009; U.S. patent application Ser. No. 13/897,807, filed Jan. 23, 2014; or WIPO Application No. PCT/US2006/014394, filed Apr. 14, 2006. In certain embodiments, the compounds is not a compound disclosed in: U.S. Pat. No. 6,989,430; U.S. application Ser. No. 12/096,463, filed Nov. 27, 2008; or WIPO Application No. PCT/US2006/046433, filed Jun. 14, 2007.

In certain embodiments, a compound of Formula (Z) is a compound of Formula (I). In certain embodiments, a compounds of Formula (Z) is not a compound of Formula (I).

Unless otherwise stated, any formulae described herein are also meant to include salts, solvates, hydrates, polymorphs, co-crystals, tautomers, stereoisomers, prodrugs, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is of an isotopically labeled form of any of the formulae described herein. For example, compounds having the present structures except for the replacement of hydrogen by deuterium or tritium, replacement of $^{19}F$ with $^{18}F$, or the replacement of a $^{12}C$ by a $^{13}C$ or $^{14}C$ are within the scope of the disclosure. In certain embodiments, the provided compound is a deuterated form of any of the formulae described herein.

A provided compound may be any possible stereoisomer of Formula (I). The ribose or ribose analog ring of Formula (I) may include at least four chiral centers, each of which may independently be in either the (R)- or (S)-configuration. In certain embodiments, a compound of Formula (I) is a stereoisomer of formula:

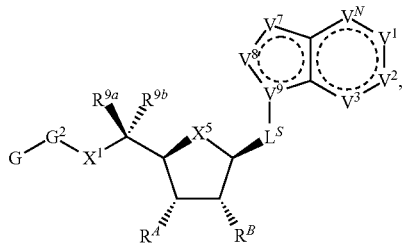

In some embodiments, a compound of Formula (I) is a stereoisomer of formula:

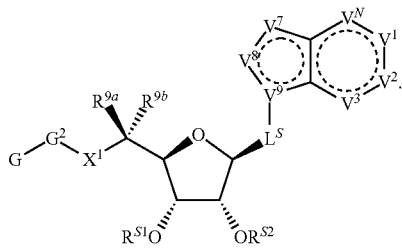

In certain embodiments, the compound of Formula (I) is a compound of Formula (II):

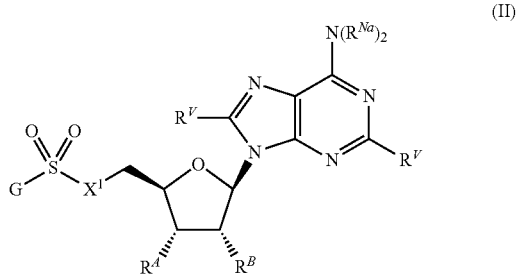

or a pharmaceutically acceptable salt, stereoisomer, or tautomer thereof, wherein G, $X^1$, $R^A$, $R^B$, $R^V$, and $R^{Na}$ are as described herein.

In certain embodiments, the compound of Formula (I) is a compound of Formula (II-A):

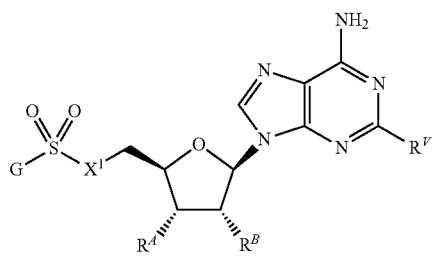
(II-A)

or a pharmaceutically acceptable salt, stereoisomer, or tautomer thereof, wherein G, $R^A$, $R^B$, $R^V$ and $X^1$ are as described herein.

In certain embodiments, the compound of Formula (I) is a compound of Formula (II-B):

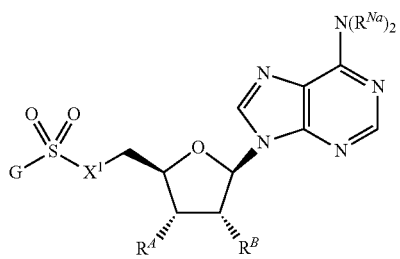
(II-B)

or a pharmaceutically acceptable salt, stereoisomer, or tautomer thereof, wherein G, $R^A$, $R^B$, $R^{Na}$, and $X^1$ are as described herein.

In certain embodiments, the compound of Formula (I) is a compound of Formula (II-C):

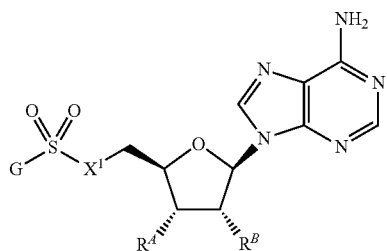
(II-C)

or a pharmaceutically acceptable salt, stereoisomer, or tautomer thereof, wherein G, $R^A$, $R^B$, and $X^1$ are as described herein.

In certain embodiments, the compound of Formula (I) is a compound of Formula (II-D):

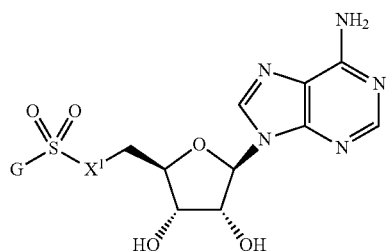
(II-D)

or a pharmaceutically acceptable salt, stereoisomer, or tautomer thereof, wherein G and $X^1$ are as described herein.

In certain embodiments, the compound of Formula (I) is a compound of Formula (II-E):

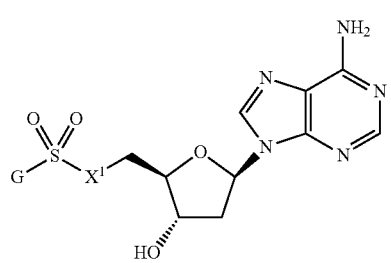
(II-E)

or a pharmaceutically acceptable salt, stereoisomer, or tautomer thereof, wherein G and $X^1$ are as described herein.

In certain embodiments, the compound of Formula (I) is a compound of Formula (II-F):

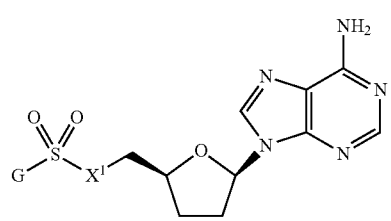
(II-F)

or a pharmaceutically acceptable salt, stereoisomer, or tautomer thereof, wherein G and $X^1$ are as described herein.

In certain embodiments, the compound of Formula (I) is a compound of Formula (II-G):

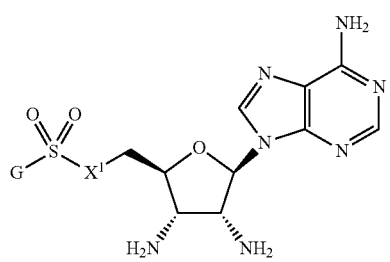
(II-G)

or a pharmaceutically acceptable salt, stereoisomer, or tautomer thereof, wherein G and $X^1$ are as described herein.

In certain embodiments, the compound of Formula (I) is a compound of Formula (III):

(III)

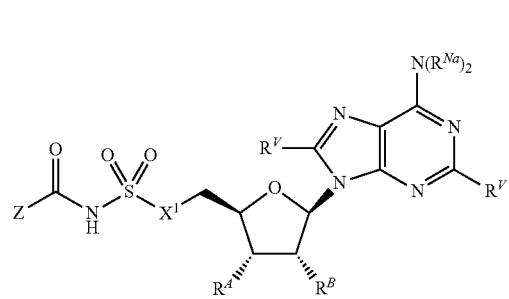

or a pharmaceutically acceptable salt, stereoisomer, or tautomer thereof, wherein Z, $X^1$, $R^A$, $R^B$, $R^V$, and $R^{Na}$ are as described herein.

In certain embodiments, the compound of Formula (I) is a compound of Formula (III-A):

(III-A)

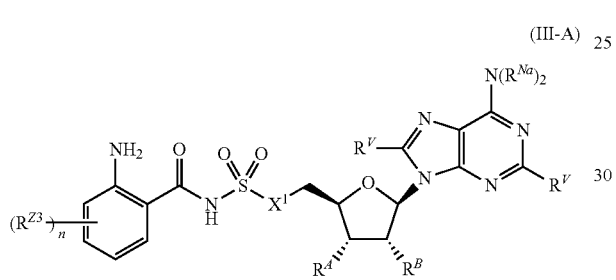

or a pharmaceutically acceptable salt, stereoisomer, or tautomer thereof, wherein $R^{Z3}$, n, $X^1$, $R^A$, $R^B$, $R^V$, and $R^{Na}$ are as described herein.

In certain embodiments, the compound of Formula (I) is a compound of Formula (III-B):

(III-B)

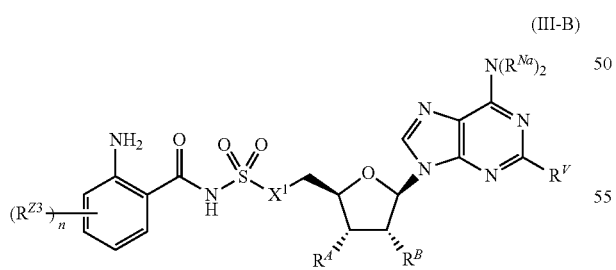

or a pharmaceutically acceptable salt, stereoisomer, or tautomer thereof, wherein $R^{Z3}$, n, $X^1$, $R^A$, $R^B$, $R^V$, and $R^{Na}$ are as described herein.

In certain embodiments, the compound of Formula (I) is a compound of Formula (III-C):

(III-C)

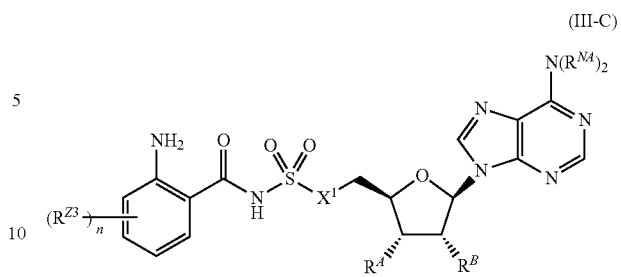

or a pharmaceutically acceptable salt, stereoisomer, or tautomer thereof, wherein $R^{Z3}$, n, $X^1$, $R^A$, $R^B$, and $R^{Na}$ are as described herein.

In certain embodiments, the compound of Formula (I) is a compound of Formula (III-D):

(III-D)

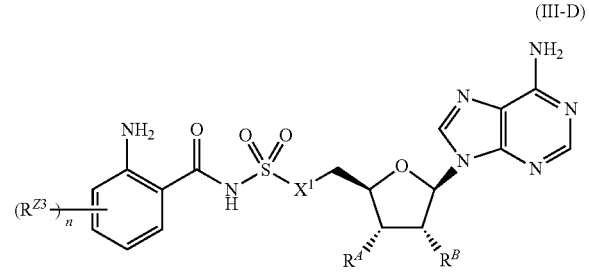

or a pharmaceutically acceptable salt, stereoisomer, or tautomer thereof, wherein $R^{Z3}$, n, $X^1$, $R^A$, and $R^B$ are as described herein.

In certain embodiments, the compound of Formula (I) is a compound of Formula (III-E):

(III-E)

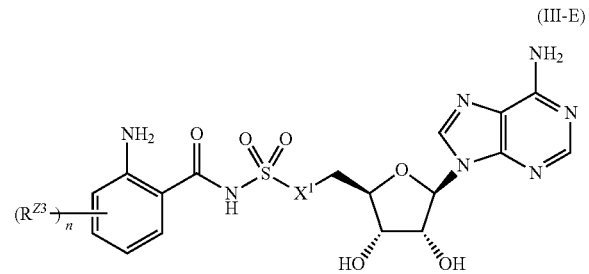

or a pharmaceutically acceptable salt, stereoisomer, or tautomer thereof, wherein $R^{Z3}$, n, and $X^1$ are as described herein.

In certain embodiments, the compound of Formula (I) is a compound of Formula (III-F):

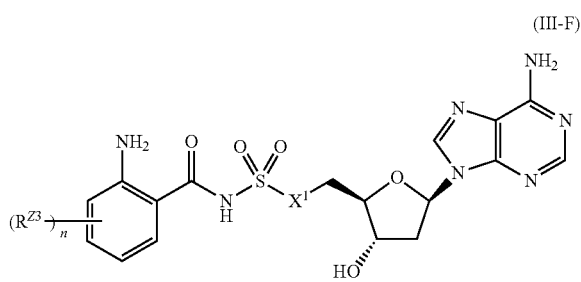

(III-F)

or a pharmaceutically acceptable salt, stereoisomer, or tautomer thereof, wherein $R^{Z3}$, n, and $X^1$ are as described herein.

In certain embodiments, the compound of Formula (I) is a compound of Formula (III-G):

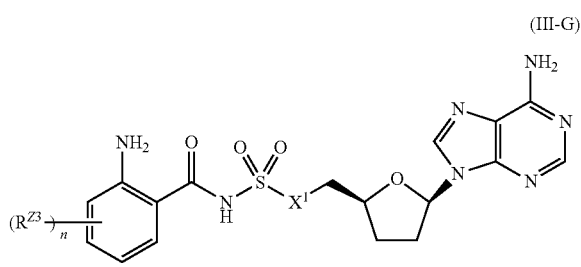

(III-G)

or a pharmaceutically acceptable salt, stereoisomer, or tautomer thereof, wherein $R^{Z3}$, n, and $X^1$ are as described herein.

In certain embodiments, the compound of Formula (I) is a compound of Formula (III-H):

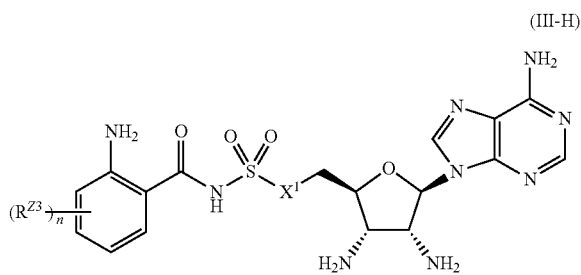

(III-H)

or a pharmaceutically acceptable salt, stereoisomer, or tautomer thereof, wherein $R^{Z3}$, n, and $X^1$ are as described herein.

In certain embodiments, the compound of Formula (I) is a compound of Formula (IV):

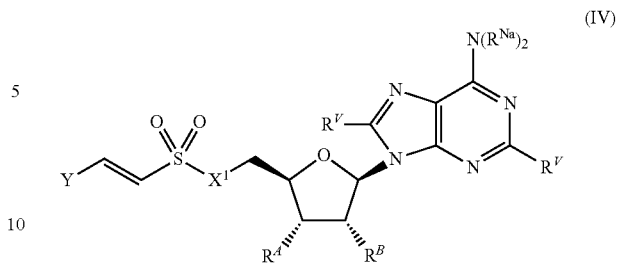

(IV)

or a pharmaceutically acceptable salt, stereoisomer, or tautomer thereof, wherein Y, $X^1$, $R^A$, $R^B$, $R^V$, and $R^{Na}$ are as described herein.

In certain embodiments, the compound of Formula (I) is a compound of Formula (IV-A):

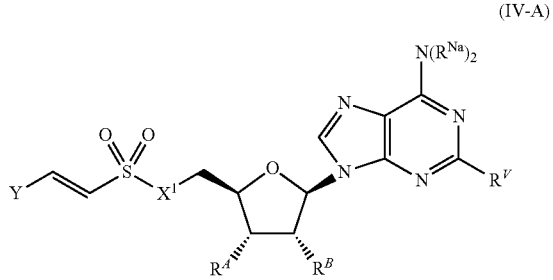

(IV-A)

or a pharmaceutically acceptable salt, stereoisomer, or tautomer thereof, wherein Y, $X^1$, $R^A$, $R^B$, $R^V$, and $R^{Na}$ are as described herein.

In certain embodiments, the compound of Formula (I) is a compound of Formula (IV-B):

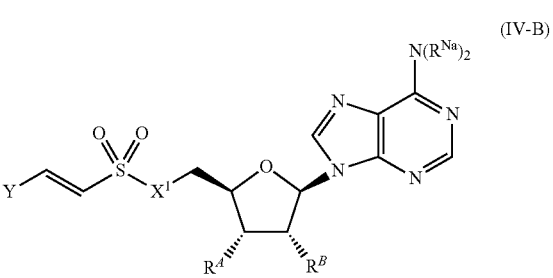

(IV-B)

or a pharmaceutically acceptable salt, stereoisomer, or tautomer thereof, wherein Y, $X^1$, $R^A$, $R^B$, and $R^{Na}$ are as described herein.

In certain embodiments, the compound of Formula (I) is a compound of Formula (IV-C):

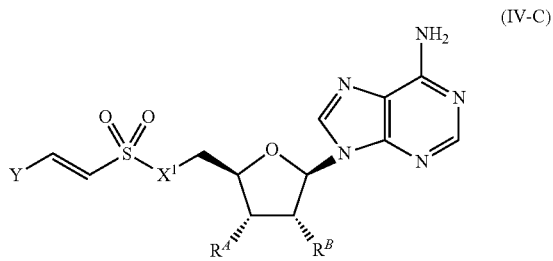

(IV-C)

or a pharmaceutically acceptable salt, stereoisomer, or tautomer thereof, wherein Y, $X^1$, $R^A$, and $R^B$ are as described herein.

In certain embodiments, the compound of Formula (I) is a compound of Formula (IV-D):

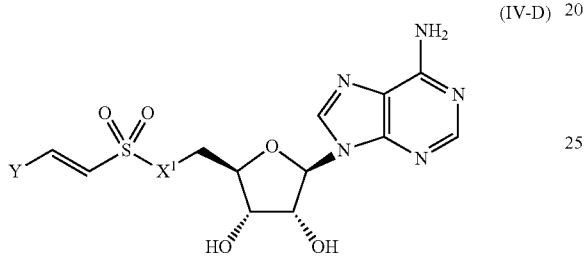

(IV-D)

or a pharmaceutically acceptable salt, stereoisomer, or tautomer thereof, wherein Y and $X^1$ are as described herein.

In certain embodiments, the compound of Formula (I) is a compound of Formula (IV-E):

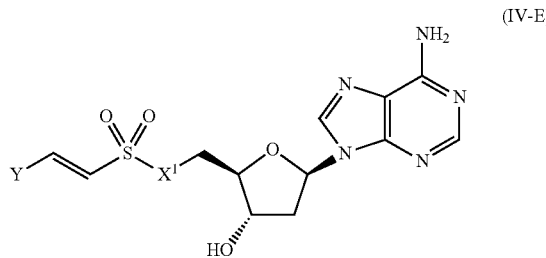

(IV-E)

or a pharmaceutically acceptable salt, stereoisomer, or tautomer thereof, wherein Y and $X^1$ are as described herein.

In certain embodiments, the compound of Formula (I) is a compound of Formula (IV-F):

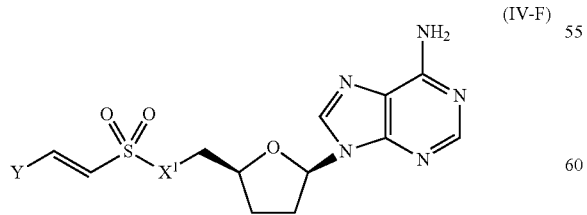

(IV-F)

or a pharmaceutically acceptable salt, stereoisomer, or tautomer thereof, wherein Y and $X^1$ are as described herein.

In certain embodiments, the compound of Formula (I) is a compound of Formula (IV-G):

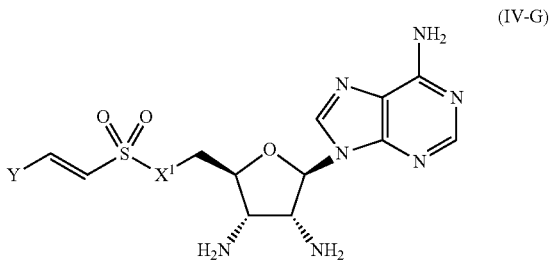

(IV-G)

or a pharmaceutically acceptable salt, stereoisomer, or tautomer thereof, wherein Y and $X^1$ are as described herein.

In certain embodiments, the compound of Formula (I) is a compound of Formula (IV-H):

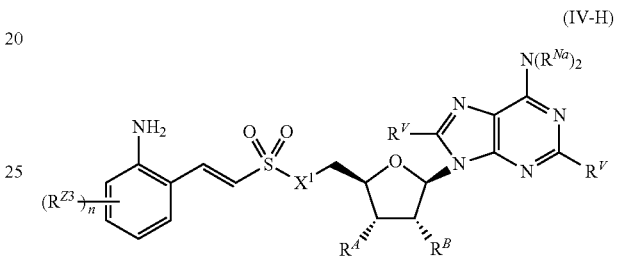

(IV-H)

or a pharmaceutically acceptable salt, stereoisomer, or tautomer thereof, wherein $R^{Z3}$, n, $X^1$, $R^A$, $R^B$, $R^V$, and $R^{Na}$ are as described herein.

In certain embodiments, the compound of Formula (I) is a compound of Formula (V):

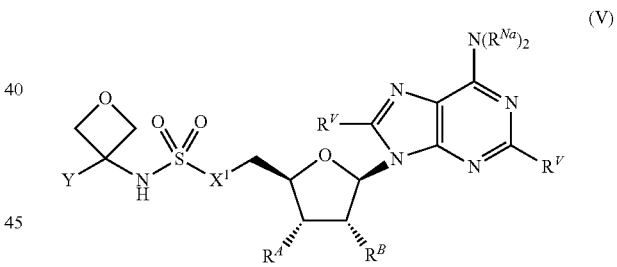

(V)

or a pharmaceutically acceptable salt, stereoisomer, or tautomer thereof, wherein Y, $X^1$, $R^A$, $R^B$, $R^V$, and $R^{Na}$ are as described herein.

In certain embodiments, the compound of Formula (I) is a compound of Formula (V-A):

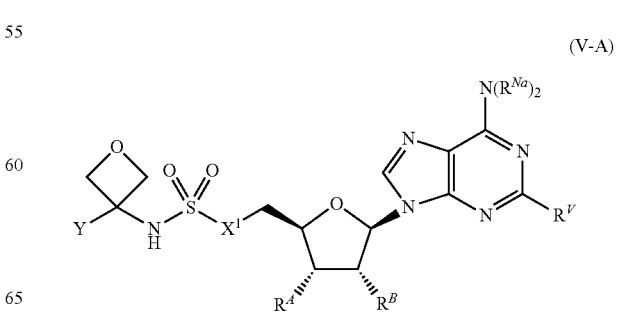

(V-A)

or a pharmaceutically acceptable salt, stereoisomer, or tautomer thereof, wherein Y, $X^1$, $R^A$, $R^B$, $R^V$, and $R^{Na}$ are as described herein.

In certain embodiments, the compound of Formula (I) is a compound of Formula (V-B):

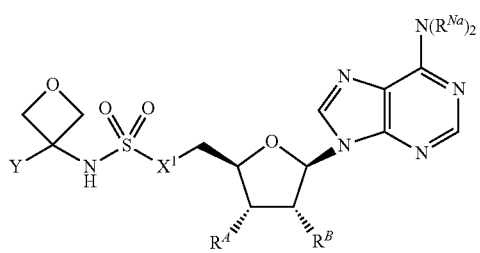

(V-B)

or a pharmaceutically acceptable salt, stereoisomer, or tautomer thereof, wherein Y, $X^1$, $R^A$, $R^B$, and $R^{Na}$ are as described herein.

In certain embodiments, the compound of Formula (I) is a compound of Formula (V-C):

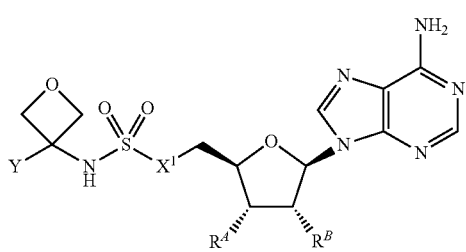

(V-C)

or a pharmaceutically acceptable salt, stereoisomer, or tautomer thereof, wherein Y, $X^1$, $R^A$, and $R^B$ are as described herein.

In certain embodiments, the compound of Formula (I) is a compound of Formula (V-D):

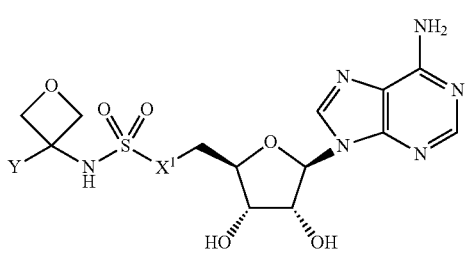

(V-D)

or a pharmaceutically acceptable salt, stereoisomer, or tautomer thereof, wherein Y and $X^1$ are as described herein.

In certain embodiments, the compound of Formula (I) is a compound of Formula (V-E):

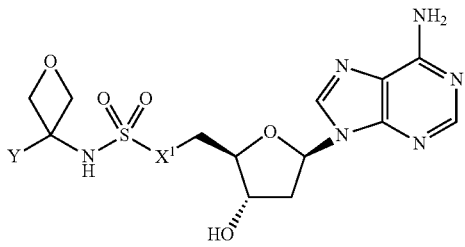

(V-E)

or a pharmaceutically acceptable salt, stereoisomer, or tautomer thereof, wherein Y and $X^1$ are as described herein.

In certain embodiments, the compound of Formula (I) is a compound of Formula (V-F):

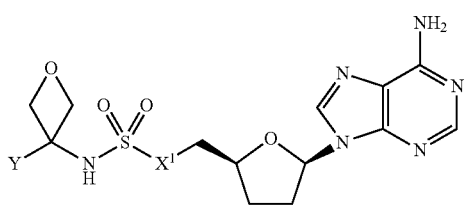

(V-F)

or a pharmaceutically acceptable salt, stereoisomer, or tautomer thereof, wherein Y and $X^1$ are as described herein.

In certain embodiments, the compound of Formula (I) is a compound of Formula (V-G):

(V-G)

or a pharmaceutically acceptable salt, stereoisomer, or tautomer thereof, wherein Y and $X^1$ are as described herein.

In certain embodiments, the compound of Formula (I) is a compound of Formula (V-H):

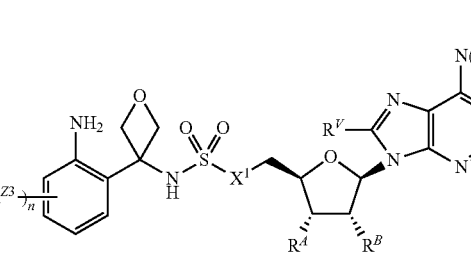

(V-H)

or a pharmaceutically acceptable salt, stereoisomer, or tautomer thereof, wherein $R^{Z1}$, $R^{Z2}$, $R^{Z3}$, $X^1$, $R^A$, $R^B$, $R^V$, and $R^{Na}$ are as described herein.

Group G

As generally defined herein, G is of formula:

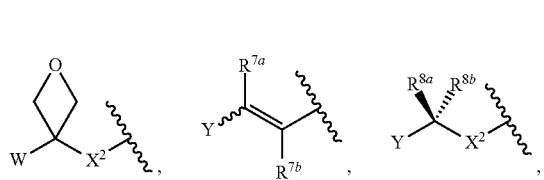

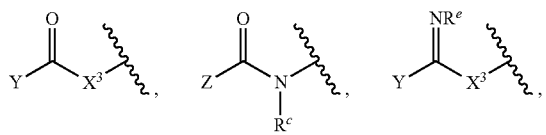

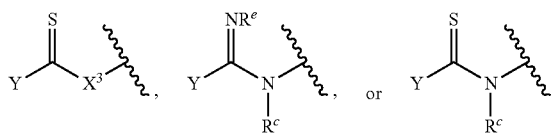

In certain embodiments, G is of formula:

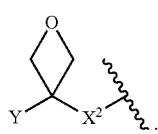

In some embodiments, G is of formula:

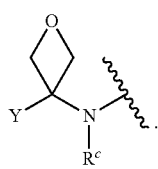

In some embodiments, G is of formula:

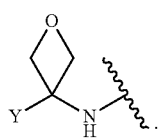

In some embodiments, G is of formula:

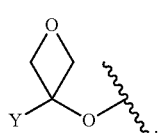

In some embodiments, G is of formula:

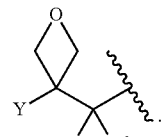

In certain embodiments, G is of formula:

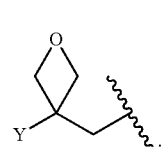

In certain embodiments, G is of formula:

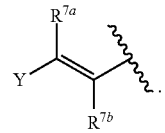

In some embodiments, G is of formula:

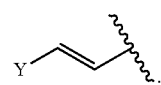

In some embodiments, G is of formula:

In certain embodiments, G is of formula:

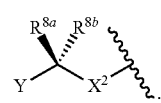

In some embodiments, G is of formula:

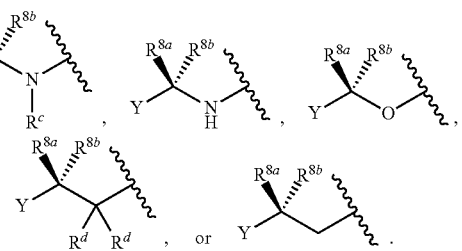

In some embodiments, G is of formula

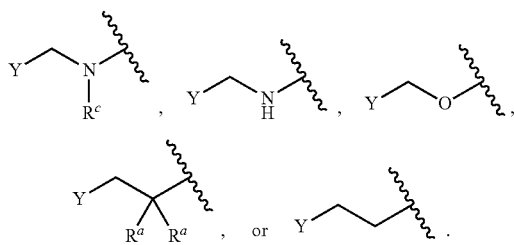

In certain embodiments, G is of formula:

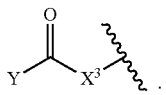

In some embodiments, G is of formula:

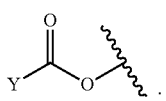

In some embodiments, G is of formula:

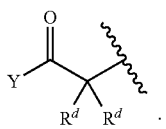

In some embodiments, G is of formula:

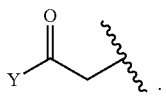

In certain embodiments, G is of formula:

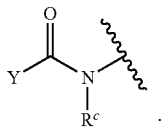

In some embodiments, G is of formula:

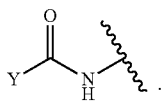

In certain embodiments, G is of the formula:

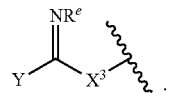

In certain embodiments, G is of the formula:

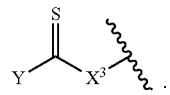

In certain embodiments, G is of the formula:

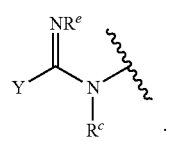

certain embodiments, G is of the formula:

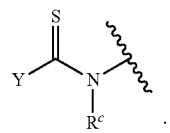

Group W

As generally defined herein, W is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —$OR^e$, —$N(R^e)_2$, optionally substituted carbocyclyl, optionally substituted heterocyclyl, optionally substituted aryl, optionally substituted heteroaryl, or of formula:

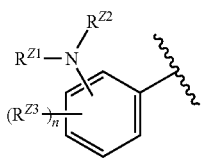

In certain embodiments, W is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —$OR^e$, —$N(R^e)_2$, optionally substituted carbocyclyl, optionally substituted heterocyclyl, optionally substituted aryl, or optionally substituted heteroaryl. In certain embodiments, W is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, W is methyl. In certain embodiments, W is ethyl, propyl, or butyl. In certain embodiments, W is optionally substituted alkenyl, e.g., optionally substituted $C_{2-6}$ alkenyl. In certain embodiments, W is vinyl, allyl, or prenyl. In certain embodiments, W is optionally substituted alkynyl, e.g., $C_{2-6}$ alkynyl.

In certain embodiments, W is optionally substituted heteroalkyl, e.g., optionally substituted $C_{1-6}$ heteroalkyl wherein one carbon is replaced with oxygen, optionally substituted $C_{1-6}$ heteroalkyl wherein one carbon is replaced with nitrogen. In certain embodiments, W is optionally substituted heteroalkenyl, e.g., optionally substituted $C_{2-6}$ heteroalkenyl wherein one carbon is replaced with oxygen, optionally substituted $C_{2-6}$ heteroalkenyl wherein one carbon is replaced with nitrogen. In certain embodiments, W is optionally substituted heteroalkynyl, e.g., optionally substituted $C_{2-6}$ heteroalkynyl wherein one carbon is replaced with oxygen, optionally substituted $C_{2-6}$ heteroalkynyl wherein one carbon is replaced with nitrogen.

In certain embodiments, W is —$OR^e$, e.g., —OH. In some embodiments, W is —$OR^e$, and $R^e$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In some embodiments, $R^e$ is methyl. In some embodiments, $R^e$ is ethyl, propyl, or butyl. In some embodiments, W is —$OR^e$, and $R^e$ is optionally substituted acyl. In some embodiments, W is —$OR^e$, and $R^e$ is an oxygen protecting group.

In certain embodiments, W is —$N(R^e)_2$. In certain embodiments, W is —$NHR^e$, e.g., —$NH_2$. In some embodiments, W is —$N(R^e)_2$, and both $R^e$ are optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In some embodiments, W is —$NHR^e$, and $R^e$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In some embodiments, at least one $R^e$ is methyl. In some embodiments, at least one $R^e$ is ethyl, propyl, or butyl. In some embodiments, W is —$NHR^e$, and $R^e$ is optionally substituted acyl. In some embodiments, W is —$NHR^e$, and $R^e$ is an oxygen protecting group. In some embodiments, W is —$N(R^e)_2$, and both $R^e$ are joined to form an optionally substituted heterocyclic ring, e.g., piperidinyl, piperizinyl. In some embodiments, W is —$N(R^e)_2$, and both $R^e$ are joined to form an optionally substituted heteroaryl ring.

In certain embodiments, W is Y, i.e., W is selected from the group consisting of optionally substituted carbocyclyl, optionally substituted heterocyclyl, optionally substituted aryl, and optionally substituted heteroaryl. Any group contemplated herein for Y is also contemplated for W.

Group Y

As generally defined herein, Y is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —$OR^e$, —$N(R^e)_2$, optionally substituted carbocyclyl, optionally substituted heterocyclyl, optionally substituted aryl, optionally substituted heteroaryl, or of formula:

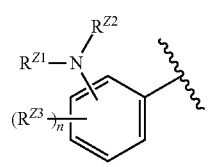

In certain embodiments, Y is optionally substituted alkyl (e.g., optionally substituted $C_{1-6}$ alkyl), optionally substituted alkenyl (e.g., optionally substituted $C_{1-6}$ alkenyl), or optionally substituted alkynyl (e.g., optionally substituted $C_{1-6}$ alkynyl). In certain embodiments, Y is optionally substituted heteroalkyl (e.g., optionally substituted $C_{1-6}$ heteroalkyl), optionally substituted heteroalkenyl (e.g., optionally substituted $C_{1-6}$ heteroalkenyl), or optionally substituted heteroalkynyl (e.g., optionally substituted $C_{1-6}$ heteroalkynyl). In certain embodiments, Y is optionally substituted alkoxy (e.g., optionally substituted $C_{1-6}$ alkoxy), optionally substituted amino, —$OR^e$, or —$N(R^e)_2$. In certain embodiments, Y is optionally substituted carbocyclyl, optionally substituted heterocyclyl, optionally substituted aryl, or optionally substituted heteroaryl. In certain embodiments, Y is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments Y is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, Y is optionally substituted aryl, e.g., optionally substituted phenyl. In certain embodiments, Y is optionally substituted heteroaryl, e.g., optionally substituted 5-6 membered heteroaryl, or optionally substituted 9-10 membered bicyclic heteroaryl. In certain embodiments, Y is optionally substituted aralkyl, e.g., optionally substituted benzyl. In certain embodiments, Y is optionally substituted heteroaralkyl, e.g., methyl substituted with a 5-6-membered heteroaryl ring.

In certain embodiments, Y is of formula:

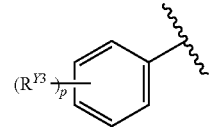

wherein p is 0, 1, 2, 3, 4, or 5; and $R^{Y3}$ is as defined herein.

In certain embodiments, Y is of formula:

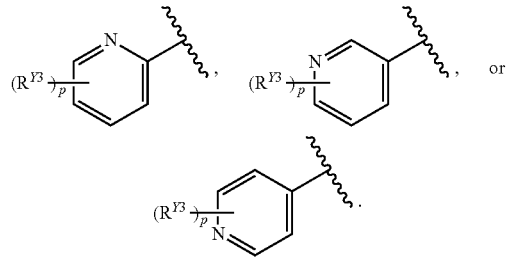

wherein p is 0, 1, 2, 3, or 4; and $R^{Y3}$ is as defined herein.

In certain embodiments, Y is of formula:

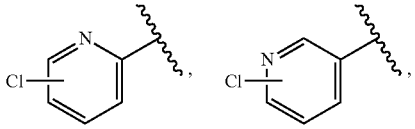

-continued

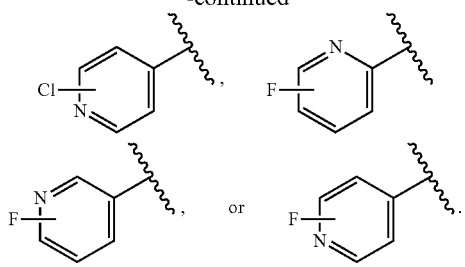

In certain embodiments, Y is of formula:

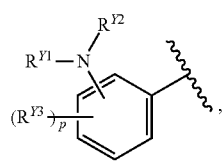

wherein p is 0, 1, 2, 3, or 4; and $R^{Y1}$, $R^{Y2}$, and $R^{Y3}$ are as defined herein.

In certain embodiments, Y is of formula:

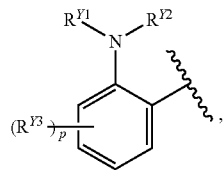

wherein p is 0, 1, 2, 3, or 4; and $R^{Y1}$, $R^{Y2}$, and $R^{Y3}$ are as defined herein.

In certain embodiments, Y is of formula:

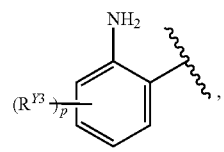

wherein p is 0, 1, 2, 3, or 4; and $R^{Y3}$ is as defined herein.

In certain embodiments, Y is of formula:

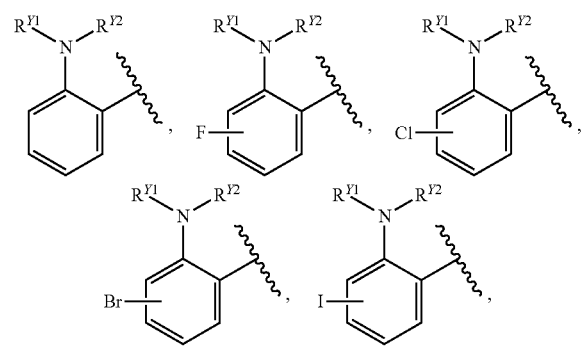

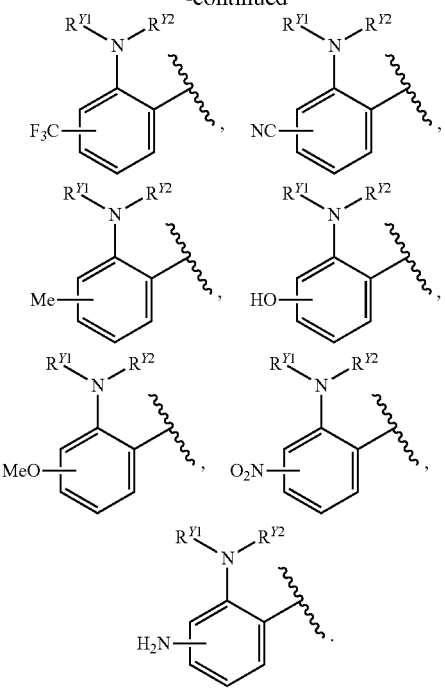

wherein $R^{Y1}$ and $R^{Y2}$ are as defined herein.

In certain embodiments, Y is of formula:

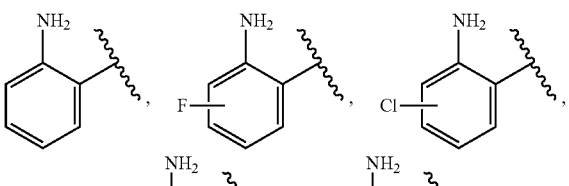

As generally defined herein, each occurrence of $R^{Y1}$ and $R^{Y2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form and optionally substituted heterocyclic or optionally substituted heteroaryl ring.

In some embodiments, $R^{Y1}$ and $R^{Y2}$ are both hydrogen. In some embodiments, $R^{Y1}$ is hydrogen, and $R^{Y2}$ is a non-hydrogen group. In some embodiments, $R^{Y2}$ is hydrogen, and $R^{Y1}$ is a non-hydrogen group. In some embodiments, both $R^{Y1}$ and $R^{Y2}$ are non-hydrogen groups.

In certain embodiments, at least one of $R^{Y1}$ and $R^{Y2}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one of $R^{Y1}$ and $R^{Y2}$ is methyl. In certain embodiments, at least one of $R^{Y1}$ and $R^{Y2}$ is ethyl, propyl, or butyl.

In certain embodiments, at least one of $R^{Y1}$ and $R^{Y2}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments at least one of $R^{Y1}$ and $R^{Y2}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one of $R^{Y1}$ and $R^{Y2}$ is optionally substituted aryl, e.g., optionally substituted phenyl. In certain embodiments, at least one of $R^{Y1}$ and $R^{Y2}$ is optionally substituted heteroaryl, e.g., optionally substituted 5-6 membered heteroaryl, or optionally substituted 9-10 membered bicyclic heteroaryl. In certain embodiments, at least one of $R^{Y1}$ and $R^{Y2}$ is optionally substituted aralkyl, e.g., optionally substituted benzyl. In certain embodiments, at least one of $R^{Y1}$ and $R^{Y2}$ is optionally substituted heteroaralkyl, e.g., methyl substituted with a 5-6-membered heteroaryl ring.

In certain embodiments, at least one of $R^{Y1}$ and $R^{Y2}$ is acyl (e.g., —C(=O)($R^e$), —C(=O)O($R^e$), —C(=O)NH($R^e$), —C(=O)N($R^e$)$_2$). In certain embodiments, at least one of $R^{Y1}$ and $R^{Y2}$ is a nitrogen protecting group. In some embodiments, at least one of $R^{Y1}$ and $R^{Y2}$ is alkoxycarbonyl (e.g., Cbz, BOC, FMOC). In some embodiments, at least one of $R^{Y1}$ and $R^{Y2}$ is acetyl (Ac), benzyl (Bn), or benzoyl (Bz). In some embodiments, at least one of $R^{Y1}$ and $R^{Y2}$ is sulfonyl (e.g., tosyl, nosyl, mesyl).

As generally defined herein, each occurrence of $R^{Y3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$.

In some embodiments, p is 0. In some embodiments, p is 1. In some embodiments, p is 2. In some embodiments, p is 3, 4 or 5. In some embodiments, at least one $R^{Y3}$ is —Cl, —Br, or —I. In some embodiments, at least one $R^{Y3}$ is —F. In certain embodiments, at least one $R^{Y3}$ is optionally substituted alkyl. In certain embodiments, at least one $R^{Y3}$ is unsubstituted $C_{1-6}$ alkyl. In certain embodiments, at least one $R^{Y3}$ is methyl. In certain embodiments, at least one $R^{Y3}$ is ethyl, propyl, or butyl. In certain embodiments, at least one $R^{Y3}$ is —CF$_3$. In certain embodiments, at least one $R^{Y3}$ optionally substituted alkenyl, e.g., optionally substituted $C_{2-6}$ alkenyl. In certain embodiments, at least one $R^{Y3}$ vinyl, allyl, or prenyl. In certain embodiments, at least one $R^{Y3}$ optionally substituted alkynyl, e.g., $C_{2-6}$ alkynyl.

In certain embodiments, at least one $R^{Y3}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments at least one $R^{Y3}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{Y3}$ is optionally substituted aryl, e.g., optionally substituted phenyl. In certain embodiments, at least one $R^{Y3}$ is optionally substituted heteroaryl, e.g., optionally substituted 5-6 membered heteroaryl, or optionally substituted 9-10 membered bicyclic heteroaryl. In certain embodiments, at least one $R^{Y3}$ is optionally substituted aralkyl, e.g., optionally substituted benzyl. In certain embodiments, at least one $R^{Y3}$ is optionally substituted heteroaralkyl, e.g., methyl substituted with a 5-6-membered heteroaryl ring.

In certain embodiments, at least one $R^{Y3}$ is —NO$_2$. In certain embodiments, at least one $R^{Y3}$ is —CN. In certain embodiments, at least one $R^{Y3}$ is —OR$^e$ (e.g., —OH, —OMe, —O($C_{1-6}$ alkyl)). In certain embodiments, at least one $R^{Y3}$ is —OR$^e$, and R$^e$ is an oxygen protecting group. In certain embodiments, at least one $R^{Y3}$ is —N(R$^e$)$_2$ (e.g., —NH$_2$, —NMe$_2$, —NH($C_{1-6}$ alkyl)). In certain embodiments, at least one $R^{Y3}$ is —NHR$^e$, and R$^e$ is a nitrogen protecting group. In certain embodiments, at least one $R^{Y3}$ is optionally substituted acyl (e.g., —C(=O)(R$^e$), —C(=O)O(R$^e$), —C(=O)NH(R$^e$), —C(=O)N(R$^e$)$_2$). In some embodiments, at least one $R^{Y3}$ is —C(=O)OMe. In some embodiments, at least one $R^{Y3}$ is —C(=O)OH.

Group Z

As generally defined herein, Z is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —OR$^e$, —N(R$^e$)$_2$, optionally substituted carbocyclyl, optionally substituted heterocyclyl, optionally substituted aryl, optionally substituted heteroaryl, or of formula:

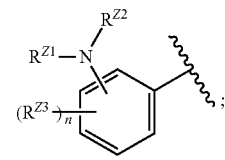

wherein n is 0, 1, 2, 3, or 4.

In certain embodiments, Z is optionally substituted alkyl (e.g., optionally substituted $C_{1-6}$ alkyl), optionally substituted alkenyl (e.g., optionally substituted $C_{1-6}$ alkenyl), or optionally substituted alkynyl (e.g., optionally substituted $C_{1-6}$ alkynyl). In certain embodiments, Z is optionally substituted heteroalkyl (e.g., optionally substituted $C_{1-6}$ heteroalkyl), optionally substituted heteroalkenyl (e.g., optionally substituted $C_{1-6}$ heteroalkenyl), or optionally substituted heteroalkynyl (e.g., optionally substituted $C_{1-6}$ heteroalkynyl). In certain embodiments, Z is optionally substituted alkoxy (e.g., optionally substituted $C_{1-6}$ alkoxy), optionally substituted amino, —$OR^e$, or —$N(R^e)_2$. In certain embodiments, Z is optionally substituted carbocyclyl (e.g., optionally substituted monocyclic 3- to 7-membered carbocyclyl). In certain embodiments, Z is optionally substituted aryl (e.g., optionally substituted 6- to 14-membered aryl, e.g., optionally substituted phenyl). In certain embodiments, Z is optionally substituted heteroaryl (e.g., optionally substituted monocyclic 5- or 6-membered heteroaryl, wherein 1, 2, 3, or 4 atoms in the heteroaryl ring system are independently oxygen, nitrogen, or sulfur). In certain embodiments, Z is optionally substituted heterocyclyl, optionally substituted 6-membered heteroaryl, or of formula:

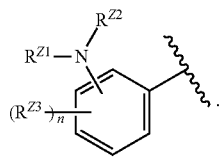

In certain embodiments, Z is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, Z is optionally substituted 6-membered heteroaryl, e.g., optionally substituted pyridyl.

In certain embodiments, Z is of formula:

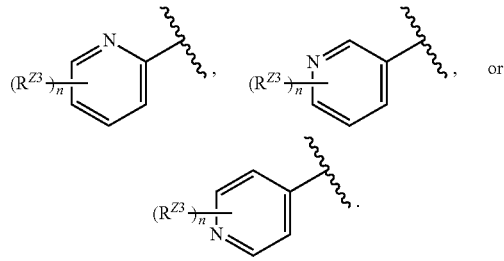

wherein n is 0, 1, 2, 3, or 4; and $R^3$ is as defined herein.

In certain embodiments, Z is of formula:

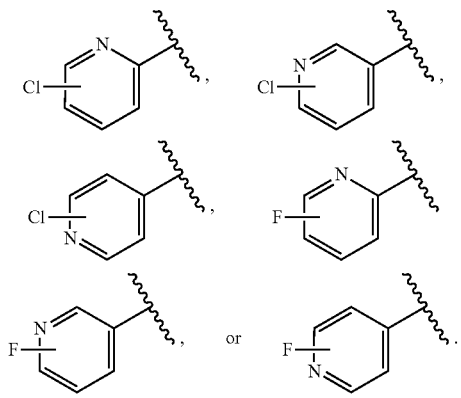

In certain embodiments, Z is of formula:

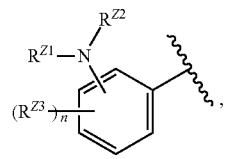

wherein n is 0, 1, 2, 3, or 4; and $R^{Z1}$, $R^{Z2}$, and $R^{Z3}$ are as defined herein.

In certain embodiments, Z is of formula:

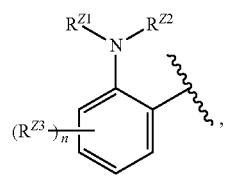

or
wherein n is 0, 1, 2, 3, or 4; and $R^{Z1}$, $R^{Z2}$, and $R^{Z3}$ are as defined herein.

In certain embodiments, Z is of formula:

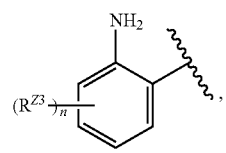

or
wherein n is 0, 1, 2, 3, or 4; and $R^3$ is as defined herein.

In certain embodiments, Z is of formula:

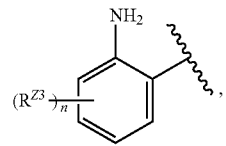

or
wherein n is 1, 2, 3, or 4; and R is as defined herein.

In certain embodiments, Z is of formula:

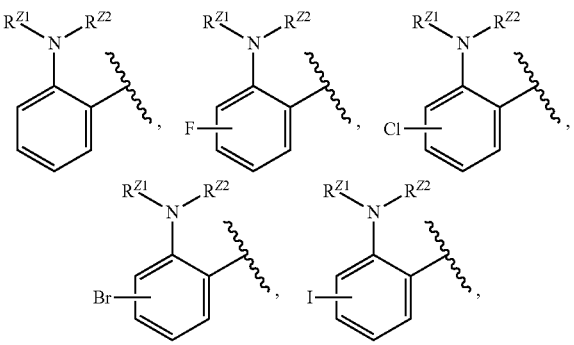

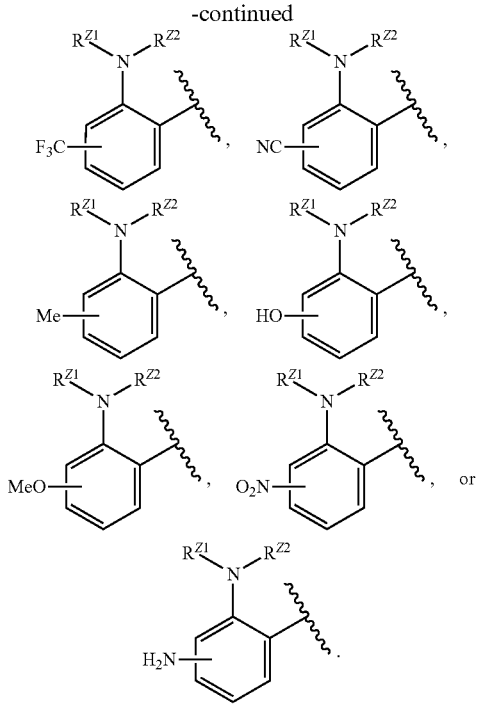

wherein $R^{Z1}$ and $R^{Z2}$ are as defined herein.

In certain embodiments, Z is of formula:

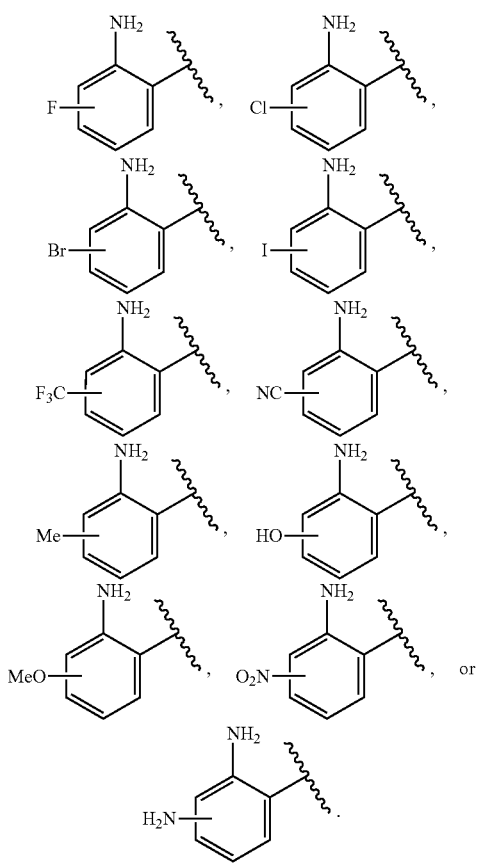

In certain embodiments, Z is of formula:

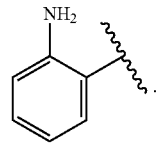

In certain embodiments, Z is not of formula:

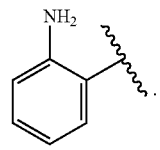

As generally defined herein, each occurrence of $R^{Z1}$ and $R^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form and optionally substituted heterocyclic or optionally substituted heteroaryl ring.

In some embodiments, $R^{Z1}$ and $R^{Z2}$ are both hydrogen. In some embodiments, $R^{Z1}$ is hydrogen, and $R^{Z2}$ is a non-hydrogen group. In some embodiments, $R^{Z2}$ is hydrogen, and $R^{Z1}$ is a non-hydrogen group. In some embodiments, both $R^{Z1}$ and $R^{Z2}$ are non-hydrogen groups.

In certain embodiments, at least one of $R^{Z1}$ and $R^{Z2}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one of $R^{Z1}$ and $R^{Z2}$ is methyl. In certain embodiments, at least one of $R^{Z1}$ and $R^{Z2}$ is ethyl, propyl, or butyl.

In certain embodiments, at least one of $R^{Z1}$ and $R^{Z2}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments at least one of $R^{Z1}$ and $R^{Z2}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one of $R^{Z1}$ and $R^{Z2}$ is optionally substituted aryl, e.g., optionally substituted phenyl. In certain embodiments, at least one of $R^{Z1}$ and $R^{Z2}$ is optionally substituted heteroaryl, e.g., optionally substituted 5-6 membered heteroaryl, or optionally substituted 9-10 membered bicyclic heteroaryl. In certain embodiments, at least one of $R^{Z1}$ and $R^{Z2}$ is optionally substituted aralkyl, e.g., optionally substituted benzyl. In certain embodiments, at least one of $R^{Z1}$ and $R^{Z2}$ is optionally substituted heteroaralkyl, e.g., methyl substituted with a 5-6-membered heteroaryl ring.

In certain embodiments, at least one of $R^{Z1}$ and $R^{Z2}$ is acyl (e.g., —C(═O)(R$^e$), —C(═O)O(R$^e$), —C(═O)NH(R$^e$), —C(═O)N(R$^e$)$_2$). In certain embodiments, at least one of $R^{Z1}$ and $R^{Z2}$ is a nitrogen protecting group. In some embodiments, at least one of $R^{Z1}$ and $R^{Z2}$ is alkoxycarbonyl (e.g., Cbz, BOC, FMOC). In some embodiments, at least one of $R^{Z1}$ and $R^{Z2}$ is acetyl (Ac), benzyl (Bn), or benzoyl (Bz). In some embodiments, at least one of $R^{Z1}$ and $R^{Z2}$ is sulfonyl (e.g., tosyl, nosyl, mesyl).

As generally defined herein, each occurrence of $R^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$.

In some embodiments, p is 0. In some embodiments, p is 1. In some embodiments, p is 2. In some embodiments, p is 3, 4 or 5. In some embodiments, at least one $R^{Z3}$ is —Cl, —Br, or —I. In some embodiments, at least one $R^{Z3}$ is —F. In certain embodiments, at least one $R^{Z3}$ is optionally substituted alkyl. In certain embodiments, at least one $R^{Z3}$ is unsubstituted $C_{1-6}$ alkyl. In certain embodiments, at least one $R^{Z3}$ is methyl. In certain embodiments, at least one $R^{Z3}$ is ethyl, propyl, or butyl. In certain embodiments, at least one $R^{Z3}$ is —CF$_3$. In certain embodiments, at least one $R^{Z3}$ optionally substituted alkenyl, e.g., optionally substituted $C_{2-6}$ alkenyl. In certain embodiments, at least one $R^{Z3}$ vinyl, allyl, or prenyl. In certain embodiments, at least one $R^{Z3}$ optionally substituted alkynyl, e.g., $C_{2-6}$ alkynyl.

In certain embodiments, at least one $R^{Z3}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments at least one $R^{Z3}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one $R^{Z3}$ is optionally substituted aryl, e.g., optionally substituted phenyl. In certain embodiments, at least one $R^{Z3}$ is optionally substituted heteroaryl, e.g., optionally substituted 5-6 membered heteroaryl, or optionally substituted 9-10 membered bicyclic heteroaryl. In certain embodiments, at least one $R^{Z3}$ is optionally substituted aralkyl, e.g., optionally substituted benzyl. In certain embodiments, at least one $R^{Z3}$ is optionally substituted heteroaralkyl, e.g., methyl substituted with a 5-6-membered heteroaryl ring.

In certain embodiments, at least one $R^{Z3}$ is —NO$_2$. In certain embodiments, at least one $R^{Z3}$ is —CN. In certain embodiments, at least one $R^{Z3}$ is —OR$^e$ (e.g., —OH, —OMe, —O(C$_{1-6}$ alkyl)). In certain embodiments, at least one $R^{Z3}$ is —OR$^e$, and R$^e$ is an oxygen protecting group. In certain embodiments, at least one $R^{Z3}$ is —N(R$^e$)$_2$ (e.g., —NH$_2$, —NMe$_2$, —NH(C$_{1-6}$ alkyl)). In certain embodiments, at least one $R^{Z3}$ is —N(R$^e$, and R$^e$ is a nitrogen protecting group. In certain embodiments, at least one $R^{Z3}$ is optionally substituted acyl (e.g., —C(=O)(R$^e$), —C(=O)O(R$^e$), —C(=O)NH(R$^e$), —C(=O)N(R$^e$)$_2$). In some embodiments, at least one $R^{Z3}$ is —C(=O)OMe. In some embodiments, at least one $R^{Z3}$ is —C(=O)OH.

Linkers $X^2$ and $X^3$

As generally defined herein, $X^2$ is a bond, —O—, —C(R$^d$)$_2$—, —(CH$_2$)$_t$—, or —NR$^f$—. In certain embodiments, $X^2$ is a bond. In certain embodiments, $X^2$ is —O—. In certain embodiments, $X^2$ is —NH—. In certain embodiments, $X^2$ is —NR$^f$—, and R$^d$ is optionally substituted C$_{1-6}$ alkyl. In certain embodiments, $X^2$ is —NR$^f$—, and R$^f$ is unsubstituted C$_{1-6}$ alkyl. In certain embodiments, $X^2$ is —NR$^f$—, and R$^f$ is methyl. In certain embodiments, $X^2$ is —NR$^f$—, and R$^d$ is ethyl, propyl, or butyl. In certain embodiments, $X^2$ is —NR$^f$—, and R$^f$ is optionally substituted acyl (e.g., —C(=O)(R$^e$), —C(=O)O(R$^e$), —C(=O)NH(R$^e$), —C(=O)N(R$^e$)$_2$). In certain embodiments, $X^2$ is —NR$^f$—, and R$^f$ is a nitrogen protecting group. In certain embodiments, $X^2$ is —C(R$^d$)$_2$—. In certain embodiments, $X^2$ is —CH$_2$—. In certain embodiments, $X^2$ is —C(R$^d$)$_2$—, and both R$^d$ are halogen. In certain embodiments, $X^2$ is —CF$_2$—. In certain embodiments, $X^2$ is —(CH$_2$)$_t$—, wherein t is 1, 2, or 3. In some embodiments, $X^2$ is —(CH$_2$)$_t$—, wherein t is 1. In some embodiments, $X^2$ is —(CH$_2$)$_t$—, wherein t is 2 or 3.

As generally defined herein, $X^3$ is a bond, —O—, —C(R$^d$)$_2$—, or —(CH$_2$)$_t$—. In certain embodiments, $X^3$ is a bond. In certain embodiments, $X^3$ is —O—. In certain embodiments, $X^3$ is —C(R$^d$)$_2$. In certain embodiments, $X^3$ is —CH$_2$—. In certain embodiments, $X^3$ is —C(R$^d$)$_2$—, and both R$^d$ are halogen. In certain embodiments, $X^3$ is —CF$_2$—. In certain embodiments, $X^3$ is —(CH$_2$)$_t$—, wherein t is 1, 2, or 3. In some embodiments, $X^3$ is —(CH$_2$)$_t$—, wherein t is 1. In some embodiments, $X^3$ is —(CH$_2$)$_t$—, wherein t is 2 or 3.

Groups $R^{7a}$ and $R^{7b}$

As generally defined herein, each of $R^{7a}$ and $R^{7b}$ is independently hydrogen, halogen, optionally substituted C$_{1-6}$ alkyl, —OR$^e$, or —N(R$^e$)$_2$. The carbon to which $R^{7a}$ and $R^{7b}$ is attached may be in either the (R) or (S) configuration. In certain embodiments, at least one of $R^{7a}$ and $R^{7b}$ is hydrogen. In certain embodiments, at least one of $R^{7a}$ and $R^{7b}$ is halogen. In some embodiments, at least one of $R^{7a}$ and $R^{7b}$ is —F. In some embodiments, at least one of $R^{7a}$ and $R^{7b}$ is —Cl, —Br, or —I. In certain embodiments, at least one of $R^{7a}$ and $R^{7b}$ is optionally substituted C$_{1-6}$ alkyl. In certain embodiments, at least one of $R^{7a}$ and $R^{7b}$ is unsubstituted C$_{1-6}$ alkyl. In certain embodiments, at least one of $R^{7a}$ and $R^{7b}$ is methyl. In certain embodiments, at least one of $R^{7a}$ and $R^{7b}$ is ethyl, propyl, or butyl.

In certain embodiments, both $R^{7a}$ and $R^{7b}$ are hydrogen. In certain embodiments, both $R^{7a}$ and $R^{7b}$ are halogen. In some embodiments, both $R^{7a}$ and $R^{7b}$ are —F. In some embodiments, both $R^{7a}$ and $R^{7b}$ are —Cl, —Br, or —I. In certain embodiments, both $R^{7a}$ and $R^{7b}$ are optionally substituted C$_{1-6}$ alkyl. In certain embodiments, both $R^{7a}$ and $R^{7b}$ are unsubstituted C$_{1-6}$ alkyl. In certain embodiments, both $R^{7a}$ and $R^{7b}$ are methyl. In certain embodiments, both $R^{7a}$ and $R^{7b}$ are ethyl, propyl, or butyl.

In certain embodiments, $R^{7a}$ is hydrogen. In certain embodiments, $R^{7a}$ is halogen. In some embodiments, $R^{7a}$ is —F. In some embodiments, at least one of $R^{7a}$ is —Cl, —Br, or —I. In certain embodiments, $R^{7a}$ is optionally substituted C$_{1-6}$ alkyl. In certain embodiments, $R^{7a}$ is unsubstituted C$_{1-6}$ alkyl. In certain embodiments, $R^{7a}$ is methyl. In certain embodiments, $R^{7a}$ is ethyl, propyl, or butyl. In certain embodiments, $R^{7a}$ is —OR$^e$, e.g., —OH. In certain embodiments, $R^{7a}$ is —N(R$^e$)$_2$. In certain embodiments, $R^{7a}$ is —NHR$^e$, e.g., —NH$_2$.

In certain embodiments, $R^{7b}$ is hydrogen. In certain embodiments, $R^{7b}$ is halogen. In some embodiments, $R^{7b}$ is —F. In some embodiments, at least one of $R^{7b}$ is —Cl, —Br, or —I. In certain embodiments, $R^{7b}$ is optionally substituted C$_{1-6}$ alkyl. In certain embodiments, $R^{7b}$ is unsubstituted C$_{1-6}$ alkyl. In certain embodiments, $R^{7b}$ is methyl. In certain embodiments, $R^{7b}$ is ethyl, propyl, or butyl. In certain embodiments, $R^{7b}$ is —OR$^e$, e.g., —OH. In certain embodiments, $R^{7b}$ is —N(R$^e$)$_2$. In certain embodiments, $R^{7b}$ is —NHR$^e$, e.g., —NH$_2$.

Groups $R^{8a}$ and $R^{8b}$

As generally defined herein, each of $R^{8a}$ and $R^{8b}$ is independently hydrogen, halogen, optionally substituted $C_{1-6}$ alkyl, —$OR^e$, or —$N(R^e)_2$. The carbon to which $R^{8a}$ and $R^{8b}$ is attached may be in either the (R) or (S) configuration. In certain embodiments, at least one of $R^{8a}$ and $R^{8b}$ is hydrogen. In certain embodiments, at least one of $R^{8a}$ and $R^{8b}$ is halogen. In some embodiments, at least one of $R^{8a}$ and $R^{8b}$ is —F. In some embodiments, at least one of $R^{8a}$ and $R^{8b}$ is —Cl, —Br, or —I. In certain embodiments, at least one of $R^{8a}$ and $R^{8b}$ is optionally substituted $C_{1-6}$ alkyl. In certain embodiments, at least one of $R^{8a}$ and $R^{8b}$ is unsubstituted $C_{1-6}$ alkyl. In certain embodiments, at least one of $R^{8a}$ and $R^{8b}$ is methyl. In certain embodiments, at least one of $R^{8a}$ and $R^{8b}$ is ethyl, propyl, or butyl.

In certain embodiments, both $R^{8a}$ and $R^{8b}$ are hydrogen. In certain embodiments, both $R^{8a}$ and $R^{8b}$ are halogen. In some embodiments, both $R^{8a}$ and $R^{8b}$ are —F. In some embodiments, both $R^{8a}$ and $R^{8b}$ are —Cl, —Br, or —I. In certain embodiments, both $R^{8a}$ and $R^{8b}$ are optionally substituted $C_{1-6}$ alkyl. In certain embodiments, both $R^{8a}$ and $R^{8b}$ are unsubstituted $C_{1-6}$ alkyl. In certain embodiments, both $R^{8a}$ and $R^{8b}$ are methyl. In certain embodiments, both $R^{8a}$ and $R^{8b}$ are ethyl, propyl, or butyl.

In certain embodiments, $R^{8a}$ is hydrogen. In certain embodiments, $R^{8a}$ is halogen. In some embodiments, $R^{8a}$ is —F. In some embodiments, at least one of $R^{8a}$ is —Cl, —Br, or —I. In certain embodiments, $R^{8a}$ is optionally substituted $C_{1-6}$ alkyl. In certain embodiments, $R^{8a}$ is unsubstituted $C_{1-6}$ alkyl. In certain embodiments, $R^{8a}$ is methyl. In certain embodiments, $R^{8a}$ is ethyl, propyl, or butyl. In certain embodiments, $R^{8a}$ is —$OR^e$, e.g., —OH. In certain embodiments, $R^{8a}$ is —$N(R^e)_2$. In certain embodiments, $R^{8a}$ is —$NHR^e$, e.g., —$NH_2$.

In certain embodiments, $R^{8b}$ is hydrogen. In certain embodiments, $R^{8b}$ is halogen. In some embodiments, $R^{8b}$ is —F. In some embodiments, at least one of $R^{8b}$ is —Cl, —Br, or —I. In certain embodiments, $R^{8b}$ is optionally substituted $C_{1-6}$ alkyl. In certain embodiments, $R^{8b}$ is unsubstituted $C_{1-6}$ alkyl. In certain embodiments, $R^{8b}$ is methyl. In certain embodiments, $R^{8b}$ is ethyl, propyl, or butyl. In certain embodiments, $R^{8b}$ is —$OR^e$, e.g., —OH. In certain embodiments, $R^{8b}$ is —$N(R^e)_2$. In certain embodiments, $R^{8b}$ is —$NHR^e$, e.g., —$NH_2$.

Linker $X^1$

As generally defined herein, $X^1$ is a bond, —O—, —$C(R^d)_2$—, —$(CH_2)_q$—, or —$NR^f$—. In certain embodiments, $X^1$ is a bond. In certain embodiments, $X^1$ is —O—. In certain embodiments, $X^1$ is —NH—. In certain embodiments, $X^1$ is —$NR^f$—, and $R^d$ is optionally substituted $C_{1-6}$ alkyl. In certain embodiments, $X^1$ is —$NR^f$—, and $R^f$ is unsubstituted $C_{1-6}$ alkyl. In certain embodiments, $X^1$ is —$NR^f$—, and $R^f$ is methyl. In certain embodiments, $X^1$ is —$NR^f$—, and $R^d$ is ethyl, propyl, or butyl. In certain embodiments, $X^1$ is —$NR^f$—, and $R^f$ is optionally substituted acyl (e.g., —C(=O)($R^e$), —C(=O)O($R^e$), —C(=O)NH($R^e$), —C(=O)N($R^e$)$_2$). In certain embodiments, $X^1$ is —$NR^f$—, and $R^f$ is a nitrogen protecting group. In certain embodiments, $X^1$ is —$C(R^d)_2$. In certain embodiments, $X^1$ is —$CH_2$—. In certain embodiments, $X^1$ is —$C(R^d)_2$—, and both $R^d$ are halogen. In certain embodiments, $X^1$ is —$CF_2$—. In certain embodiments, $X^1$ is —$(CH_2)_q$—, wherein q is 1, 2, or 3. In some embodiments, $X^1$ is —$(CH_2)_q$—, wherein q is 1. In some embodiments, $X^1$ is —$(CH_2)_q$—, wherein q is 2 or 3.

In certain embodiments, both $X^1$ and $X^2$ are bonds. In certain embodiments, both $X^1$ and $X^2$ are —O—. In certain embodiments, both $X^1$ and $X^2$ are —$NR^f$—. In certain embodiments, both $X^1$ and $X^2$ are —NH—. In certain embodiments, both $X^1$ and $X^2$ are —$C(R^d)_2$—. In certain embodiments, $X^1$ is —$(CH_2)_q$—, and $X^2$ is —$(CH_2)_t$—, wherein each of q and t is independently 1, 2, or 3. In certain embodiments, both $X^1$ and $X^2$ are —$CH_2$—. In certain embodiments, $X^1$ is a bond, and $X^2$ is —O—. In certain embodiments, $X^1$ is a bond, and $X^2$ is —$NR^f$—. In certain embodiments, $X^1$ is a bond, and $X^2$ is —NH—. In certain embodiments, $X^1$ is a bond, and $X^2$ is —$C(R^d)_2$—. In certain embodiments, $X^1$ is a bond, and $X^2$ is —$(CH_2)_t$—. In certain embodiments, $X^1$ is —O—, and $X^2$ is a bond. In certain embodiments, $X^1$ is —O—, and $X^2$ is —$NR^f$—. In certain embodiments, $X^1$ is —O—, and $X^2$ is —NH—. In certain embodiments, $X^1$ is —O—, and $X^2$ is —$C(R^d)_2$—. In certain embodiments, $X^1$ is —O—, and $X^2$ is —$CH_2$—. In certain embodiments, $X^1$ is —O—, and $X^2$ is —$(CH_2)_t$—. In certain embodiments, $X^1$ is —$NR^f$—, and $X^2$ is a bond. In certain embodiments, $X^1$ is —NH—, and $X^2$ is a bond. In certain embodiments, $X^1$ is —$NR^f$—, and $X^2$ is —O—. In certain embodiments, $X^1$ is —NH—, and $X^2$ is —O—. In certain embodiments, $X^1$ is —$NR^f$—, and $X^2$ is —$C(R^d)_2$—. In certain embodiments, $X^1$ is —$NR^f$—, and $X^2$ is —$CH_2$—. In certain embodiments, $X^1$ is —$NR^f$—, and $X^2$ is —$(CH_2)_t$—. In certain embodiments, $X^1$ is —NH—, and $X^2$ is —$C(R^d)_2$—. In certain embodiments, $X^1$ is —NH—, and $X^2$ is —$CH_2$—. In certain embodiments, $X^1$ is —NH—, and $X^2$ is —$(CH_2)_t$—. In certain embodiments, $X^1$ is —$C(R^d)_2$—, and $X^2$ is a bond. In certain embodiments, $X^1$ is —$C(R^d)_2$—, and $X^2$ is —$NR^f$—. In certain embodiments, $X^1$—$C(R^d)_2$—, and $X^2$ is —NH—. In certain embodiments, $X^1$ is —$C(R^d)_2$—, and $X^2$ is —O—. In certain embodiments, $X^1$ is —$C(R^d)_2$—, and $X^2$ is —$(CH_2)_t$—. In certain embodiments, $X^1$ is —$CH_2$—, and $X^2$ is a bond. In certain embodiments, $X^1$ is —$CH_2$—, and $X^2$ is —$NR^f$—. In certain embodiments, $X^1$—$CH_2$—, and $X^2$ is —NH—. In certain embodiments, $X^1$ is —$CH_2$—, and $X^2$ is —O—. In certain embodiments, $X^1$ is —$(CH_2)_q$—, and $X^2$ is a bond. In certain embodiments, $X^1$ is —$(CH_2)_q$—, and $X^2$ is —O—. In certain embodiments, $X^1$ is —$(CH_2)_q$—, and $X^2$ is a —$NR^f$— bond. In certain embodiments, $X^1$ is —$(CH_2)_q$—, and $X^2$ is —NH—. In certain embodiments, $X^1$ is —$(CH_2)_q$—, and $X^2$ is —$C(R^d)_2$—.

In certain embodiments, both $X^1$ and $X^3$ are bonds. In certain embodiments, both $X^1$ and $X^3$ are —O—. In certain embodiments, both $X^1$ and $X^3$ are —NH—. In certain embodiments, both $X^1$ and $X^3$ are —$C(R^d)_2$—. In certain embodiments, $X^1$ is —$(CH_2)_q$—, and $X^3$ is —$(CH_2)_t$—, wherein each of q and t is independently 1, 2, or 3. In certain embodiments, both $X^1$ and $X^3$ are —$CH_2$—. In certain embodiments, $X^1$ is a bond, and $X^3$ is —O—. In certain embodiments, $X^1$ is a bond, and $X^3$ is —$C(R^d)_2$—. In certain embodiments, $X^1$ is a bond, and $X^3$ is —$(CH_2)_t$—. In certain embodiments, $X^1$ is —O—, and $X^3$ is a bond. In certain embodiments, $X^1$ is —O—, and $X^3$ is —$C(R^d)_2$—. In certain embodiments, $X^1$ is —O—, and $X^3$ is —$CH_2$—. In certain embodiments, $X^1$ is —O—, and $X^3$ is —$(CH_2)_t$—. In certain embodiments, $X^1$ is —$NR^f$—, and $X^3$ is a bond. In certain embodiments, $X^1$ is —NH—, and $X^3$ is a bond. In certain embodiments, $X^1$ is —$NR^f$—, and $X^3$ is —O—. In certain embodiments, $X^1$ is —NH—, and $X^3$ is —O—. In certain embodiments, $X^1$ is —$NR^f$—, and $X^3$ is —$C(R^d)_2$—. In certain embodiments, $X^1$ is —$NR^f$—, and $X^3$ is —$CH_2$—. In certain embodiments, $X^1$ is —$NR^f$—, and $X^3$ is —$(CH_2)_t$—. In certain embodiments, $X^1$ is —NH—, and $X^3$ is —$C(R^d)_2$—. In certain embodiments, $X^1$ is —NH—, and $X^3$ is —$CH_2$—. In certain embodiments, $X^1$ is —NH—, and $X^3$ is —$(CH_2)_t$—. In certain embodiments, $X^1$ is —$C(R^d)_2$—, and X³ is a bond. In certain embodiments, X¹ is —C(R$^d$)$_2$—, and X³ is —O—. In certain embodiments, X¹ is —C(R$^d$)$_2$—, and X³ is —(CH$_2$)$_t$—. In certain embodiments, X¹ is —CH$_2$—, and X³ is a bond. In certain embodiments, X¹ is —CH$_2$—, and X³ is —O—. In certain embodiments, X¹ is —(CH$_2$)$_q$—, and X³ is a bond. In certain embodiments, X¹ is —(CH$_2$)$_q$—, and X³ is —O—. In certain embodiments, X¹ is —(CH$_2$)$_q$—, and X³ is —C(R$^d$)$_2$—.

Group G²

As generally defined herein, G² is —S(=O)$_2$—, —P(=O)(R$^e$)—, —P(=O)(OR$^e$)—, —P(=O)(N(R$^e$)$_2$)—, —P(=S)(R$^e$)—, —P(=S)(OR$^e$)—, —P(=S)(N(R$^e$)$_2$)—, —Si(OR$^e$)$_2$—, —C(=O)—, —C(=S)—, —C(=NR$^f$)—, —(CH$_2$)$_h$—,

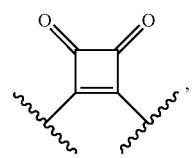 [SMILES: *c1c(*)c(=O)c1=O]

or optionally substituted monocyclic 5- or 6-membered heteroarylene, wherein 1, 2, 3, or 4 atoms in the heteroarylene ring system are independently oxygen, nitrogen, or sulfur.

In certain embodiments, G² is —S(=O)$_2$—, —P(=O)(OR$^e$)—, —P(=O)(N(R$^e$)$_2$)—, —Si(OR$^e$)$_2$—, or is of formula:

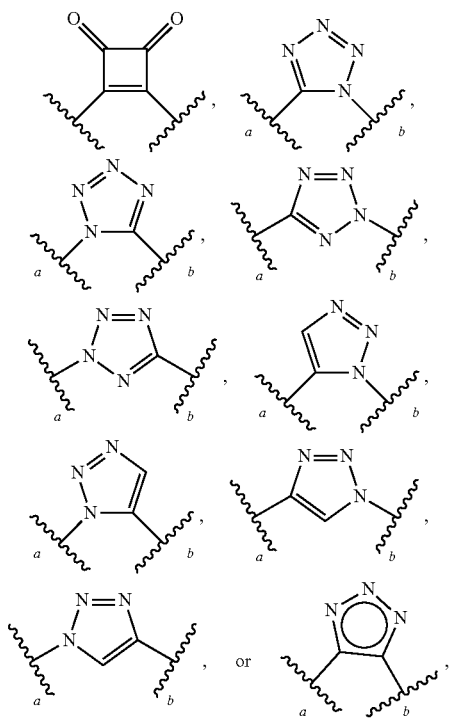

wherein G² is oriented such that the position labeled a is attached to L, and the position labeled b is attached to X¹.

In certain embodiments, G² is —S(=O)$_2$— or is of formula:

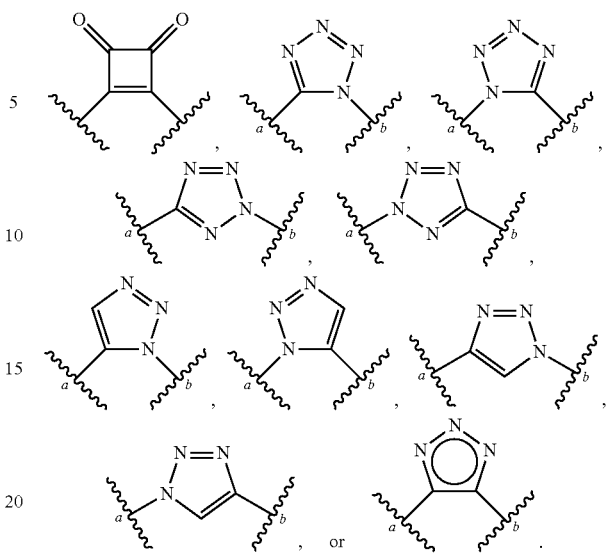

In certain embodiments, G² is —S(=O)$_2$—.

In certain embodiments, G² is —P(=O)(R$^e$)—. In certain embodiments, G² is —P(=O)(OR$^e$)—. In certain embodiments, G² is —P(=O)(OH)—. In certain embodiments, G² is —P(=O)(OR$^e$)—, and R$^e$ is optionally substituted alkyl. In certain embodiments, G² is —P(=O)(OR$^e$)—, and R$^e$ is unsubstituted C$_{1-6}$ alkyl. In certain embodiments, G² is —P(=O)(OMe)-. In certain embodiments, G is —P(=O)(OR$^e$)—, and R$^e$ is optionally substituted acyl. In certain embodiments, G² is —P(=O)(OR$^e$)—, and R$^e$ is an oxygen protecting group (e.g., silyl, TBDPS, TBDMS, TIPS, TES, TMS, MOM, THP, t-Bu, Bn, allyl, acetyl, pivaloyl, or benzoyl).

In certain embodiments, G² is —P(=O)(N(R$^e$)$_2$)—. In certain embodiments, G² is —P(=O)(NHR$^e$)—. In certain embodiments, G² is —P(=O)(NH$_2$)—. In certain embodiments, G² is —P(=O)(N(R$^e$)$_2$)—, and each R$^e$ is independently optionally substituted alkyl. In certain embodiments, G² is —P(=O)(N(R$^e$)$_2$)—, and each R$^e$ is independently unsubstituted C$_{1-6}$ alkyl. In certain embodiments, G² is —P(=O)(NHR$^e$)—, and R$^e$ is optionally substituted alkyl. In certain embodiments, G² is —P(=O)(NHR$^e$)—, and R$^e$ is unsubstituted C$_{1-6}$ alkyl. In certain embodiments, G² is —P(=O)(NHR$^e$)—, and R$^e$ is optionally substituted acyl. In certain embodiments, G² is —P(=O)(NHR$^e$)—, and R$^e$ is a nitrogen protecting group (e.g., Bn, Boc, Cbz, Fmoc, trifluoroacetyl, triphenylmethyl, acetyl, tosyl, nosyl, brosyl, mesyl, or triflyl). In certain embodiments, G² is —P(=O)(N(R$^e$)$_2$)—, and both R$^e$ are joined to form an optionally substituted heterocyclic ring (e.g., piperidinyl, piperizinyl). In certain embodiments, G² is —P(=S)(R$^e$)—, —P(=S)(OR$^e$)—, or —P(=S)(N(R$^e$)$_2$)—.

In certain embodiments, G² is —Si(OR$^e$)$_2$⁻. In certain embodiments, G² is —Si(OH)$_2$—.

In certain embodiments, G² is —Si(OR$^e$)(OH)—. In certain embodiments, G² is —Si(OMe)(OH)—. In certain embodiments, G² is —Si(OMe)$_2$-. In certain embodiments, G² is —Si(OR$^e$)$_2$—, and each R$^e$ is independently optionally substituted alkyl. In certain embodiments, G² is —Si(OR$^e$)$_2$—, and each R$^e$ is independently unsubstituted C$_{1-6}$ alkyl. In certain embodiments, G² is —Si(OR$^e$)(OH)—, and R$^e$ is optionally substituted alkyl. In certain embodiments, G² is —Si(OR$^e$)(OH)—, and R$^e$ is unsubstituted C$_{1-6}$ alkyl. In certain embodiments, G² is —Si(ORᵉ)₂—, each Rᵉ is an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, G² is —Si(ORᵉ)₂—, and both Rᵉ are joined to form an optionally substituted heterocyclic ring.

In certain embodiments, G² is —C(=O)—. In certain embodiments, G² is —C(=S)—. In certain embodiments, G² is —C(=NRᶠ)—. In certain embodiments, G² is —C(=NH)—.

In certain embodiments, G² is —(CH₂)ₕ—, and h is 1. In certain embodiments, G² is —(CH₂)ₕ—, and h is 2. In certain embodiments, G² is —(CH₂)ₕ—, and h is 3.

In certain embodiments, G² is of formula:

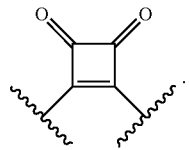 [SMILES: *c1c(*)c(=O)c1=O]

In certain embodiments, G² is optionally substituted monocyclic 5- or 6-membered heteroarylene, wherein 1, 2, 3, or 4 atoms in the heteroarylene ring system are independently oxygen, nitrogen, or sulfur. In certain embodiments, G² is furanylene, thienylene, pyrrolylene, oxazolylene, isoxazolylene, thiazolylene, isothiazolylene, imidazolylene, or pyrazolylene. In certain embodiments, G² is of formula:

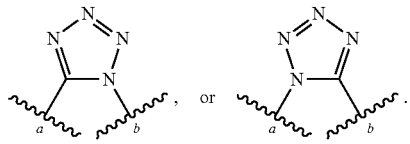 [SMILES: *c1nnnn1* ; *c1nnnn1*]

In certain embodiments, G² is of formula:

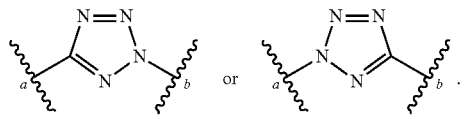 [SMILES: *c1nnn(*)n1 ; *c1nnn(*)n1]

In certain embodiments, G² is of formula:

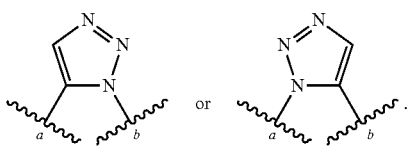 [SMILES: *c1cnnn1* ; *c1cnnn1*]

In certain embodiments, G² is of formula:

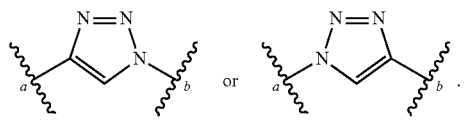 [SMILES: *c1cn(*)nn1 ; *c1cn(*)nn1]

In certain embodiments, G² is of formula:

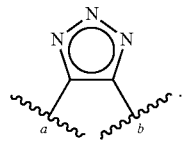

Groups $R^{9a}$ and $R^{9b}$

As generally defined herein, each of $R^{9a}$ and $R^{9b}$ is independently hydrogen, halogen, optionally substituted $C_{1-6}$ alkyl, —ORᵉ, or —N(Rᵉ)₂. The carbon to which $R^{9a}$ and $R^{9b}$ is attached may be in either the (R) or (S) configuration. In certain embodiments, at least one of $R^{9a}$ and $R^{9b}$ is hydrogen. In certain embodiments, at least one of $R^{9a}$ and $R^{9b}$ is halogen. In some embodiments, at least one of $R^{9a}$ and $R^{9b}$ is —F. In some embodiments, at least one of $R^{9a}$ and $R^{9b}$ is —Cl, —Br, or —I. In certain embodiments, at least one of $R^{9a}$ and $R^{9b}$ is optionally substituted $C_{1-6}$ alkyl. In certain embodiments, at least one of $R^{9a}$ and $R^{9b}$ is unsubstituted $C_{1-6}$ alkyl. In certain embodiments, at least one of $R^{9a}$ and $R^{9b}$ is methyl. In certain embodiments, at least one of $R^{9a}$ and $R^{9b}$ is ethyl, propyl, or butyl.

In certain embodiments, both $R^{9a}$ and $R^{9b}$ are hydrogen. In certain embodiments, both $R^{9a}$ and $R^{9b}$ are halogen. In some embodiments, both $R^{9a}$ and $R^{9b}$ are —F. In some embodiments, both $R^{9a}$ and $R^{9b}$ are —Cl, —Br, or —I. In certain embodiments, both $R^{9a}$ and $R^{9b}$ are optionally substituted $C_{1-6}$ alkyl. In certain embodiments, both $R^{9a}$ and $R^{9b}$ are unsubstituted $C_{1-6}$ alkyl. In certain embodiments, both $R^{9a}$ and $R^{9b}$ are methyl. In certain embodiments, both $R^{9a}$ and $R^{9b}$ are ethyl, propyl, or butyl.

In certain embodiments, $R^{9a}$ is hydrogen. In certain embodiments, $R^{9a}$ is halogen. In some embodiments, $R^{9a}$ is —F. In some embodiments, at least one of $R^{9a}$ is —Cl, —Br, or —I. In certain embodiments, $R^{9a}$ is optionally substituted $C_{1-6}$ alkyl. In certain embodiments, $R^{9a}$ is unsubstituted $C_{1-6}$ alkyl. In certain embodiments, $R^{9a}$ is methyl. In certain embodiments, $R^{9a}$ is ethyl, propyl, or butyl. In certain embodiments, $R^{9a}$ is —ORᵉ, e.g., —OH. In certain embodiments, $R^{9a}$ is —N(Rᵉ)₂. In certain embodiments, $R^{9a}$ is —NHRᵉ, e.g., —NH₂.

In certain embodiments, $R^{9b}$ is hydrogen. In certain embodiments, $R^{9b}$ is halogen. In some embodiments, $R^{9b}$ is —F. In some embodiments, at least one of $R^{9b}$ is —Cl, —Br, or —I. In certain embodiments, $R^{9b}$ is optionally substituted $C_{1-6}$ alkyl. In certain embodiments, $R^{9b}$ is unsubstituted $C_{1-6}$ alkyl. In certain embodiments, $R^{9b}$ is methyl. In certain embodiments, $R^{9b}$ is ethyl, propyl, or butyl. In certain embodiments, $R^{9b}$ is —ORᵉ, e.g., —OH. In certain embodiments, $R^{9b}$ is —N(Rᵉ)₂. In certain embodiments, $R^{9b}$ is —NHRᵉ, e.g., —NH₂.

Groups A-B and $X^5$

As generally defined herein, A-B is —(Rᴬ)₂C—C(Rᴮ)₂— or —RᴬC=CRᴮ—. In some embodiments, A-B is —(Rᴬ)₂C—C(Rᴮ)₂—. In some embodiments, A-B is —(Rᴬ)(H)C—C(H)(Rᴮ)—. In some embodiments, A-B is —RᴬC=CRᴮ—. In some embodiments, A-B is —HC=CH—. In some embodiments, A-B is —(N(Rᵉ)₂)(H)C—C(H)(N(Rᵉ)₂)—. In some embodiments, A-B is —(NHRᵉ)(H)C—C(H)(NHRᵉ)—. In some embodiments, A-B is —(NH₂)(H)C—C(H)(NH₂)—. In some embodiments, A-B is —(OR^{S1})(H)C—C(H)(OR^{S2})—. In some embodiments, A-B is —(OH)(H)C—C(H)(OH)—. In some embodiments, A is —CF₂— or —CCl₂—. In some embodiments, B is —CF$_2$— or —CCl$_2$—. In some embodiments, A is —CHF— or —CHCl—. In some embodiments, B is —CHF— or —CHCl—.

As generally defined herein, each occurrence of R$^A$ is independently hydrogen, halogen, optionally substituted alkyl, optionally substituted acyl, —OR$^{S1}$, or —N(R$^e$)$_2$. In some embodiments, at least one R$^A$ is hydrogen. In some embodiments, at least one R$^A$ is halogen. In some embodiments, at least one R$^A$ is unsubstituted C$_{1-6}$ alkyl, e.g., methyl. In some embodiments, at least one R$^A$ is optionally substituted acyl. In some embodiments, at least one R$^A$ is —OR$^{S1}$, e.g., —OH. In some embodiments, at least one R$^A$ is —N(R$^e$)$_2$, e.g., —NH$_2$.

As generally defined herein, each occurrence of R$^B$ is independently hydrogen, halogen, optionally substituted alkyl, optionally substituted acyl, —OR$^{S2}$, or —N(R$^e$)$_2$. In some embodiments, at least one R$^B$ is hydrogen. In some embodiments, at least one R$^B$ is halogen. In some embodiments, at least one R$^B$ is unsubstituted C$_{1-6}$ alkyl, e.g., methyl. In some embodiments, at least one R$^B$ is optionally substituted acyl. In some embodiments, at least one R$^B$ is —OR$^{S1}$, e.g., —OH. In some embodiments, at least one R$^B$ is —N(R$^e$)$_2$, e.g., —NH$_2$.

As generally defined herein, each of R$^{S1}$ and R$^{S2}$ is independently hydrogen, optionally substituted C$_{1-6}$ alkyl, optionally substituted acyl, or an oxygen protecting group, or R$^{S1}$ and R$^{S2}$ are joined to form an optionally substituted heterocyclic ring. The carbon to which R$^{S1}$ is attached may be in either the (R) or (S) configuration. The carbon to which R$^{S2}$ is attached may be in either the (R) or (S) configuration.

In certain embodiments, at least one of R$^{S1}$ and R$^{S2}$ is hydrogen. In certain embodiments, at least one of R$^{S1}$ and R$^{S2}$ is optionally substituted C$_{1-6}$ alkyl. In certain embodiments, at least one of R$^{S1}$ and R$^{S2}$ is unsubstituted C$_{1-6}$ alkyl. In certain embodiments, at least one of R$^{S1}$ and R$^{S2}$ is methyl. In certain embodiments, at least one of R$^{S1}$ and R$^{S2}$ is ethyl, propyl, or butyl. In certain embodiments, at least one of R$^{S1}$ and R$^{S2}$ is acyl (e.g., —C(=O)(R$^e$), —C(=O)O(R$^e$), —C(=O)NH(R$^e$), —C(=O)N(R$^e$)$_2$). In certain embodiments, at least one of R$^{S1}$ and R$^{S2}$ is an oxygen protecting group. In some embodiments, at least one of R$^{S1}$ and R$^{S2}$ is silyl (e.g., TMS, TBDMS, TIPS). In some embodiments, at least one of R$^{S1}$ and R$^{S2}$ is acetyl (Ac), benzyl (Bn), benzoyl (Bz), or methoxymethyl ether (MOM).

In certain embodiments, both R$^{S1}$ and R$^{S2}$ are hydrogen. In certain embodiments, both R$^{S1}$ and R$^{S2}$ are optionally substituted C$_{1-6}$ alkyl. In certain embodiments, both R$^{S1}$ and R$^{S2}$ are unsubstituted C$_{1-6}$ alkyl. In certain embodiments, both R$^{S1}$ and R$^{S2}$ are methyl. In certain embodiments, both R$^{S1}$ and R$^{S2}$ are ethyl, propyl, or butyl. In certain embodiments, both R$^{S1}$ and R$^{S2}$ are acyl (e.g., —C(=O)(R$^e$), —C(=O)O(R$^e$), —C(=O)NH(R$^e$), —C(=O)N(R$^e$)$_2$). In certain embodiments, both R$^{S1}$ and R$^{S2}$ are oxygen protecting groups. In some embodiments, both R$^{S1}$ and R$^{S2}$ are silyl (e.g., TMS, TBDMS, TIPS). In some embodiments, both R$^{S1}$ and R$^{S2}$ are acetyl (Ac), benzyl (Bn), benzoyl (Bz), or methoxymethyl ether (MOM).

In certain embodiments, R$^{S1}$ is hydrogen. In certain embodiments, R$^{S1}$ is optionally substituted C$_{1-6}$ alkyl. In certain embodiments, R$^{S1}$ is unsubstituted C$_{1-6}$ alkyl. In certain embodiments, R$^{S1}$ is methyl. In certain embodiments, R$^{S1}$ is ethyl, propyl, or butyl. In certain embodiments, R$^{S1}$ is acyl (e.g., —C(=O)(R$^e$), —C(=O)O(R$^e$), —C(=O)NH(R$^e$), —C(=O)N(R$^e$)$_2$). In certain embodiments, R$^{S1}$ is an oxygen protecting group. In some embodiments, R$^{S1}$ is silyl (e.g., TMS, TBDMS, TIPS). In some embodiments, R$^{S1}$ is acetyl (Ac), benzyl (Bn), benzoyl (Bz), or methoxymethyl ether (MOM).

In certain embodiments, R$^{S2}$ is hydrogen. In certain embodiments, R$^{S2}$ is optionally substituted C$_{1-6}$ alkyl. In certain embodiments, R$^{S2}$ is unsubstituted C$_{1-6}$ alkyl. In certain embodiments, R$^{S2}$ is methyl. In certain embodiments, R$^{S2}$ is ethyl, propyl, or butyl. In certain embodiments, R$^{S2}$ is acyl (e.g., —C(=O)(R$^e$), —C(=O)O(R$^e$), —C(=O)NH(R$^e$), —C(=O)N(R$^e$)$_2$). In certain embodiments, R$^{S2}$ is an oxygen protecting group. In some embodiments, R$^{S2}$ is silyl (e.g., TMS, TBDMS, TIPS). In some embodiments, R$^{S2}$ is acetyl (Ac), benzyl (Bn), benzoyl (Bz), or methoxymethyl ether (MOM).

In certain embodiments, R$^{S1}$ and R$^{S2}$ are joined to form an optionally substituted heterocyclic ring. In certain embodiments, R$^{S1}$ and R$^{S2}$ are taken together to form a cyclic acetal (e.g., —C(CH$_3$)$_2$—).

As generally defined herein, X$^5$ is —O—, —S—, —C(R$^e$)$_2$—, or —NR$^c$—. In certain embodiments, X$^5$ is —O—. In certain embodiments, X$^5$ is —S—. In certain embodiments, X$^5$ is —C(R$^e$)$_2$—. In certain embodiments, X$^5$ is —CH$_2$—, —CHMe-, or —CMe$_2$-. In certain embodiments, X$^5$ is —NR$^c$—, e.g., —NH—. In some embodiments, X$^5$ is —NR$^c$—, wherein R$^c$ is a nitrogen protecting group, e.g., —NAc—.

Groups L$^S$, V$^1$, V$^2$, V$^3$, V$^7$, V$^8$, and V$^9$.

As generally defined herein, L$^S$ is a bond, —O—, —NR$^c$—, optionally substituted alkylene, optionally substituted alkenylene, optionally substituted alkynylene, optionally substituted acylene, or optionally substituted arylene. In certain embodiments, L$^S$ is a bond. In certain embodiments, L$^S$ is —O—. In certain embodiments, L$^S$ is —NR$^c$—, e.g. —NH—. In certain embodiments, L$^S$ is optionally substituted alkylene. In certain embodiments, L$^S$ is optionally substituted arylene. In certain embodiments, L$^S$ is unsubstituted C$_{1-4}$ alkylene, e.g., methylene, ethylene. In certain embodiments, L$^S$ is optionally substituted alkenylene, e.g., —HC=CH—. In certain embodiments, L$^S$ is optionally substituted alkynylene, e.g., —C≡C—. In certain embodiments, L$^S$ is optionally substituted acylene. In some embodiments, L$^S$ is —C(=O)—, —C(=O)O—, —OC(=O)—, —C(=O)NR$^c$—, —NR$^c$C(=O)—, —C(=O)NH—, or —NHC(=O)—.

As generally defined herein, each of V$^1$, V$^2$, V$^3$, V$^7$, V$^8$, and V$^9$ is independently N, NR$^V$, or CR$^V$, valence permitting depending on the other ring positions. In certain embodiments, V$^1$ is N. In certain embodiments, V$^1$ is CR$^V$. In certain embodiments, V$^1$ is NR$^V$. In some embodiments, V$^1$ is CH. In certain embodiments, V$^2$ is N. In certain embodiments, V$^2$ is CR$^V$. In certain embodiments, V$^2$ is CR$^V$, and R$^V$ is hydrogen, halogen, optionally substituted alkyl, optionally substituted alkynyl, optionally substituted aryl, optionally substituted heteroaryl, or —N(R$^e$)$_2$. In certain embodiments, V$^2$ is CR$^V$, and R$^V$ is optionally substituted phenyl.

In certain embodiments, V$^2$ is CR$^V$, and R$^V$ is optionally substituted heteroaryl (e.g., optionally substituted monocyclic 5- or 6-membered heteroaryl, wherein 1, 2, 3, or 4 atoms in the heteroaryl ring system are independently oxygen, nitrogen, or sulfur). In certain embodiments, V$^2$ is CR$^V$, R$^V$ is —NH(R$^e$), and R$^e$ is optionally substituted phenyl. In certain embodiments, V$^2$ is CR$^V$, R$^V$ is —NH(R$^e$), and R$^e$ is optionally substituted heteroaryl (e.g., optionally substituted monocyclic 5- or 6-membered heteroaryl, wherein 1, 2, 3, or 4 atoms in the heteroaryl ring system are independently oxygen, nitrogen, or sulfur). In certain embodiments, V$^2$ is NR$^V$. In some embodiments, V$^2$ is CH. In certain embodiments, V$^3$ is N. In certain embodiments, V$^3$ is CR$^V$. In certain embodiments, V$^3$ is NR$^V$. In some embodiments, V$^3$ is CH. In certain embodiments, V$^7$ is N. In certain embodiments, V$^7$ is CR$^V$. In certain embodiments, V$^7$ is NR$^V$. In some embodiments, V$^7$ is CH. In certain embodiments, V is N. In certain embodiments, V$^8$ is CR$^V$. In certain embodiments, V$^8$ is CR$^V$, and R$^V$ is hydrogen or halogen. In certain embodiments, V is NR$^V$. In some embodiments, V is CH. In certain embodiments, V$^9$ is N. In certain embodiments, V$^9$ is CR$^V$. In certain embodiments, V$^9$ is NR$^V$. In some embodiments, V$^9$ is CH.

For each occurrence of V$^1$, V$^2$, V$^3$, V$^7$, V$^8$, and V$^9$ which is NR$^V$ or CR$^V$, R$^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$. In certain embodiments, R$^V$ is halogen. In certain embodiments, R$^V$ is —F. In certain embodiments, R$^V$ is —Cl, —Br, or —F. In certain embodiments, R$^V$ is optionally substituted C$_{1-6}$ alkyl. In certain embodiments, R$^V$ is unsubstituted C$_{1-6}$ alkyl. In certain embodiments, R$^V$ is methyl. In certain embodiments, R$^V$ is ethyl, propyl, or butyl. In certain embodiments, R$^V$ is —NO$_2$. In certain embodiments, R$^V$ is —CN. In certain embodiments, R$^V$ is —OR$^e$ (e.g. —OH, —OMe, —O(C$_{1-6}$ alkyl)) In certain embodiments, R$^V$ is —OR$^e$, and R$^e$ is an oxygen protecting group. In certain embodiments, R$^V$ is —N(R$^e$)$_2$ (e.g., —NH$_2$, —NMe$_2$, —NH(C$_{1-6}$ alkyl)). In certain embodiments, R$^V$ is —NHR$^e$, and R$^e$ is a nitrogen protecting group. In certain embodiments, R$^V$ is optionally substituted acyl (e.g., —C(=O)(R$^e$), —C(=O)O(R$^e$), —C(=O)NH(R$^e$), —C(=O)N(R$^e$)$_2$). In some embodiments, R$^V$ is —C(=O)OMe. In some embodiments, R$^V$ is —C(=O)OH.

In certain embodiments, R$^V$ is optionally substituted alkyl, e.g., optionally substituted C$_{1-6}$ alkyl, optionally substituted C$_{1-2}$ alkyl, optionally substituted C$_{2-3}$ alkyl, optionally substituted C$_{3-4}$ alkyl, optionally substituted C$_{4-5}$ alkyl, or optionally substituted C$_{5-6}$ alkyl. In certain embodiments, R$^V$ is methyl. In certain embodiments, R$^V$ is ethyl, propyl, or butyl. In certain embodiments, R$^V$ is optionally substituted alkenyl, e.g., optionally substituted C$_{2-6}$ alkenyl. In certain embodiments, R$^V$ is vinyl, allyl, or prenyl. In certain embodiments, R$^V$ is optionally substituted alkynyl, e.g., C$_{2-6}$ alkynyl.

In certain embodiments, R$^V$ is optionally substituted carbocyclyl, e.g., optionally substituted C$_{3-6}$ carbocyclyl, optionally substituted C$_{3-4}$ carbocyclyl, optionally substituted C$_{4-5}$ carbocyclyl, or optionally substituted C$_{5-6}$ carbocyclyl. In certain embodiments R$^V$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, R$^V$ is optionally substituted aryl, e.g., optionally substituted phenyl. In certain embodiments, R$^V$ is optionally substituted heteroaryl, e.g., optionally substituted 5-6 membered heteroaryl, or optionally substituted 9-10 membered bicyclic heteroaryl. In certain embodiments, R$^V$ is optionally substituted aralkyl, e.g., optionally substituted benzyl. In certain embodiments, R$^V$ is optionally substituted heteroaralkyl, e.g., methyl substituted with a 5-6-membered heteroaryl ring.

In certain embodiments, the group attached to L$^S$ is of formula:

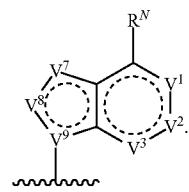

In certain embodiments, the group attached to L$^S$ is of formula:

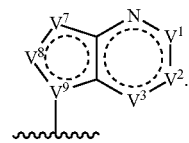

In certain embodiments, the group attached to L$^S$ is of formula:

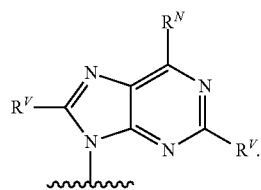

In certain embodiments, the group attached to L$^S$ is of formula:

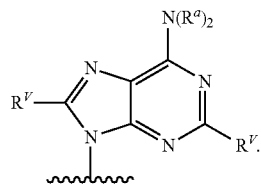

In certain embodiments, the group attached to L$^S$ is of formula:

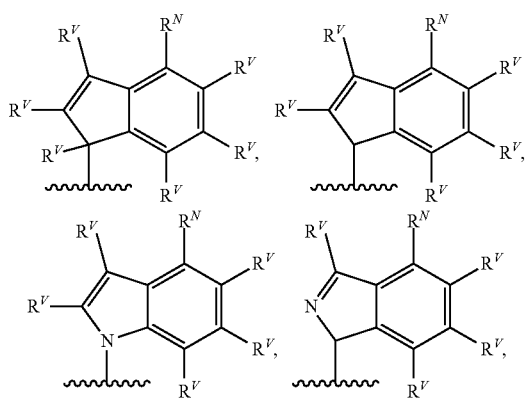

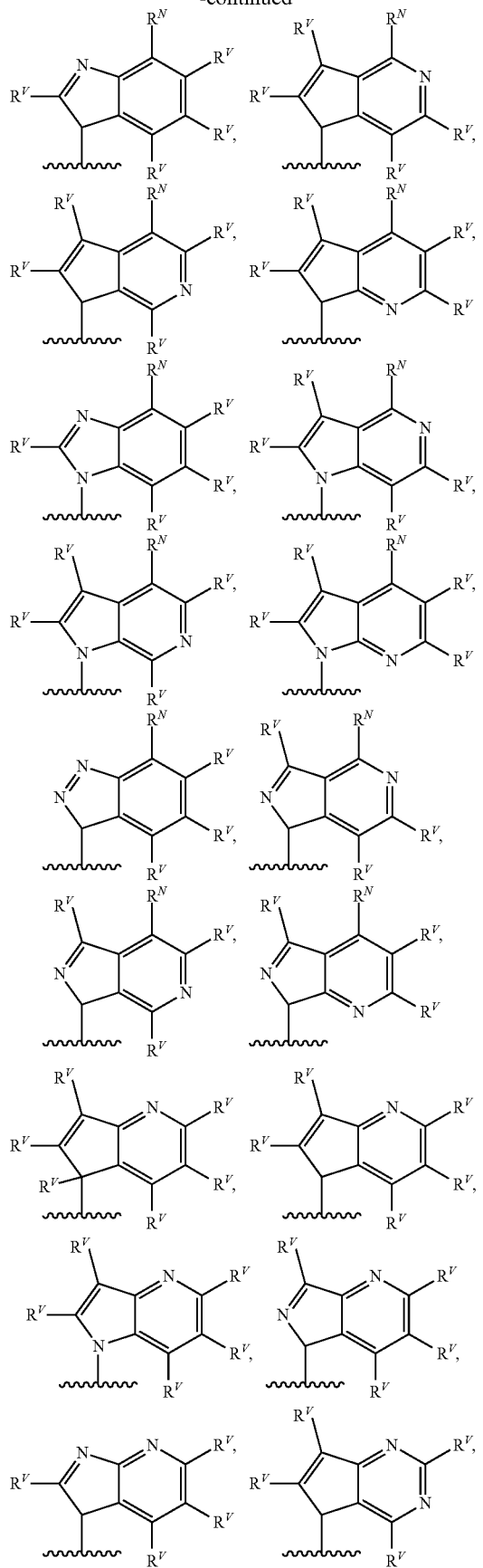
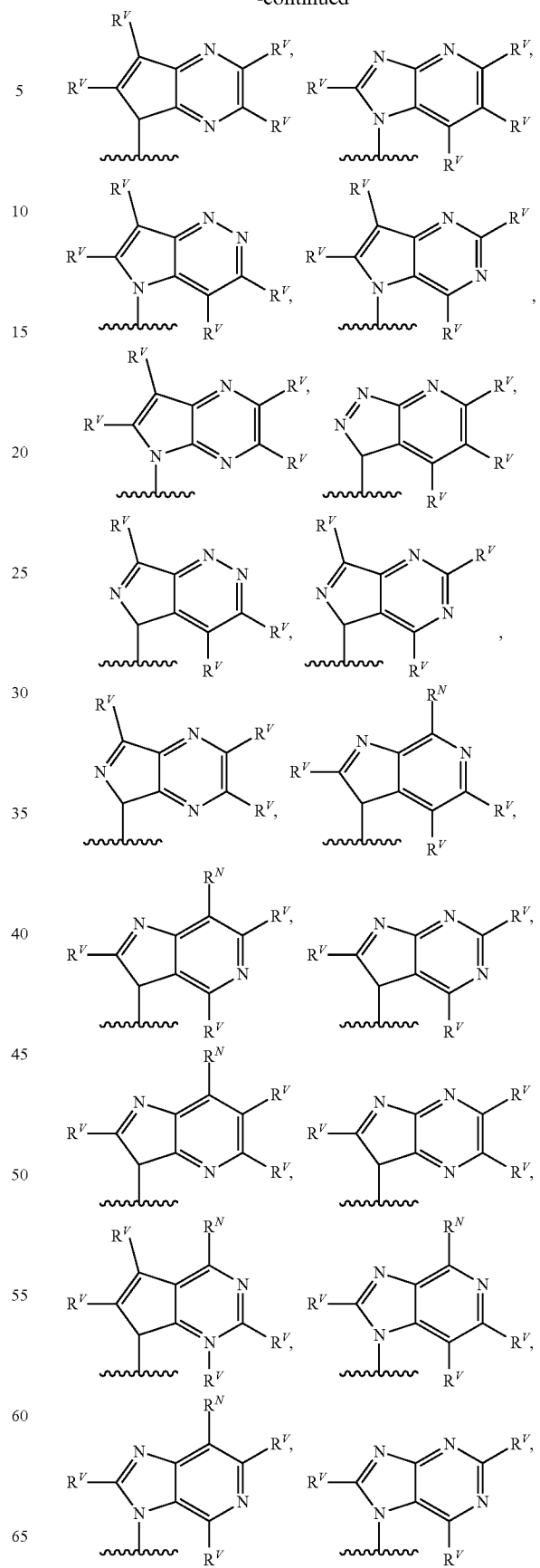

-continued

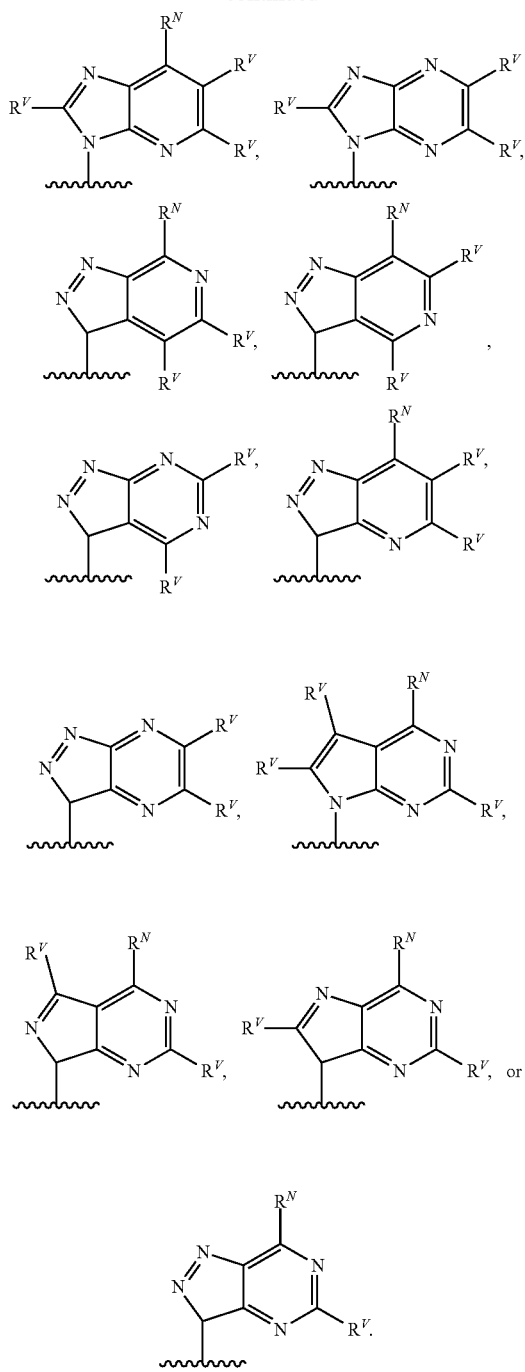

In certain embodiments, the group attached to $L^S$ is of formula:

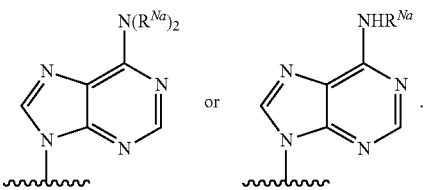

In certain embodiments, the group attached to $L^S$ is of formula:

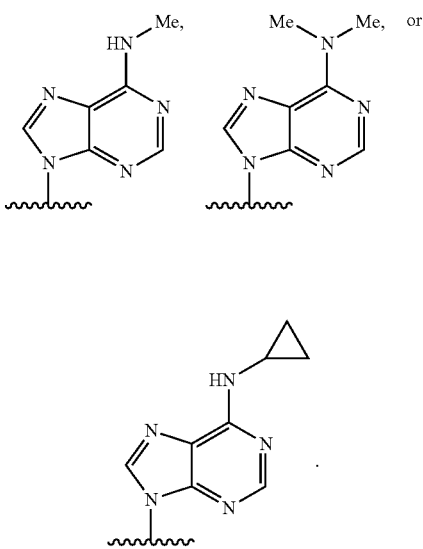

In certain embodiments, the group attached to $L^S$ is of formula:

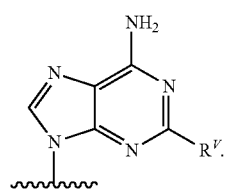

In certain embodiments, the group attached to $L^S$ is of formula:

In certain embodiments, the group attached to $L^S$ is of formula:

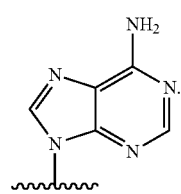

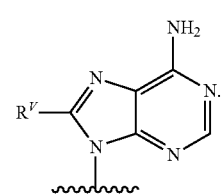

In certain embodiments, the group attached to $L^S$ is of formula:

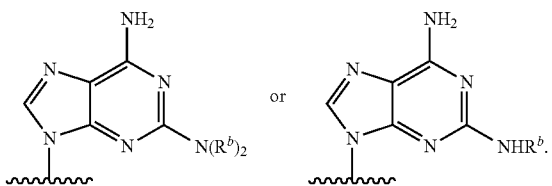

In certain embodiments, the group attached to $L^S$ is of formula:

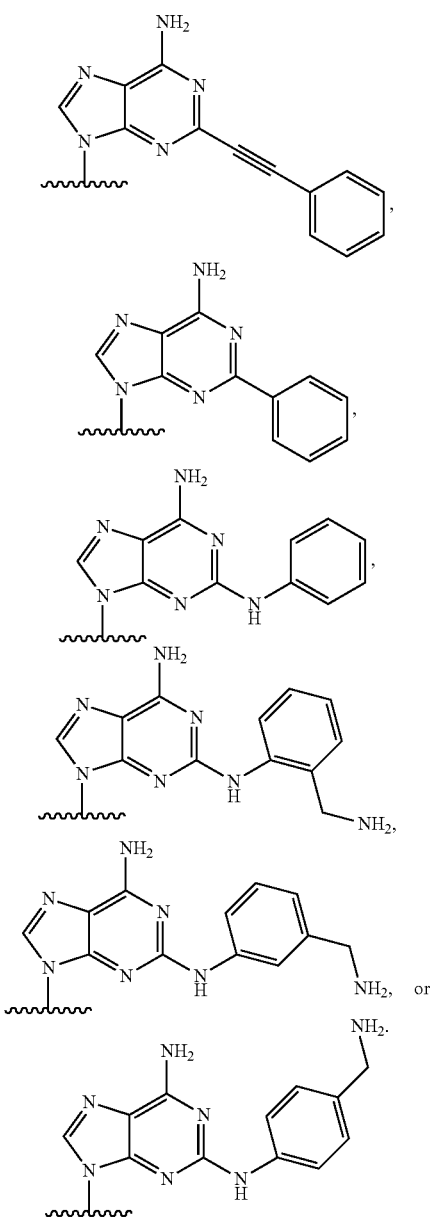

Group $V^N$ and $R^N$

As generally defined herein, $V^N$ is N, $NR^V$, or $CR^V$, valence permitting depending on the other ring positions. In certain embodiments, $V^N$ is N. In certain embodiment $V^N$ is $NR^V$. In certain embodiments, $V^N$ is $CR^V$. In certain embodiments, $V^N$ is CH.

As generally defined herein, $R^N$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^e$, or —$N(R^{Na})_2$.

In certain embodiments, $R^N$ is hydrogen. In certain embodiments, $R^N$ is halogen. In certain embodiments, $R^N$ is —F. In certain embodiments, $R^N$ is —Cl, —Br, or —F. In certain embodiments, $R^N$ is —$NO_2$. In certain embodiments, $R^N$ is —CN. In certain embodiments, $R^N$ is —$OR^e$ (e.g. —OH, —OMe, —O($C_{1-6}$ alkyl)). In certain embodiments, $R^N$ is —$OR^e$, and $R^e$ is an oxygen protecting group. In certain embodiments, $R^N$ is —$N(R^{Na})_2$ (e.g., —$NH_2$, —$NMe_2$, —NH($C_{1-6}$ alkyl)). In certain embodiments, $R^N$ is —$NHR^{Na}$, and $R^{Na}$ is a nitrogen protecting group. In certain embodiments, $R^N$ is optionally substituted acyl (e.g., —C(=O)($R^e$), —C(=O)O($R^e$), —C(=O)NH($R^e$), —C(=O)N($R^e$)$_2$). In some embodiments, $R^N$ is —C(=O)OMe. In some embodiments, $R^N$ is —C(=O)OH.

In certain embodiments, $R^N$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^N$ is methyl. In certain embodiments, $R^N$ is ethyl, propyl, or butyl. In certain embodiments, $R^N$ is optionally substituted alkenyl, e.g., optionally substituted $C_{2-6}$ alkenyl. In certain embodiments, $R^N$ is vinyl, allyl, or prenyl. In certain embodiments, $R^N$ is optionally substituted alkynyl, e.g., $C_{2-6}$ alkynyl.

In certain embodiments, $R^N$ is optionally substituted carbocyclyl, e.g., optionally substituted $C_{3-6}$ carbocyclyl, optionally substituted $C_{34}$ carbocyclyl, optionally substituted $C_{4-5}$ carbocyclyl, or optionally substituted $C_{5-6}$ carbocyclyl. In certain embodiments $R^N$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^N$ is optionally substituted aryl, e.g., optionally substituted phenyl. In certain embodiments, $R^N$ is optionally substituted heteroaryl, e.g., optionally substituted 5-6 membered heteroaryl, or optionally substituted 9-10 membered bicyclic heteroaryl. In certain embodiments, $R^N$ is optionally substituted aralkyl, e.g., optionally substituted benzyl. In certain embodiments, $R^N$ is optionally substituted heteroaralkyl, e.g., methyl substituted with a 5-6-membered heteroaryl ring.

As generally defined herein, $R^{Na}$ is independently hydrogen, optionally substituted $C_{1-6}$ alkyl, optionally substituted acyl, or a nitrogen protecting group, or both $R^{Na}$ are joined to form and optionally substituted heterocyclic or optionally substituted heteroaryl ring. In certain embodiments, at least one occurrence of $R^{Na}$ is hydrogen. In certain embodiments, at least one occurrence of $R^{Na}$ is optionally substituted $C_{1-6}$ alkyl. In certain embodiments, at least one occurrence of $R^{Na}$ is unsubstituted $C_{1-6}$ alkyl. In certain embodiments, at least one occurrence of $R^{Na}$ is methyl. In certain embodiments, at least one occurrence of $R^{Na}$ is ethyl, propyl, or butyl. In certain embodiments, at least one occurrence of $R^{Na}$ is acyl (e.g., —C(=O)($R^e$), —C(=O)O($R^e$), —C(=O)NH($R^e$), —C(=O)N($R^e$)$_2$). In certain embodiments, at least one occurrence of $R^{Na}$ is a nitrogen protecting group. In some embodiments, at least one occurrence of $R^{Na}$ is alkoxycarbonyl (e.g., Cbz, BOC, FMOC). In some embodiments, at least one occurrence of $R^{Na}$ is acetyl (Ac), benzyl (Bn), or benzoyl (Bz). In some embodiments, at least one occurrence of $R^{Na}$ is sulfonyl (e.g., tosyl, nosyl, mesyl).

In certain embodiments, both occurrences of $R^{Na}$ are hydrogen. In certain embodiments, both occurrences of $R^{Na}$ are optionally substituted $C_{1-6}$ alkyl. In certain embodiments, both occurrences of $R^{Na}$ are unsubstituted $C_{1-6}$ alkyl. In certain embodiments, both occurrences of $R^{Na}$ are methyl. In certain embodiments, both occurrences of $R^{Na}$ are ethyl, propyl, or butyl. In certain embodiments, both occurrences of $R^{Na}$ are acyl (e.g., —C(=O)($R^e$), —C(=O)O($R^e$), —C(=O)NH($R^e$), —C(=O)N($R^e$)$_2$). In certain embodiments, both occurrences of $R^{Na}$ are nitrogen protecting groups. In some embodiments, both occurrences of $R^{Na}$ are alkoxycarbonyl (e.g., Cbz, BOC, FMOC). In some embodiments, both occurrences of $R^{Na}$ are acetyl (Ac), benzyl (Bn), or benzoyl (Bz). In some embodiments, both occurrences of $R^{Na}$ are sulfonyl (e.g., tosyl, nosyl, mesyl).

In certain embodiments, one occurrence of $R^{Na}$ is hydrogen, and the other occurrence of $R^{Na}$ is optionally substituted $C_{1-6}$ alkyl. In certain embodiments, one occurrence of $R^{Na}$ is hydrogen, and the other occurrence of $R^{Na}$ unsubstituted $C_{1-6}$ alkyl. In certain embodiments, one occurrence of $R^{Na}$ is hydrogen, and the other occurrence of $R^{Na}$ is methyl. In certain embodiments, one occurrence of $R^{Na}$ is hydrogen, and the other occurrence of $R^{Na}$ is ethyl, propyl, or butyl. In certain embodiments, one occurrence of $R^{Na}$ is hydrogen, and the other occurrence of $R^{Na}$ is acyl (e.g., —C(=O)($R^e$), —C(=O)O($R^e$), —C(=O)NH($R^e$), —C(=O)N($R^e$)$_2$). In certain embodiments, one occurrence of $R^{Na}$ is hydrogen, and the other occurrence of $R^{Na}$ is a nitrogen protecting group. In some embodiments, one occurrence of $R^{Na}$ is hydrogen, and the other occurrence of $R^{Na}$ is alkoxycarbonyl (e.g., Cbz, BOC, FMOC). In some embodiments, one occurrence of $R^{Na}$ is hydrogen, and the other occurrence of $R^{Na}$ is acetyl (Ac), benzyl (Bn), or benzoyl (Bz). In some embodiments, one occurrence of $R^{Na}$ is hydrogen, and the other occurrence of $R^{Na}$ is sulfonyl (e.g., tosyl, nosyl, mesyl).

In certain embodiments, both occurrences of $R^{Na}$ are joined to form an optionally substituted heterocyclic ring (e.g., a 5- to 6-membered optionally substituted heterocyclic ring). In certain embodiments, both occurrences of $R^{Na}$ are joined to form an optionally substituted heteroaryl ring (e.g., a 5- to 6-membered optionally substituted heteroaryl ring).

In certain embodiments, the compound of Formula (I) is a compound listed in Table 1, or a pharmaceutically acceptable salt, solvate, hydrate, polymorph, co-crystal, tautomer, stereoisomer, or prodrug thereof.

TABLE 1

Exemplary compounds of Formula (I).

| No. | Structure |
|---|---|
| DST-Pqs1 (1) | 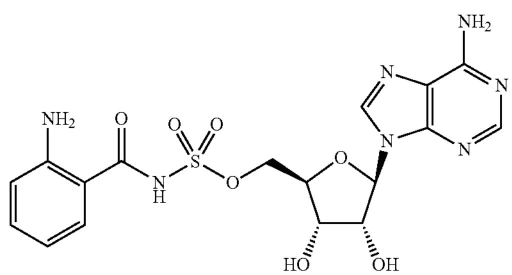 [SMILES: Nc1ccccc1C(=O)NS(=O)(=O)OC[C@H]1O[C@@H](n2cnc3c(N)ncnc32)[C@H](O)[C@@H]1O] |
| DST-Pqs2 (2) | 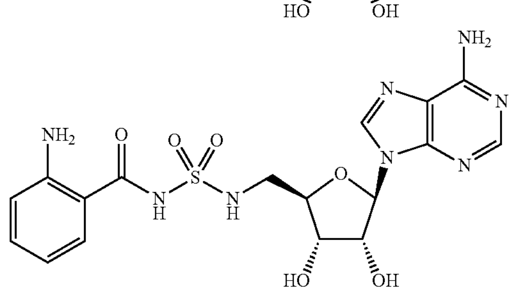 |
| DST-Pqs6 (6) | 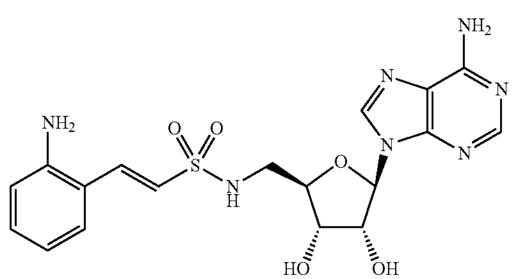 [SMILES: Nc1ccccc1/C=C/S(=O)(=O)NC[C@H]1O[C@@H](n2cnc3c(N)ncnc32)[C@H](O)[C@@H]1O] |

TABLE 1-continued

Exemplary compounds of Formula (I).

| No. | Structure |
|---|---|
| DST-Pqs8 | 2-chloropyridine-3-carbonyl sulfamoyl adenosine |
| DST-Pqs9 | 3-amino-2-naphthoyl sulfamoyl adenosine |
| DST-Pqs10 | 2-amino-4-(trifluoromethyl)benzoyl sulfamoyl adenosine |
| DST-Pqs11 | 2-amino-4-fluorobenzoyl sulfamoyl adenosine |
| DST-Pqs12 | 2-amino-6-fluorobenzoyl sulfamoyl adenosine |

TABLE 1-continued

Exemplary compounds of Formula (I).

| No. | Structure |
|---|---|
| DST-Pqs13 | 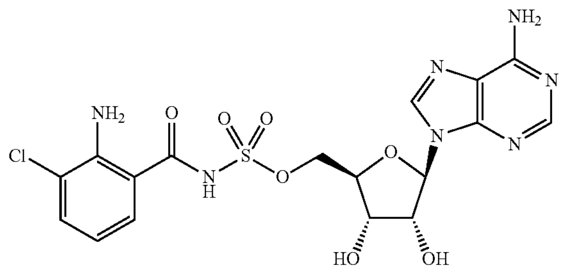 [SMILES: Nc1c(Cl)cccc1C(=O)NS(=O)(=O)OC[C@H]1O[C@@H](n2cnc3c(N)ncnc32)[C@H](O)[C@@H]1O] |
| DST-Pqs14 | 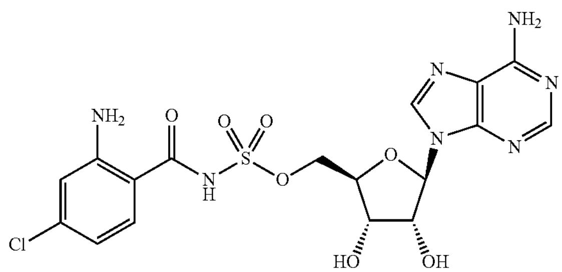 [SMILES: Nc1cc(Cl)ccc1C(=O)NS(=O)(=O)OC[C@H]1O[C@@H](n2cnc3c(N)ncnc32)[C@H](O)[C@@H]1O] |
| DST-Pqs15 | 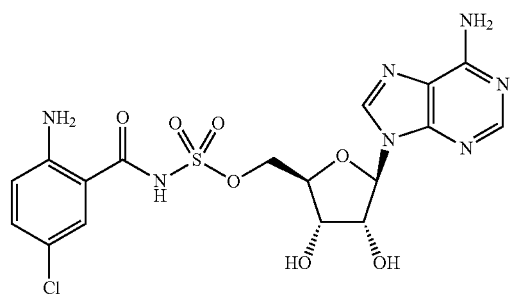 [SMILES: Nc1ccc(Cl)cc1C(=O)NS(=O)(=O)OC[C@H]1O[C@@H](n2cnc3c(N)ncnc32)[C@H](O)[C@@H]1O] |
| DST-Pqs16 | 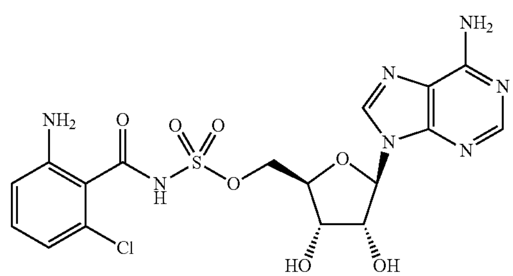 |
| DST-Pqs17 | 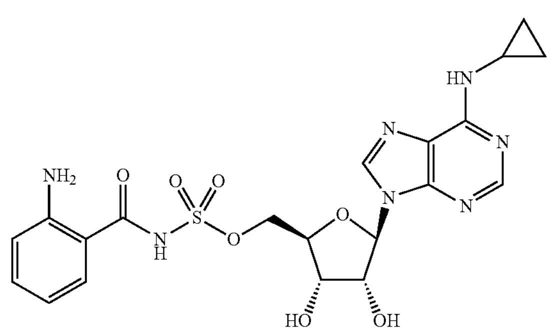 [SMILES: Nc1ccccc1C(=O)NS(=O)(=O)OC[C@H]1O[C@@H](n2cnc3c(NC4CC4)ncnc32)[C@H](O)[C@@H]1O] |

TABLE 1-continued
Exemplary compounds of Formula (I).
| No. | Structure |
|---|---|
| DST-Pqs18 | 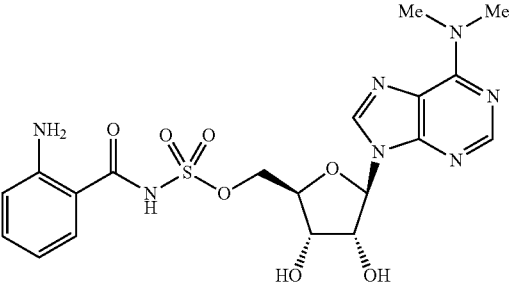 [SMILES: CN(C)c1ncnc2c1ncn2[C@@H]1O[C@H](COS(=O)(=O)NC(=O)c2ccccc2N)[C@@H](O)[C@H]1O] |
| JI-C-2013-451 | 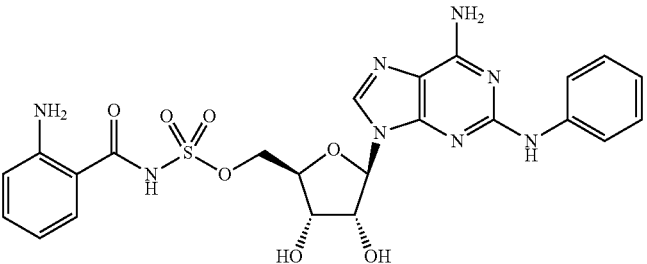 [SMILES: Nc1ccccc1C(=O)NS(=O)(=O)OC[C@H]1O[C@@H](n2cnc3c(N)nc(Nc4ccccc4)nc32)[C@H](O)[C@@H]1O] |
| JI-C-2013-454 | 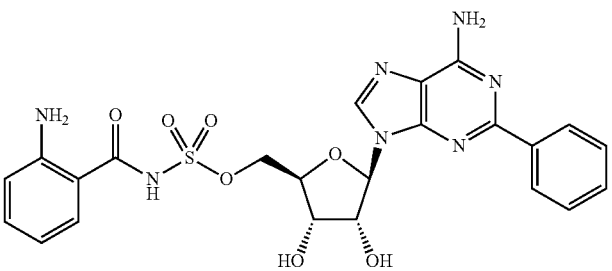 [SMILES: Nc1ccccc1C(=O)NS(=O)(=O)OC[C@H]1O[C@@H](n2cnc3c(N)nc(-c4ccccc4)nc32)[C@H](O)[C@@H]1O] |
| JI-C-2013-456 | 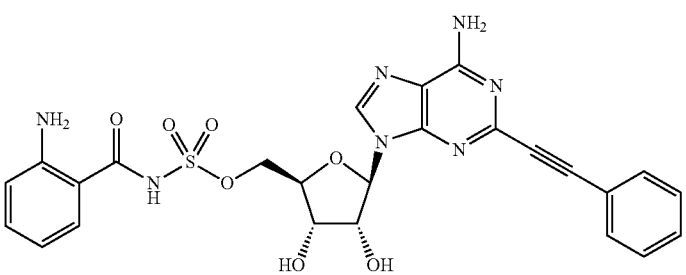 [SMILES: Nc1ccccc1C(=O)NS(=O)(=O)OC[C@H]1O[C@@H](n2cnc3c(N)nc(C#Cc4ccccc4)nc32)[C@H](O)[C@@H]1O] |
| JI-C-2014-008 | 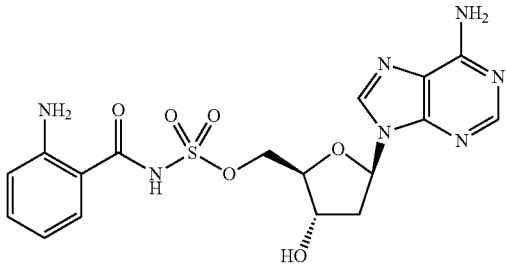 [SMILES: Nc1ccccc1C(=O)NS(=O)(=O)OC[C@H]1O[C@@H](n2cnc3c(N)ncnc32)C[C@@H]1O] |

TABLE 1-continued

Exemplary compounds of Formula (I).

| No. | Structure |
|---|---|
| JI-C-2014-025 | 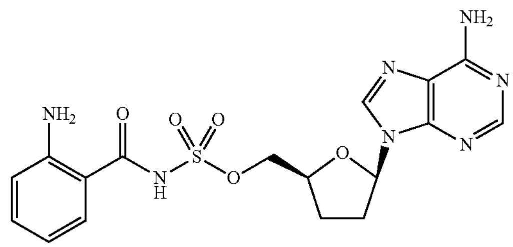 [SMILES: Nc1ccccc1C(=O)NS(=O)(=O)OC[C@@H]1CC[C@H](n2cnc3c(N)ncnc32)O1] |
| JI-C-2013-189 | 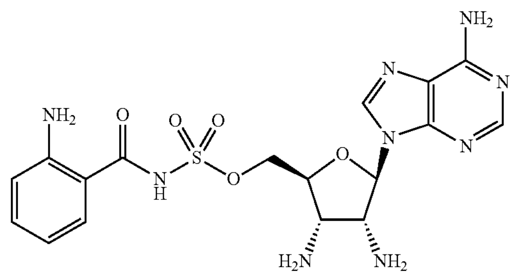 [SMILES: Nc1ccccc1C(=O)NS(=O)(=O)OC[C@H]1O[C@@H](n2cnc3c(N)ncnc32)[C@H](N)[C@@H]1N] |
| DST-Pqs27 | 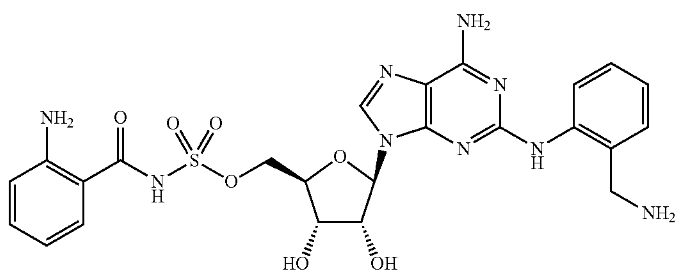 [SMILES: NCc1ccccc1Nc1nc(N)c2ncn([C@@H]3O[C@H](COS(=O)(=O)NC(=O)c4ccccc4N)[C@@H](O)[C@H]3O)c2n1] |
| DST-Pqs28 | 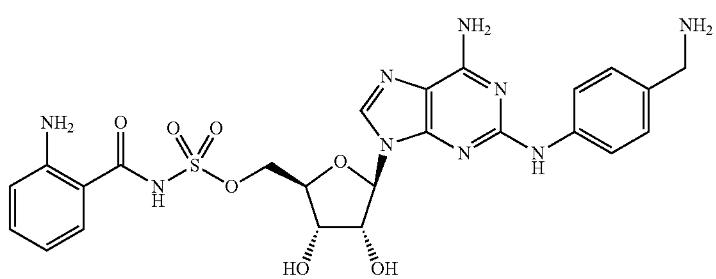 [SMILES: NCc1ccc(Nc2nc(N)c3ncn([C@@H]4O[C@H](COS(=O)(=O)NC(=O)c5ccccc5N)[C@@H](O)[C@H]4O)c3n2)cc1] |
| DST-Pqs29 | 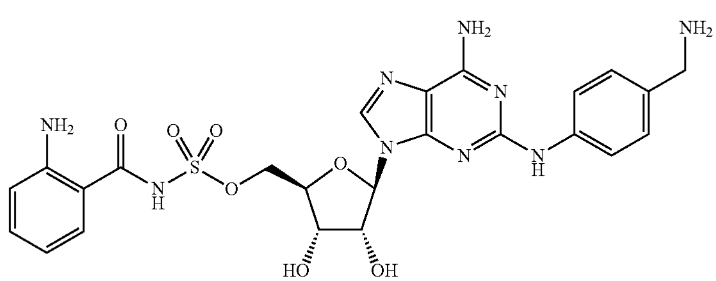 [SMILES: NCc1ccc(Nc2nc(N)c3ncn([C@@H]4O[C@H](COS(=O)(=O)NC(=O)c5ccccc5N)[C@@H](O)[C@H]4O)c3n2)cc1] |

TABLE 1-continued

Exemplary compounds of Formula (I).

| No. | Structure |
|---|---|
| DST-Pqs19 | 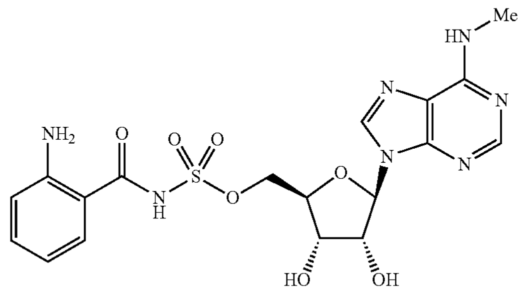 [SMILES: CNc1ncnc2c1ncn2[C@@H]1O[C@H](COS(=O)(=O)NC(=O)c2ccccc2N)[C@@H](O)[C@H]1O] |
| DST-Pqs30 | 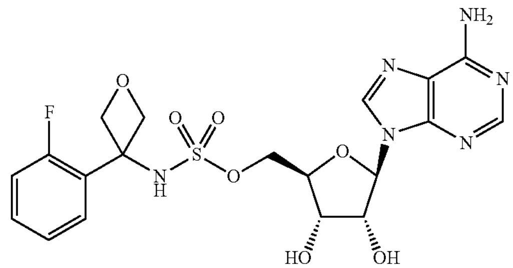 [SMILES: Nc1ncnc2c1ncn2[C@@H]1O[C@H](COS(=O)(=O)NC2(c3ccccc3F)COC2)[C@@H](O)[C@H]1O] |
| DST-Pqs31 | 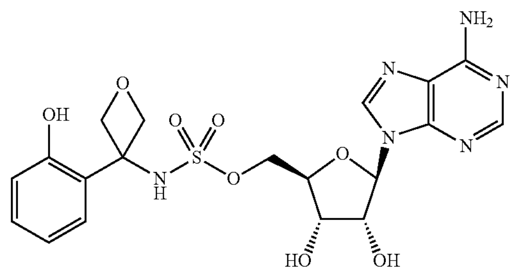 [SMILES: Nc1ncnc2c1ncn2[C@@H]1O[C@H](COS(=O)(=O)NC2(c3ccccc3O)COC2)[C@@H](O)[C@H]1O] |
| DST-Pqs32 | 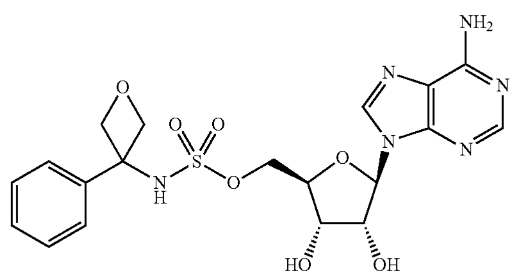 [SMILES: Nc1ncnc2c1ncn2[C@@H]1O[C@H](COS(=O)(=O)NC2(c3ccccc3)COC2)[C@@H](O)[C@H]1O] |
| DST-Pqs33 | 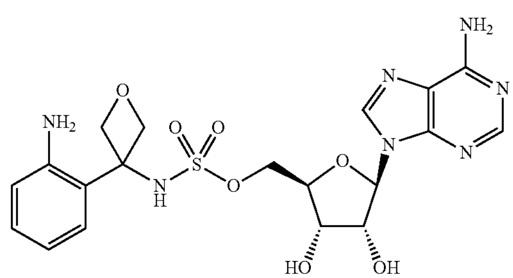 |

Additional exemplary compounds of Formula (I) include, but are not limited to:
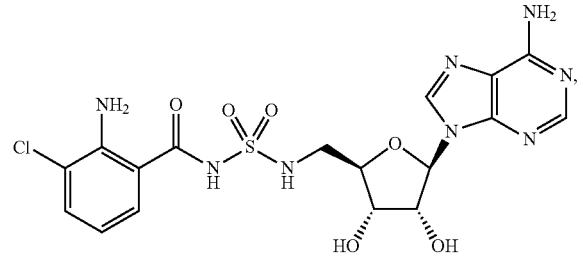
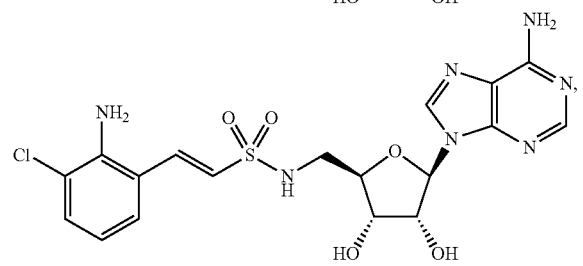
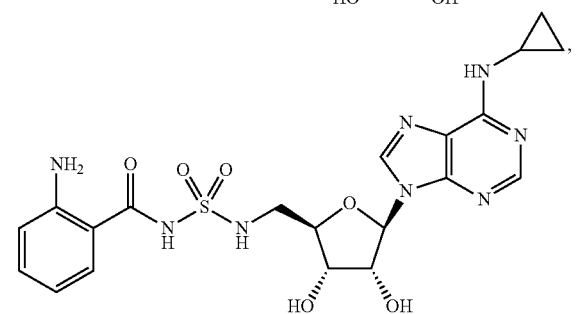
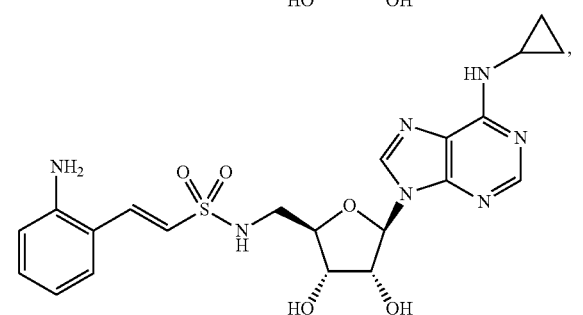
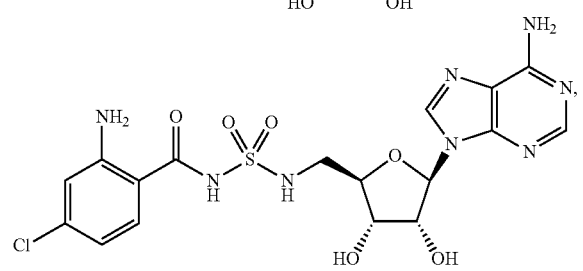
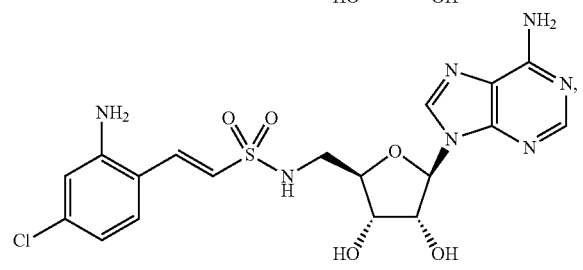
-continued
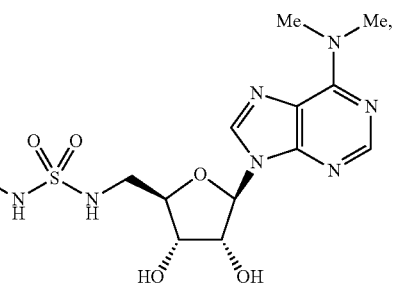
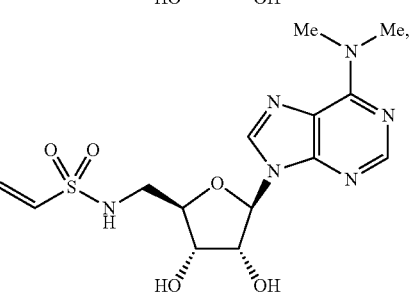
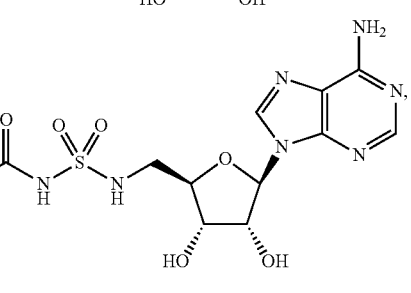
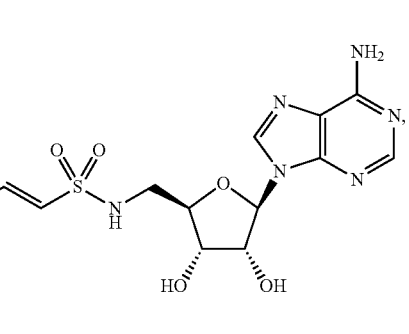
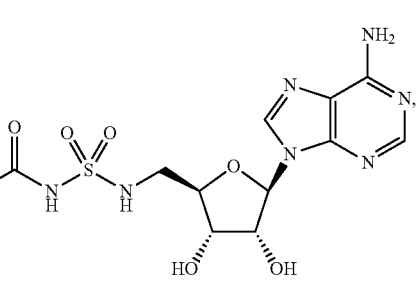
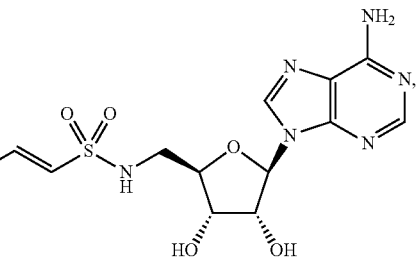

69
-continued
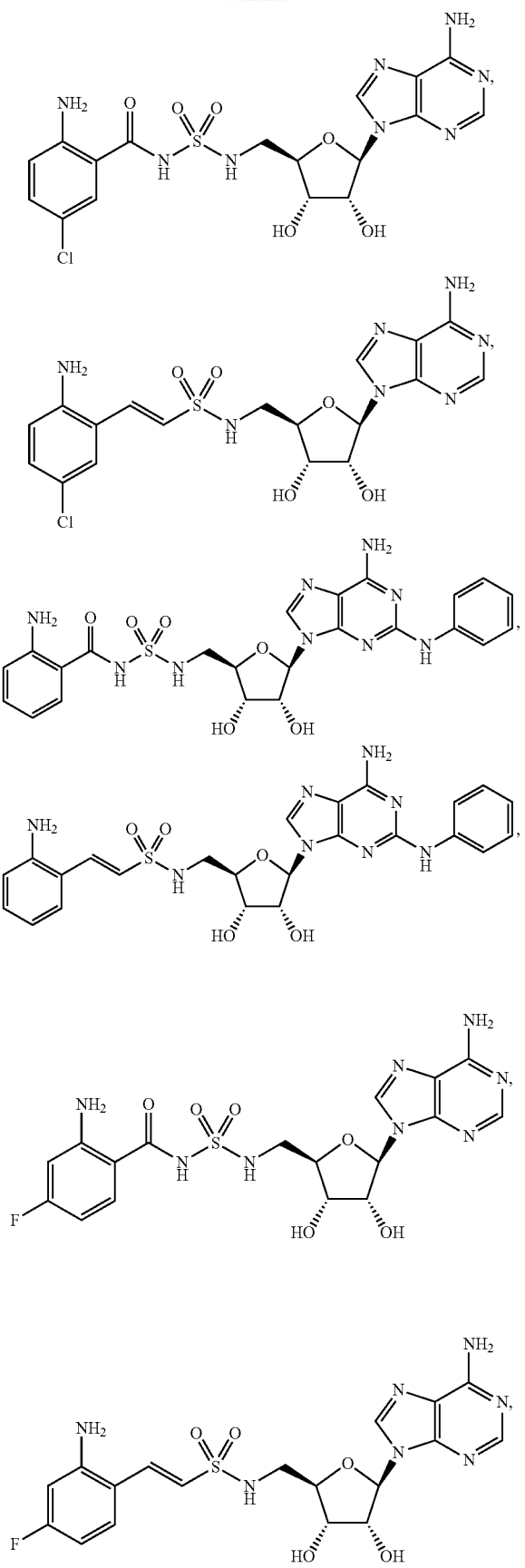
70
-continued
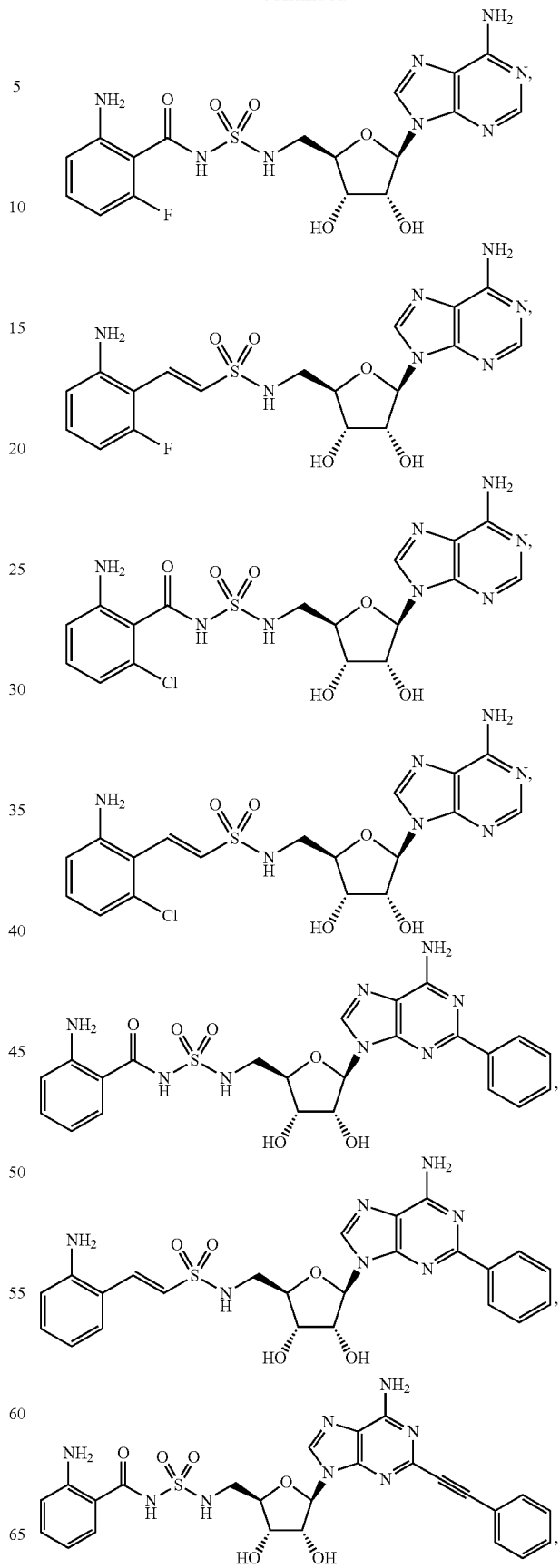

71
-continued
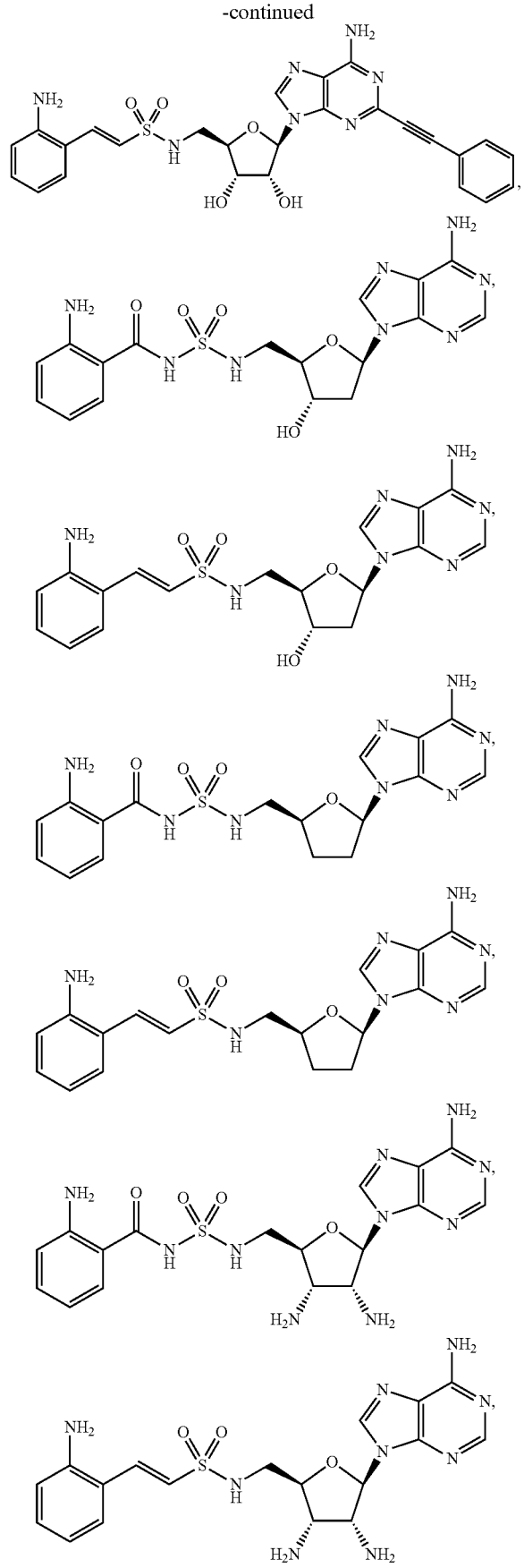
72
-continued
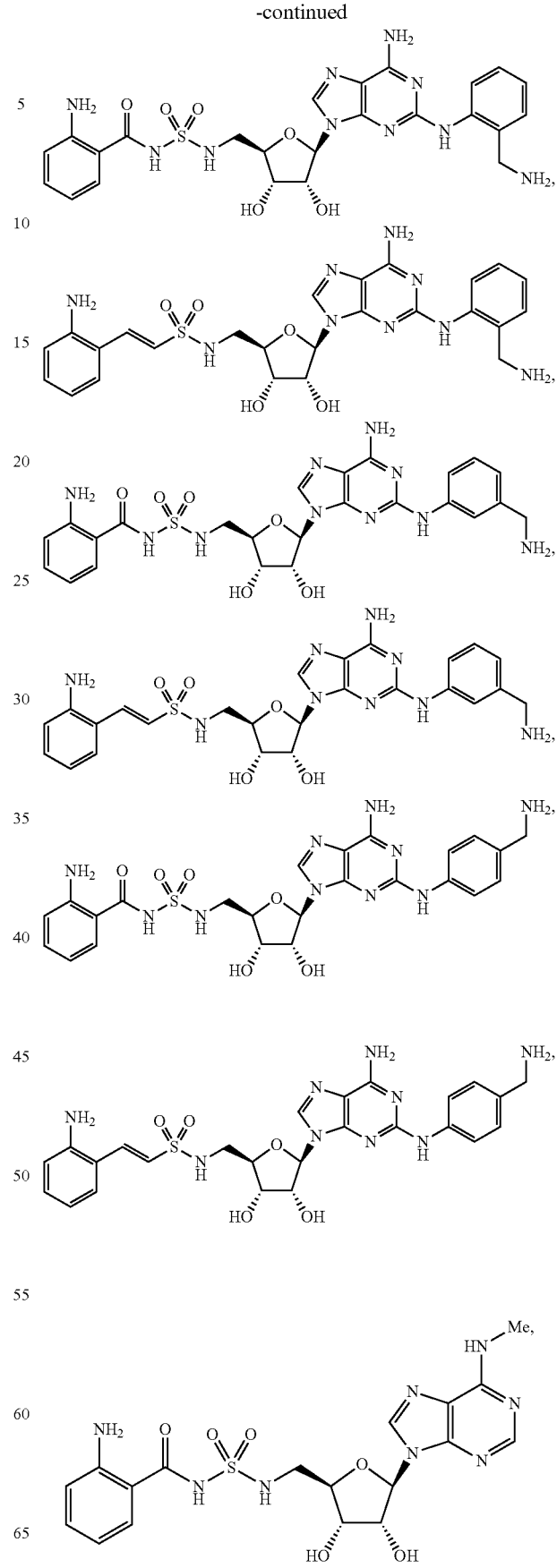

-continued

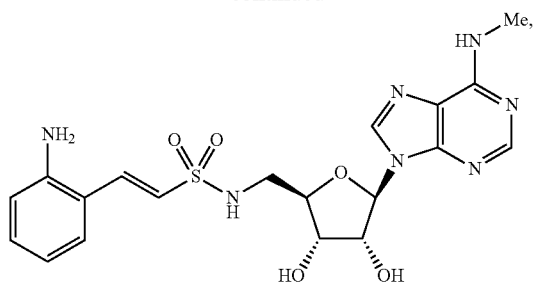
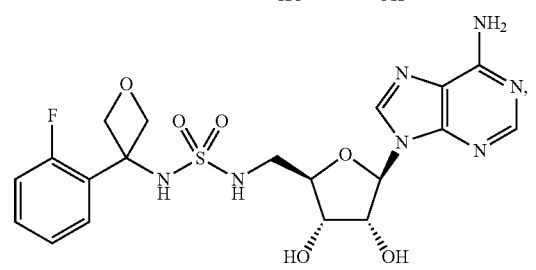
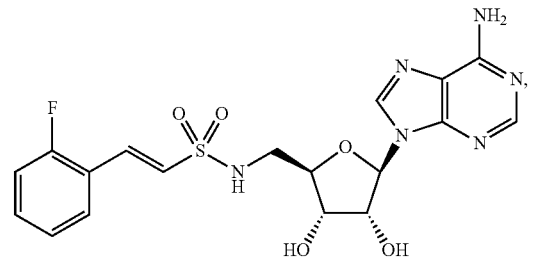
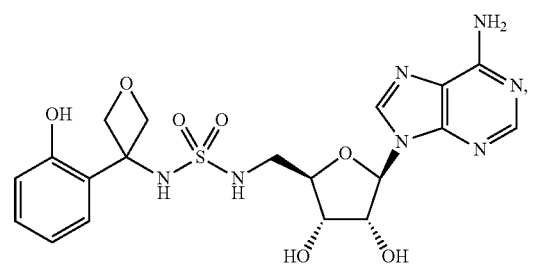
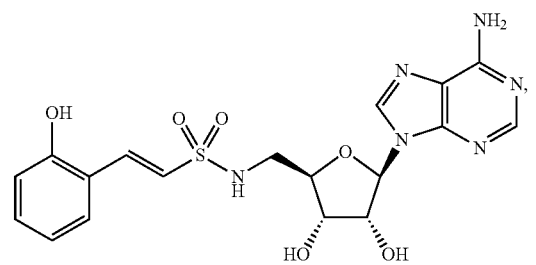
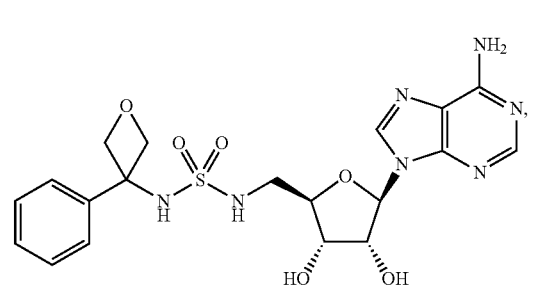

-continued

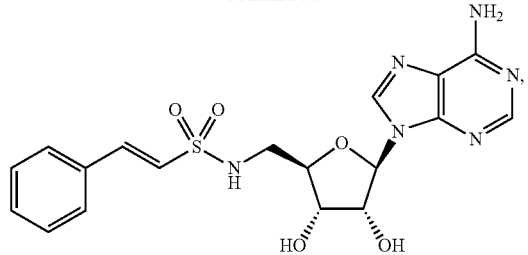
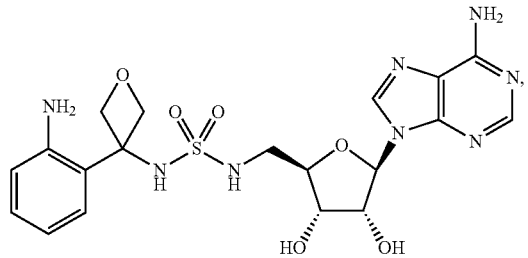
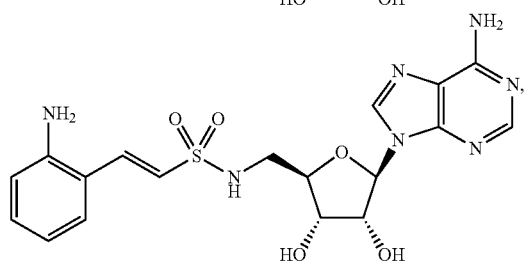

and pharmaceutically acceptable salts, solvates, hydrates, polymorphs, co-crystals, tautomers, stereoisomers, and prodrugs thereof.

Compounds of Formula (I) and (Z) comprise a linker between the 5-membered ribose or ribose analog ring and group W, Y, or Z. In certain embodiments, the linker is selected from Table 2.

TABLE 2

Exemplary linkers of compounds of Formula (I) or (Z).

| Linker |
| --- |
| 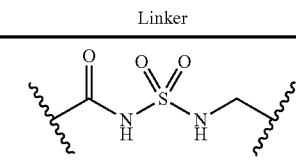 |
| 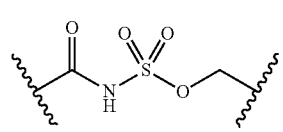 [SMILES: *COS(=O)(=O)NC(*)=O] |
| 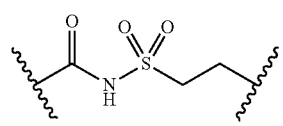 [SMILES: *CCS(=O)(=O)NC(*)=O] |
| 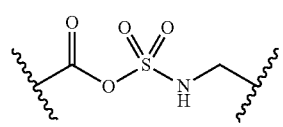 [SMILES: *CNS(=O)(=O)OC(*)=O] |

TABLE 2-continued

Exemplary linkers of compounds of Formula (I) or (Z).

TABLE 2-continued

Exemplary linkers of compounds of Formula (I) or (Z).

TABLE 2-continued

Exemplary linkers of compounds of Formula (I) or (Z).

TABLE 2-continued

Exemplary linkers of compounds of Formula (I) or (Z).

TABLE 2-continued

Exemplary linkers of compounds of Formula (I) or (Z).

TABLE 2-continued
Exemplary linkers of compounds of Formula (I) or (Z).
Linker
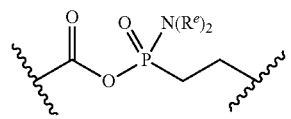
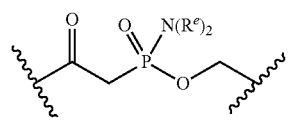
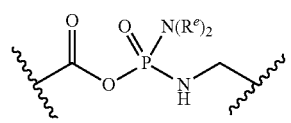
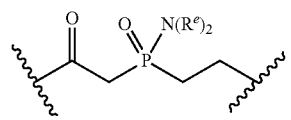
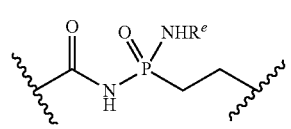
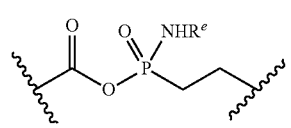
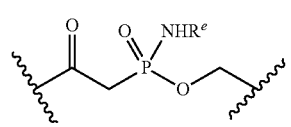
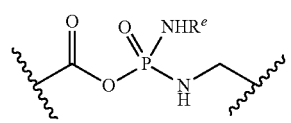
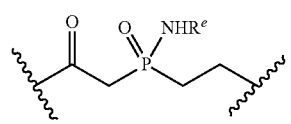
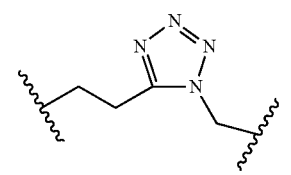 [SMILES: *CCc1nnnn1C*]
TABLE 2-continued
Exemplary linkers of compounds of Formula (I) or (Z).
Linker
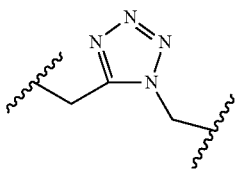 [SMILES: *Cc1nnnn1C*]
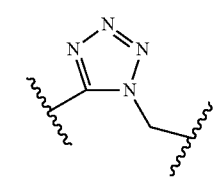 [SMILES: *Cn1nnnc1*]
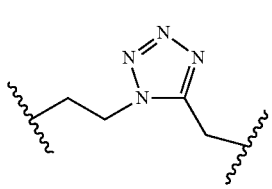 [SMILES: *CCn1nnnc1C*]
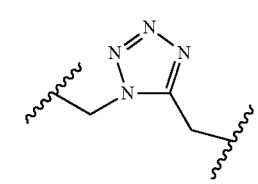 [SMILES: *Cc1nnnn1C*]
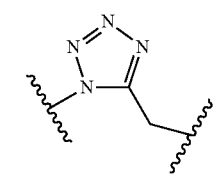 [SMILES: *Cc1nnnn1*]
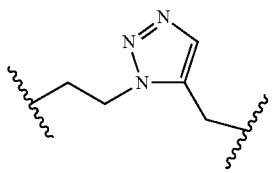 [SMILES: *CCn1nncc1C*]
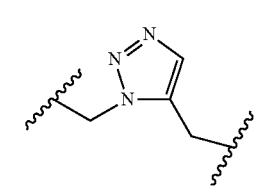 [SMILES: *Cc1cnnn1C*]
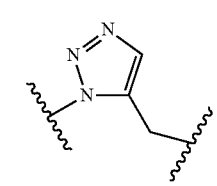 [SMILES: *Cc1cnnn1*]

TABLE 2-continued
Exemplary linkers of compounds of Formula (I) or (Z).
Linker
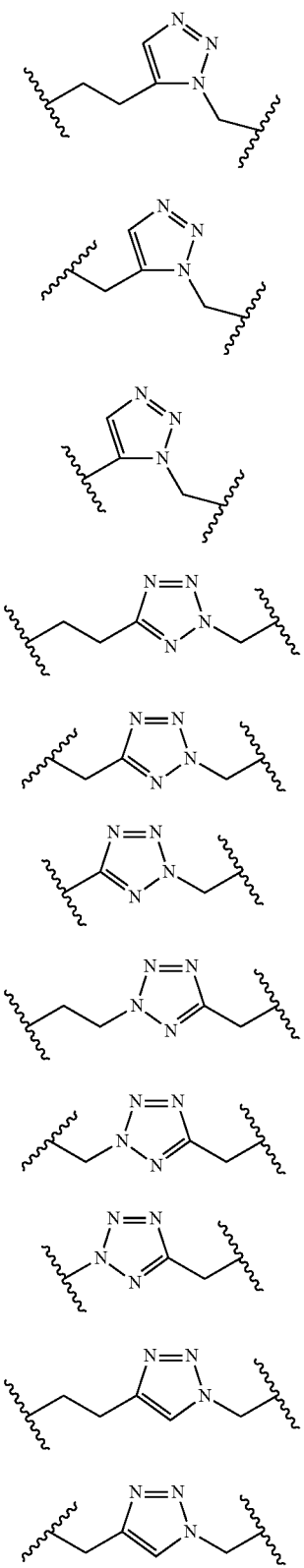
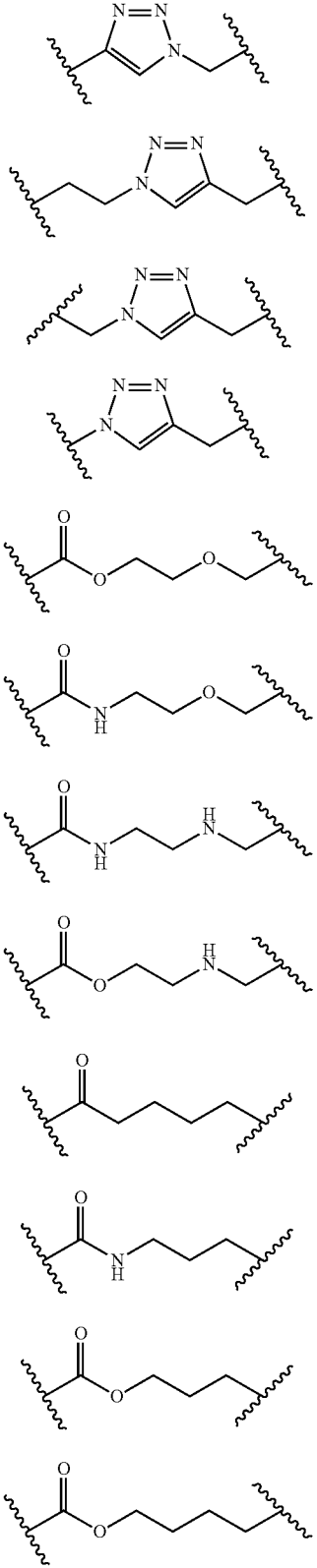

TABLE 2-continued
Exemplary linkers of compounds of Formula (I) or (Z).
Linker
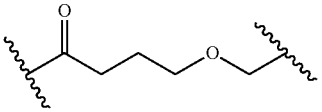 [SMILES: *COCCCC(*)=O]
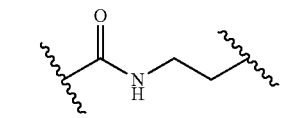 [SMILES: *CCNC(*)=O]
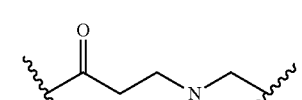
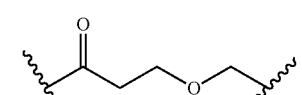
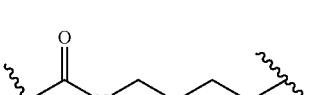
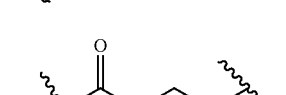
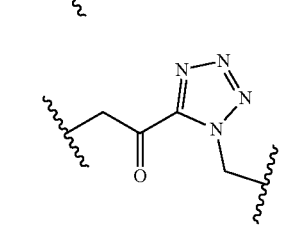
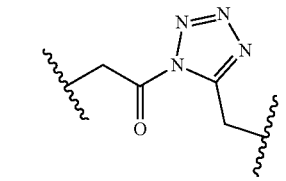 [SMILES: *CC(=O)n1nnnc1C*]
TABLE 2-continued
Exemplary linkers of compounds of Formula (I) or (Z).
Linker
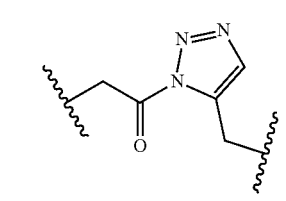 [SMILES: *CC(=O)n1nncc1C*]
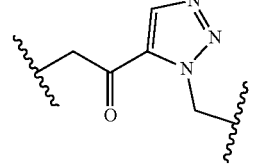
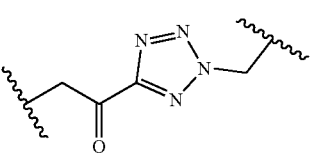 [SMILES: *CC(=O)c1nnn(C*)n1]
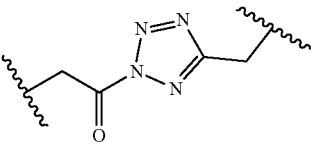 [SMILES: *CC(=O)n1nnc(C*)n1]
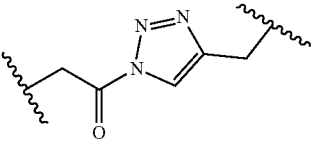 [SMILES: *CC(=O)n1cc(C*)nn1]
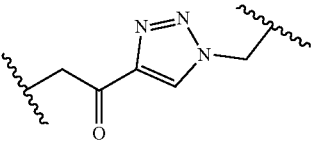 [SMILES: *CC(=O)c1cn(C*)nn1]
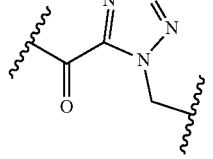
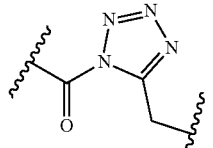
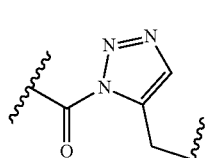

TABLE 2-continued
Exemplary linkers of compounds of Formula (I) or (Z).
Linker
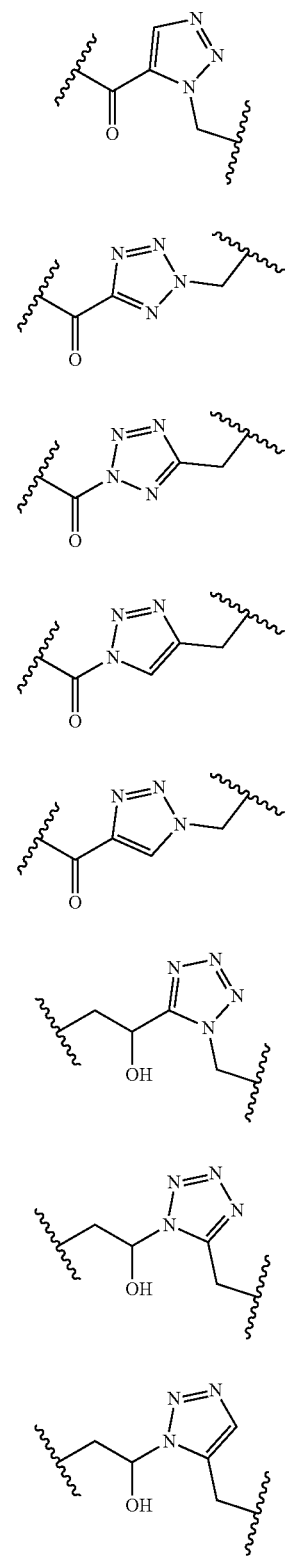
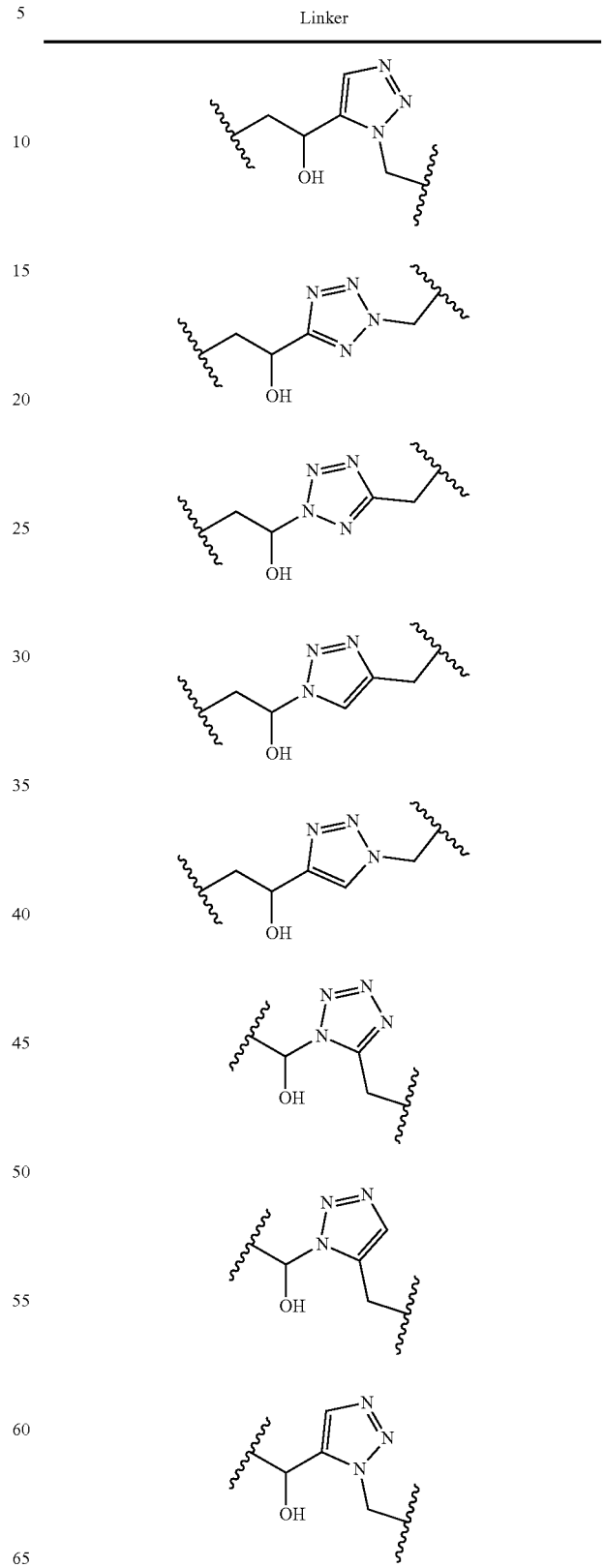

TABLE 2-continued

Exemplary linkers of compounds of Formula (I) or (Z).

Linker

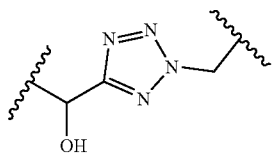 [SMILES: *Cn1nnc(C(*)O)n1]
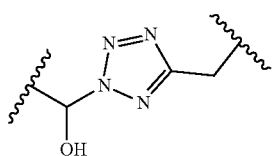 [SMILES: *Cc1nnn(C(*)O)n1]
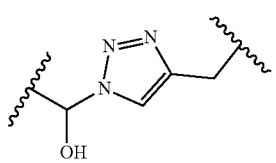 [SMILES: *Cc1cn(C(*)O)nn1]
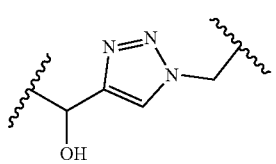 [SMILES: *Cn1cc(C(*)O)nn1]
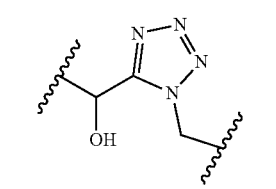 [SMILES: *Cn1nnnc1C(*)O]
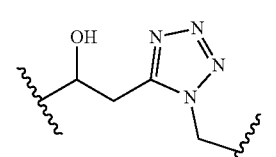
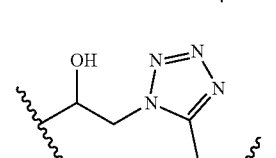
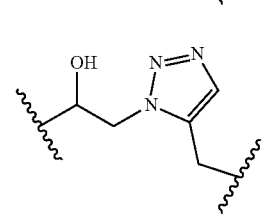
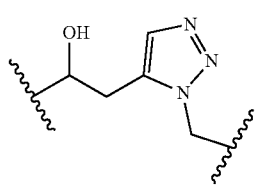 [SMILES: *Cn1nncc1CC(*)O]
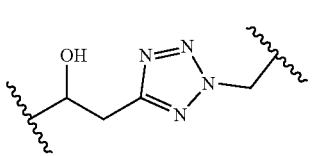 [SMILES: *Cn1nnc(CC(*)O)n1]
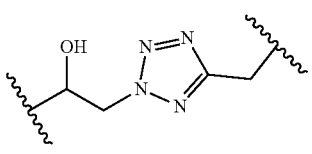 [SMILES: *Cc1nnn(CC(*)O)n1]
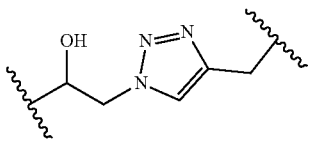 [SMILES: *Cc1cn(CC(*)O)nn1]
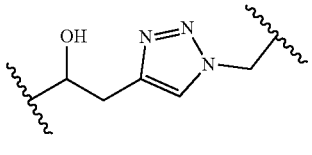 [SMILES: *Cn1cc(CC(*)O)nn1]

Methods of Preparation

Compounds of the invention may be synthesized according to the schemes below and those presented in the Examples. The reagents and conditions described are intended to be exemplary and not limiting. As one of skill in the art would appreciate, various analogs may be prepared by modifying the synthetic reaction, for example, using different starting materials, different reagents, or different reaction conditions (e.g., temperature, solvent, concentration). The synthesis of sulfonyl AMP analogs is described in Lu et al., *ChemBioChem* (2012) 13, 129-136; Lu et al., *Bioorg. Med. Chem. Lett.* (2008) 18, 5963-5966; Cisar et al., *J. Am. Chem. Soc.* (2007) 129, 7752-7753; U.S. patent application Ser. No. 11/911,525, filed Apr. 14, 2006; U.S. patent application Ser. No. 13/897,807, filed May 20, 2013; and WIPO application PCT/US2006/014394, filed Apr. 14, 2006, each of which is incorporated herein by reference.

In one aspect, the present invention provides methods for the preparation of compounds of Formula (I) and intermediates thereto. Exemplary synthetic methods are shown in Schemes 1 to 6. Unless otherwise stated, variables depicted in the schemes below are as defined for compounds of Formula (I).

Scheme 1.

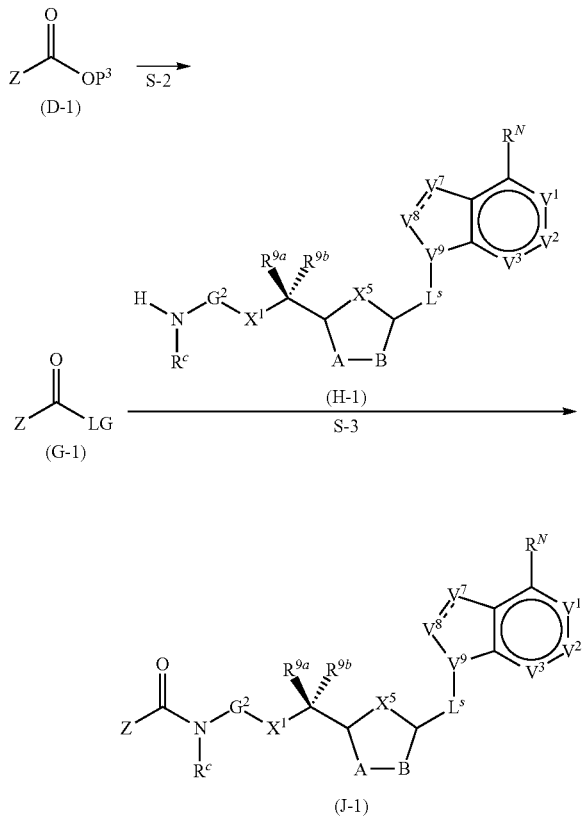

When G is

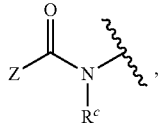

a compound of Formula (I) may be prepared according to Scheme 1. Step S-2 comprises converting a compound of Formula (D-1) to a compound of Formula (G-1). In some embodiments, LG is —OH. In some embodiments, the step of converting comprises deprotection of P³. In some embodiments, LG is halogen (e.g., —Cl, —Br, —I). In some embodiments, the step of converting is performed in the presence of an acid (e.g., TFA). In some embodiments, the step of converting is performed in the presence of a halogenating reagent (e.g., —Cl₂, —Br₂, —I₂, SOCl₂, POCl₃, N-halosuccinimide).

Step S-3 comprises coupling a compound of Formula (G-1) and a sulfonyl compound of Formula (H-1) to form a compound of Formula (J-1). A compound of Formula (J-1) is a compound of Formula (I). In some embodiments, LG is halogen (e.g., —Cl, —Br, —I). In some embodiments, LG is —OH. In some embodiments, LG is —OH, and X² is —O—. In some embodiments, the step of coupling is performed in the presence of a carbodiimide (e.g., DCC, EDC). In some embodiments, the step of coupling is performed in the presence of a base (e.g., DMAP).

Scheme 2.

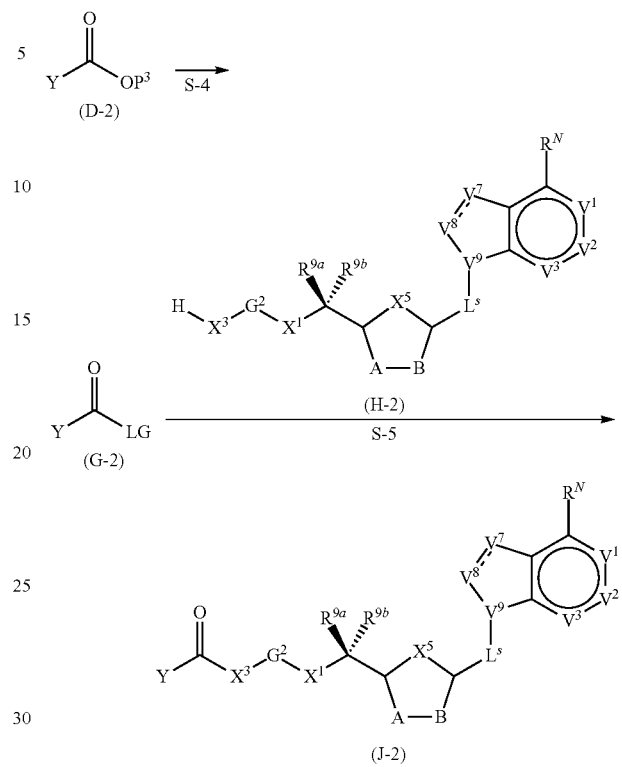

When G is

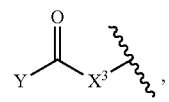

a compound of Formula (I) may be prepared according to Scheme 1. Step S-4 comprises converting a compound of Formula (D-2) to a compound of Formula (G-2). In some embodiments, LG is —OH. In some embodiments, the step of converting comprises deprotection of P³. In some embodiments, LG is halogen (e.g., —Cl, —Br, —I). In some embodiments, the step of converting is performed in the presence of an acid (e.g., TFA). In some embodiments, the step of converting is performed in the presence of a halogenating reagent (e.g., —Cl₂, —Br₂, —I₂, SOCl₂, POCl₃, N-halosuccinimide).

Step S-5 comprises coupling a compound of Formula (G-2) and a sulfonyl compound of Formula (H-2) to form a compound of Formula (J-2). A compound of Formula (J-2) is a compound of Formula (I). In some embodiments, X³ is —NR$^c$—. In some embodiments, X³ is —NH—. In some embodiments, X³ is —O—. In some embodiments, LG is halogen (e.g., —Cl, —Br, —I). In some embodiments, LG is —OH. In some embodiments, LG is —OH, and X³ is —O—. In some embodiments, LG is —OH, and X³ is —NH—. In some embodiments, the step of coupling is performed in the presence of a carbodiimide (e.g., DCC, EDC). In some embodiments, the step of coupling is performed in the presence of a base (e.g., DMAP).

Scheme 3.

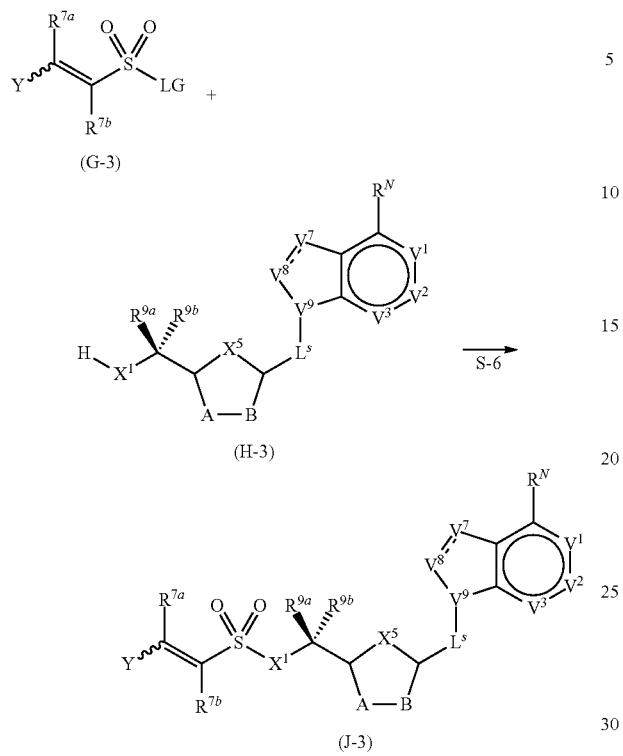

When G is

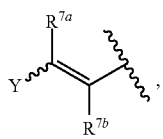

a compound of Formula (I) may be prepared according to Scheme 3. Step S-6 comprises coupling a sulfonyl compound of Formula (G-3) with a compound of Formula (H-3) to form a compound of Formula (J-3). A compound of Formula (J-3) is a compound of Formula (I). In some embodiments, $X^1$ is —O—. In some embodiments, $X^1$ is —NR$^c$—. In some embodiments, $X^1$ is —NH—. In some embodiments, LG is halogen (e.g., —Cl, —Br, —I). In some embodiments, LG is —OH. In some embodiments, LG is —Cl, and $X^1$ is —O—. In some embodiments, LG is —Cl, and $X^1$ is —NH—. In some embodiments, the step of coupling is performed in the presence of a base (e.g., pyridine, lutidine, DMAP). In certain embodiments, a method of preparing a compound of Formula (I) further comprises reducing the double bond of a compound of Formula (J-3) to a single bond.

Scheme 4.

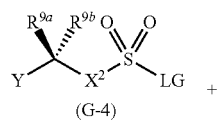

a compound of Formula (I) may be prepared according to Scheme 4. Step S-7 comprises coupling a sulfonyl compound of Formula (G-4) with a compound of Formula (H-4) to form a compound of Formula (J-4). A compound of Formula (J-4) is a compound of Formula (I). In some embodiments, $X^1$ is —O—. In some embodiments, $X^1$ is —NR$^c$—. In some embodiments, $X^1$ is —NH—. In some embodiments, LG is halogen (e.g., —Cl, —Br, —I). In some embodiments, LG is —OH. In some embodiments, LG is —Cl, and $X^1$ is —O—. In some embodiments, LG is —Cl, and $X^1$ is —NH—. In some embodiments, the step of coupling is performed in the presence of a base (e.g., pyridine, lutidine, DMAP).

Scheme 5.

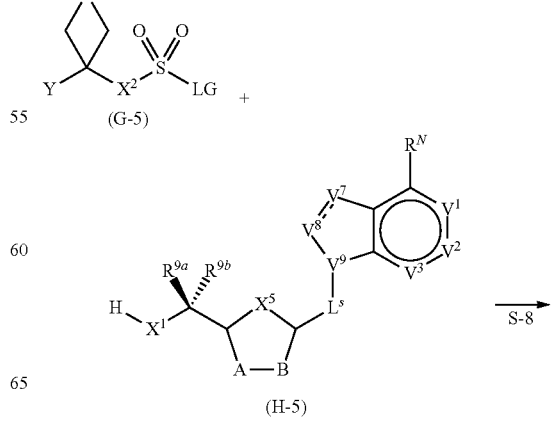

-continued

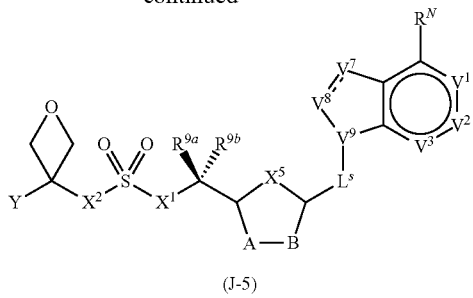

(J-5)

When G is

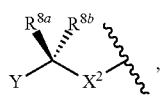

a compound of Formula (I) may be prepared according to Scheme 5. Step S-8 comprises coupling a sulfonyl compound of Formula (G-5) with a compound of Formula (H-5) to form a compound of Formula (J-5). A compound of Formula (J-5) is a compound of Formula (I). In some embodiments, $X^1$ is —O—. In some embodiments, $X^1$ is —$NR^c$—. In some embodiments, $X^1$ is —NH—. In some embodiments, LG is halogen (e.g., —Cl, —Br, —I). In some embodiments, LG is —OH. In some embodiments, LG is —Cl, and $X^1$ is —O—. In some embodiments, LG is —Cl, and $X^1$ is —NH—. In some embodiments, the step of coupling is performed in the presence a base (e.g., pyridine, lutidine, DMAP).

Scheme 6.

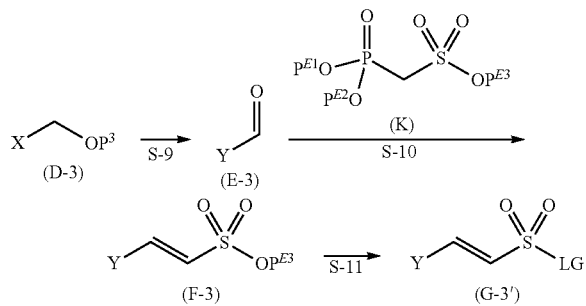

Intermediate (G-3') may be prepared according to Scheme 6. Step S-9 comprises oxidizing a compound of Formula (D-3) to an aldehyde of Formula (E-3). In certain embodiments, $P^3$ is H. In certain embodiments, $P^3$ is a non-hydrogen group, and Step S-9 further comprises deprotection of $P^3$. In some embodiments, the step of oxidizing comprises a Swern oxidation, Pfitzner-Moffatt oxidation, Corey-Kim oxidation, or Dess-Martin oxidation. In some embodiments, the step of oxidizing is performed in the presence of pyridiniumchlorochromate (PCC), oxalyl chloride, a carbodiimide (e.g., DCC, EDC), an N-halosuccinimide (e.g., NCS, NBS, NIS), or Dess-Martin periodinane (DMP). In some embodiments, the step of oxidizing is performed in the presence of dimethylsulfoxide or dimethylsulfide.

Step S-10 comprises coupling an aldehyde of Formula (E-3) and a sulfonyl phosphonate of Formula (K) to form a sulfonate of Formula (F-3). In certain embodiments, $P^{E1}$, $P^{E2}$, and $P^{E3}$ are unsubstituted $C_{1-6}$ alkyl (e.g., methyl, ethyl, propyl). In certain embodiments, $P^{E1}$, $P^{E2}$, and $P^{E3}$ are ethyl. In some embodiments, the step of coupling comprises a Horner-Wadsworth-Emmons coupling. In some embodiments, the step of coupling is performed in the presence of a base (e.g., an organolithium species (e.g., n-BuLi, tert-BuLi).

Step S-11 comprises converting a sulfonate of Formula (F-3) to a sulfonyl compound of Formula (G-3'). A compound of Formula (G-3') is a compound of Formula (G-3). In some embodiments, LG is —OH. In some embodiments, the step of converting comprises deprotection of $P^{E3}$. In some embodiments, LG is halogen (e.g., —Cl, —Br, —I). In some embodiments, the step of converting is performed in the presence of an acid (e.g., TFA). In some embodiments, the step of converting is performed in the presence of a halogenating reagent (e.g., —$Cl_2$, —$Br_2$, —$I_2$, $SOCl_2$, $POCl_3$, N-halosuccinimide).

$P^3$ is hydrogen, optionally substituted $C_{1-6}$ alkyl, optionally substituted acyl, or an oxygen protecting group.

LG is a leaving group. Exemplary leaving groups include, but are not limited to, halogen (e.g., F, Cl, Br, I), sulfonic acid ester (e.g., tosylate, mesylate, triflate), —OH, alkoxy, aryloxy, alkoxycarbonyloxy, aryloxycarbonyloxy, alkylcarbonyloxy, and arylcarbonyloxy.

Each of $P^{E1}$, $P^{E2}$, and $P^{E3}$ are hydrogen, substituted $C_{1-6}$ alkyl, optionally substituted acyl, or an oxygen protecting group.

The method of preparing a compound of Formula (I) or an intermediate thereto optionally further comprises one or more steps of protecting a nitrogen, oxygen, or sulfur atom, or deprotecting a nitrogen, oxygen, or sulfur atom. In certain embodiments, the step of deprotecting or protecting comprises replacing $R^{S1}$, $R^{S2}$, or both $R^{S1}$ and $R^{S2}$. In certain embodiments, the step of deprotecting or protecting comprises replacing one $R^{Na}$ or both $R^{Na}$ of group $R^N$. In certain embodiments, the step of deprotecting or protecting comprises replacing both $R^{S1}$ and $R^{S2}$, and replacing one $R^{Na}$, or both $R^{Na}$, or group $R^N$.

Pharmaceutical Compositions and Administration

The present invention also provides pharmaceutical compositions comprising a compound described herein (e.g., a compound of Formula (I)), or a pharmaceutically acceptable salt, solvate, hydrate, co-crystal, polymorph, tautomer, stereoisomer, or prodrug thereof, and optionally a pharmaceutically acceptable excipient. In certain embodiments, the pharmaceutical composition described herein comprises a compound of Formula (I), or a pharmaceutically acceptable salt, stereoisomer, or tautomer thereof, and a pharmaceutically acceptable excipient. In certain embodiments, the composition is useful for treating a patient with cystic fibrosis. In certain embodiments, the composition useful for eradication of a biofilm in a subject. In certain embodiments, the composition useful for preventing the formation of a biofilm in a subject.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating an infectious disease (e.g., bacterial infection, e.g., *P. aeruginosa* infection)) in a subject in need thereof. In certain embodiments, the effective amount is an amount effective for preventing an infectious disease (e.g., bacterial infection, e.g., *P. aeruginosa* infection)) in a subject in need thereof. In certain embodiments, the effective amount is an amount effective for reducing the risk of developing an infectious disease (e.g., bacterial infection, e.g., *P. aeruginosa* infection)) in a subject in need thereof. In certain embodiments, the effective amount is an amount effective for inhibiting PQS biosynthesis (e.g., inhibiting anthranilate-CoA synthetase (PqsA)) in an infection in a subject. In certain embodiments, the effective amount is an amount effective for inhibiting the biosynthesis of virulence factors (e.g., pyocyanin) in an infection in a subject. In certain embodiments, the effective amount is an amount effective for inhibiting menaquinone biosynthesis (e.g., inhibiting anthranilate-CoA ligase (PqsA)) in an infectious microorganism. In certain embodiments, the effective amount is an amount effective for inhibiting the biosynthesis of virulence factors (e.g., pyocyanin) in an infectious microorganism.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal.

In certain embodiments, the animal is a transgenic animal (e.g., transgenic mice and transgenic pigs). In certain embodiments, the subject is a fish or reptile.

In certain embodiments, the effective amount is an amount effective for inhibiting PQS biosynthesis by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting menaquinone biosynthesis by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting an adenylate-forming enzyme (e.g., an acyl-CoA synthetase) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting adenylate-forming enzyme (e.g., an acyl-CoA synthetase) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting anthranilate-CoA synthetase (PqsA) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting anthranilate-CoA synthetase (PqsA) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for a range of inhibition between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting PQS biosynthesis in an infectious microorganism), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., infectious disease, proliferative disease, hematological disease, or painful condition). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-diabetic agents, anti-proliferative agents, anti-cancer agents, anti-angiogenesis agents, anti-inflammatory agents, anti-bacterial agents, anti-viral agents, cardiovascular agents, and pain-relieving agents. In certain embodiments, the additional pharmaceutical agent is a binder or inhibitor of an AMP-producing synthetase. In certain embodiments, the additional pharmaceutical agent is a binder or inhibitor of anthranilate-CoA synthetase (PqsA). In certain embodiments, the additional pharmaceutical agent inhibits cellular respiration. In certain embodiments, the additional pharmaceutical agent inhibits biosynthesis of a virulence factor. In certain embodiments, the additional pharmaceutical agent inhibits biosynthesis of pyocyanin. In certain embodiments, the additional pharmaceutical agent inhibits biosynthesis of PQS, PqsE, lectin, HCN, or a rhamnolipid. In certain embodiments, the additional pharmaceutical agent inhibits protein synthesis. In certain embodiments, the additional pharmaceutical agent downregulates expression of PqsABCDE, PqsR, PqsH, or PhnAB. In certain embodiments, the additional pharmaceutical agent binds a ribosome. In certain embodiments, the additional pharmaceutical agent is an antibiotic. In certain embodiments, the additional pharmaceutical agent is an anti-bacterial agent.

In certain embodiments, the additional pharmaceutical agent is a β-lactam antibiotic. Exemplary β-lactam antibiotics include, but are not limited to: β-lactamase inhibitors (e.g., avibactam, clavulanic acid, tazobactam, sulbactam); carbacephems (e.g., loracarbef); carbapenems (e.g., doripenem, imipenem, ertapenem, meropenem); cephalosporins ($1^{st}$ generation) (e.g., cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cephalosporin C); cephalosporins ($2^{nd}$ generation) (e.g., cefaclor, cefamandole, cefbuperzone, cefmetazole, cefonicid, ceforanide, cefotetan, cefotiam, cefoxitin, cefminox, cefprozil, cefuroxime, cefuzonam); cephalosporins ($3^{rd}$ generation) (e.g., cefcapene, cefdaloxime, cefdinir, cefditorin, cefetamet, cefixime, cefmenoxime, cefodizime, cefoperazone, cefotaxime, cefovecin, cefpimizole, cefpiramide, cefpodoxime, ceftamere, ceftazidime, cefteram, ceftibuten, ceftiofur, ceftiolene, ceftizoxime, ceftriaxone, latamoxef); cephalosporins ($4^{th}$ generation) (e.g., cefepime, cefluprenam, cefoselis, cefozopran, cefpirome, cefquinome, flomoxef); cephalosporins ($5^{th}$ generation) (e.g., ceftaroline fosamil, ceftobiprole, ceftolozane); cephems (e.g., cefaloram, cefaparole, cefcanel, cefedrolor, cefempidone, cefetrizole, cefivitril, cefmepidium cefoxazole, cefrotil, cefsulodin, cefsumide, ceftioline, ceftioxime, cefuracetime, nitrocefin); monobactams (e.g., aztreonam, carumonam, norcadicin A, tabtoxinine β-lactam, tigemonam); penicillins/penams (e.g., amoxicillin, amoxicillin/clavulanate, ampicillin, ampicillin/flucloxacillin, ampicillin/sulbactam, azidocillin, azlocillin, bacampicillin, benzathine benzylpenicillin, benzathine phenoxymethylpenicillin, carbenicillin, carindacillin, clometocillin, cloxacillin, dicloxacillin, epicillin, flucloxacillin, hetacllin, mecillinam, mezlocillin, meticillin, metampiciillin, nafcillin, oxacillin, penamacillin, penicillin G, penicillin V, phenaticillin, piperacillin, piperacillin/tazobactam, pivampicillin, pivmecillinam, procaine benzylpenicillin, propicillin, sulbenicillin, talampicillin, temocllin, ticarcillin, ticarcillin/clavulanate); and penems/carbapenems (e.g., biapenem, doripenem, ertapenem, faropenem, imipenem, imipenem/cilastatin, lenapenem, meropenem, panipenem, razupenem, tebipenem, thienamycin, tomopenem).

In certain embodiments, the additional pharmaceutical agent is a non-β-lactam antibiotic. Exemplary non-β-lactam antibiotics include, but are not limited to: aminoglycosides (e.g., amikacin, dibekacin, gentamicin, kanamycin, neomycin, netilmicin, tobramycin, paromomycin, sisomicin, streptomycin, spectinomycin); ansamycins (e.g., geldanamycin, herbimycin); glycopeptides (e.g., belomycin, dalbavancin, oritavancin, ramoplanin, teicoplanin, telavancin, vancomycin); glycylcyclines (e.g., tigecycline); lincosamides (e.g., clindamycin, lincomycin); lipopeptides (e.g., anidulafungin, caspofungin, cilofungin, daptomycin, echinocandin B, micafungin, mycosubtilin); macrolides (e.g., azithromycin, carbomycin A, clarithromycin, dirithromycin, erythromycin, josmycin, kitasamycin, midecamycin, oleandomycin, roxithromycin, solithromycin, spiramycin, troleandomycin, telithromycin, tylosin); nitrofurans (e.g., furazolidone, furylfuramide, nitrofurantoin, nitrofurazone, nifuratel, nifurquinazol, nifurtoinol, nifuroxazide, nifurtimox, nifurzide, ranbezolid); nitroimidazoles (e.g., metronidazole, nimorazole, tinadazole); oxazolidinones (e.g., cycloserine, linezolid, posizolid radezolid, tedizolid); polypeptides (e.g., actinomycin, bacitracin, colistin, polymyxin B); quinolones (e.g., balofloxacin, besifloxacin, cinoxacin, ciprofloxacin, clinafloxacin, danofloxacin, delafloxacin, difloxacin, enoxacin, enrofloxacin, flerofloxacin, flumequine, gatifloxacin, gemifloxacin, grepafloxacin, ibafloxacin, JNJ-Q2, levofloxacin, lomefloxacin, marbofloxacin, moxifloxacin, nadifloxacin, nalidixic acid, nemonoxacin, norfloxacin, ofloxacin, orbifloxacin, oxilinic acid, pazufloxacin, pefloxacin, piromidic acid, pipemidic acid, prulifloxacin, rosoxacin, rufloxacin, sarafloxacin, sparfloxacin, sitafloxacin, temafloxacin, tosufloxacin, trovafloxacin); rifamycins (e.g., rifamycin B, rifamycin S, rifamycin SV, rifampicin, rifabutin, rifapentine, rifalazil, rifaximin); sulfonamides (e.g., co-trimoxazole, mafenide, pediazole, sulfacetamide, sulfadiazine, silver sulfadiazine, sulfadimidine, sulfadimethoxine, sulfadoxine, sulfafurazole, sulfamethizole, sulfamethoxazole, sulfamethoxypyridazine, sulfametopyrazine, sulfametoxydiazine, sulfamoxole, sulfanilamide, sulfanitran, sulfasalazine, sulfisomidine, sulfonamidochrysoidine, trimethoprim); tetracyclines (e.g., 6-deoxytetracycline, aureomycin, chlortetracycline, demeclocycline, doxycycline, lymecycline, meclocycline, methacycline, minocycline, oxytetracycline, PTK-0796, sancycline, rolitetracycline, tetracycline, terramycin); tuberactinomycins (e.g., tuberactinomycin A, tuberactinomycin O, viomycin, enviomycin, capreomycin); arsphenamine; chloramphenicol; dalfoprisitin; fosfomycin; fusidic acid; fidaxomycin; gramicidin; lysozyme; mupirocin; platensimycin; pristinamycin; sparsomycin; quinupristin; quinupristin/dalfopristin; teixobactin; and thiamphenicol.

In certain embodiments, the additional pharmaceutical agent is a carbapenem. In some embodiments, the additional pharmaceutical agent is doripenem, imipenem, or meropenem.

In certain embodiments, the additional pharmaceutical agent is a glycylcycline. In some embodiments, the additional pharmaceutical agent is tigecycline.

In certain embodiments, the additional pharmaceutical agent is a aminoglycoside. In some embodiments, the additional pharmaceutical agent is gentamycin, amikacin, or tobramycin.

In certain embodiments, the additional pharmaceutical agent is a quinolone. In some embodiments, the additional pharmaceutical agent is ciprofloxacin or levofloxacin.

In certain embodiments, the additional pharmaceutical agent is a cephalosporin. In some embodiments, the additional pharmaceutical agent is ceftazidime, cefepime, cefoperazone, cefpirome, ceftobirprole, or ceftaroline fosamil.

In certain embodiments, the additional pharmaceutical agent is a penicillin. In some embodiments, the additional pharmaceutical agent is an antipseudomonal penicillin or extended spectrum penicillin. In certain embodiments, the additional pharmaceutical agent is a carboxypenicillin or a ureidopenicillin. In some embodiments, the additional pharmaceutical agent is carbenicillin, ticarcillin, mezlocillin, azlocillin, piperacillin, or mecillinam.

In certain embodiments, the additional pharmaceutical agent is a polymyxin. In some embodiments, the additional pharmaceutical agent is polymyxin B or colistin.

In certain embodiments, the additional pharmaceutical agent is a monobactam. In some embodiments, the additional pharmaceutical agent is aztreonam.

In certain embodiments, the additional pharmaceutical agent is a β-lactamase inhibitor. In some embodiments, the additional pharmaceutical agent is sulbactam.

In certain embodiments, the additional pharmaceutical agent is gentamicin, amikacin, tobramycin, ciprofloxacin, levofloxacin, ceftazidimine, cefepime, cefoperazone, cefpirome, ceftobiprole, ceftaroline fosamil, carbenicllin, ticarcillin, mezlocillin, azlocillin, piperacillin, meropenem, imipenem, doripenem, polymyxin B, colistin, aztreonam, tigecycline, or sulbactam.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating an infectious disease (e.g., bacterial infection (e.g., *P. aeruginosa* infection)) in a subject in need thereof. In certain embodiments, the kits are useful for preventing an infectious disease (e.g., bacterial infection (e.g., *P. aeruginosa* infection)) in a subject in need thereof. In certain embodiments, the kits are useful for reducing the risk of developing an infectious disease (e.g., bacterial infection (e.g., *P. aeruginosa* infection)) in a subject in need thereof. In certain embodiments, the kits are useful for inhibiting biosynthesis of virulence factors in an infection in a subject or in an infectious microorganism. In certain embodiments, the kits are useful for inhibiting PQS biosynthesis (e.g., inhibiting anthranilate-CoA synthetase (PqsA)) in an infection in a subject or in an infectious microorganism. In certain embodiments, the kits are useful for treating a patient with cystic fibrosis. In certain embodiments, the kits are useful for eradication of a biofilm in a patient. In certain embodiments, the kits are useful for preventing the formation of a biofilm in a patient.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating an infectious disease (e.g., bacterial infection (e.g., *P. aeruginosa* infection)) in a subject in need thereof. In certain embodiments, the kits and instructions provide for preventing an infectious disease (e.g., bacterial infection (e.g., *P. aeruginosa* infection)) in a subject in need thereof. In certain embodiments, the kits and instructions provide for reducing the risk of developing an infectious disease (e.g., bacterial infection (e.g., *P. aeruginosa* infection)) in a subject in need thereof. In certain embodiments, the kits and instructions provide for inhibiting biosynthesis of virulence factors in an infection in a subject or in an infectious microorganism. In certain embodiments, the kits and instructions provide for inhibiting menaquinone biosynthesis (e.g., inhibiting anthranilate-CoA synthetase (PqsA)) in an infection in a subject or in an infectious microorganism. A kit described herein may include one or more additional pharmaceutical agents described herein as a separate composition.

Methods of Treatment and Uses

The present invention also provides methods that may be useful for the treatment and/or prevention of a disease. In certain embodiments, the disease is an infectious disease. In certain embodiments, the infectious disease is a bacterial infection. In certain embodiments, the infectious disease is a parasitic infection. In certain embodiments, the infectious disease is associated with another disease or condition, for example, in subjects with a weakened immune system as a result of HIV infection, AIDS, lupus, cancer, cystic fibrosis, or diabetes, or subjects with burns. In certain embodiments, the bacterial infection is an infection caused by Gram-positive bacteria. In certain, embodiments, the bacterial infection is an infection caused by Gram-negative bacteria. In certain embodiments, the bacterial infection is a *Staphylococcus* infection, a *Bacillus* infection, or an *Escherichia* infection. In certain embodiments, the bacterial infection is a *Pseudomonas* infection. In some embodiments, the bacterial infection is *Pseudomonas aeruginosa* infection. In some embodiments, the bacterial infection is infection of multiple species of bacterium. In some embodiments, the bacterial infection is infection of multiple species of bacterium, one of which is *P. aeruginosa*.

The compounds described herein (e.g., compounds of Formula (I)) may exhibit inhibitory activity towards an adenylate-forming enzyme (e.g., an acyl-CoA synthetase), may exhibit the ability to inhibit anthranilate-CoA synthetase (PqsA), may exhibit the ability to inhibit the biosynthesis of virulence factors in an infectious microorganism, may exhibit the ability to inhibit PQS biosynthesis, may exhibit a therapeutic effect and/or preventative effect in the treatment of infectious diseases (e.g., bacterial infections, e.g., *P. aeruginosa*)), and/or may exhibit a therapeutic and/or preventative effect superior to existing agents for treatment of an infectious disease.

The compounds described herein (e.g., compounds of Formula (I)) may exhibit selective inhibition of anthranilate-CoA synthetase (PqsA) versus inhibition of other proteins. In certain embodiments, the selectivity versus inhibition of another protein is between about 2 fold and about 10 fold. In certain embodiments, the selectivity is between about 10 fold and about 50 fold. In certain embodiments, the selectivity is between about 50 fold and about 100 fold. In certain embodiments, the selectivity is between about 100 fold and about 500 fold. In certain embodiments, the selectivity is between about 500 fold and about 1000 fold. In certain embodiments, the selectivity is between about 1000 fold and about 5000 fold. In certain embodiments. In certain embodiments, the selectivity is between about 5000 fold and about 10000 fold. In certain embodiments, or at least about 10000 fold.

The present invention provides methods that may be useful for the treatment of an infectious disease by administering a compound described herein, or pharmaceutically acceptable salt, solvate, hydrate, polymorph, co-crystal, tautomer, stereoisomer, or prodrug thereof, or pharmaceutical composition thereof, to a subject in need thereof. In certain embodiments, the compound is administered as a pharmaceutically acceptable salt, stereoisomer, or tautomer thereof. In certain embodiments, the compound is administered as a pharmaceutically acceptable salt of the compound. In certain embodiments, the compound is administered as a specific stereoisomer or mixture of stereoisomers of the compound. In certain embodiments, the compound is administered as a specific tautomer or mixture of tautomers of the compound. In certain embodiments, the compound is administered as a pharmaceutical composition as described herein comprising the compound.

The present invention also provides uses of the inventive compounds, and pharmaceutically acceptable salts, solvates, hydrates, polymorphs, co-crystals, tautomers, stereoisomers, prodrugs, and pharmaceutical compositions thereof, in the manufacture of medicaments for the treatment and prevention of diseases. In certain embodiments, the disease is an infectious disease. In certain embodiments, the infectious disease is a bacterial infection. In certain embodiments, the infectious disease is a parasitic infection. In certain embodiments, the infectious disease may be associated with another disease or condition, for example, in subjects with a weakened immune system as a result of HIV infection, AIDS, lupus, cancer, cystic fibrosis, or diabetes, or subjects with burns. In certain embodiments, the infectious disease may arise as complication of another disease or condition, for example, in subjects with a weakened immune system as a result of HIV infection, AIDS, lupus, cancer, cystic fibrosis or diabetes. In certain embodiments, the bacterial infection is an infection caused by Gram-positive bacteria. In certain, embodiments, the bacterial infection is an infection caused by Gram-negative bacteria. In certain embodiments, the bacterial infection is a *Staphylococcus* infection, a *Bacillus* infection, or an *Escherichia* infection. In certain embodiments, the bacterial infection is a *Pseudomonas* infection. In some embodiments the bacterial infection is *Pseudomonas aeruginosa* infection.

Certain methods described herein include methods of treating a bacterial infection, methods of treating an infection in a subject, or methods of contacting an infectious microorganism with a compound described herein (e.g. a compound of Formula (I)). Any of these methods may involve a specific class of bacteria or type of bacteria. In certain embodiments, the bacterial infection is caused by Gram-positive bacteria. In certain, embodiments, the bacterial infection caused by Gram-negative bacteria. In certain embodiments the bacteria is from the genus *Staphylococcus*, *Escherichia*, or *Bacillus*. In certain embodiments the bacteria is from the genus *Pseudomonas*.

In certain embodiments, the microbial infection is an infection with a bacteria, i.e., a bacterial infection. In certain embodiments, the compounds of the invention exhibit antibacterial activity. For example, in certain embodiments, the compound has a mean inhibitory concentration, with respect to a particular bacterium, of less than 50 µg/mL, preferably less than 25 µg/mL, more preferably less than 5 µg/mL, and most preferably less than 1 µg/mL.

Exemplary bacteria include, but are not limited to, Gram positive bacteria (e.g., of the phylum Actinobacteria, phylum Firmicutes, or phylum Tenericutes); Gram negative bacteria (e.g., of the phylum Aquificae, phylum Deinococcus—*Thermus*, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacteria is a member of the phylum Proteobacteria and the genus *Pseudomonas*, e.g., the bacterial infection is a *Pseudomonas* infection. Exemplary *Pseudomonas* bacteria include, but are not limited to, *P. aeruginosa*, *P. anguilliseptica*, *P. agarici*, *P. luteola*, *P. oryzihabitans*, *P. plecoglossida*, *P. syringae*, and *P. tolaasii*. In certain embodiments, the bacteria is *P. aeruginosa*.

In certain embodiments, the methods of the invention include administering to the subject an effective amount of a compound described herein (e.g., a compound of Formula (I)), or a pharmaceutically acceptable salt, stereoisomer, or tautomer thereof, or a pharmaceutical composition thereof. In certain embodiments, the effective amount is a therapeutically effective amount. In certain embodiments, the effective amount is a prophylactically effective amount.

In another aspect, the present invention provides methods for inhibiting the biosynthesis of virulence factors in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting the biosynthesis of virulence factors in an infectious microorganism, by contacting the sample with a compound described herein (e.g., a compound of Formula (I)), or a pharmaceutically acceptable salt, stereoisomer, or tautomer thereof, or a pharmaceutical composition thereof.

In some embodiments, the virulence factor is pyocyanin. In some embodiments, the virulence factor is lectin, HCN, or a rhamnolipid. In some embodiments, the virulence factor is PQS. In some embodiments, the virulence factor is PqsE.

In another aspect, the present invention provides methods for inhibiting PQS biosynthesis in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting PQS biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

Inhibiting PQS biosynthesis may decrease levels of one or more PQS metabolite and/or virulence factors. In some embodiments, the PQS metabolite is anthranilyl-S-CoA. In some embodiments, the PQS metabolite is 2-heptyl-4-hydroxyquinoline (HHQ). In some embodiments, the PQS metabolite is 3,4-dihydroxy-2-heptylquinoline (PQS). In some embodiments, the virulence factor is pyocyanin. In some embodiments, the virulence factor is another virulence factor described herein.

In another aspect, the present invention provides methods for inhibiting HHQ biosynthesis in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting HHQ biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting pyocyanin in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting pyocyanin biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting biofilm formation, in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting biofilm formation by contacting the biofilm with a compound described herein (e.g., a compound of Formula (I)), or a pharmaceutically acceptable salt, stereoisomer, or tautomer thereof, or a pharmaceutical composition thereof.

In another aspect, the present invention provides methods for eradicating a biofilm in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for eradicating a biofilm by contacting the biofilm with a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting an adenylate-forming enzyme (e.g., an acyl-CoA synthetase) in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting an adenylate-forming enzyme (e.g., an acyl-CoA synthetase) in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting anthranilate-CoA synthetase (PqsA) in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present invention provides methods for inhibiting anthranilate-CoA synthetase (PqsA) in an infectious microorganism, by contacting the sample with a compound described herein (e.g., a compound of Formula (I)), or a pharmaceutically acceptable salt, stereoisomer, or tautomer thereof, or a pharmaceutical composition thereof.

The present invention also provides methods of using a compound described herein (e.g., a compound of Formula (I)), or a pharmaceutically acceptable salt, solvate, hydrate, polymorph, co-crystal, tautomer, stereoisomer, or prodrug thereof, or pharmaceutical compositions thereof, in research studies in the field of disease pathology, biochemistry, cell biology, and other fields associated with infectious diseases. The compounds of the invention can be used to study the roles of biomolecules (e.g., anthranilate-CoA synthetase, anthranilic acid, anthranilate-AMP, anthranilyl-S-CoA, HHQ, PQS, pyocyanin). The compounds of the invention can be used to study the biosynthesis of a virulence factor in a microorganism. The compounds of the invention can be used to study quorum sensing in a microorganism. In certain embodiments, the method comprises use of the compound or composition thereof to inhibit the biosynthesis of virulence factors, inhibitor PQS biosynthesis, or disrupt quorum sensing. In certain embodiments, the method comprises use of the compound or composition thereof to inhibit anthranilate-CoA synthetase (PqsA). In certain embodiments, the method comprises determining the concentration of a biomolecule in a subject or biological sample.

Certain methods described herein, may comprise administering one or more additional pharmaceutical agent in combination with the compounds described herein. The additional pharmaceutical agents include, but are not limited to, anti-diabetic agents, anti-proliferative agents, anti-cancer agents, anti-angiogenesis agents, anti-inflammatory agents, anti-bacterial agents, anti-viral agents, cardiovascular agents, and pain-relieving agents. In certain embodiments, the additional pharmaceutical agent is an antibiotic. In certain embodiments, the additional pharmaceutical agent is an anti-bacterial agent. In certain embodiments, the additional pharmaceutical agent is a binder or inhibitor of an AMP-producing synthetase. In certain embodiments, the additional pharmaceutical agent is a binder or inhibitor of anthranilate-CoA synthetase (PqsA). In certain embodiments, the additional pharmaceutical agent inhibits the biosynthesis of a virulence factor. In certain embodiments, the additional pharmaceutical agent inhibits PQS biosynthesis.

In certain embodiments, the additional pharmacetucial agent is a β-lactam antibiotic. Exemplary β-lactam antibiotics include, but are not limited to: β-lactamase inhibitors (e.g., avibactam, clavulanic acid, tazobactam, sulbactam); carbacephems (e.g., loracarbef); carbapenems (e.g., doripenem, imipenem, ertapenem, meropenem); cephalosporins ($1^{st}$ generation) (e.g., cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cephalosporin C); cephalosporins ($2^{nd}$ generation) (e.g., cefaclor, cefamandole, cefbuperzone, cefmetazole, cefonicid, ceforanide, cefotetan, cefotiam, cefoxitin, cefminox, cefprozil, cefuroxime, cefuzonam); cephalosporins ($3^{rd}$ generation) (e.g., cefcapene, cefdaloxime, cefdinir, cefditoren, cefetamet, cefixime, cefmenoxime, cefodizime, cefoperazone, cefotaxime, cefovecin, cefpimizole, cefpiramide, cefpodoxime, ceftamere, ceftazidime, cefteram, ceftibuten, ceftiofur, ceftiolene, ceftizoxime, ceftriaxone, latamoxef); cephalosporins ($4^{th}$ generation) (e.g., cefepime, cefluprenam, cefoselis, cefozopran, cefpirome, cefquinome, flomoxef); cephalosporins ($5^{th}$ generation) (e.g., ceftaroline fosamil, ceftobiprole, ceftolozane); cephems (e.g., cefaloram, cefaparole, cefcanel, cefedrolor, cefempidone, cefetrizole, cefivitril, cefmepidium cefoxazole, cefrotil, cefsulodin, cefsumide, ceftioline, ceftioxime, cefuracetime, nitrocefin); monobactams (e.g., aztreonam, carumonam, norcadicin A, tabtoxinine β-lactam, tigemonam); penicillins/penams (e.g., amoxicillin, amoxicillin/clavulanate, ampicillin, ampicillin/flucloxacillin, ampicillin/sulbactam, azidocillin, azlocillin, bacampacillin, benzathine benzylpenicillin, benzathine phenoxymethylpenicillin, carbenicillin, carindacillin, clometocillin, cloxacillin, dicloxacillin, epicillin, flucloxacillin, hetacllin, mecillinam, mezlocillin, meticillin, metampiciillin, nafcillin, oxacillin, penamacillin, penicillin G, penicillin V, phenaticillin, piperacillin, piperacillin/tazobactam, pivampicillin, pivmecillinam, procaine benzylpenicillin, propicillin, sulbenicillin, talampicillin, temocllin, ticarcillin, ticarcillin/clavulanate); and penems/carbapenems (e.g., biapenem, doripenem, ertapenem, faropenem, imipenem, imipenem/cilastatin, lenapenem, meropenem, panipenem, razupenem, tebipenem, thienamycin, tomopenem).

In certain embodiments, the additional pharmacetucial agent is a non-β-lactam antibiotic. Exemplary non-β-lactam antibiotics include, but are not limited to: aminoglycosides (e.g., amikacin, dibekacin, gentamicin, kanamycin, neomycin, netilmicin, tobramycin, paromomycin, sisomicin, streptomycin, spectinomycin); ansamycins (e.g., geldanamycin, herbimycin); glycopeptides (e.g., belomycin, dalbavancin, oritavancin, ramoplanin, teicoplanin, telavancin, vancomycin); glycylcyclines (e.g., tigecycline); lincosamides (e.g., clindamycin, lincomycin); lipopeptides (e.g., anidulafungin, caspofungin, cilofungin, daptomycin, echinocandin B, micafungin, mycosubtilin); macrolides (e.g., azithromycin, carbomycin A, clarithromycin, dirithromycin, erythromycin, josmycin, kitasamycin, midecamycin, oleandomycin, roxithromycin, solithromycin, spiramycin, troleandomycin, telithromycin, tylosin); nitrofurans (e.g., furazolidone, furylfuramide, nitrofurantoin, nitrofurazone, nifuratel, nifurquinazol, nifurtoinol, nifuroxazide, nifurtimox, nifurzide, ranbezolid); nitroimidazoles (e.g., metronidazole, nimorazole, tinadazole); oxazolidinones (e.g., cycloserine, linezolid, posizolid radezolid, tedizolid); polypeptides (e.g., actinomycin, bacitracin, colistin, polymyxin B); quinolones (e.g., balofloxacin, besifloxacin, cinoxacin, ciprofloxacin, clinafloxacin, danofloxacin, delafloxacin, difloxacin, enoxacin, enrofloxacin, fleroxacin, flumequine, gatifloxacin, gemifloxacin, grepafloxacin, ibafloxacin, JNJ-Q2, levofloxacin, lomefloxacin, marbofloxacin, moxifloxacin, nadifloxacin, nalidixic acid, nemonoxacin, norfloxacin, ofloxacin, orbifloxacin, oxilinic acid, pazufloxacin, pefloxacin, piromidic acid, pipemidic acid, prulifloxacin, rosoxacin, rufloxacin, sarafloxacin, sparfloxacin, sitafloxacin, temafloxacin, tosufloxacin, trovafloxacin); rifamycins (e.g., rifamycin B, rifamycin S, rifamycin SV, rifampicin, rifabutin, rifapentine, rifalazil, rifaximin); sulfonamides (e.g., co-trimoxazole, mafenide, pediazole, sulfacetamide, sulfadiazine, silver sulfadiazine, sulfadimidine, sulfadimethoxine, sulfadoxine, sulfafurazole, sulfamethizole, sulfamethoxazole, sulfamethoxypyridazine, sulfametopyrazine, sulfametoxydiazine, sulfamoxole, sulfanilamide, sulfanitran, sulfasalazine, sulfisomidine, sulfonamidochrysoidine, trimethoprim); tetracyclines (e.g., 6-deoxytetracycline, aureomycin, chlortetracycline, demeclocycline, doxycycline, lymecycline, meclocycline, methacycline, minocycline, oxytetracycline, PTK-0796, sancycline, rolitetracycline, tetracycline, terramycin); tuberactinomycins (e.g., tuberactinomycin A, tuberactinomycin O, viomycin, enviomycin, capreomycin); arsphenamine; chloramphenicol; dalfoprisitin; fosfomycin; fusidic acid; fidaxomycin, gramicidin; lysozyme; mupirocin; platensimycin; pristinamycin; sparsomycin; quinupristin; quinupristin/dalfopristin; teixobactin; and thiamphenicol.

In certain embodiments, the additional pharmaceutical agent is a carbapenem. In some embodiments, the additional pharmaceutical agent is doripenem, imipenem, or meropenem.

In certain embodiments, the additional pharmaceutical agent is a glycylcycline. In some embodiments, the additional pharmacetucial agent is tigecycline.

In certain embodiments, the additional pharmaceutical agent is a aminoglycoside. In some embodiments, the additional pharmaceutical agent is gentamycin, amikacin, or tobramycin.

In certain embodiments, the additional pharmaceutical agent is a quinolone. In some embodiments, the additional pharmaceutical agent is ciprofloxacin or levofloxacin.

In certain embodiments, the additional pharmaceutical agent is a cephalosporin. In some embodiments, the additional pharmaceutical agent is ceftazidime, cefepime, cefoperazone, cefpirome, ceftobirprole, or ceftaroline fosamil.

In certain embodiments, the additional pharmaceutical agent is a penicillin. In some embodiments, the additional pharmaceutical agent is an antipseudomonal penicillin or extended spectrum penicillin. In certain embodiments, the additional pharmaceutical agent is a carboxypenicillin or a ureidopenicillin. In some embodiments, the additional pharmaceutical agent is carbenicillin, ticarcillin, mezlocillin, azlocillin, piperacillin, or mecillinam.

In certain embodiments, the additional pharmaceutical agent is a polymyxin. In some embodiments, the additional pharmaceutical agent is polymyxin B or colistin.

In certain embodiments, the additional pharmaceutical agent is a monobactam. In some embodiments, the additional pharmaceutical agent is aztreonam.

In certain embodiments, the additional pharmaceutical agent is a β-lactamase inhibitor. In some embodiments, the additional pharmaceutical agent is sulbactam.

In certain embodiments, the additional pharmaceutical agent is gentamicin, amikacin, tobramycin, ciprofloxacin, levofloxacin, ceftazidimine, cefepime, cefoperazone, cefpirome, ceftobiprole, ceftaroline fosamil, carbenicllin, ticarcillin, mezlocillin, azlocillin, piperacillin, meropenem, imipenem, doripenem, polymyxin B, colistin, aztreonam, tigecycline, or sulbactam.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⌇ is a single bond where the stereochemistry of the moieties immediately attached thereto is not specified, --- is absent or a single bond, ═ or ≡ is a single or double bond, and ≡ is a single, double, or triple bond. If drawn in a ring, ⃝ indicates that each bond of the ring is a single or double bond, valency permitting. The precise of arrangement of single and double bonds will be determined by the number, type, and substitution of atoms in the ring, and if the ring is multicyclic or polycyclic. In general, any ring atom (e.g., C or N), can have a double bond with a maximum of one adjacent atom.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2CL$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl").

In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

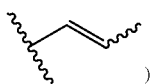
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any one of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$)$_2$)$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino.

In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any one of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2H$), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)$NR^{bb}SO_2R^{aa}$, —C(=S)N($R^{bb}$)$_2$), and imines (—C(=$NR^{bb}$)$R^{aa}$, —C(=$NR^{bb}$)$OR^{aa}$, —C(=$NR^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —$OR^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

The term "leaving group" is given its ordinary meaning in the art of synthetic organic chemistry and refers to an atom or a group capable of being displaced by a nucleophile. See, for example, Smith, March Advanced Organic Chemistry 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$], B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The invention is not intended to be limited in any manner by the above exemplary listing of substituents.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal contains a compound of the present invention and one or more other component, including but not limited to, atoms, ions, molecules, or solvent molecules. In certain embodiments, a co-crystal contains a compound of the present invention and one or more solvent molecules. In certain embodiments, a co-crystal contains a compound of the present invention and one or more acid or base. In certain embodiments, a co-crystal contains a compound of the present invention and one or more components related to said compound, including not limited to, an isomer, tautomer, salt, solvate, hydrate, synthetic precursor, synthetic derivative, fragment or impurity of said compound.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "condition," "disease," and "disorder" are used interchangeably.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition (i.e., "therapeutic treatment"), and also contemplates an action that occurs before a subject begins to suffer from the specified disease or condition (i.e., "prophylactic treatment").

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

As used herein the term "inhibit" or "inhibition" in the context of enzymes, for example, in the context of anthranilate-CoA synthetase (PqsA), refers to a reduction in the activity of the enzyme. In some embodiments, the term refers to a reduction of the level of enzyme activity, e.g., PqsA activity, to a level that is statistically significantly lower than an initial level, which may, for example, be a baseline level of enzyme activity. In some embodiments, the term refers to a reduction of the level of enzyme activity, e.g., PqsA activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein the term "infectious microorganism" refers to a species of infectious fungi, bacteria, or protista, or to a virus. In certain embodiments, the infectious microorganism is a fungi. In certain embodiments, the infectious microorganism is a bacteria. In certain embodiments, the infectious microorganism is a protista. In certain embodiments, the infectious microorganism is a virus.

An "infection" or "infectious disease" refers to an infection with a microorganism, such as a fungus, bacteria or virus. In certain embodiments, the infection is an infection with a fungus, i.e., a fungal infection. In certain embodiments, the infection is an infection with a virus, i.e., a viral infection. In certain embodiments, the infection is an infection with bacteria, i.e., a bacterial infection. Various infections include, but are not limited to, skin infections, GI infections, urinary tract infections, genito-urinary infections, sepsis, blood infections, and systemic infections.

As used herein, the term "anthranilate-CoA synthetase" or "PqsA" refers to an enzyme of the menaquinone biosynthesis pathway which converts anthranilic acid to anthranilyl-S-CoA. PqsA may also refer to the encoding RNA and DNA sequences of the PqsA protein. In some embodiments, a PqsA inhibitor provided herein is specific for a PqsA from a species, e.g., for *P. aeuroginosa* PqsA. The term PqsA further includes, in some embodiments, sequence variants and mutations (e.g., naturally occurring or synthetic PqsA sequence variants or mutations), and different PqsA isoforms. In some embodiments, the term PqsA includes protein or encoding sequences that are homologous to a PqsA protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with a PqsA sequence, for example, with a PqsA sequence provided herein. PqsA protein and encoding gene sequences are well known to those of skill in the art, and exemplary protein sequences include, but are not limited to, the following sequences. Additional PqsA sequences, e.g., PqsA homologues from other bacteria species, will be apparent to those of skill in the art, and the invention is not limited to the exemplary sequences provided herein.

>gi|15596193|ref|NP_249687.1|anthranilate-CoA Ligase [*Pseudomonas aeruginosa* PAO1]

```
                                              (SEQ ID NO: 1)
MSTLANLTEVLFRLDFDPDTAVYHYRGQTLSRLQCRTYILSQASQLARLL

KPGDRVVLALNDSPSLACLFLACIAVGAIPAVINPKSREQALADIAADCQ

ASLVVREADAPSLSGPLAPLTLRAAAGRPLLDDFSLDALVGPADLDWSAF

HRQDPAAACFLQYTSGSTGAPKGVMHSLRNTLGFCRAFATELLALQAGDR

LYSIPKMFFGYGMGNSLFFPWFSGASALLDDTWPSPERVLENLVAFRPRV

LFGVPAIYASLRPQARELLSSVRLAFSAGSPLPRGEFEFWAAHGLEICDG

IGATEVGHVFLANRPGQARADSTGLPLPGYECRLVDREGHTIEEAGRQGV

LLVRGPGLSPGYWRASEEQQARFAGGWYRTGDLFERDESGAYRHCGREDD

LFKVNGRWVVPTQVEQAICRHLPEVSEAVLVPTCRLHDGLRPTLFVTLAT
```

-continued

PLDDNQILLAQRIDQHLAEQIPSHMLPSQLHVLPALPRNDNGKLARAELR

HLADTLYHDNLPEERAC

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Synthesis and Activity of PqSA Inhibitors

Bosynthesis of the quinolone HHQ is thought to involve PqsA-E, with final conversion to PQS involving oxidation by PqsH (See, e.g., FIG. 1). Also, see, e.g., Dulcey et al. Chem. Biol. (2013) 20, 1481-1491; Dubern et al. Mol. BioSyst. (2008) 4, 882. Inhibitors of the cyclase PqsD and the thioesterase activity of PqsE, direct antagonists of the MvfR receptor, a dual inhibitor of PqsD and MvfR, as well as an inhibitor of the upstream enzyme KynU, which is one source of the anthranilic acid precursor, have been reported. See, e.g., Pistorius et al. ChemBioChem (2011) 12, 850; Weidel et al. (2013) J. Med. Chem. 56, 6146-6155; Hinsberger et al. (2014) Eur. J. Med. Chem. 76, 343-351; Storz et al. (2012) J. Am. Chem. Soc. 134, 16143-16146; Storz et al. (2013) ACS Chem. Biol. 8, 2794-2801; Storz et al. (2014) Org. Biomol. Chem. 12, 6094-6104; Sahner et al. (2013) J. Med. Chem. 56, 8656-8664; Sahner et al. (2015) 96, 14; Zender et al. (2016) ACS Chem. Biol. 11, 1755-1763; Lu et al. (2012) Chem. Biol. 19, 381-390; Klein et al. (2012) ACS Chem. Biol. 7, 1496-1501; Lu et al. (2014) Angew. Chem., Int. Ed. 53, 1109-1112; Lu et al. (2014) Eur. J. Med. Chem. 79, 173-183; Zender et al. (2013) J. Med. Chem. 56, 6761-6774; Ilangovan et al. (2013) PLoS Pathog. 9, e1003508; Starkey et al. (2014) PLoS Pathog. 10, e1004321; Thomann et al. (2016) ACS Chem. Biol. 11, 1279-1286; Kasper et al. (2016) ACS Chem. Biol. 11, 1106. Some efforts to target this pathway have focused on PqsA, an acyl-CoA synthetase (ligase) that catalyzes a key step in quinolone biosynthesis. See, e.g., Coleman et al. (2008) J. Bacteriol. 190, 1247. PqsA converts anthranilic acid to anthranilyl-CoA via a two step process involving initial ATP-dependent adenylation of anthranilic acid to form a tightly bound anthranilyl-AMP intermediate, followed by thioesterification with CoA to form anthranilyl-CoA. PqsA has been validated previously as a promising therapeutic target using both genetic and pharmacological approaches. pqsA-mutants do not produce HHQ or PQSand are poor biofilm producers in vitro. See, e.g., Deziel et al. (2004) Proc. Natl. Acad. Sci. U.S.A 101, 1339; Kim et al. (2010) Immunology 129, 578-588; Miisken et al. (2010) Microbiology 156, 431. They also exhibit attenuated virulence in a mouse burn infection model, reduced dissemination in a mouse lung infection model, and less biofilm formation and increased susceptibility to clearance by ciprofloxacin in a mouse tumor infection model. See, e.g., Deziel et al. (2005) Mol. Microbiol. 55, 998; Lesic et al. (2007) PLoS Pathog. 3, e126; Komor et al. (2012) Microbes Infect. 14, 951. There is no known human orthologue of PqsA, although related aliphatic acyl-CoA synthetases are used in metabolism. Thus, selective PqsA inhibitors would not be expected to impact host cell viability. Moreover, haloanthranilate substrate analogues that act as either PqsA substrates or inhibitors have been shown to inhibit PQS production in cell culture and to decrease both nolone production and mortality in the mouse burn model.

Acyl-CoA synthetases belong to a superfamily of structurally and mechanistically related adenylate-forming enzymes that also includes nonribosomal peptide synthetase (NRPS) adenylation domains and firefly luciferase. Some have used 5'-O—(N-acylsulfamoyl)adenosines (acyl-AMS) and related compounds to inhibit such enzymes by mimicking the cognate, tightly bound acyl-AMP intermediates. See, e.g., Ferreras et al. (2005) Nat. Chem. Biol. 1, 29-32; Lun et al. (2013) Antimicrob. Agents Chemother. 57, 5138-5140; Cisar et al. (2007) J. Am. Chem. Soc. 129, 7752-7753; Lu et al. (2008) Bioorg. Med. Chem. Lett. 18, 5963-5966; Lu et al. (2012) ChemBioChem 13, 129-136; Matarlo et al. (2015) Biochemistry 54, 6514-6524; Ferreras et al. (2008) Chem. Biol. 15, 51; Lu et al. (2010) J. Am. Chem. Soc. 132, 1748; Olsen et al. (2010) Nature 463, 906-912; Finking et al. (2003) Chem-BioChem 4, 903-906; Koroniak et al. (2003) Org. Lett. 5, 2033-2036; Brown et al. (2005) Biochemistry 44, 3112-3121; Branchini et al. (2005) Bioorg. Med. Chem. Lett. 15, 3860-3864; May et al. (2005) FEBS J. 272, 2993-3003; Somu et al. (2006) J. Med. Chem. 49, 31; Miethke et al. (2006) FEBS J. 273, 409-419; Pfleger et al. (2007) Biochemistry 46, 4147-4157; Tian et al. (2008) Biochemistry 47, 12434-12447. Ciulli et al. (2008) ChemBioChem 9, 2606-2611; Arora et al. (2009) Nat. Chem. Biol. 5, 166-173; Drake et al. (2010) Biochemistry 49, 9292-9305; Sikora et al. (2010) Biochemistry 49, 3648.

Ishida and co-workers first applied this inhibitor design strategy to mechanistically related aminoacyl-tRNA synthetases and were inspired by the sulfamoyladenosine class of natural products that includes nucleocidin and ascamycin. See, e.g., Ueda et al. (1991) Biochim. Biophys. Acta, Protein Struct. Mol. Enzymol. 1080, 126-134; Waller et al. (1957) J. Am. Chem. Soc. 79, 1011-1012; Morton et al. (1969) J. Am. Chem. Soc. 91, 1535; Isono et al. (1984) J. Antibiot. 37, 670-672.

Figure 5:
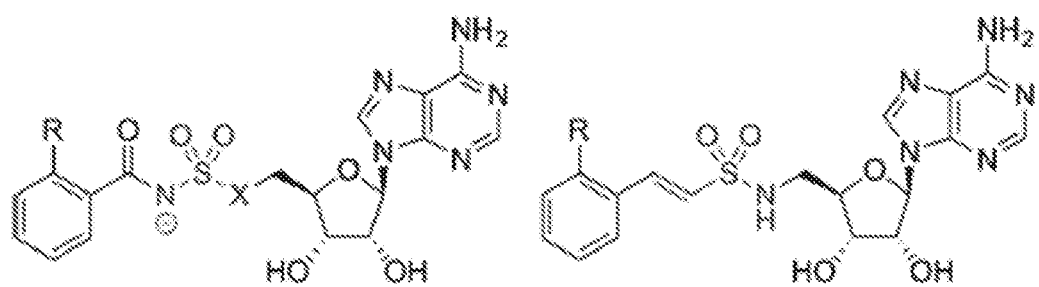
FIG. 5 shows inhibition of PqsA by designed sulfonyladenosine inhibitors. Assays were performed with 60 nM PqsA. [b]Calculated based on Dixon plots. [c]Competitive inhibitor with respect to ATP (Ki=16.5±2.6 nM, calculated based on Morrison equation) and uncompetitive with respect to anthranilate and CoA.

Compound of the present invention are effective inhibitors of PqsA and quinolone biosynthesis. For example, anthranilyl-AMS (1, FIG. 5) or its sulfamide analogue, anthranilyl-AMSN (2), are effective inhibitors of PqsA and quinolone biosynthesis. The close structural analogues salicyl-AMS (3), salicyl-AMSN (4), and benzoyl-AMS (5) provide structure-activity relationship data. See, e.g., Ferreras et al. (2005) Nat. Chem. Biol. 1, 29-32; Somu et al. (2006) J. Med. Chem. 49, 31. It was envisioned that the corresponding vinyl sulfonamides anthranilyl-AVSN (6) and salicyl-AVSN (7) could inhibit PqsA through covalent binding to the incoming CoA thiol nucleophile during the second half-reaction, forming a mimic of the tetrahedral intermediate. See, e.g., Qiao et al. (2007) J. Am. Chem. Soc. 129, 6350. This vinyl sulfonamide inhibitor design strategy was previously used to target the NRPS salicylate adenylation domain MbtA, which is involved in bacterial siderophore biosynthesis, and we have also successfully applied this strategy to an acyl-CoA synthetase MenE, which is involved in bacterial menaquinone biosynthesis, as well as E1 activating enzymes involved in jugation of ubiquitin and ubiquitin-like modifier proteins. Data for these and other inhibitors of PqsA can be found in Table E1.

The acyl-AMS sulfamate (1, 3, 5) and acyl-AMSN sulfamide (2, 4) inhibitors were readily synthesized by acylation of a protected sulfamoyladenosine or corresponding sulfamide, respectively, followed by global deprotection using aqueous TFA. The sulfamidoadenosine precursor was prepared conveniently by Mitsunobu substitution of the 5'-alcohol of 2',3'-acetonide-protected adenosine with mono-N-

Boc-sulfamide. The acyl-AVSN vinyl sulfonamides (6, 7) were synthesized by Mitsunobu substitution with the corresponding Boc-arylvinylsulfonamides directly, followed by deprotection. See, e.g., Sundlov et al. (2012) *Chem. Biol.* 19, 188.

Example 1. Synthesis of the Compounds

General Synthetic Procedures

Reagents were obtained from Aldrich Chemical or Acros Organics and used without further purification. Optima or HPLC grade solvents were obtained from Fisher Scientific, degassed with Ar, and purified on a solvent drying system. Reactions were performed in flame-dried glassware under positive Ar pressure with magnetic stirring.

TLC was performed on 0.25 mm E. Merck silica gel 60 F254 plates and visualized under UV light (254 nm) or by staining with potassium permanganate (KMnO4), cerium ammonium molybdenate (CAM), or iodine ($I_2$). Silica flash chromatography was performed on E. Merck 230-400 mesh silica gel 60. Samples were lyophilized using a Labconco Freezone 2.5 instrument.

NMR spectra were recorded on a Bruker Avance III 500 instrument or Bruker Avance III 600 instrument at 24° C. in $CDCl_3$ unless otherwise indicated. Spectra were processed using Bruker TopSpin or nucleomatica iNMR software, and chemical shifts are expressed in ppm relative to TMS ($^1$H, 0 ppm) or residual solvent signals: $CDCl_3$ ($^1$H, 7.24 ppm; $^{13}$C, 77.23 ppm), $CD_3OD$ ($^1$H, 3.31 ppm; $^{13}$C, 49.15 ppm), $D_2O$ ($^1$H, 4.80 ppm); coupling constants are expressed in Hz. Mass spectra were obtained at the MSKCC Analytical Core Facility on a ity SQD LC-MS by electrospray (ESI) ionization or atmospheric pressure chemical ionization (AP-CI).

General Procedure for Ion-Exchange

A solution of the acylsulfamate/sulfamide in a form of protonated or triethylammonium salt was dissolved in minimum amount of $H_2O$. The solution was added to a short column of Dowex 50WX8-100-Na$^+$ and incubated for 10 minutes before eluting with $H_2O$. The fractions containing the product were combined and lyophilized to afford the sodium salt as white solid. The Dowex cation exchange resin was converted to the sodium form by sequentially washing the column with MeOH, 1 N aqueous NaOH, and $H_2O$ until the column washes reached neutral pH.

Experimental Procedures

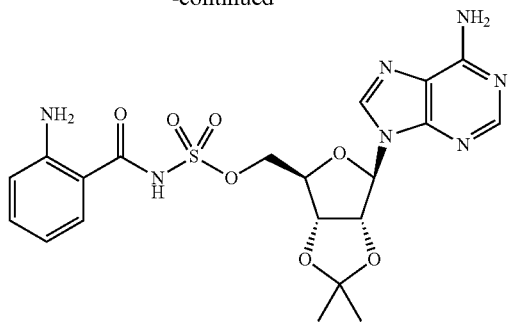

5'-O—[N-(2-Aminobenzoyl)sulfamoyl]-2',3'-O-isopropylideneadenosine

To a solution of isatoic anhydride (359 mg, 2.2 mmol, 1.1 equiv.) in DMF (6.0 mL) at room temperature was added isopropylidene sulfamoyl adenosine (Castro-Pichel, J.; Garcia-Lopez, M. T.; De las Heras, F. G. *Tetrahedron* 1987, 43, 383) (773 mg, 2.0 mmol, 1.0 equiv.) and $Cs_2CO_3$ (1.3 g, 4.0 mmol, 2.0 equiv.). The reaction was stirred 12 hours at room temperature and then concentrated under reduced pressure. Purification by flash chromatography (10-20% MeOH in EtOAc with 1% $Et_3N$) afforded the title compound (879 mg, 87%) as a white solid ($Et_3N$ salt). $^1$H NMR (600 MHz, $CD_3OD$) δ 8.49 (s, 1H), 8.16 (s, 1H), 7.90 (dd, J=8.0, 1.7 Hz, 1H), 7.09-7.12 (m, 1H), 6.66 (dd, J=8.2, 1.1 Hz, 1H), 6.52-6.55 (m, 1H), 6.23 (d, J=3.2 Hz, 1H), 5.39 (dd, J=6.0, 3.2 Hz, 1H), 5.15 (dd, J=6.0, 2.2 Hz, 1H), 4.56 (d, J=2.2 Hz, 1H), 4.20-4.38 (m, 2H), 3.14 (q, J=7.3 Hz, 4H), 1.59 (s, 3H), 1.34 (s, 3H), 1.24 (t, J=7.3 Hz, 6H) ppm. $^{13}$C NMR (151 MHz, $CD_3OD$): δ 176.92, 157.26, 153.94, 151.28, 150.43, 141.48, 133.13, 132.58, 120.10, 119.93, 117.94, 116.75, 115.21, 91.91, 85.69, 83.42, 69.61, 47.80, 27.46, 25.46, 9.19 ESI-MS m/z=506.08 [M+H]$^+$. HRMS (ESI) m/z: calcd. for $C_{20}H_{24}N_7O_7S$ [M+H]+ 506.1458, found 506.1470.

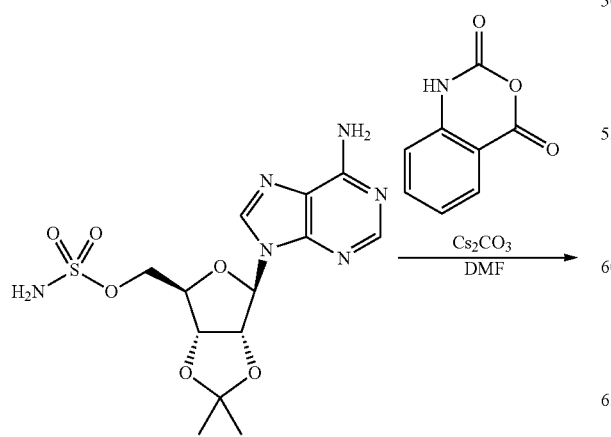

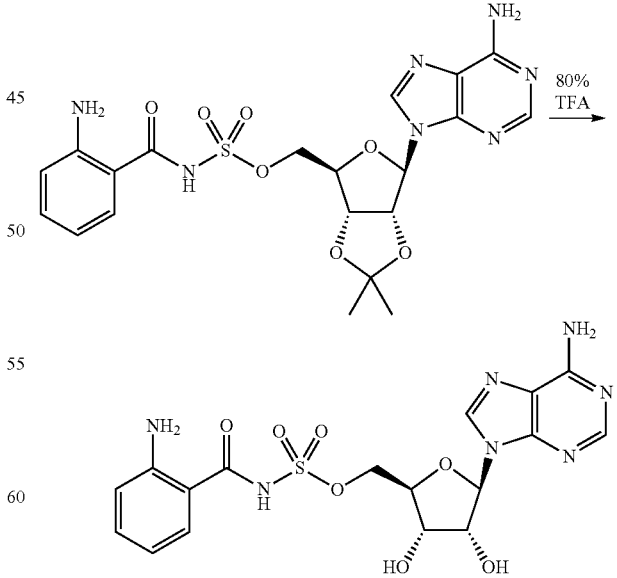

Anthranilyl-AMS

To the above isopropylidene protected compound (750 mg, 1.48 mmol) was added 80% aqueous TFA (10 mL).

After 2 hours, the reaction mixture was concentrated under reduced pressure. Purification by flash chromatography (10-20% MeOH in EtOAc with 1% Et$_3$N) afforded the title compound as an Et$_3$N salt (580 mg, 84%). The Et$_3$N salt was converted to sodium salt using the general procedure for ion-exchange to afford the title product as a white solid (500 mg, 100%). $^1$H NMR (500 MHz, CD$_3$OD) δ8.57 (s, 1H), 8.18 (s, 1H), 7.92 (dd, J=8.0, 1.6 Hz, 1H), 7.11 (ddt, J=8.5, 7.1, 1.2 Hz, 2H), 6.67 (dd, J=8.1, 1.1 Hz, 1H), 6.55 (ddd, J=8.1, 7.0, 1.1 Hz, 1H), 6.10 (d, J=6.0 Hz, 1H), 4.73 (t, J=5.5 Hz, 1H), 4.43 (dd, J=5.1, 3.0 Hz, 1H), 4.29-4.41 (m, 3H) ppm. $^{13}$C NMR (151 MHz, D$_2$O): 175.98, 155.36, 152.55, 148.81, 147.73, 132.52, 130.45, 119.39, 118.55, 117.46, 117.41, 86.96, 82.40, 73.44, 70.11, 68.48; ESI-MS m/z=465.96 [M+H]$^+$. HRMS (ESI) m/z: calcd. for C$_{17}$H$_{18}$N$_7$O$_7$S [M−H]− 464.0988, found 464.1006.

Procedures for Scheme E2

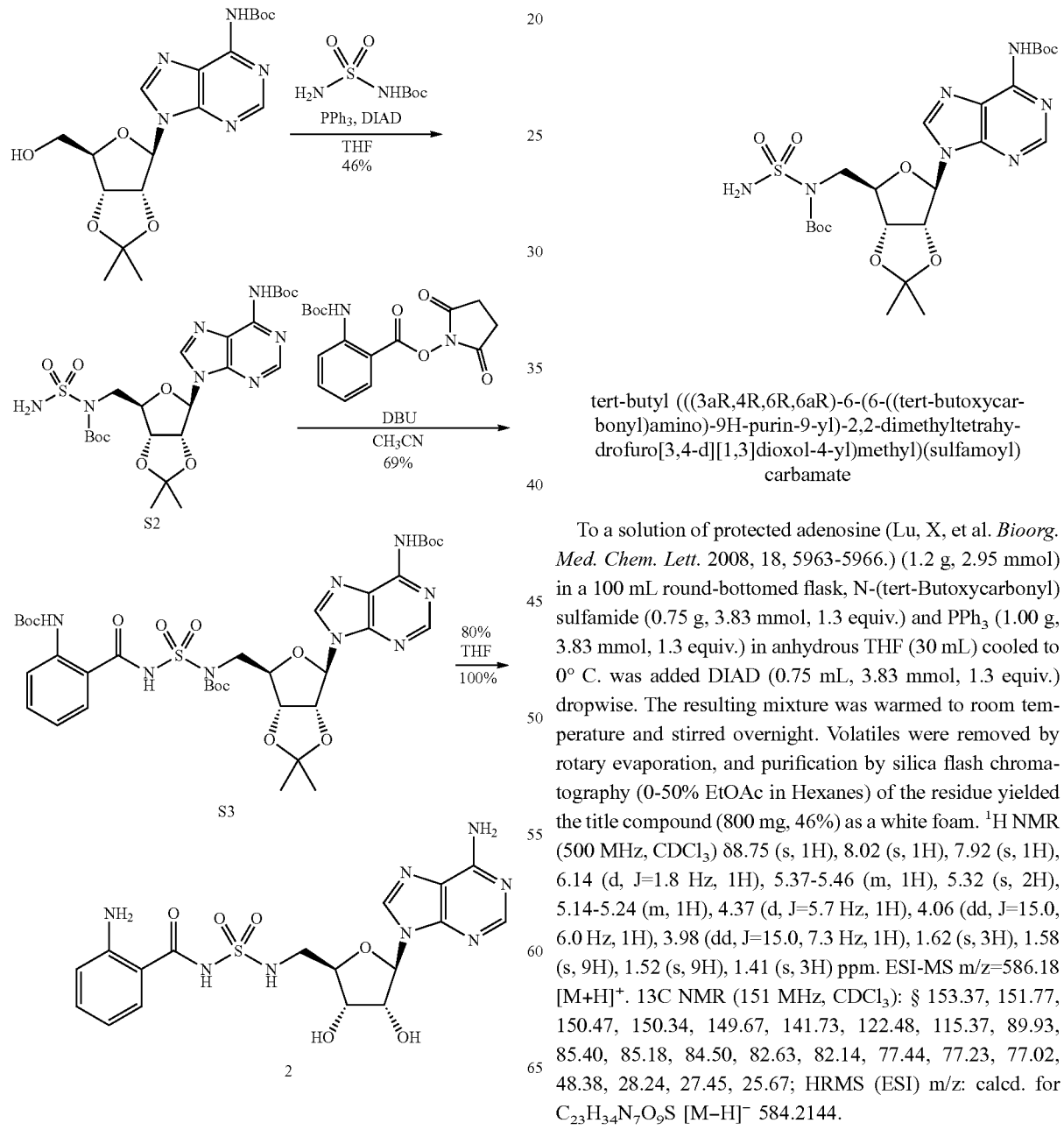

Scheme E1. Synthesis of anthranilyl-AMSN (2)

tert-butyl (((3aR,4R,6R,6aR)-6-(6-((tert-butoxycarbonyl)amino)-9H-purin-9-yl)-2,2-dimethyltetrahydrofuro[3,4-d][1,3]dioxol-4-yl)methyl)(sulfamoyl) carbamate To a solution of protected adenosine (Lu, X, et al. *Bioorg. Med. Chem. Lett.* 2008, 18, 5963-5966.) (1.2 g, 2.95 mmol) in a 100 mL round-bottomed flask, N-(tert-Butoxycarbonyl)sulfamide (0.75 g, 3.83 mmol, 1.3 equiv.) and PPh$_3$ (1.00 g, 3.83 mmol, 1.3 equiv.) in anhydrous THF (30 mL) cooled to 0° C. was added DIAD (0.75 mL, 3.83 mmol, 1.3 equiv.) dropwise. The resulting mixture was warmed to room temperature and stirred overnight. Volatiles were removed by rotary evaporation, and purification by silica flash chromatography (0-50% EtOAc in Hexanes) of the residue yielded the title compound (800 mg, 46%) as a white foam. $^1$H NMR (500 MHz, CDCl$_3$) δ8.75 (s, 1H), 8.02 (s, 1H), 7.92 (s, 1H), 6.14 (d, J=1.8 Hz, 1H), 5.37-5.46 (m, 1H), 5.32 (s, 2H), 5.14-5.24 (m, 1H), 4.37 (d, J=5.7 Hz, 1H), 4.06 (dd, J=15.0, 6.0 Hz, 1H), 3.98 (dd, J=15.0, 7.3 Hz, 1H), 1.62 (s, 3H), 1.58 (s, 9H), 1.52 (s, 9H), 1.41 (s, 3H) ppm. ESI-MS m/z=586.18 [M+H]$^+$. 13C NMR (151 MHz, CDCl$_3$): § 153.37, 151.77, 150.47, 150.34, 149.67, 141.73, 122.48, 115.37, 89.93, 85.40, 85.18, 84.50, 82.63, 82.14, 77.44, 77.23, 77.02, 48.38, 28.24, 27.45, 25.67; HRMS (ESI) m/z: calcd. for C$_{23}$H$_{34}$N$_7$O$_9$S [M−H]− 584.2144.

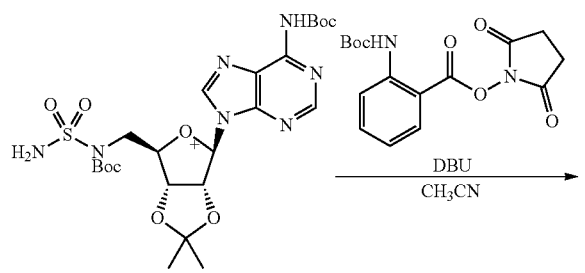
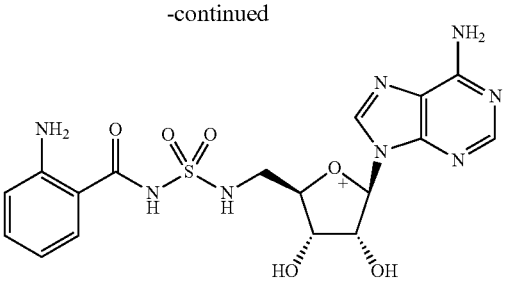

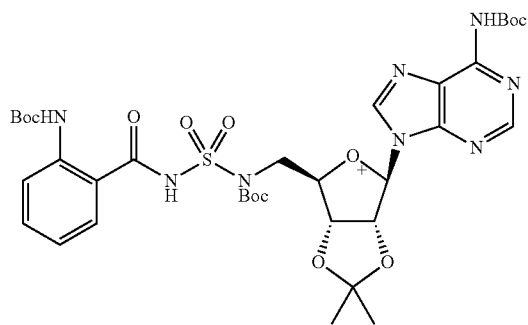

Protected Anthranilyl-AMSN

To a solution of the protected AMSN (800 mg, 1.37 mmol, 1 equiv.) and the NHS ester (Tanaka F., et al. *J. Am. Chem. Soc.*, 1996, 118, 2332-2339) (502 mg, 1.50 mmol, 1.1 equiv.) dissolved in 20 mL of $CH_3CN$ in a 50-mL round bottomed flask was added DBU (420 mg, 2.74 mmol, 2.0 equiv.) dropwise. The mixture was stirred at room temperature for 3 and EtOAc (20 mL). The aqueous layer was extracted with EtOAc (3×20 mL), dried ($Na_2SO_4$), and concentrated by rotary evaporation. Purification by silica flash chromatography (50-100% EtOAc in Hexanes) yielded the title compound (760 mg, 69%) as a white solid. $^1$H NMR (500 MHz, $CD_3OD$) δ 8.61 (s, 1H), 8.40 (s, 1H), 8.13 (dd, J=8.4, 1.1 Hz, 1H), 8.06 (dd, J=8.0, 1.7 Hz, 1H), 7.34 (ddd, J=8.6, 7.1, 1.7 Hz, 1H), 6.90 (ddd, J=8.3, 7.2, 1.2 Hz, 1H), 6.20 (d, J=2.3 Hz, 1H), 5.49 (dd, J=6.3, 2.3 Hz, 1H), 5.29 (dd, J=6.3, 3.5 Hz, 1H), 4.56 (td, J=6.5, 3.5 Hz, 1H), 4.18 (dd, J=14.9, 6.8 Hz, 1H), 3.92 (dd, J=14.9, 6.2 Hz, 1H), 1.58 (s, 9H), 1.55 (s, 3H), 1.38 (s, 9H), 1.37 (s, 9H), 1.33 (s, 3H) ppm. $^{13}$C NMR (126 MHz, $CD_3OD$): δ 155.25, 154.61, 153.37, 152.43, 152.04, 151.45, 144.34, 141.67, 133.19, 132.68, 124.09, 123.55, 122.10, 119.73, 115.50, 91.62, 87.16, 85.78, 85.40, 83.94, 82.89, 80.98, 28.66, 28.47, 28.36, 27.54, 25.58. HRMS (ESI) m/z: calcd. for $C_{35}H_{47}N_8O_{12}S$ [M−H]$^−$ 803.3034, found 803.3000.

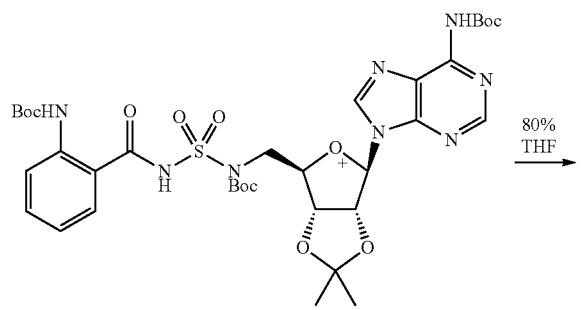

Anthranilyl-AMSN

To the above global protected compound (700 mg, 0.87 mmol) in a 25-mL round bottomed flask was added 80% aqueous TFA (5 mL). After 2 hours, the reaction mixture was diluted with water (20 mL) and extracted with ether (5×25 mL). The aqueous layer was lyophilized to give the title compound as a white solid (400 mg, quantitative). $^1$H NMR (500 MHz, $CD_3OD$) δ 8.51 (s, 1H), 8.39 (s, 1H), 7.51 (dd, J=8.2, 1.5 Hz, 1H), 7.15-7.32 (m, 1H), 6.74 (d, J=8.4 Hz, 1H), 6.51-6.66 (m, 1H), 5.95 (d, J=6.8 Hz, 1H), 4.80-4.83 (m, 1H), 4.34 (dd, J=5.4, 2.6 Hz, 1H), 4.27-4.32 (m, 1H), 3.42-3.51 (m, 1H), 3.35 (d, J=3.2 Hz, 1H) ppm. ESI-MS m/z=465.08 [M+H]. $^{13}$C NMR (151 MHz, $CD_3OD$): δ 169.88, 153.01, 151.97, 149.47, 147.39, 144.68, 135.03, 129.99, 121.39, 118.29, 116.95, 113.24, 91.79, 85.98, 74.96, 73.03, 46.24; HRMS (ESI) m/z: calcd. for $C_{17}H_{21}N_8O_6S$ [M+H]$^+$ 465.1305, found 465.1300.

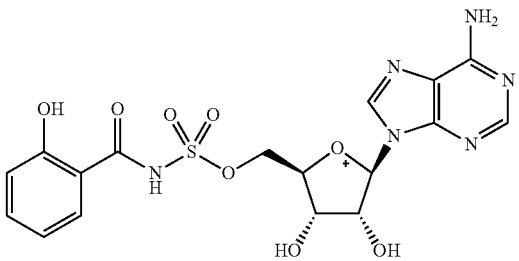 [SMILES: Nc1ncnc2c1ncn2[C@@H]1[OH+][C@H](COS(=O)(=O)NC(=O)c2ccccc2O)[C@@H](O)[C@H]1O]

Salicyl-AMS

This compound was prepared as previously described (Ferreras, J. A.; Ryu, J. S.; Di Lello, F.; Tan, D. S.; Quadri, L. E. *Nat. Chem. Biol.* 2005, 1, 29) and converted to a sodium salt using the general procedure for ion exchange. $^1$H NMR (600 MHz, $D_2O$) δ 8.18 (s, 1H), 8.06 (s, 1H), 7.55 (dd, J=7.9, 1.7 Hz, 1H), 7.27 (ddd, J=8.3, 7.2, 1.8 Hz, 1H), 6.71 (ddd, J=8.2, 7.2, 1.1 Hz, 1H), 6.64 (dd, J=8.3, 1.2 Hz, 1H), 5.91 (d, J=5.2 Hz, 1H), 4.76 (t, J=5.4 Hz, 1H), 4.45-4.51 (m, 3H), 4.35 (td, J=4.5, 2.9 Hz, 1H) ppm. ESI-MS m/z=466.97 [M+H]$^+$. 13C NMR (151 MHz, $D_2O$): δ 174.47, 158.57, 155.24, 152.40, 148.63, 139.75, 134.07, 129.38 119.13, 118.56, 117.88, 116.39, 87.33, 82.15, 73.16, 70.01, 69.32; HRMS (ESI) m/z: calcd. for $C_{17}H_{17}N_6O_8S$ [M−H]$^−$ 465.0829, found 465.0812.

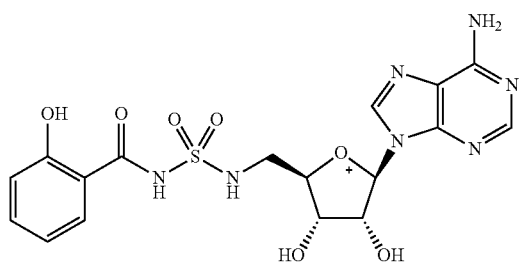 [SMILES: Nc1ncnc2c1ncn2[C@@H]1[OH+][C@H](CNS(=O)(=O)NC(=O)c2ccccc2O)[C@@H](O)[C@H]1O]

Salicyl-AMSN

This compound was prepared as previously described (Somu, R. V., et al., *J. Med. Chem.* 2006, 49, 31) and converted to a sodium salt using the general procedure for ion exchange. $^1$H NMR (500 MHz, D$_2$O) δ8.22 (s, 1H), 8.19 (s, 1H), 7.63-7.74 (m, 1H), 7.35 (t, J=7.8 Hz, 1H), 6.84 (t, J=7.6 Hz, 1H), 6.78 (d, J=8.3 Hz, 1H), 5.91 (d, J=6.1 Hz, 1H), 4.84 (t, J=5.8 Hz, 1H), 4.36-4.46 (m, 1H), 4.30 (q, J=4.4 Hz, 1H), 3.35-3.50 (m, 2H) ppm. ESI-MS m/z=465.92 [M+H]$^+$. $^{13}$C NMR (151 MHz, D2O): δ 173.98, 158.55, 155.41, 152.53, 148.46, 140.60, 133.79, 129.18, 119.18, 118.41, 116.47, 87.96, 83.39, 72.92, 71.15, 45.14. HRMS (ESI) m/z: calcd. for C17H20N7O7S [M+H]+ 466.1145, found 466.1130.

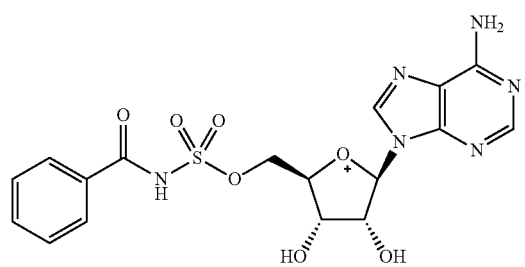 [SMILES: Nc1ncnc2c1ncn2[C@@H]1[OH+][C@H](COS(=O)(=O)NC(=O)c2ccccc2)[C@@H](O)[C@H]1O]

Benzoyl-AMS

This compound was prepared as previously described (Qiao, C., et al., *J. Med. Chem.* 2007, 50, 6080) and converted to a sodium salt using the general procedure for ion exchange. $^1$H NMR (600 MHz, CD$_3$OD) δ8.56 (s, 1H), 8.16 (s, 1H), 8.04 (t, J=1.2 Hz, 1H), 8.02 (d, J=1.5 Hz, 1H), 7.41-7.45 (m, 1H), 7.32-7.37 (m, 2H), 6.10 (d, J=5.9 Hz, 1H), 4.73 (dd, J=5.9, 5.0 Hz, 1H), 4.44 (dd, J=5.0, 3.2 Hz, 1H), 4.41 (dd, J=11.2, 3.3 Hz, 1H), 4.37 (dd, J=11.1, 3.1 Hz, 1H), 4.33 (q, J=3.2 Hz, 1H) ppm. ESI-MS m/z=451.09 [M+H]$^+$. $^{13}$C NMR (151 MHz, CD3OD): δ 175.35, 157.22, 153.82, 150.81, 141.16, 138.90, 132.08, 129.88, 128.79, 120.11, 89.16, 84.72, 76.14, 72.43, 69.25; HRMS (ESI) m/z: calcd. for C$_{17}$H$_{17}$N$_6$O$_7$S [M–H]$^-$ 449.0879, found 449.0859.

Scheme E2. Synthesis of anthranilyl-AVSN (6)

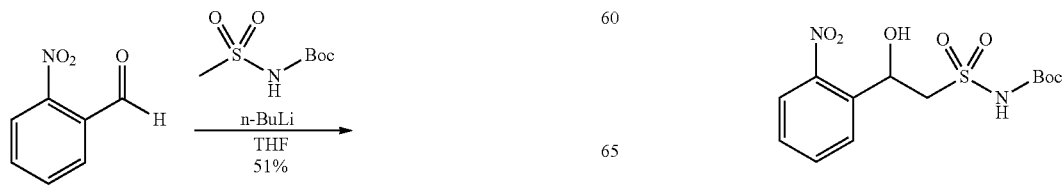

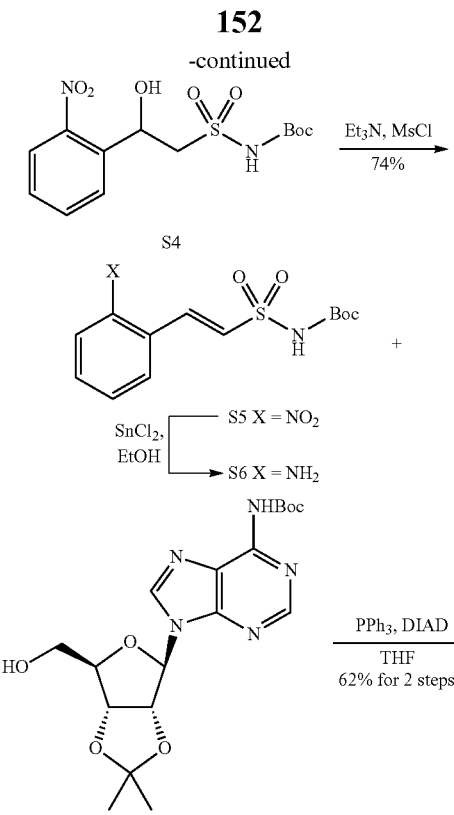

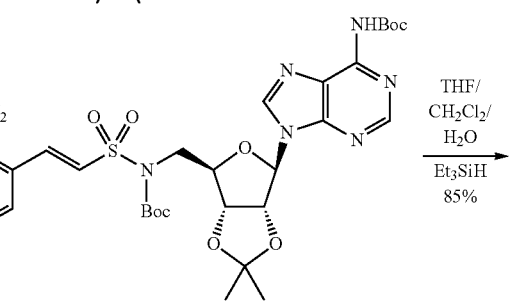

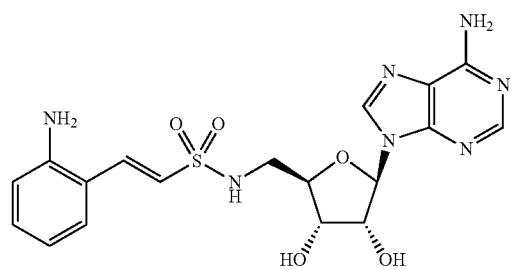

Procedures for Scheme E2 tert-Butyl ((2-hydroxy-2-(2-nitrophenyl)ethyl)sulfonyl)carbamate (S4)

In a 100-mL roundbottom flask, tert-butyl (methylsulfonyl)carbamate 1 (600 mg, 3.07 mmol, 1.0 equiv) was dissolved in 15 mL of THF and the solution was cooled to −78° C. n-BuLi (3.84 mL, 6.14 mmol, 2.0 equiv, 1.6 M in hexanes) was added dropwise. The resulting solution was allowed to warm to 0° C. over 1 h, then cooled again to −78° C. A precooled (−78° C.) solution of 2-nitrobenzaldehyde (464 mg, 3.07 mmol, 1.0 equiv) in 6 mL of THF was added dropwise and the reaction mixture was allowed to warm to −40° C. over 1 h. The reaction mixture was quenched with 1 N HCl and the aqueous layer was separated and extracted with EtOAc (2×100 mL). The combined organic extracts were washed with brine, dried (Na2SO4), filtered, and concentrated by rotary evaporation. Purification by silica flash chromatography (0-50% EtOAc in hexanes) afforded the benzylic alcohol S4 (542 mg, 51%) as a light yellow oil. TLC: Rf 0.4 (1:1 hexanes/EtOAc); $^1$H NMR (600 MHz): δ 8.04 (d, J=7.8 Hz, 1H), 7.98 (d, J=7.8 Hz, 1H), 7.73 (t, J=7.4 Hz, 1H), 7.51 (t, J=7.4 Hz, 1H), 5.85 (d, J=9.5 Hz, 1H), 4.11 (dd, J=9.6, 14.8 Hz, 1H), 3.54 (dd, J=9.6, 14.8 Hz, 1H), 1.52 (s, 9H); $^{13}$C NMR (151 MHz): δ 149.6, 146.8, 138.6, 136.0, 134.4, 129.6, 128.4, 124.5, 85.0, 65.0, 59.8, 41.2, 28.2; ESI-MS m/z calcd. for $C_{13}H_{18}N_2O_7SNa$ [M+Na]+ 369.1, found 369.1.

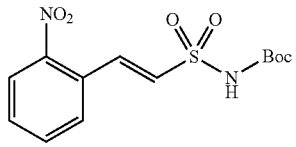 [SMILES: CC(C)(C)OC(=O)NS(=O)(=O)/C=C/c1ccccc1[N+](=O)[O-]]

tert-Butyl (E)-((2-nitrostyryl)sulfonyl)carbamate (S5)

In a 50-mL roundbottom flask, benzyl alcohol S4 (500 mg, 1.45 mmol, 1.0 equiv) was dissolved in 14.5 mL of $CH_2Cl_2$ and the solution was cooled to 0° C. Triethylamine (0.6 mL, 4.35 mmol, 3.0 equiv) was added followed by methanesulfonyl chloride (0.168 mL, 2.18 mmol, 1.5 equiv). The resulting solution was stirred at 0° C. for 2 h, then heated to reflux for 6 h. The mixture was quenched with saturated sodium bicarbonate solution and the aqueous layer was separated and extracted with $CH_2Cl_2$ (2×50 mL). The combined organic extracts were washed with brine, dried ($Na_2SO_4$), filtered, and concentrated by rotary evaporation. Purification by silica flash chromatography (0-40% EtOAc in hexanes) afforded 2-nitrophenylvinyl sulfonamide S5 (351 mg, 74%) as a light yellow oil. TLC: $R_f$ 0.42 (2:1 hexanes/EtOAc); $^1$H NMR (600 MHz): δ 8.18 (d, J=15.4 Hz, 1H), 8.14 (d, J=8.2 Hz, 1H), 7.72 (t, J=7.5 Hz, 1H), 7.65-7.62 (m, 2H), 7.36 (s, 1H), 7.05 (d, J=15.4 Hz, 1H), 1.52 (s, 9H); $^{13}$C-NMR (151 MHz): δ 149.3, 148.0, 139.7, 134.0, 131.3, 129.6, 129.0, 128.5, 125.3, 84.7, 31.6, 28.0; ESI-MS m/z calcd. for $C_{13}H_{16}N_2O_6SNa$ [M+Na]$^+$ 351.1, found 351.2.

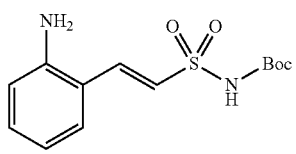 [SMILES: CC(C)(C)OC(=O)NS(=O)(=O)/C=C/c1ccccc1N]

tert-Butyl (E)-((2-aminostyryl)sulfonyl)carbamate (S6)

In a 5-mL conical vial, 2-nitrophenylvinyl sulfonamide S5 (300 mg, 0.92 mmol, 1.0 equiv) and $SnCl_2.2H2O$ (1.04 g, 4.6 mmol, 5.0 equiv) were dissolved in 2 mL of EtOH and heated at 40° C. for 1 h. The solution was allowed to cool to room temperature, poured onto ice (10 g), and basified with 5% aqueous sodium bicarbonate. The resulting mixture was extracted with EtOAc (3×50 mL), dried ($Na_2SO_4$), and concentrated by rotary evaporation. The crude 2-aminophenylvinyl sulfonamide S6 was used for the next step without purification.

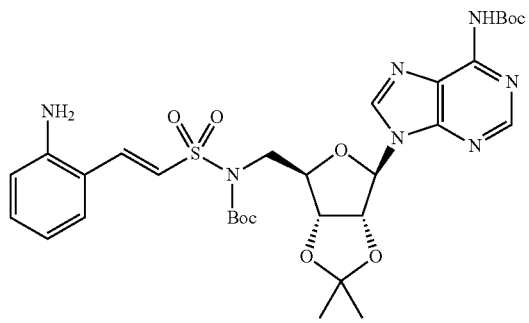 [SMILES: CC(C)(C)OC(=O)Nc1ncnc2c1ncn2[C@@H]1O[C@H](CN(C(=O)OC(C)(C)C)S(=O)(=O)/C=C/c2ccccc2N)[C@H]2OC(C)(C)O[C@H]21]

Protected Anthranilyl-AVSN (S7)

To solution of the crude vinyl sulfonamide S6 (0.92 mmol, 1.0 equiv), N-Boc-2',3'-O-isopropylideneadenosine, prepared as previously described 4 (1.2 g, 2.95 mmol (374 mg, 0.92 mmol, 1.0 equiv) and $PPh_3$ (362 mg, 1.38 mmol, 1.5 equiv) in 3.0 mL of THF at 0° C. was added a solution of DIAD (0.27 mL, 1.38 mmol, 1.5 equiv). The solution was gradually warmed to room temperature and stirred for 16 h. The mixture was then concentrated and purified by flash chromatography (20-100% EtOAc/hexanes) to afford the title compound (392 mg, 62%) as a foam. TLC: Rf 0.2 (2:8 hexanes/EtOAc); $^1$H NMR (500 MHz): δ 8.77 (s, 1H), 8.05 (s, 1H), 7.91 (s, 1H), 7.52 (d, J=15.0 Hz, 1H), 7.22-7.19 (m, 2H), 6.86 (d, J=15.0 Hz, 1H), 6.76 (t, J=7.5 Hz, 1H), 6.70 (d, J=8.0 Hz, 1H), 6.15 (s, 1H), 5.51 (dd, J=6.0, 1.5 Hz, 1H), 5.17 (dd, J=6.5, 3.5 Hz, 1H), 4.52 (s, 1H), 4.01-3.97 (m, 4H), 1.60 (s, 3H), 1.56 (s, 9H), 1.47 (s, 9H), 1.37 (s, 3H); $^{13}$C NMR (151 MHz): δ 153.1, 150.9, 150.4, 150.0, 149.5, 146.0, 141.9, 139.5, 132.2, 128.5, 124.3, 122.3, 119.0, 117.6, 117.0, 114.6, 90.5, 85.7, 84.8, 84.3, 82.5, 82.3, 47.5, 28.1, 28.0, 27.9, 27.1, 25.3; ESI-MS m/z calcd. for $C_{31}H_{41}N_7O_9SNa$ [M+Na]$^+$ 710.3, found 710.3.

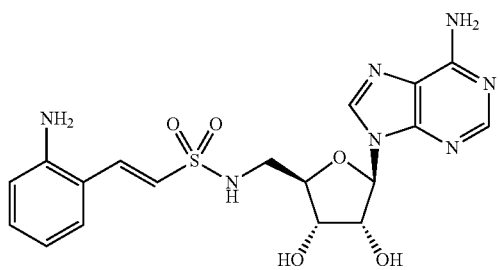 [SMILES: Nc1ccccc1/C=C/S(=O)(=O)NC[C@H]1O[C@@H](n2cnc3c(N)ncnc32)[C@H](O)[C@@H]1O]

Anthranilyl-AVSN (6)

In a 10-mL roundbottom flask, 2-aminophenylvinyl sulfonamide S7 (70 mg, 0.1 mmol) was dissolved in CH2Cl2 (1 mL). 80% Aqueous TFA (1 mL) was added and the solution was stirred at 0° C. for 1 h, then at room temperature for 4 h. The resulting solution was azeotroped with toluene (2×10 mL) and concentrated by rotary evaporation. Purification by silica flash chromatography (10:1 EtOAc/MeOH) afforded anthranilyl-AVSN 6 (39 mg, 85%) as a waxy solid. TLC: Rf 0.20 (9:1 EtOAc/MeOH); $^1$H NMR (500 MHz, CD3OD): 7 exchangable proton δ 8.29 (s, 2H), 7.65 (d, J=15.0 Hz, 1H), 7.34 (d, J=8.0 Hz, 1H), 7.15 (t, J=8.0 Hz, 1H), 6.84-6.78 (m, 2H), 6.68 (t, J=7.5 Hz, 1H), 5.96 (d, J=6.5 Hz, 1H), 4.39 (dd, J=5.0, 3.0 Hz, 1H), 4.28 (d, J=3.0 Hz, 1H), 3.43-3.37 (m, 3H). $^{13}$C NMR (151 MHz): δ 156.6, 152.3, 150.0, 148.4, 142.7, 138.3, 132.7, 128.8, 125.0, 121.1, 119.4, 119.0, 118.3, 91.3, 85.9, 74.6, 72.9, 45.6; ESI-MS m/z calcd. for $C_{18}H_{21}N_7O_5SNa$ $[M+Na]^+$ 470.1, found 470.2.

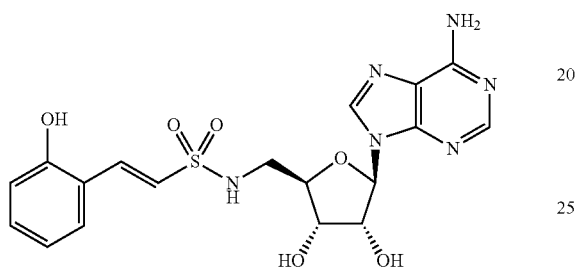

Salicyl-AVSN (7)

This compound was prepared as previously described, e.g., in Sundlov, J. A.; Shi, C.; Wilson, D. J.; Aldrich, C. C.; Gulick, A. M. *Chem. Biol.* 2012, 19, 188-198.

Scheme E3. Synthesis of HHQ-d$_4$ and PQS-d$_4$ standards for LC-MS analysis

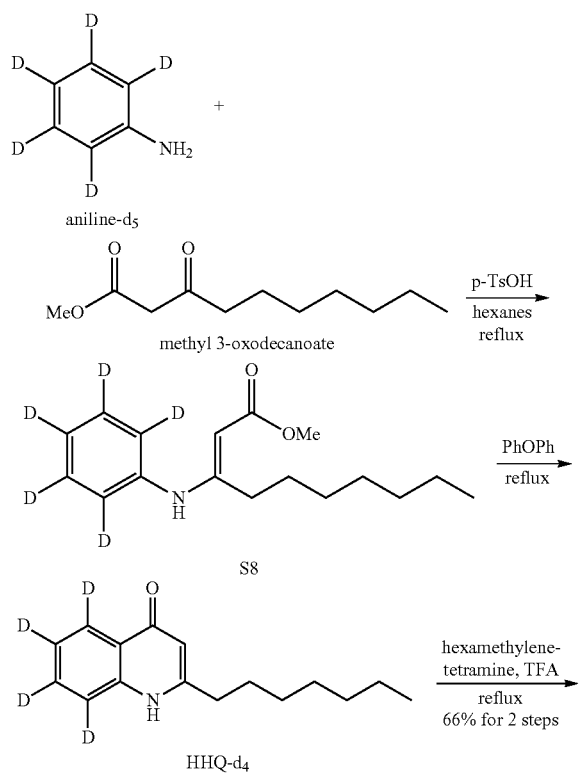

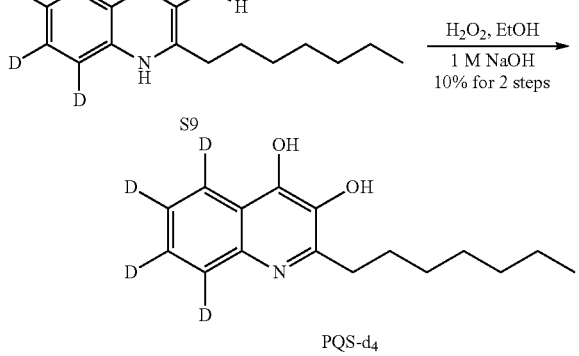

Procedures for Scheme E3

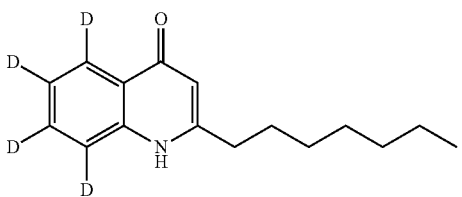 [SMILES: [2H]c1c([2H])c([2H])c2c(=O)cc(CCCCCCC)[nH]c2c1[2H]]

2-Heptylquinolin-4(1H)-one-5,6,7,8-d$_4$ (HHQ-d$_4$)

In a 100-mL roundbottom flask, aniline-d$_5$ (1.0 g, 10.2 mmol, 1.0 equiv) and methyl 3-oxodecanoate (2.5 g, 12.50 mmol, 1.2 equiv) were dissolved in dry hexanes (35 mL). p-Toluenesulfonic acid (100 mg) was added and the mixture heated to reflux for 12 h under a Dean-Stark trap to remove water. The mixture was allowed to cool to room temperature then concentrated by rotary evaporation. The crude enamine S8 was used without further purification.

In a 25-mL roundbottom flask equipped with a distillation head and collecting flask, diphenyl ether (8 mL) was heated to reflux (280° C.). The crude enamine S8 was added dropwise over 10 min, then the mixture was stirred at reflux (280° C.) for an additional 30 min as the methanol byproduct was removed by distillation. The mixture was then cooled to room temperature, whereupon it solidified. Purification by silica flash chromatography (1:1 EtOAc/hexanes→EtOAc→1:19 MeOH/EtOAc) afforded HHQ-d$_4$ (1.4 g, 68% over 2 steps) as a white solid. TLC: R$_f$ 0.4 (19:1 EtOAc/CH$_3$OH). $^1$H-NMR (600 MHz, CD$_3$OD): 1 exchangable proton δ 6.22 (s, 1H), 2.71 (t, J=7.8 Hz, 2H), 1.75 (q, J=7.6 Hz, 2H), 1.45-1.25 (m, 8H), 0.89 (t, J=6.8 Hz, 3H). $^{13}$C-NMR (151 MHz) δ 180.65, 157.17, 141.55, 125.41, 108.81, 35.02, 32.89, 30.22, 30.20, 30.19, 30.15, 30.13, 23.69, 14.41. ESI-MS for $C_{16}H_{17}D_4NO$ m/z (rel int): (pos) 270.2 ($[M+Na]^+$, 100).

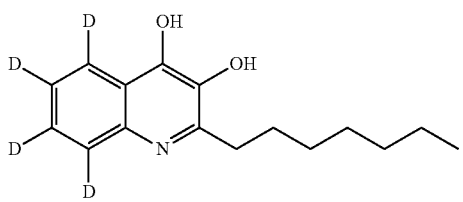 [SMILES: [2H]c1c([2H])c([2H])c2c(O)c(O)c(CCCCCCC)nc2c1[2H]]

2-Heptylquinoline-5,6,7,8-d4-3,4-diol (PQS-d4)

In a 50-mL roundbottom flask, HHQ-d4 (1.14 g, 4.6 mmol, 1.0 equiv), hexamethylenetetramine (323 mg, 2.3 mmol, 0.5 equiv) were dissolved in trifluoroacetic acid (7.0 ml) and heated to reflux for 27 h. Methanol (11 ml) and water (11 ml) were added, and heating was continued for 50 min. Hydrochloric acid (2.5 M, 5 ml) was added, and heating was continued for 30 min. The mixture was allowed to cool to room temperature, then the precipitate was removed by filtration and washed with water to provide the crude aldehyde S9 (1.0 g), which was used without further purification.

In a 25-mL roundbottom flask, aldehyde S9 was dissolved in ethanol (3 mL). Aqueous 30% hydrogen peroxide (0.453 g, 3.99 mmol) was added followed by aqueous sodium hydroxide (1.08 M, 0.75 ml). The mixture was stirred at room temperature for 6 h, then diluted with water and filtered. The resulting solid was washed with water. Purification by silica flash chromatography (1:1 EtOAc/hexanes to EtOAc) afforded PQS-d4 (121 mg, 10% over 2 steps) as a white solid. TLC: Rf 0.2 (EtOAc only). 1H-NMR (600 MHz, CD3OD): 2 exchangable protons δ 2.91 (t, J=7.8 Hz, 2H), 1.80 (p, J=7.6 Hz, 2H), 1.51-1.30 (m, 8H), 0.92 (t, J=6.7 Hz, 3H). 13C-NMR (151 MHz) δ 139.61, 139.60, 138.67, 123.56, 32.92, 30.44, 30.17, 29.82, 29.37, 23.70, 14.42. ESI-MS for C16H17D4NO2 m/z (rel int): (pos) 286.2 ([M+Na]+, 100).

Example 2. Biological Assays

Microorganisms

*Pseudomonas aeruginosa* strains PA14 (from Laurence G. Rahme, Department of Microbiology and Molecular Genetics, Harvard Medical School, Boston, Mass., United States of America) was employed.

then vertexed and centrifuged at 13,000 g for 5 minutes, and the supernatant was transferred to a 96-well plates for LC-MS/MS analysis. Bacterial growth was measured by recording OD600 at 20 h to provide the data in FIG. 7A.

Analytical Conditions for PQS and HHQ Quantification

Liquid chromatography tandem mass spectrometry (LC-MS/MS) was carried out on an Agilent Technologies 6410 triple quad LC-MS/MS system with autosampler in electrospray ionization (ESI) mode, with an Agilent Zorbax Eclipse XDB-C18 reverse phase column (50×4.6 mm, 5 μm) using a flow rate of 0.5 mL/minute and an isocratic mobile phase of 60% $CH_3CN$ in 0.1% aqueous formic acid over 5 minutes. Positive electrospray in MRM mode was employed to quantify PQS and HHQ, using the ion transitions HHQ 244 to 159, $d^4$-HHQ 248 to 163, PQS 260 to 175, and $d^4$-PQS 264 to 179; shown in Table E3.

TABLE E3

| quinolone | ion transitions ($H_4$) | ion transitions ($d_4$) | linear range of detection (injected) | linear range of detection (culture) |
|---|---|---|---|---|
| HHQ | 244 → 159 | 248 → 163 | 0.01-10 μM | 0.1-100 μM |
| PQS | 260 → 175 | 264 → 179 | 0.01-10 μM | 0.1-100 μM |

Incubation, Sample Preparation, and LC-MS/MS Analysis

*P. aeruginosa* PA14 (OD600=0.5, 1,000 uL, LB media, 37° C., n=8 samples) were incubated with the appropriate inhibitor [anthranilyl-AMS (1), anthranilyl-AMSN (2), or 6FABA] (1000 μM, 30 min), centrifuged (15,000 rpm, 4° C., 5 min) and the supernatant removed. The pellet was washed with cold PBS (resuspend, centrifuge, decant 4×200 μL), and lysed by freeze-thaw cycles (200 μL PBS, 20 cycles). For each 200 μL sample (supernatant, 4 washes, lysate), 200 μL MeOH containing 2 μM benzoyl-AMS (5) internal standard was added (2-fold dilution of sample to 400 μL total volume with 1 μM internal standard final concentration). LC-MS/MS analysis was carried out as described in the preceding section, using an isocratic mobile phase of 30% CH3CN in 0.1% aq formic acid over 5 min. Positive electrospray in MRM mode was employed to quantify the inhibitor, using the ion transitions indicated (benzoyl-AMS 451 to 136). The on of inhibitor was calculated based on CFU determination of the culture prior to centrifugation as described in Table E4 below.

TABLE E4

| inhibitor | ion transitions (inhibitor) | linear range of detection (injected) | avg # cells | avg intracellular volume | linear range of detection (intracellular) |
|---|---|---|---|---|---|
| 1 | 466 → 136 | 0.006-100 μM | $7.913 \times 10^8$ | 0.791 μL | 3.036-50,600 μM |
| 2 | 465 → 136 | 0.006-100 μM | $1.203 \times 10^9$ | 1.203 μL | 1.992-33,200 μM |
| 6FABA | 156 → 138 | 0.049-100 μM | $2.122 \times 10^9$ | 2.122 μL | 9.212-18,800 μM |

Cultivation and Samples Preparation

The production of PQS and HHQ by strain PA14 was performed in triplicate in 14-mL round bottom falcon tubes containing 3-mL cultures in LB medium. Tubes were incubated at 37° C. in an orbital shaker at 225 rpm. Cultures were inoculated with 15-hour culture in LB in order to obtain a starting $OD_{600}$=0.05, with or without inhibitors added. For PQS and HHQ analysis, a 20 μl aliquot was taken at time points as indicated. Each sample was diluted with 180 μL of methanol containing the internal standard (100 μM of $d^4$-PQS or $d^4$-HHQ) and 2% acetic acid. The solution was Pyocyanin Quantification Production of pyocyanin by *P. aeruginosa* strain PA14 was performed in triplicate in roundbottom glass tubes containing 5-mL cultures in LB medium. Tubes tilted at ~60° angle were incubated at 37° C. in an orbital shaker at 200 rpm. Cultures were inoculated with 15-h preculture in LB in order to obtain a starting $OD_{600\ nm}$=0.05, with or without inhibitors added. At 24 h, 1 mL of each culture was thoroughly vortexed and centrifuged (12,000 g, 5 min). Next, 0.8 mL of the supernatant was removed and the $OD_{690\ nm}$ was measured. The ratio of the absorbance compound-treated or MvfR⁻ cultures and untreated controls was calculated to provide the data in FIG. 7B.

In Vivo PQS Synthesis Inhibition Assays

In vivo PQS synthesis inhibition assays were performed using reported methods, e.g., the methods reported in Coleman et al., *Journal of Bacteriology*, 2008, 190, 1247-1255. The following is an example of such an assay. *P. aeruginosa* strain PAO1 was maintained at −70° C. in 10% skim milk (Becton Dickinson). *P. aeruginosa* was grown at 37° C. with shaking in PTSB medium (Ohman et al., 1980, *J. Bacteriol.* 142:836-842), and freshly plated cells from skim milk stocks were used to begin the experiments. Cultures of *Escherichia coli* strain Rosetta 2(DE3) (EMD-Novagen) were grown at 37° C. with shaking in Luria-Bertani broth (Parsek et al., 1999, *Proc. Natl. Acad. Sci. USA*, 96:4360-4365) supplemented with 30 µg of chloramphenicol/ml and 100 µg of ampicillin/ml to maintain plasmids when appropriate. One-milliliter aliquots of a *P. aeruginosa* strain PAO1 subculture, adjusted to an $A_{660}$ of 0.05 with fresh medium, were added to tubes with and without anthranilate analogs at a final concentration of 1 mM, and the tubes were incubated for 24 hours at 37° C. with shaking (the enzymes were purchased from Sigma-Aldrich, Inc.). At 24 hours, culture optical densities were measured to ensure that no growth inhibition had occurred, and 900 al of acidified ethyl acetate was added to 300 al of cell culture. After vortexing for 1 minute and centrifugation at 16,000×g for 5 minutes, an 800-1 aliquot of the organic layer was transferred to a new tube and the solvent was evaporated to dryness. For thin-layer chromatography (TLC) analysis, the dried extract was dissolved in 50 al of 1:1 acidified ethyl acetate-acetonitrile and 5 al of each extract was resolved by TLC as described previously (Calfee et al., 2001, *Proc. Natl. Acad. Sci. USA*, 98:11633-11637). Fifty nanograms of synthetic PQS was also loaded as a standard. The resolved plates were photographed under long-wave UV light. For the comparison of PQS production in untreated strain PAO1 versus that in analog-treated strain PAO1, extracts in decreasing amounts were resolved by TLC as described above and digitized images of the resulting PQS spots were quantitated using ImageQuant software (version 3.3; Molecular Dynamics). Exemplary results are shown in Table E1 and FIG. 2B.

TABLE E1

$IC_{50}$ and % inhibition values of exemplary compounds for inhibition of *P. aeruginosa* PqsA.

| Compound | $IC_{50}$ (µM) | % inhibition at 10 µM |
|---|---|---|
| DST-Pqs1 | 0.3094 | 98.6 ± 2.3 |
| DST-Pqs2 | 0.2127 | 100 |
| DST-Pqs6 | — | — |
| DST-Pqs8 | — | 10.3 ± 5.3 |
| DST-Pqs9 | — | <1 |
| DST-Pqs10 | — | 1.1 ± 2.6 |
| DST-Pqs11 | 0.1074 | 100 |
| DST-Pqs12 | 0.5159 | 100 |
| DST-Pqs13 | 1.227 | 97.2 ± 1.2 |
| DST-Pqs14 | 0.8283 | 98.6. ± 1.3 |
| DST-Pqs15 | 1.525 | 97.3 ± 0.9 |
| DST-Pqs16 | 0.5516 | 100 |
| DST-Pqs17 | — | 1.3 ± 3.0 |
| DST-Pqs18 | — | 21.3 ± 1.9 |
| JI-C-2013-451 | 2.066 | 95.1 ± 0.2 |
| JI-C-2013-454 | 24.96 | 42.7 ± 0.2 |
| JI-C-2013-456 | 1.461 | 95.9 ± 0.4 |
| JI-C-2014-008 | 0.4443 | 99.8 ± 0.2 |
| JI-C-2014-025 | 4.995 | 91.2 ± 0.9 |
| JI-C-2013-189 | 7.218 | 77.8 ± 0.2 |
| DST-Pqs27 | 5.244 | 84.8 ± 1.5 |
| DST-Pqs28 | 44.87 | 9.5 ± 3.9 |
| DST-Pqs29 | 6.561 | 76.0 ± 1.3 |
| DST-Pqs19 | 39.22 | 32.1 ± 2.8 |
| DST-Pqs30 | — | <1 |
| DST-Pqs31 | — | <1 |
| DST-Pqs32 | — | 2.3 ± 0.9 |
| DST-Pqs33 | — | 4.6 ± 2.9 |

PqsA Inhibition Assays

PqsA inhibitors were evaluated using a quantitative spectrophotometric assay with recombinant PqsA, detecting formation of anthranilyl-CoA at 365 nm. See, e.g., Coleman et al. (2008) *J. Bacteriol.* 190, 1247. Both anthranilyl-AMS (1) and anthranilyl-AMSN ATP (2) were potent inhibitors of PqsA, with $K_i$ values of 205 and 170 nM, respectively (See FIG. 5). Further analysis of these "tight-binding inhibitors" using the Morrison equation indicated that both anthranilyl-AMS (1) and anthranilyl-AMSN (2) are competitive inhibitors with respect to ATP (Ki=16.5±2.6 nM; 10.5±2.3 nM, respectively) and uncompetitive inhibitors with respect to anthranilate and CoA. See, e.g., Morrison et al. *Biochim. Biophys. Acta, Enzymol.* 185, 269-286; Williams et al. (1979) *Methods Enzymol.* 63, 437. Interestingly, both salicyl-AMS (3) and salicyl-AMSN (4) exhibited potency similar to that of the cognate anthranilyl inhibitors, indicating that an o-phenolic moiety is tolerated by PqsA. This is generally consistent with the previous finding that salicylate, while not accepted as a substrate, does inhibit PqsA. Benzoyl-AMS (5) was a somewhat weaker inhibitor, indicating the importance of an ortho substituent on the aromatic ring. This is again consistent with previous biochemical studies indicating that benzoate, while accepted as a PqsA substrate, exhibits a much weaker $K_m$ compared to anthranilate (150 µM vs 8 µM). In contrast, the corresponding vinyl sulfonamide analogues 6 and 7 were not as effective, at least on the short time scale of this assay. This is consistent with previous studies within this structural superfamily of enzymes, in which we have shown that related vinyl sulfonamides are effective but slow-binding inhibitors of another acyl-CoA synthetase MenE when assayed in the presence of CoA, while Aldrich et al. have reported that salicyl-AVSN (7) is a weak inhibitor of the salicylate adenylation enzyme MbtA the absence of the corresponding thiol nucleophile MbtB. See, e.g., Qiao et al. (2007) *J. Am. Chem. Soc.* 129, 6350.

PqsA Spectrophotometric Assay Methods

Reactions were performed at 37° C. in a 0.5 mL volume in a Varian Cary 100 UV-visible spectrophotometer with Cary WinUV software. Reaction mixtures contained 100 mM HEPES, pH 8.0, 0.2 mM dithiothreitol, 2 mM MgCl2, ~3.3 µg PqsA protein (~60 nM final), and depending on which substrate varied, 1 mM ATP (disodium salt), 0.5 mM coenzyme A (tri-lithium salt), 0.5 mM sodium anthranilate, and inhibitor (usually as a DMSO stock solution). Reactions were blanked and preincubated with all components except anthranilate at 37° C. for 1 min, then initiated by addition of anthranilate. Formation of anthraniloyl-CoA was monitored ance at 365 nm (ε=5.5 mM−1 cm−1) for 1 min. Data were analyzed using GraphPad Prism 6 software.

Inhibition of P. aeruginosa Quinolone Production

Figure 2A:
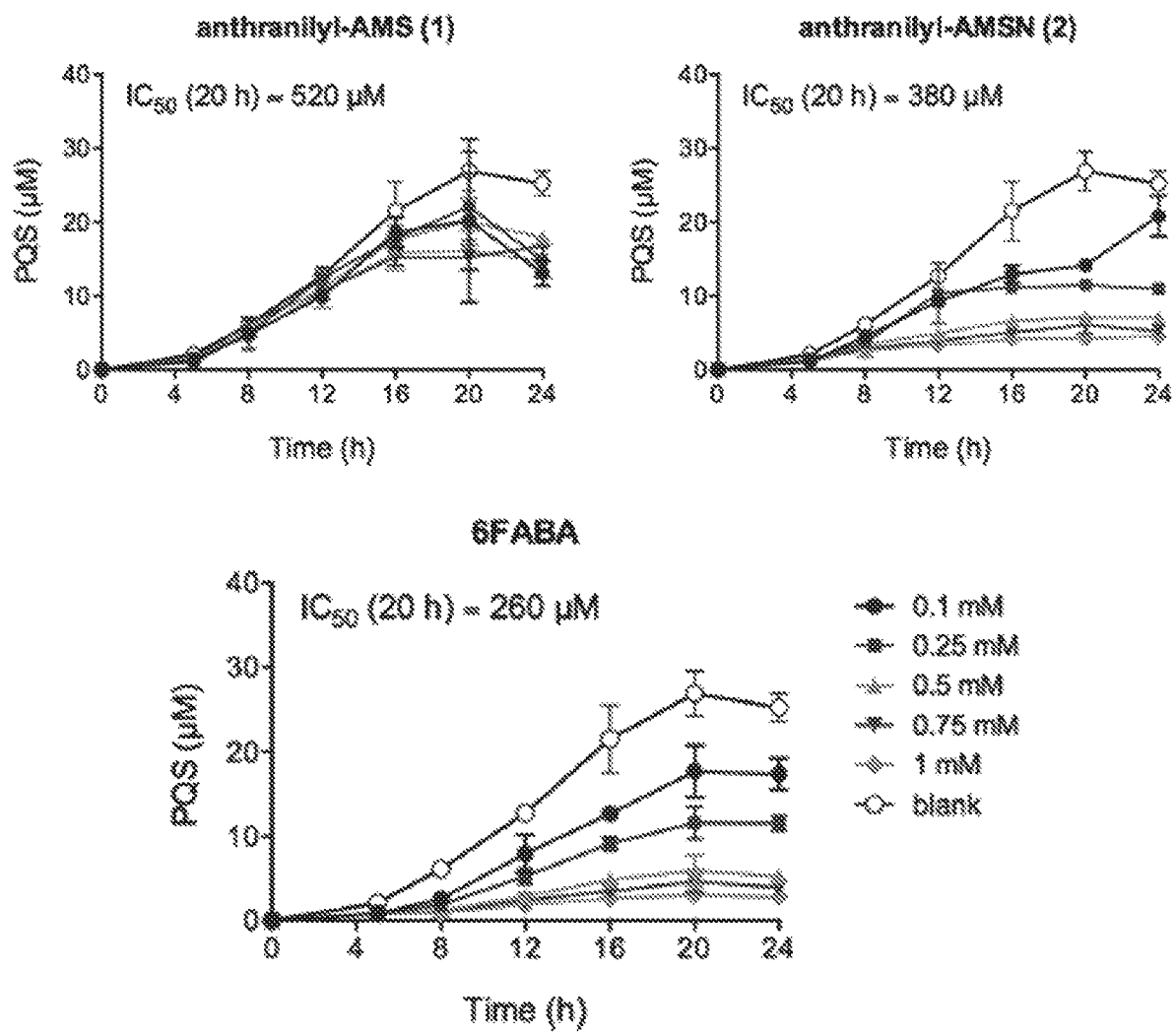
FIG. 2A shows the timecourses of PQS and HHQ biosynthesis inhibition by anthranilyl-AMS, anthranilyl-AMSN, and 6-fluoroanthranilate (6FABA).
Figure 2A:
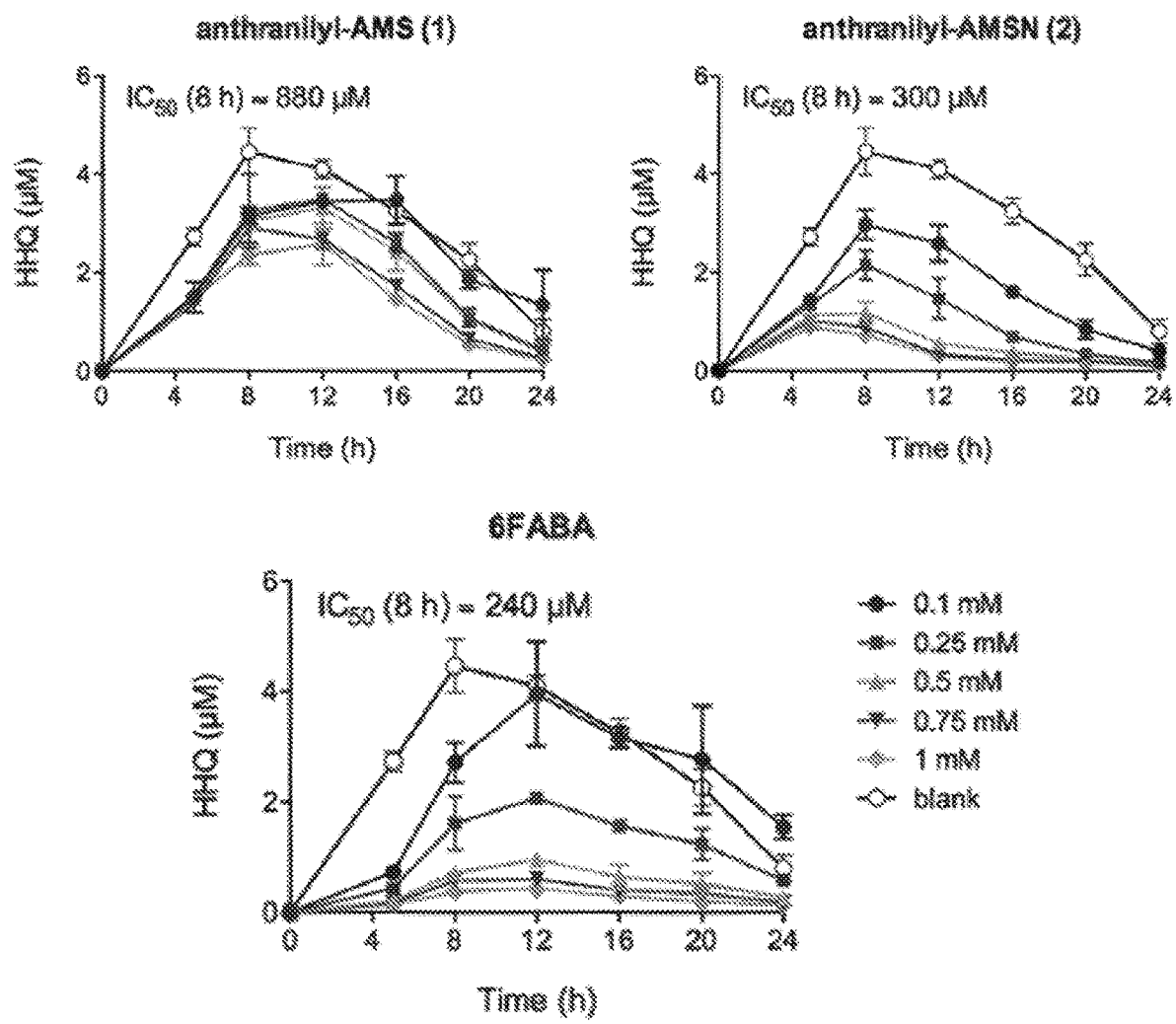
Figure 3:
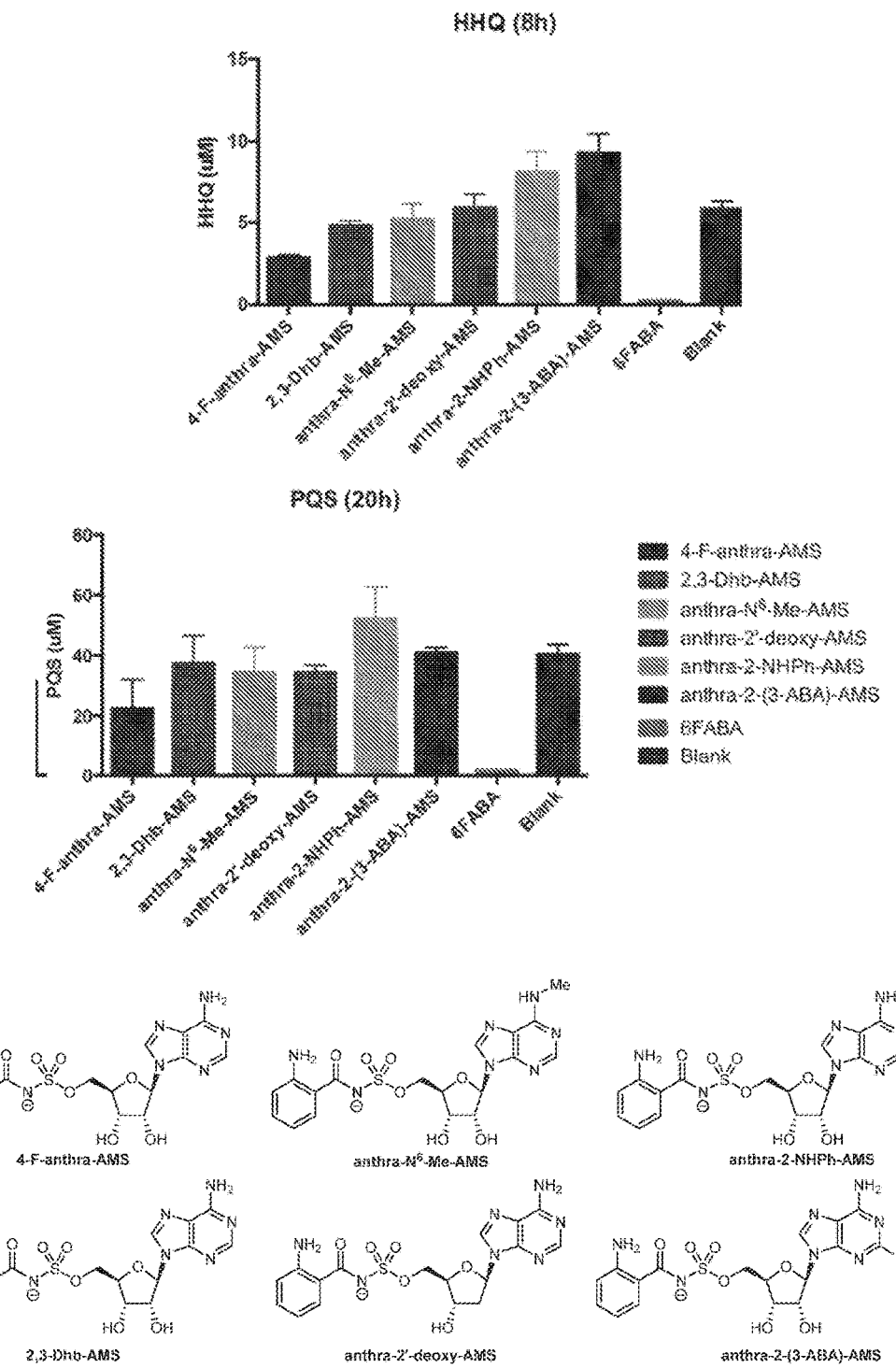
FIG. 3. Graph of HHQ and PQS concentration (μM) in *P. aeruginosa* PA14 cell cultures after 8 hours (HHQ) or 24 hours (PQS) in the presence of 1.5 mM anthranilyl-AMS, 6-fluoroanthranilyl-AMS, 2,3-dihydroxybenzoyl-AMS, anthranilyl-2'-deoxy-AMS, anthranilyl-2-phenylamino- AMS, anthranilyl-2-(3-aminomethyl)phenylamino-AMS, and 6-fluroanthranilate (6FABA).
Figure 4A:
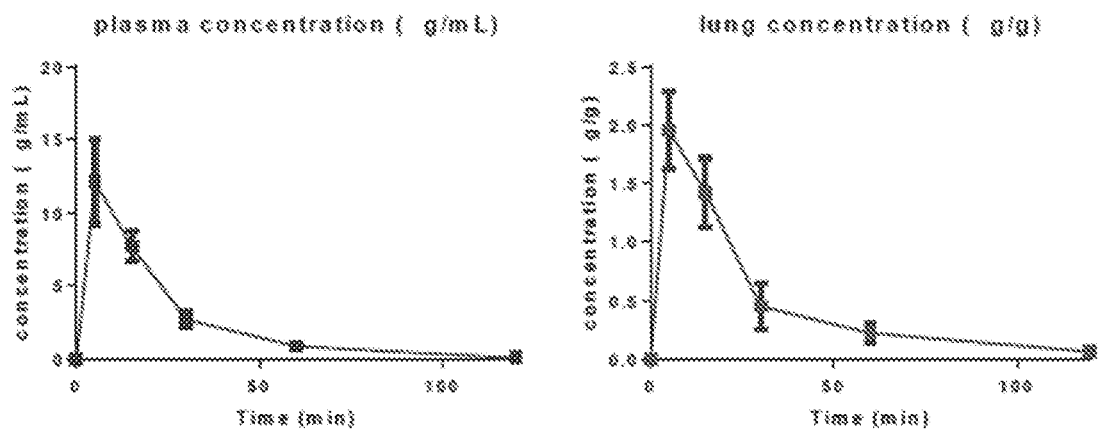
FIG. 4A shows pharmacokinetic graphs of the concentration of anthranilyl-AMS in mouse plasma and lungs over 2 hours, following a single-dose intraperitoneal injection of 10 mg/kg.
Figure 4B:
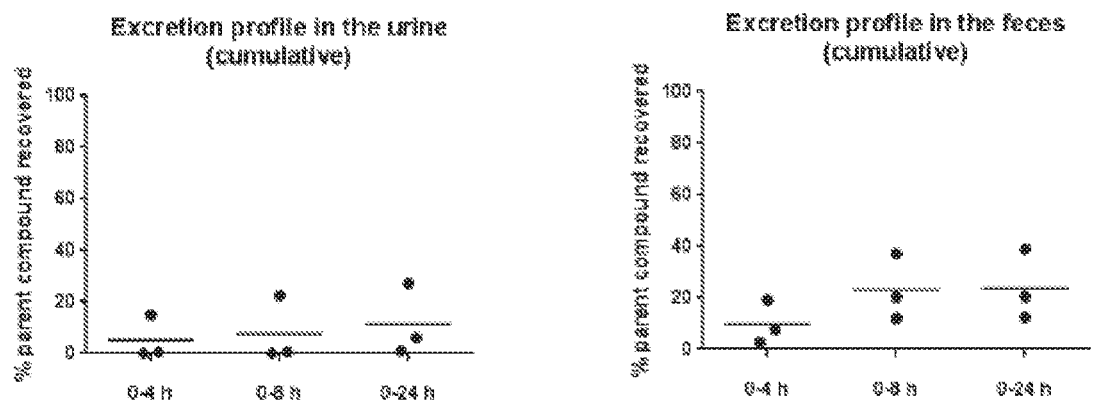
FIG. 4B shows excretion profiles showing the percentage of anthranilyl-AMS recovered from mice in urine and feces over 24 hours, following a single-dose intraperitoneal injection of 10 mg/kg.
Figure 6:
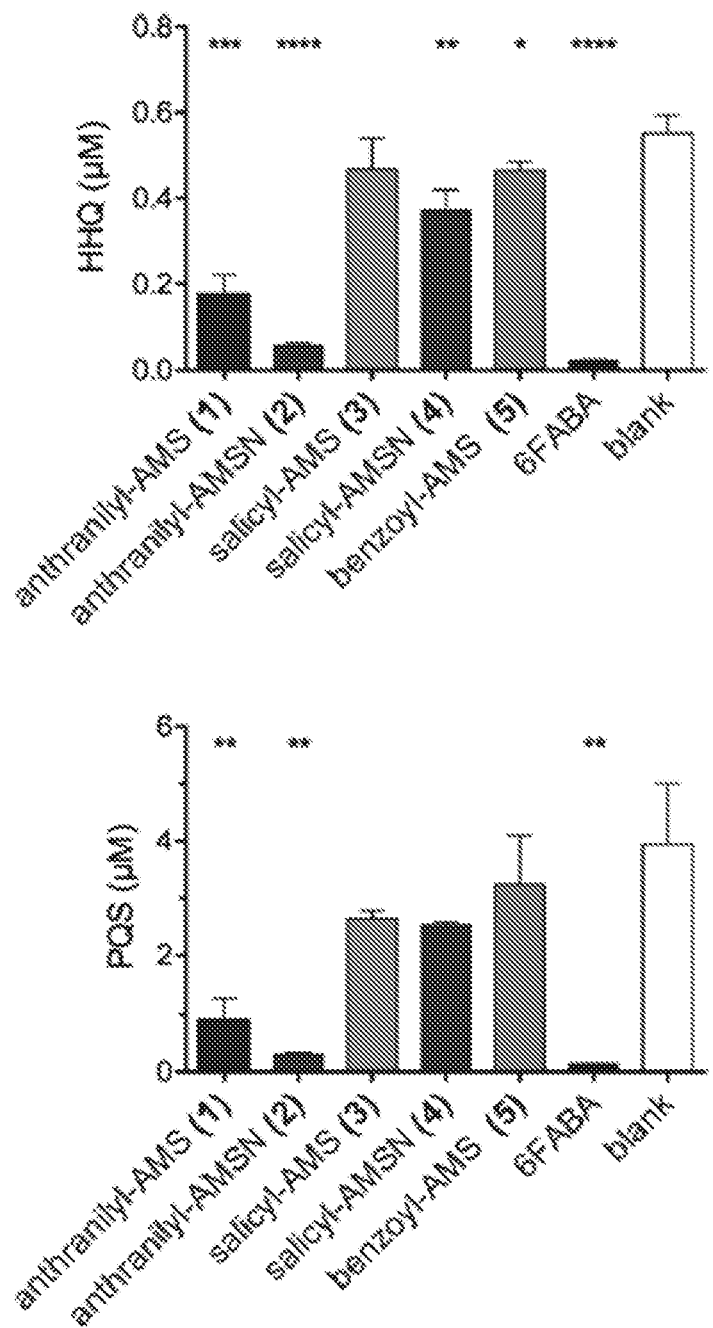
FIG. 6 shows Inhibition of HHQ (8 hours) and PQS (20 h) quinolone production in *P. aeruginosa* strain PA14 (1.5 mM inhibitors). Statistical significance relative to the blank was assessed using a two-tailed unpaired Student t-test with 95% confidence intervals; $*p<0.05$, $p<0.01$, $*p<0.001$, and $***01$.
Figure 7A:
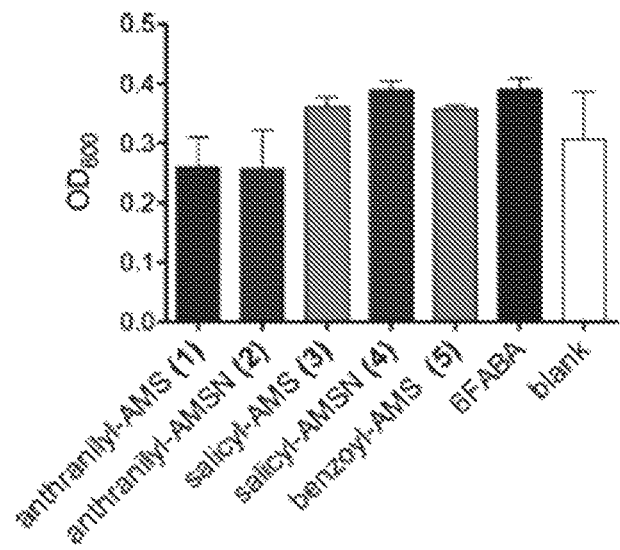
FIG. 7A shows that *P. aeruginosa* PA14 growth is not affected by PqsA inhibitors (1.5 mM) at 20 h.

PqsA inhibitors 1-5 were evaluated for their ability to inhibit HHQ and PQS quinolone production in P. aeruginosa strain PA14 (FIG. 6). HHQ and PQS concentrations were determined by LC-MS/MS quantitation relative to deuterated internal standards. 6-Fluoroanthranilate (6FABA), a substrate analogue reported previously to inhibit quinolone production at millimolar concentrations, was used as a positive control. Compounds were initially tested at 1.5 mM concentration, and HHQ and PQS were quantified at 8 and 20 hours, respectively. These time points were selected based on an initial time course study of quinolone production in the absence of inhibitors, with HHQ or PQS production peaking at these respective time points. The parent inhibitor anthranilyl-AMS (1) exhibited good inhibition of both HHQ and PQS production under these conditions (67% and 77% inhibition, respectively), whereas the sulfamide analogue anthranilyl-AMSN (2) was more potent (90% and 92% inhibition, respectively), consistent with its increased biochemical potency against PqsA. Salicyl-AMS (3), salicyl-AMSN (4), and benzoyl-AMS (5) were less potent inhibitors of quinolone production, despite their similar biochemical potencies against PqsA. This could be due to differences in cell penetration, stability, and/or target specificity. Finally, because inhibitors of the quinolone quorum sensing pathway should not impact bacterial growth, we confirmed that none of the six inhibitors above inhibited growth over 20 h (FIG. 7A). Encouraged by the ability of anthranilyl-AMS (1) and anthranilyl-AMSN (2) to inhibit HHQ and PQS quinolone production, the activity of these two inhibitors and 6FABA were investigated in greater detail. In untreated controls, HHQ and PQS production peaked at 8 and 20 hours, respectively. Previously reported time course studies have similarly shown that HHQ levels peak at 6-8 hours while PQS levels continue to rise. See, e.g., Deziel et al. (2004) Proc. Natl. Acad. Sci. U.S.A 101, 1339; Kesarwani et al. (2011) PLoS Pathog. 7, e1002192. All three inhibitors were able to decrease quinolone production in a dose- and time-dependent manner (FIG. 2A). While none of the inhibitors blocked quinolone production completely at any of the concentrations tested, both anthranilyl-AMSN (2) and 6FABA were able to inhibit or delay quinolone production at concentrations as low as 100 µM. Such a perturbation might still be sufficient to impact P. aeruginosa virulence in vivo. Indeed, 6FABA and related haloanthranilate substrate analogues have been shown to increase survival significantly in a mouse burn infection model, despite the fact that they only reduce HHQ levels partially compared to untreated controls in tissue directly underlying the infection site. See, e.g., Lesic et al. (2007) PLoS Pathog. 3, e126. Anthranilyl-AMS (1) exhibited the same trend of inhibition, albeit again with lower potency.

Effect on P. aeruginosa Pyocyanin Production

Figure 7B:
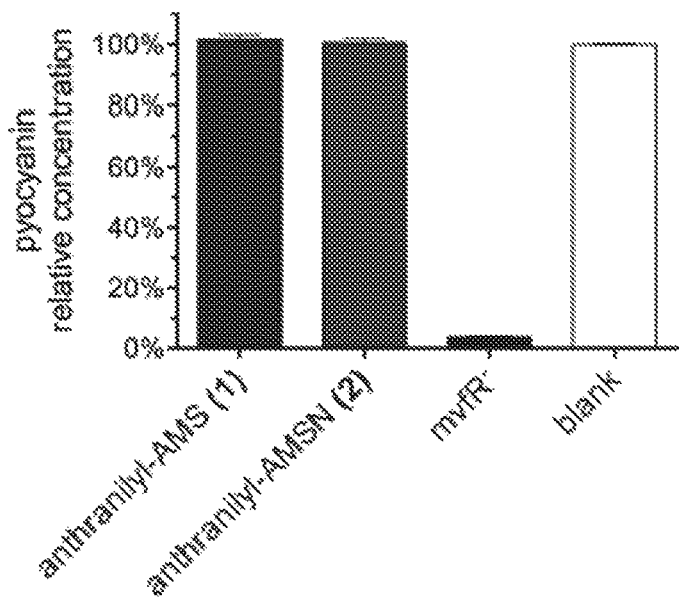
FIG. 7B shows that *P. aeruginosa* PA14 production of pyocyanin is not inhibited by PqsA inhibitors (1.0 mM) at 24 h.

The ability of these PqsA inhibitors to block production of the virulence factor pyocyanin was investigated. Although both anthranilyl-AMS (1) and anthranilyl-AMSN (2) were able to reduce HHQ and PQS production at 1 mM concentration (1, 47 and 40% inhibition, respectively; 2, 84% and 84% inhibition, respectively; FIG. 2A), neither inhibited pyocyanin production at this concentration (FIG. 7B). Of note, MvfR antagonists and PqsD inhibitors that similarly inhibit quinolone production but not pyocyanin production have been reported previously. See, e.g., Starkey et al. (2014) PLoS Pathog. 10, e1004321; Storz et al. (2012) J. Am. Chem. Soc. 134, 16143; Thomann et al. (2016) ACS Chem. Biol. 11, 1279. Haloanthranilate substrate analogues have been reported to inhibit both quinolone and pyocyanin production but may impact multiple targets in this complex signaling network. This is indicative of the complex relationship between HHQ and PQS quinolone biosynthesis, induction of the MvfR regulon, and production of pyocyanin.

Accumulation of Compounds in P. aeruginosa

Figure 8:
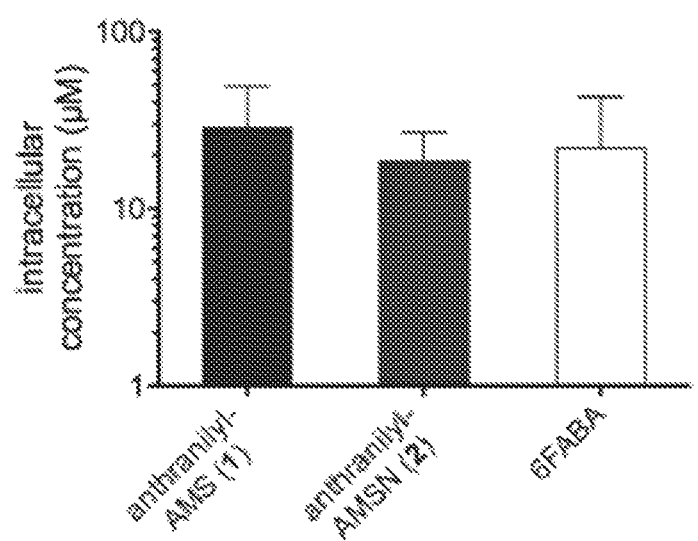
FIG. 8 shows compound accumulation in *P. aeruginosa* strain PA14 after incubation with 1000 µM extracellular concentration for 30 min.

It is well-known that P. aeruginosa has high intrinsic resistance to small-molecule antibiotics due to limited membrane permeability and high efflux. See, e.g., Bonomo et al. (2006) Clin. Infect. Dis. 43, S49-S54; Zavascki et al. (2010) Expert Rev. Anti-Infect. Ther. 8, 71. This may be the basis for the difference between the potent biochemical activity of PqsA inhibitors and their cellular potencies in P. aeruginosa. Thus, compound accumulation studies were carried out with anthranilyl-AMS (1), anthranilyl-AMSN (2), and 6FABA in P. aeruginosa PA14 using an LC-MS/MS quantitation approach (FIG. 8). See, e.g., Davis et al. (2014) ACS Chem. Biol. 9, 2535. Cells were grown in LB to early log phase ($OD_{600}$≈0.5), treated with 1000 µM compound for 30 min, then centrifuged and rapidly washed four times with cold PBS to remove surface-associated compound. The cells were lysed by multiple freeze-thaw cycles, centrifuged, and precipitated with methanol containing an internal standard (benzoyl-AMS, 5). Compound concentration in the lysate was quantitated by LC-MS/MS relative to the internal standard and the intracellular concentration was calculated based on CFU determination of the culture just prior to washing. Anthranilyl-AMS (1), anthranilyl-AMSN (2), and 6FABA accumulated to 20-30 µM intracellular concentration under these conditions, corresponding to 2-3% penetration relative to the 1000 µM extracellular concentration applied. These results suggest that limited penetration of anthranilyl-AMS (1) and anthranilyl-AMSN (2) into P. aeruginosa contributes to the differences between their biochemical and cellular potencies observed above, although other factors such as metabolic stability and/or off-target binding must also be considered. These integrated data provide a basis to correlate biochemical inhibition, bacterial compound accumulation, and cellular activity and indicate that membrane penetration and/or efflux evasion are keys to improving the cellular activity of these rationally designed PqsA inhibitors.

Calculation of Intracellular Concentration

Figure 9:
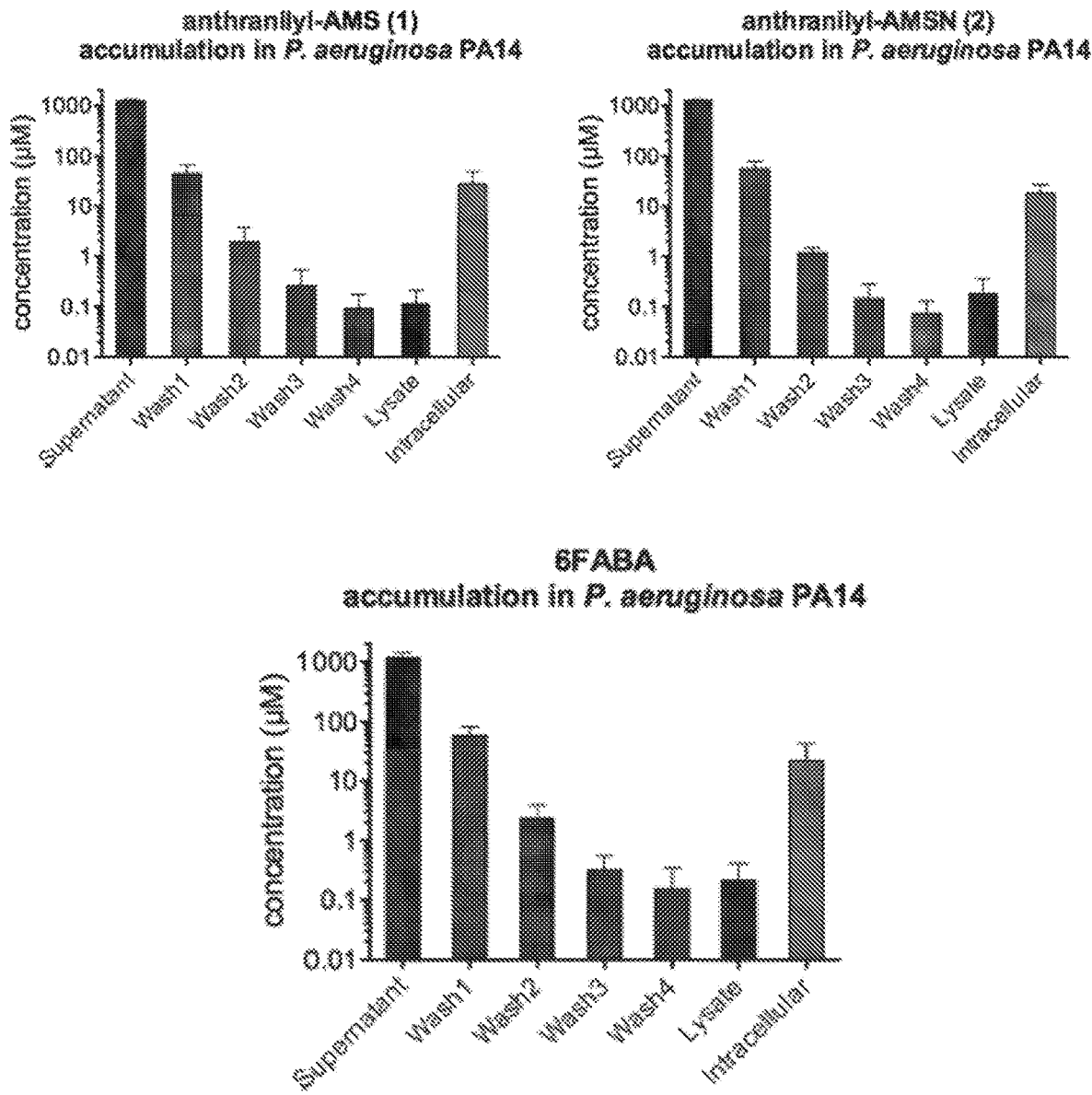
FIG. 9 shows compound concentrations detected in supernatant, washes, and lysates from incubations with *P. aeruginosa* strain PA14, with estimated intracellular concentrations calculated based on CFUs.

The total number of cells was determined via viable cell counts and plating of colony forming units (CFUs). After incubation with analyte, serial dilutions in fresh media were plated on agar. Colonies were grown for 24 hours and plates containing 25-250 colonies were used to calculate the total number of cells. Volume of a bacterial cell was estimated as 1×10−15 L and total cell volume and intracellular analyte concentration were calculated based on this value. After intracellular concentration was evaluated for each individual sample, outliers were removed by applying Grubbs' test to the dataset (n=8) repeatedly until no more outliers were detected. See FIG. 9.

Pharmacokinetics Studies

Twenty-four female mice were weighed and administered anthranilyl-AMS intraperitoneally at 10 mg/kg dose. The animals assigned for 24 hours sampling after dosing were kept in metabolic cages to collect urine and feces at an interval of 0 to 4, 4 to 8, and 8 to 24 hours. Approximately 60 µL of blood samples were collected from retro orbital plexus at 0.08, 0.25, 0.5, 1, 2, 4, 8, and 24 hours following i.p. administration. The blood samples were collected from three mice under light isoflurane anesthesia at each time point in labeled micro centrifuge tube containing $K_2EDTA$ solution. Blood samples were centrifuged at 4000 rpm for 10 minutes at 4±2° C. Immediately after plasma collection the animals were humanely euthanized by carbon dioxide asphyxiation, and lung samples were collected from each mouse at 0.08, 0.25, 0.5, 1, 2, 4, 8, and 24 hours. The tissue samples were then homogenized using ice-cold phosphate buffer saline (pH 7.4), and the total homogenate volume was three times of the tissue weight. The collected feces were weighed and homogenized with 9 volumes of ice-cold phosphate buffer saline (pH 7.4), and homogenates were stored below −70° C. until analysis. All samples were stored below −70° C. until sample analysis. The plasma and tissue samples were processed using protein precipitation with acetonitrile (ACN) and analyzed with fit for purpose LC-MS/MS method. Pharmacokinetic parameters were calculated using the non-compartmental analysis tool of Phoenix WinNonlin® (Version 6.3). Exemplary results are shown in Table E2.

TABLE E2

Pharmacokinetic data for anthranilyl-AMS in mice

| | | |
|---|---|---|
| $C_{max}$ (µg/mL) | plasma | 12.1 ± 2.9 |
| | lung | 2.0 ± 0.3 |
| $T_{1/2}$ (min) | plasma | 63.6 |
| | lung | 130 |
| AUC | plasma | 300.0 |
| (µg · min/mL or µg · min/g) | lung | 63.9 |
| lung/plasma ratio | | 0.21 |
| plasma protein binding | | 90.3 |

Cytotoxicity Screening
Cell Viability Assay (CellTiter Glow)

Promega Cell Titer-Glo utilizes the ATP dependent conversion of Luciferin to Oxyluciferin by a recombinant Luciferase in order to quantify the number of metabolically active cells in a sample. Quantification is possible because the number of RLU's detected is linearly proportional to the amount of ATP produced by metabolically active cells in culture at the time of lysis. Therefore, the relative cytotoxicity of each compound can be tested by quantifying the amount of ATP present in each microtiter well as compared to control groups.

Figure 10:
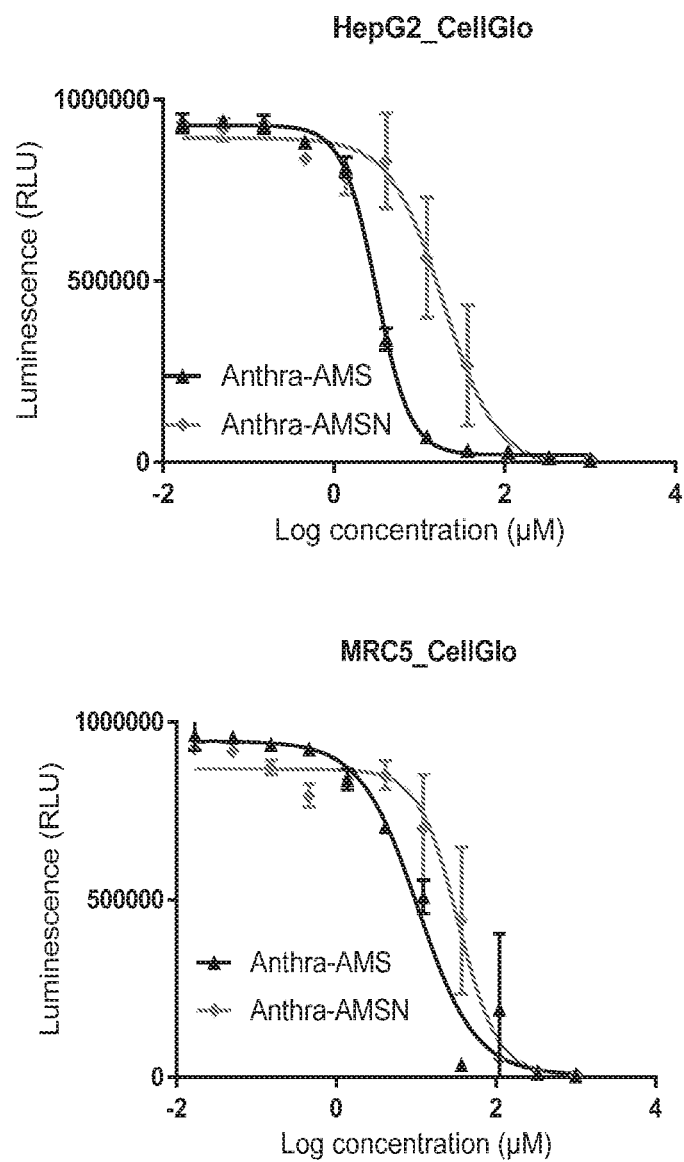
FIG. 10 shows cytotoxicity cell viability assay (CellTiter Glo). Based on luminescence readout, Anthra-AMS and Anthra-AMSN show significant toxicity in the tested range. This effect is consistently seen in both cell lines, HepG2 and MRC5. Table E5 summarizes the calculated $IC_{50}$ values of the tested compounds.

HepG2 and MRC5 were plated at a density of 1500 cells/25 al in well in the assay plate and allowed to settle overnight. 0.1 µL of compounds was then transferred from the source plate, into the cell assay plates. The cells were left to incubate with the compounds for 48 hrs, after which, 25 µL of Promega Cell Titer-Glo was added to each well, and allowed to incubate at room temperature with shaking for 20 minutes. RLU's for each well were then recorded on a BioTek Synergy NEO. DMSO was used as negative control Based on luminescence readout, Anthra-AMS and Anthra-AMSN show significant toxicity in the tested range (See FIG. 10). This effect is consistently seen in both cell lines. Table E5 summarizes the calculated $IC_{50}$ values of the tested compounds.

Cell Health and Viability Image Based Study (Fluorescence Microscopy)

The multiparametric assay developed surveys a number of elements of cell health simultaneously. Using a combination of 2 dyes, we are able to simultaneously measure nuclear morphology, membrane integrity and cell proliferation. All measurements are made on live cells after an incubation time of 24H. Hoechst 33342 is used to measure total number of cells, nuclear morphology and cell proliferation. The nuclear impermeable dye Syto17 is used to assess the nuclear membrane integrity by measuring the nuclear translocation of the dye when the membrane gets porous after incubation with a toxic compound.

Cells were plated at a density of 1500 cells/25 al in well in a 384 wells plate the day before incubation with the drugs. The following day, 0.1 al of the source plate are added to the assay plate. Then, 25 al of a fluorophores mixture containing Hoechst 33342, Syto17 diluted in EMEM was added to each well. Plates are read after 48 h incubation in the ImageXpress instrument (Molecular Devices) using the appropriate filters. Images are analyzed using an application of MetaXpress software (Molecular Devices) and data are presented using Prism software. Low Signal Control (C23): 5 µM Staurosporine; High Signal Control (C24): DMSO.

Figure 11:
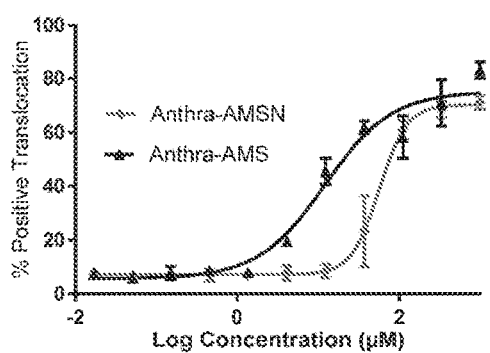
FIG. 11 shows results of cell health and viability image-based study (Fluorescence Microscopy). Based on the imaging results, Anthra-AMS and Anthra-AMSN show significant toxicity in the tested range. This effect is consistently seen in both cell lines and both parameters assessed. Table E5 summarizes the calculated $IC_{50}$ values of the tested compounds.
Figure 11:
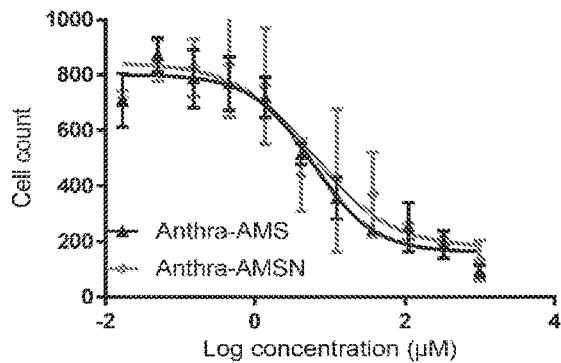
Figure 11:
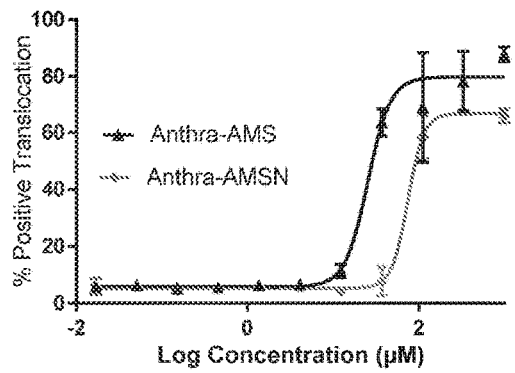
Figure 11:
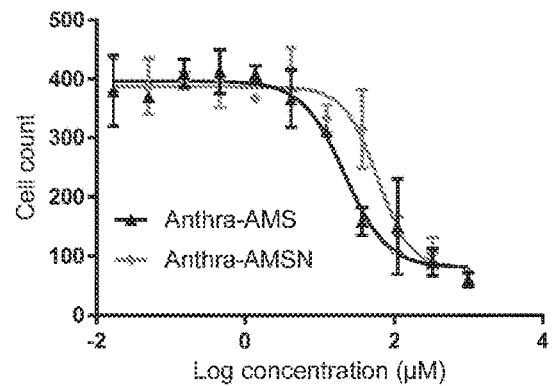

Based on the imaging results, Anthra-AMS and Anthra-AMSN show significant toxicity in the tested range (See FIG. 11). This effect is consistently seen in both cell lines and both parameters assessed. In conclusion, Anthra-AMS and Anthra-AMSN showed toxicity in both cell HepG2 and MRC5 lines and the data are in agreement between the 3 parameters tested.

TABLE E5

Potency of the compounds in HepG2 and MRC5 cells, tested using luminescence and imaging methods

| Compound name | Highest dose tested (µM) | CellTiter Glo (IC50 in µM) | | Cell Count (IC50 in µM) | | Nuclear membrane integrity (IC50 in µM) | |
|---|---|---|---|---|---|---|---|
| | | MRC5 | HepG2 | MRC5 | HepG2 | MRC5 | HepG2 |
| Anthra-AMS | 1000 | 10.6 | 3.1 | 21.5 | 5.9 | 25.47 | 12.09 |
| Anthra-AMSN | 1000 | 33.7 | 19.2 | 58.8 | 6 | 74.26 | 56.31 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any one of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

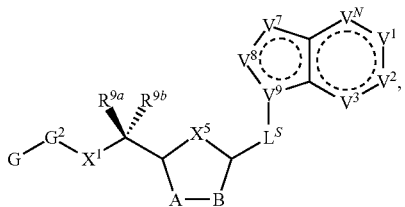

or a pharmaceutically acceptable salt, stereoisomer, or tautomer thereof, wherein:

$G^2$ is —S(=O)$_2$—, —P(=O)(R$^e$)—, —P(=O)(OR$^e$)—, —P(=O)(N(R$^e$)$_2$)—, —P(=S)(R$^e$)—, —P(=S)(OR$^e$)—, —P(=S)(N(R$^e$)$_2$)—, —Si(OR$^e$)$_2$—, —C(=O)—, —C(=S)—, —C(=NR$^f$)—, —(CH$_2$)$_h$—,

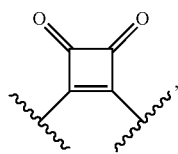 [SMILES: *c1c(*)c(=O)c1=O]

or optionally substituted monocyclic 5- or 6-membered heteroarylene, wherein 1, 2, 3, or 4 atoms in the heteroarylene ring system are independently oxygen, nitrogen, or sulfur;

G is of formula:

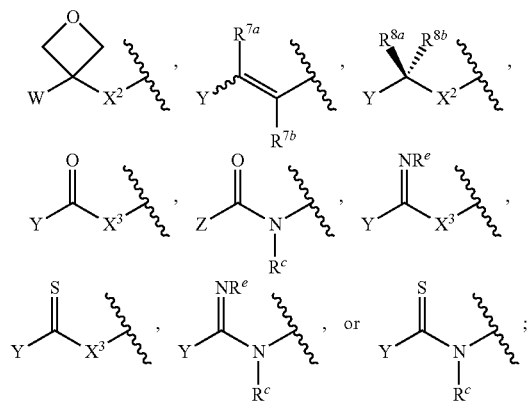

each of W, Y, and Z is independently optionally substituted heteroaryl or of the formula:

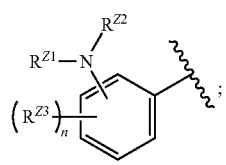

n is 0, 1, 2, 3, or 4;
each of $R^{Z1}$ and $R^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form an optionally substituted heterocyclic or optionally substituted heteroaryl ring;

each occurrence of $R^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$, or two $R^{Z3}$ are joined to form an optionally substituted aryl or optionally substituted heteroaryl ring;

$X^1$ is a bond, —O—, —C(R$^d$)$_2$—, —(CH$_2$)$_q$—, —NH—, or —NR$^f$—;

$X^2$ is a bond, —O—, —C(R$^d$)$_2$—, —(CH$_2$)$_t$—, —NH—, or —NR$^f$—;

each instance of R$^f$ is optionally substituted C$_{1-6}$ alkyl, optionally substituted acyl, or a nitrogen protecting group;

$X^3$ is a bond, —O—, —C(R$^d$)$_2$—, or —(CH$_2$)$_t$—;

A-B is —(R$^A$)$_2$C—C(R$^B$)$_2$— or —R$^A$C=CR$^B$—, wherein each occurrence of R$^A$ is independently hydrogen, halogen, optionally substituted alkyl, optionally substituted acyl, —OR$^{S1}$, or —N(R$^e$)$_2$, and each occurrence of R$^B$ is independently hydrogen, halogen, optionally substituted alkyl, optionally substituted acyl, —OR$^{S2}$, or —N(R$^e$)$_2$, $X^5$ is —O—, —S—, —C(R$^d$)$_2$—, or —NR$^c$—;

each of $R^{7a}$ and $R^{7b}$ is independently hydrogen, halogen, optionally substituted C$_{1-6}$ alkyl, —OR$^e$, or —N(R$^e$)$_2$;

each of $R^{8a}$ and $R^{8b}$ is independently hydrogen, halogen, optionally substituted C$_{1-6}$ alkyl, —OR$^e$, or —N(R$^e$)$_2$;

each of $R^{9a}$ and $R^{9b}$ is independently hydrogen, halogen, optionally substituted C$_{1-6}$ alkyl, —OR$^e$, or —N(R$^e$)$_2$;

each of $R^{S1}$ and $R^{S2}$ is independently hydrogen, optionally substituted C$_{1-6}$ alkyl, optionally substituted acyl, or an oxygen protecting group, or $R^{S1}$ and $R^{S2}$ are joined to form an optionally substituted heterocyclic ring;

$L^S$ is a bond, —O—, —NR$^c$—, optionally substituted alkylene, optionally substituted alkenylene, optionally substituted alkynylene, optionally substituted acylene, or optionally substituted arylene;

each of $V^1$, $V^2$, $V^3$, $V^7$, $V^8$, and $V^9$ is independently N or CR$^V$, wherein each R$^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$;

$V^N$ is N, NR$^N$, or CR$^N$;

$R^N$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^{Na}$)$_2$, each occurrence of $R^{Na}$ independently hydrogen, optionally substituted C$_{1-6}$ alkyl, optionally substituted acyl, or a nitrogen protecting group, or both R$^{Na}$ are joined to form and optionally substituted heterocyclic or optionally substituted heteroaryl ring;

each occurrence of R$^d$ is independently hydrogen, halogen, optionally substituted C$_{1-6}$ alkyl, —OR$^e$, or —N(R$^e$)$_2$;

each occurrence of $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two $R^e$ are joined to form and optionally substituted heterocyclic or optionally substituted heteroaryl ring;

each occurrence of $R^c$ is independently hydrogen, optionally substituted $C_{1-6}$ alkyl, optionally substituted acyl, or a nitrogen protecting group;

each of h, q, and t is independently 1, 2, or 3; and

⟳ indicates that each bond of the ring is a single or double bond;

provided that the compound is not any of the following:

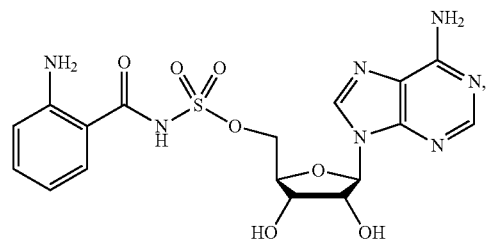

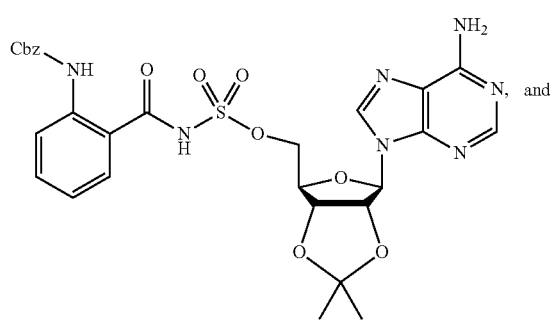

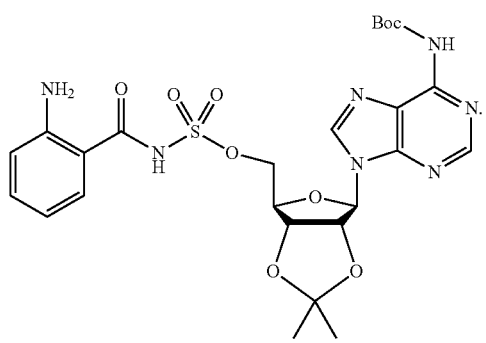

2. The compound of claim 1, wherein the compound is of Formula (II):

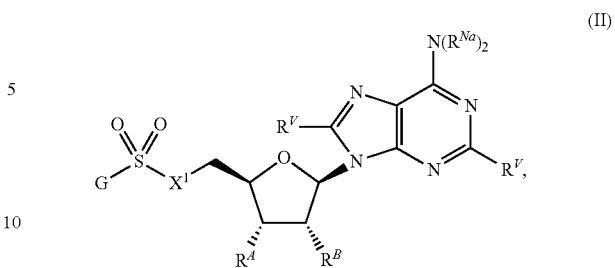

(II)

or a pharmaceutically acceptable salt, stereoisomer, or tautomer thereof.

3. The compound of claim 1, wherein the compound is of one of the following formulae:

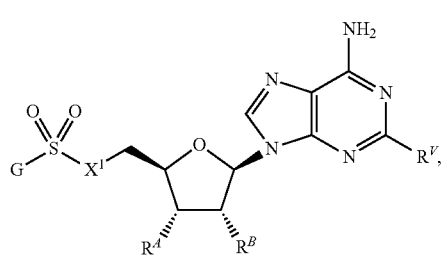

(II-A)

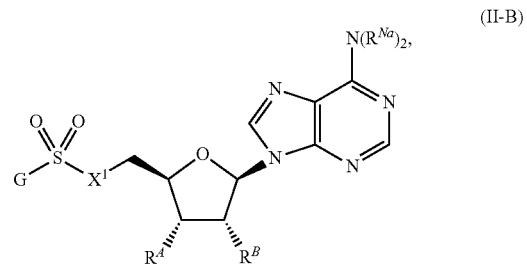

(II-B)

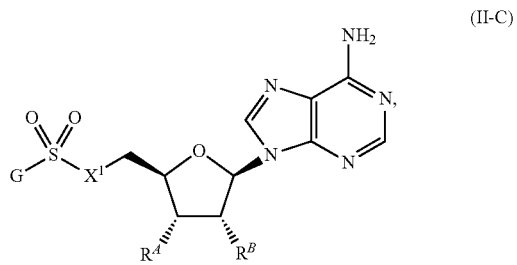

(II-C)

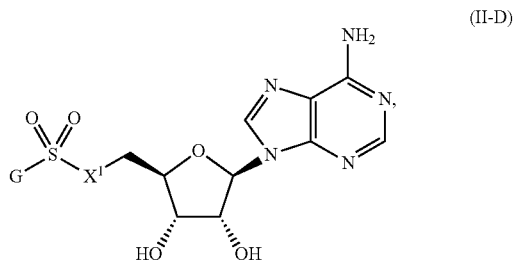

(II-D)

(II-E)
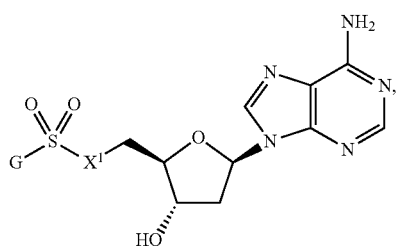
(II-F)
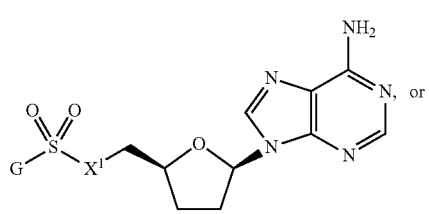
or
(II-G)
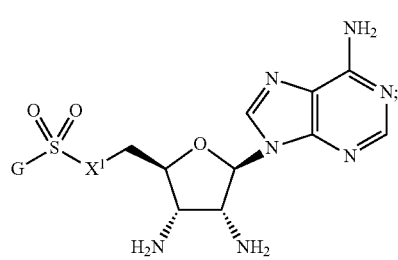
or a pharmaceutically acceptable salt, stereoisomer, or tautomer thereof.
4. The compound of claim 1, wherein the compound is of formula:
(III)
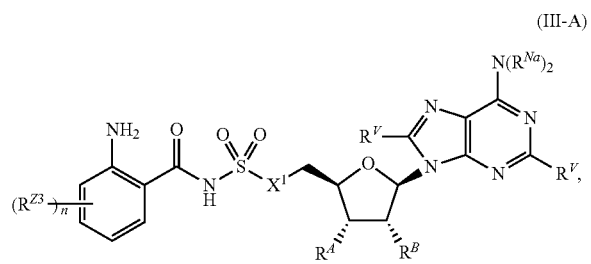
or a pharmaceutically acceptable salt, stereoisomer, or tautomer thereof.
5. The compound of claim 1, wherein the compound is of one of the following formulae:
(III-A)
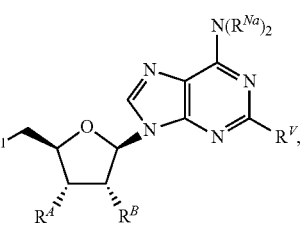
(III-B)
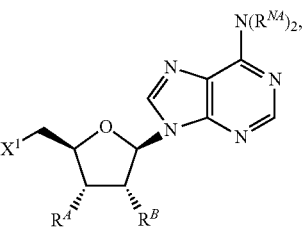
(III-C)
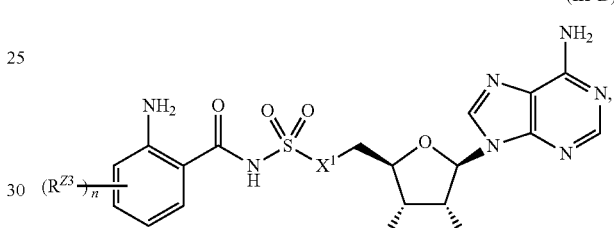
(III-D)
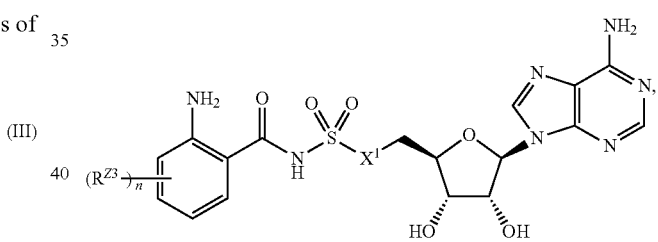
(III-E)
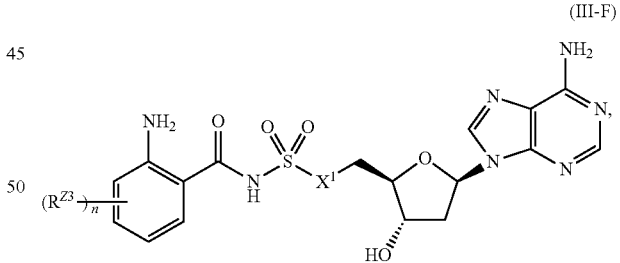
(III-F)
(III-G)
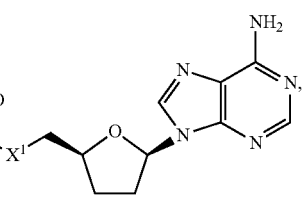

-continued (III-H)

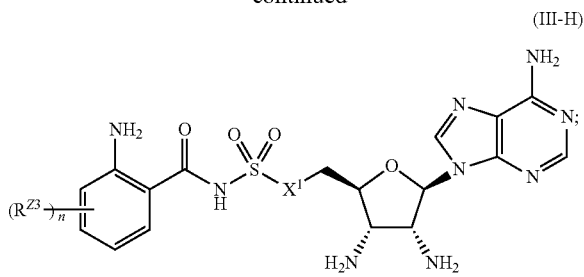

or a pharmaceutically acceptable salt, stereoisomer, or tautomer thereof.

6. A compound of Formula (IV):

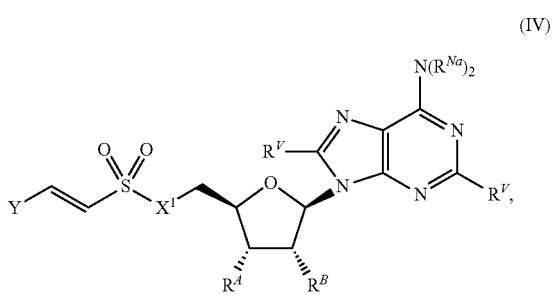
(IV)

or a pharmaceutically acceptable salt, stereoisomer, or tautomer thereof; wherein:
Y is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —OR$^e$, —N(R$^e$)$_2$, optionally substituted carbocyclyl, optionally substituted heterocyclyl, optionally substituted aryl, optionally substituted heteroaryl, or of formula:

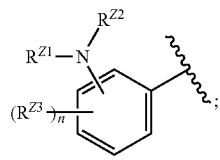

n is 0, 1, 2, 3, or 4;
each of R$^{Z1}$ and R$^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or R$^{Z1}$ and R$^{Z2}$ are joined to form an optionally substituted heterocyclic or optionally substituted heteroaryl ring;
each occurrence of R$^{Z3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$, or two R$^{Z3}$ are joined to form an optionally substituted aryl or optionally substituted heteroaryl ring;

X$^1$ is a bond, —O—, —C(R$^d$)$_2$—, —(CH$_2$)$_q$—, —NH— or —NR$^f$—;
q is 1, 2, or 3;
R$^f$ is optionally substituted C$_{1-6}$ alkyl, optionally substituted acyl, or a nitrogen protecting group;
R$^A$ is hydrogen, halogen, optionally substituted alkyl, optionally substituted acyl, —OR$^{S1}$, or —N(R$^e$)$_2$;
R$^B$ is hydrogen, halogen, optionally substituted alkyl, optionally substituted acyl, —OR$^{S2}$, or —N(R$^e$)$_2$;
each of R$^{S1}$ and R$^{S2}$ is independently hydrogen, optionally substituted C$_{1-6}$ alkyl, optionally substituted acyl, or an oxygen protecting group, or R$^{S1}$ and R$^{S2}$ are joined to form an optionally substituted heterocyclic ring;
each R$^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$;
each occurrence of R$^{Na}$ independently hydrogen, optionally substituted C$_{1-6}$ alkyl, optionally substituted acyl, or a nitrogen protecting group, or both R$^{Na}$ are joined to form and optionally substituted heterocyclic or optionally substituted heteroaryl ring;
each occurrence of R$^d$ is independently hydrogen, halogen, optionally substituted C$_{1-6}$ alkyl, —OR$^e$, or —N(R$^e$)$_2$; and
each occurrence of R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two R$^e$ are joined to form and optionally substituted heterocyclic or optionally substituted heteroaryl ring;
provided that the compound is not the following:

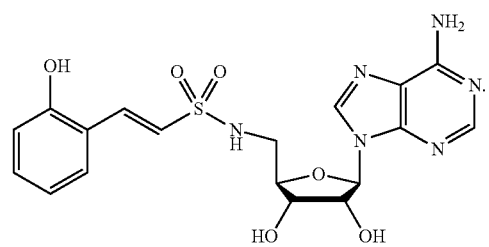

7. The compound of claim 6, wherein the compound is of one of the following formulae:

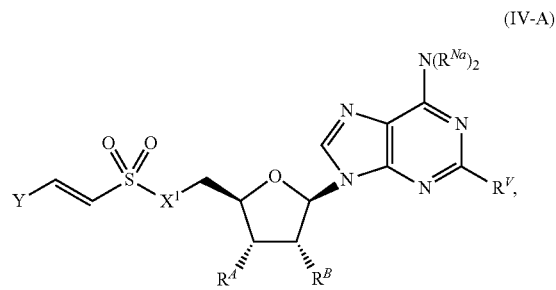
(IV-A)

-continued

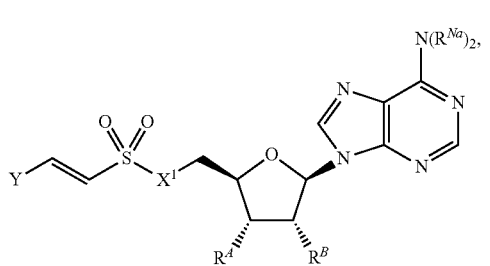
(IV-B)

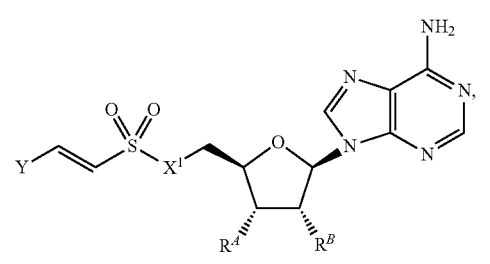
(IV-C)

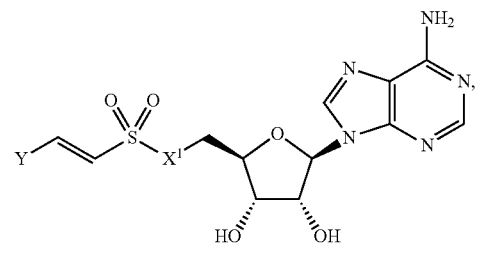
(IV-D)

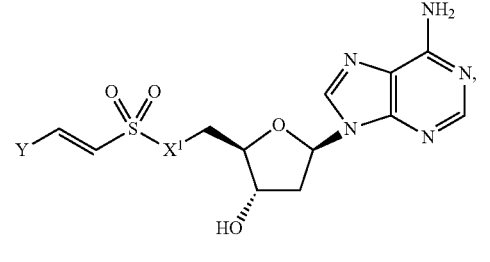
(IV-E)

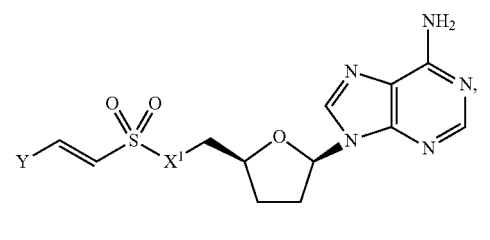
(IV-F)

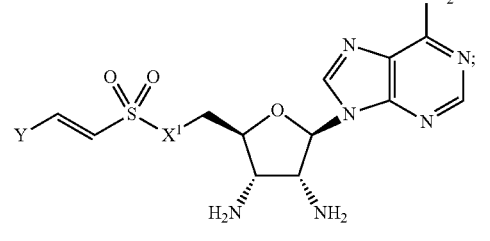
(IV-G)

or a pharmaceutically acceptable salt, stereoisomer, or tautomer thereof.

8. The compound of claim 6, wherein the compound is of formula:

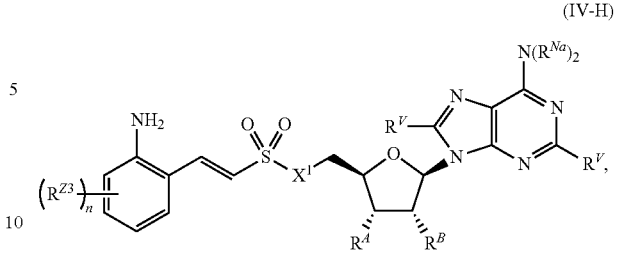
(IV-H)

or a pharmaceutically acceptable salt, stereoisomer, or tautomer thereof.

9. A compound of Formula (V):

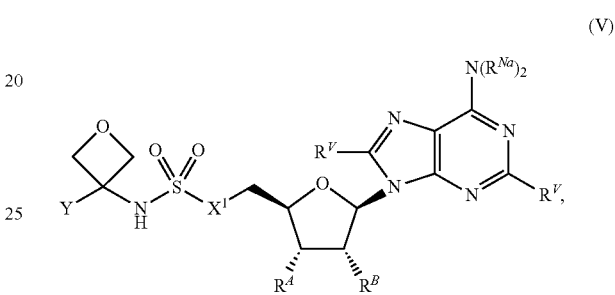
(V)

or a pharmaceutically acceptable salt, stereoisomer, or tautomer thereof; wherein:

Y is optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —$OR^e$, —$N(R^e)_2$, optionally substituted carbocyclyl, optionally substituted heterocyclyl, optionally substituted aryl, optionally substituted heteroaryl, or of formula:

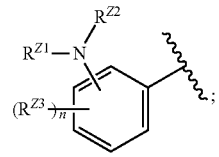

n is 0, 1, 2, 3, or 4;

each of $R^{Z1}$ and $R^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form an optionally substituted heterocyclic or optionally substituted heteroaryl ring;

each occurrence of $R^{Z3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$NO_2$, —CN, —$OR^e$, or —$N(R^e)_2$, or two $R^{Z3}$ are joined to form an optionally substituted aryl or optionally substituted heteroaryl ring;

$X^1$ is a bond, —O—, —C(R$^d$)$_2$—, —(CH$_2$)$_q$—, —NH— or —NR$^f$—;

q is 1, 2, or 3;

R$^f$ is optionally substituted C$_{1-6}$ alkyl, optionally substituted acyl, or a nitrogen protecting group;

R$^A$ is hydrogen, halogen, optionally substituted alkyl, optionally substituted acyl, —OR$^{S1}$, or —N(R$^e$)$_2$;

R$^B$ is hydrogen, halogen, optionally substituted alkyl, optionally substituted acyl, —OR$^{S2}$, or —N(R$^e$)$_2$;

each of R$^{S1}$ and R$^{S2}$ is independently hydrogen, optionally substituted C$_{1-6}$ alkyl, optionally substituted acyl, or an oxygen protecting group, or R$^{S1}$ and R$^{S2}$ are joined to form an optionally substituted heterocyclic ring;

each R$^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$;

each occurrence of R$^{Na}$ independently hydrogen, optionally substituted C$_{1-6}$ alkyl, optionally substituted acyl, or a nitrogen protecting group, or both R$^{Na}$ are joined to form and optionally substituted heterocyclic or optionally substituted heteroaryl ring;

each occurrence of R$^d$ is independently hydrogen, halogen, optionally substituted C$_{1-6}$ alkyl, —OR$^e$, or —N(R$^e$)$_2$; and each occurrence of R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two R$^e$ are joined to form and optionally substituted heterocyclic or optionally substituted heteroaryl ring.

10. The compound of claim 9, wherein the compound is of one of the following formulae:

(V-A)

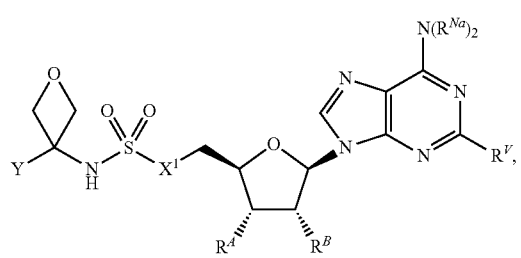

(V-B)

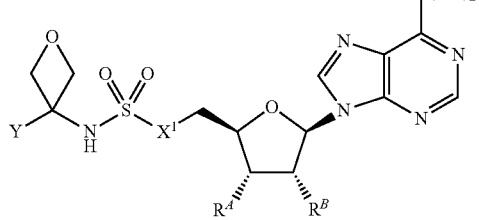

(V-C)

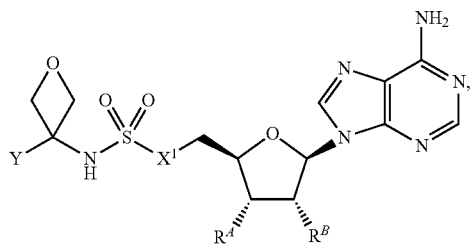

(V-D)

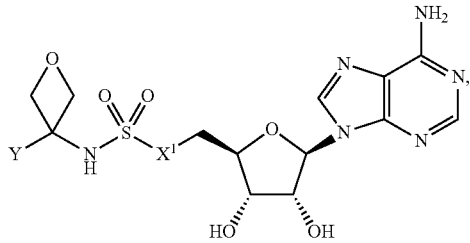

(V-E)

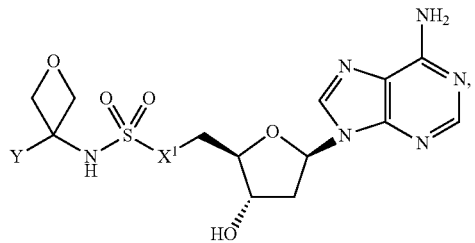

(V-F)

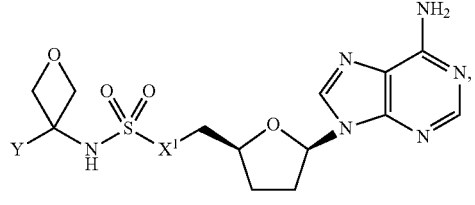

(V-G)

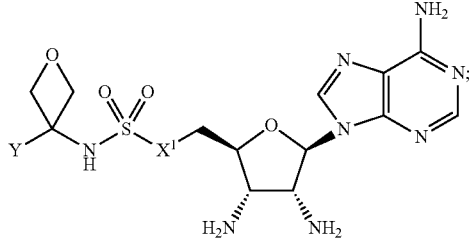

or a pharmaceutically acceptable salt, stereoisomer, or tautomer thereof.

11. The compound of claim 9, wherein the compound is of formula:

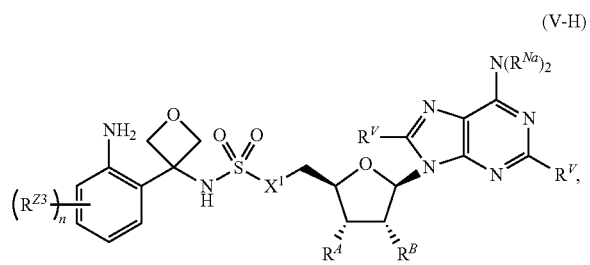
or a pharmaceutically acceptable salt, stereoisomer, or tautomer thereof.
12. The compound of claim 1, wherein the compound is selected from the group consisting of:
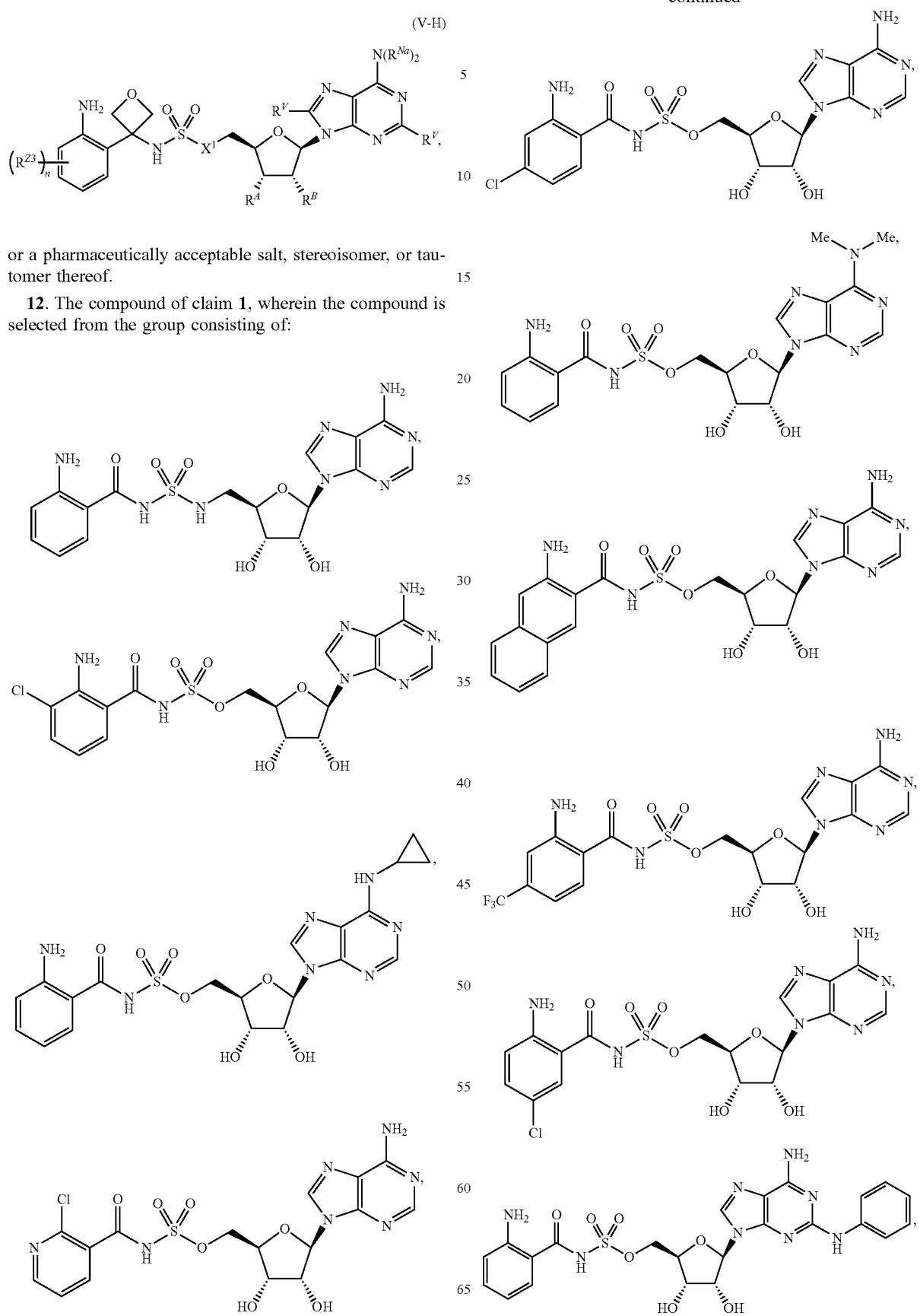

-continued
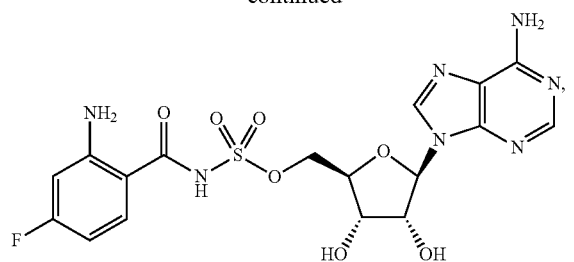
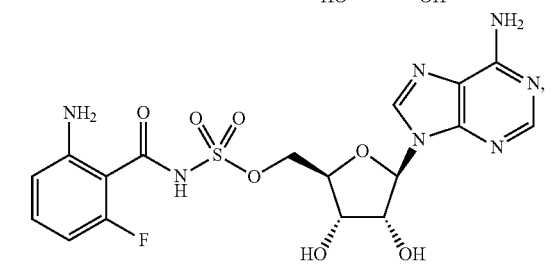
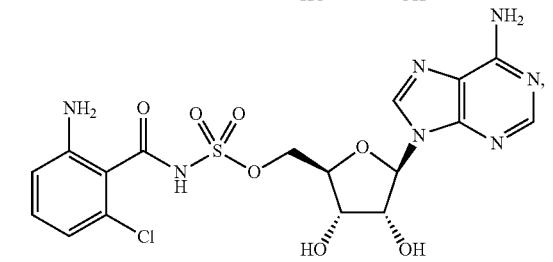
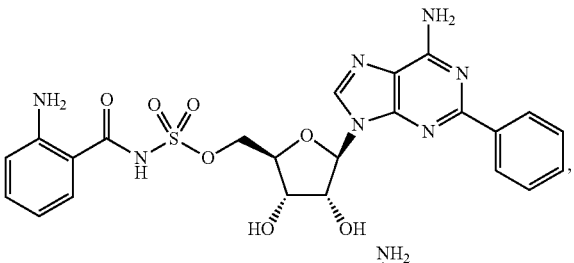
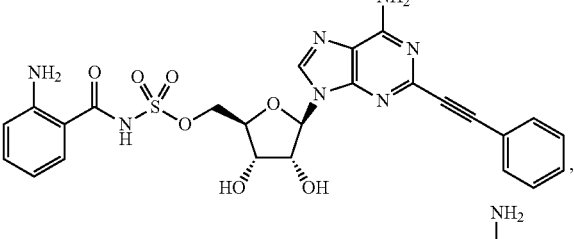
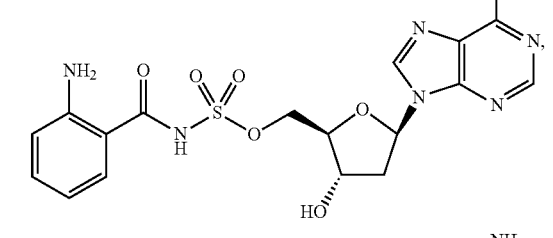
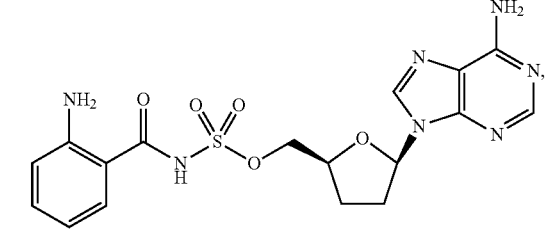
-continued
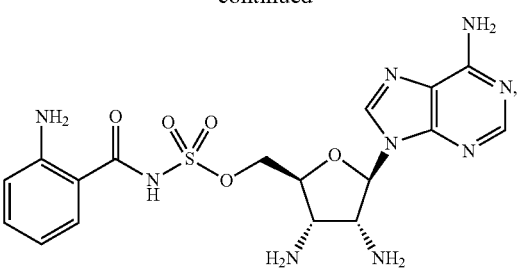
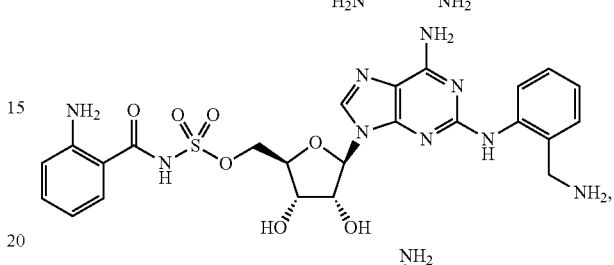
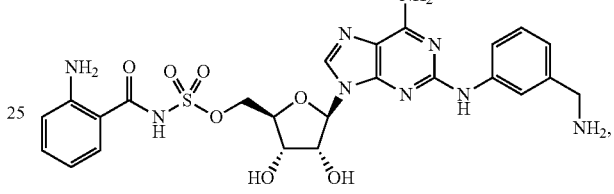
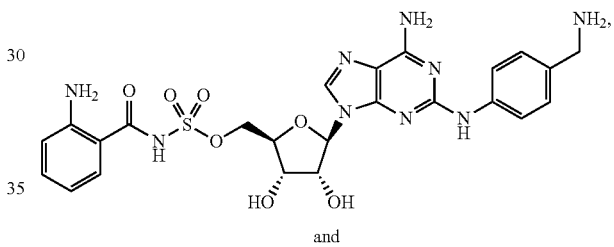
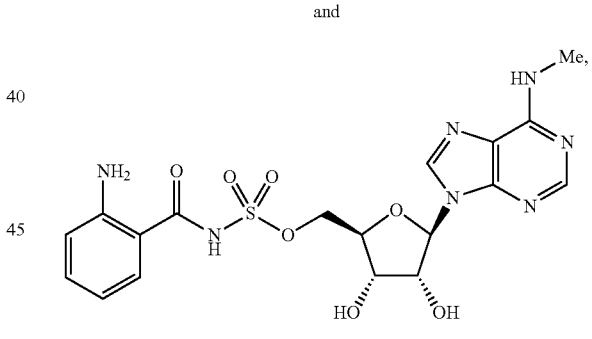
and pharmaceutically acceptable salts, stereoisomers, and tautomers thereof.
13. The compound of claim 1, wherein the compound is selected from the group consisting of:
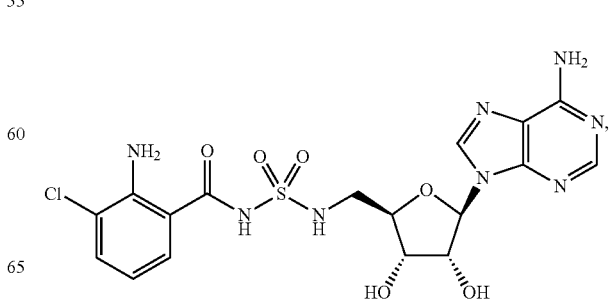

185
-continued
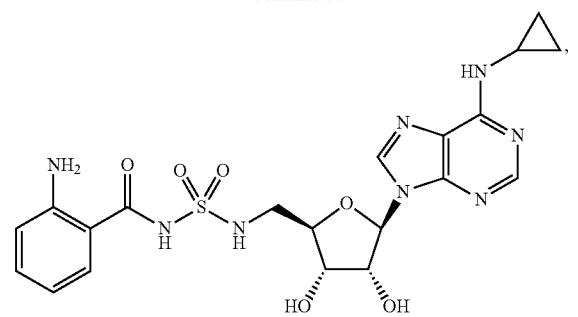
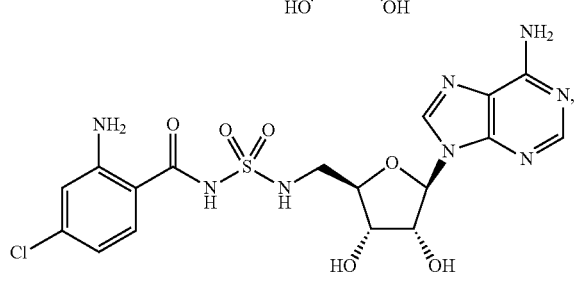
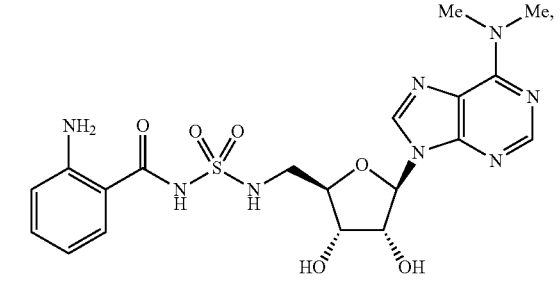
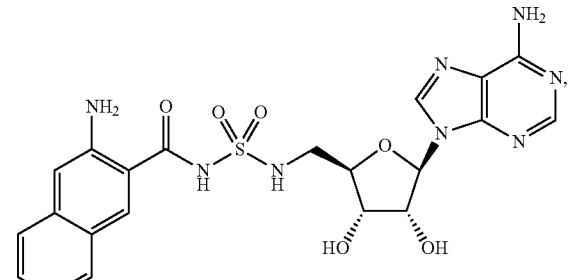
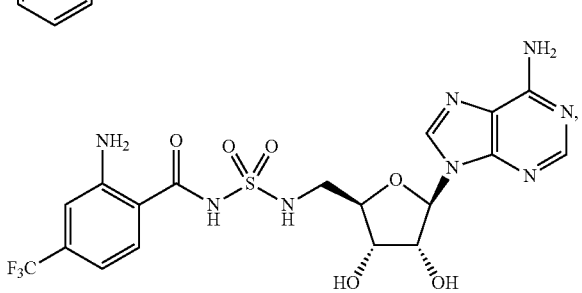
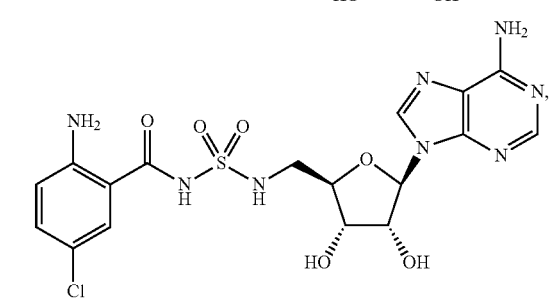
186
-continued
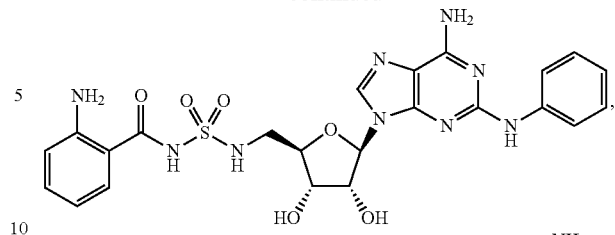
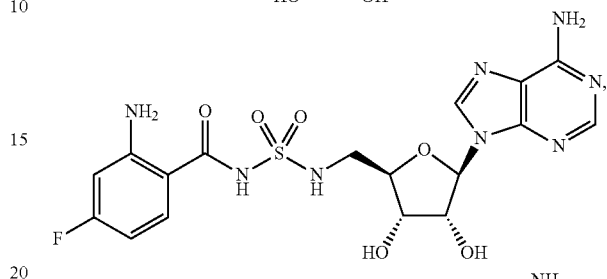
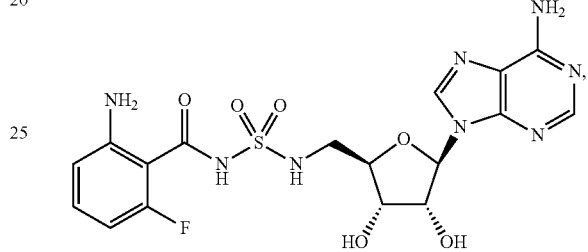
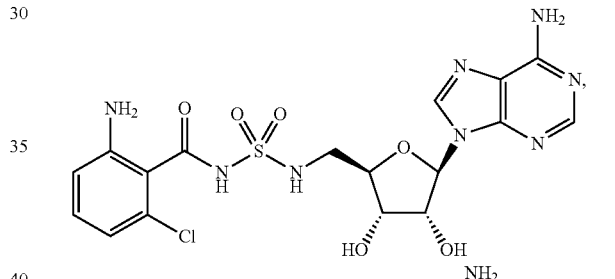
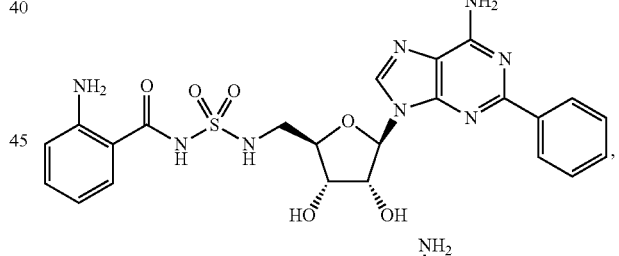
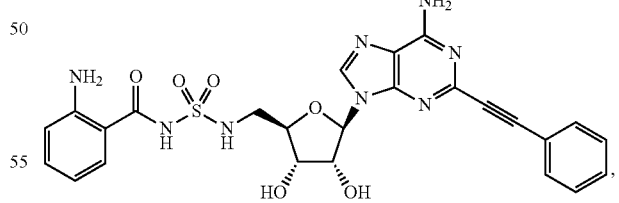
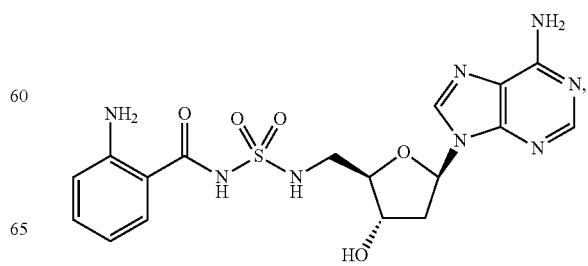

-continued

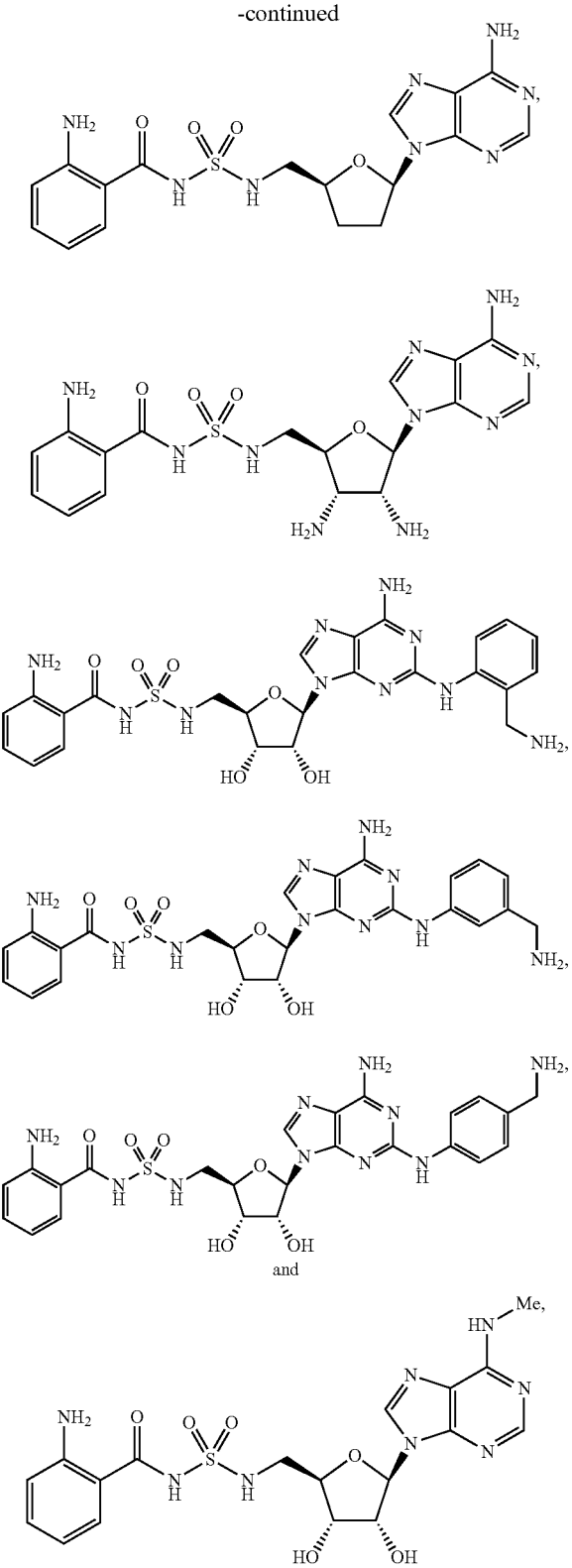

and pharmaceutically acceptable salts, stereoisomers, and tautomers thereof.

14. A pharmaceutical composition comprising a compound of claim 1, or a pharmaceutically acceptable salt, stereoisomer, or tautomer thereof, and a pharmaceutically acceptable excipient.

15. A method of treating a *Pseudomonas* infection in a subject in need thereof comprising administering to the subject an effective amount of a compound of Formula (I):

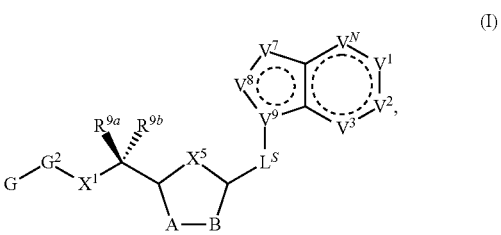

(I)

or a pharmaceutically acceptable salt, stereoisomer, or tautomer thereof, wherein:

G² is —S(=O)₂—, —P(=O)(Rᵉ)—, —P(=O)(ORᵉ)—, —P(=O)(N(Rᵉ)₂)—, —P(=S)(Rᵉ)—, P(=S)(ORᵉ)—, —P(=S)(N(Rᵉ)₂)—, —Si(ORᵉ)₂—, —C(=O)—, —C(=S)—, —C(=NRᶠ)—,

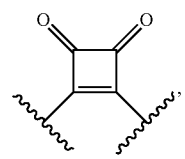 [SMILES: *c1c(*)c(=O)c1=O]

or optionally substituted monocyclic 5- or 6-membered heteroarylene, wherein 1, 2, 3, or 4 atoms in the heteroarylene ring system are independently oxygen, nitrogen, or sulfur;

G is of formula:

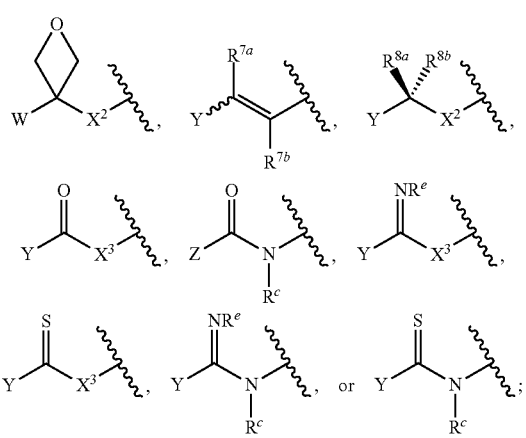

each of W, Y, and Z is independently optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —ORᵉ, —N(Rᵉ)₂, optionally substituted carbocyclyl, optionally substituted heterocyclyl, optionally substituted aryl, optionally substituted heteroaryl, or of formula:

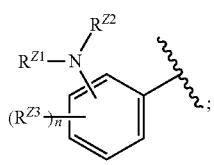

n is 0, 1, 2, 3, or 4;

each of $R^{Z1}$ and $R^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form an optionally substituted heterocyclic or optionally substituted heteroaryl ring;

each occurrence of $R^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$NO_2$, —CN, —$OR^e$, or —$N(R^e)_2$, or two $R^{Z3}$ are joined to form an optionally substituted aryl or optionally substituted heteroaryl ring;

$X^1$ is a bond, —O—, —$C(R^d)_2$—, —$(CH_2)_q$—, —NH—, or —$NR^f$—;

$X^2$ is a bond, —O—, —$C(R^d)_2$—, —$(CH_2)_t$—, —NH—, or —$NR^f$—;

$X^3$ is a bond, —O—, —$C(R^d)_2$—, or —$(CH_2)_t$—;

$R^f$ is optionally substituted $C_{1-6}$ alkyl, optionally substituted acyl, or a nitrogen protecting group;

A-B is —$(R^A)_2C$—$C(R^B)_2$— or —$R^AC$=$CR^B$—, wherein each occurrence of $R^A$ is independently hydrogen, halogen, optionally substituted alkyl, optionally substituted acyl, —$OR^{S1}$, or —$N(R^e)_2$, and each occurrence of $R^B$ is independently hydrogen, halogen, optionally substituted alkyl, optionally substituted acyl, —$OR^{S2}$, or —$N(R^e)_2$;

$X^5$ is —O—, —S—, —$C(R^d)_2$—, or —$NR^c$—;

each of $R^{7a}$ and $R^{7b}$ is independently hydrogen, halogen, optionally substituted $C_{1-6}$ alkyl, —$OR^e$, or —$N(R^e)_2$;

each of $R^{8a}$ and $R^{8b}$ is independently hydrogen, halogen, optionally substituted $C_{1-6}$ alkyl, —$OR^e$, or —$N(R^e)_2$;

each of $R^{9a}$ and $R^{9b}$ is independently hydrogen, halogen, optionally substituted $C_{1-6}$ alkyl, —$OR^e$, or —$N(R^e)_2$;

each of $R^{S1}$ and $R^{S2}$ is independently hydrogen, optionally substituted $C_{1-6}$ alkyl, optionally substituted acyl, or an oxygen protecting group, or $R^{S1}$ and $R^{S2}$ are joined to form an optionally substituted heterocyclic ring;

$L^S$ is a bond, —O—, —$NR^c$—, optionally substituted alkylene, optionally substituted alkenylene, optionally substituted alkynylene, optionally substituted acylene, or optionally substituted arylene;

each of $V^1$, $V^2$, $V^3$, $V^7$, $V^8$, and $V^9$ is independently N or $CR^V$, wherein each $R^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$NO_2$, —CN, —$OR^e$, or —$N(R^e)_2$;

$V^N$ is N, $NR^N$, or $CR^N$;

$R^N$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$NO_2$, —CN, —$OR^e$, or —$N(R^{Na})_2$;

each occurrence of $R^{Na}$ independently hydrogen, optionally substituted $C_{1-6}$ alkyl, optionally substituted acyl, or a nitrogen protecting group, or both $R^{Na}$ are joined to form and optionally substituted heterocyclic or optionally substituted heteroaryl ring;

each occurrence of $R^d$ is independently hydrogen, halogen, optionally substituted $C_{1-6}$ alkyl, —$OR^e$, or —$N(R^e)_2$;

each occurrence of $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two $R^e$ are joined to form and optionally substituted heterocyclic or optionally substituted heteroaryl ring;

each occurrence of $R^c$ is independently hydrogen, optionally substituted $C_{1-6}$ alkyl, optionally substituted acyl, or a nitrogen protecting group;

each of h, q, and t is independently 1, 2, or 3; and

⌇ indicates that each bond of the ring is a single or double bond.

16. A method of inhibiting PQS biosynthesis in an infection in a subject or in a microorganism, the method comprising administering to the subject or contacting the microorganism with a compound of Formula (I):

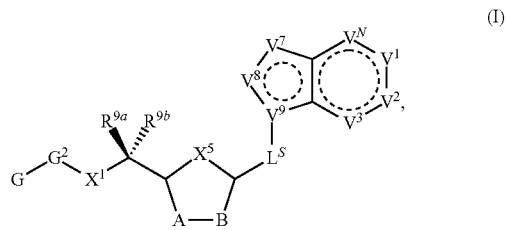

(I)

or a pharmaceutically acceptable salt, stereoisomer, or tautomer thereof, wherein:

$G^2$ is —$S(=O)_2$—, —$P(=O)(R^e)$—, —$P(=O)(OR^e)$—, —$P(=O)(N(R^e)_2)$—, —$P(=S)(R^e)$—, $P(=S)(OR^e)$—, —$P(=S)(N(R^e)_2)$—, —$Si(OR^e)_2$—, —$C(=O)$—, —$C(=S)$—, —$C(=NR^f)$—,

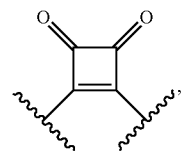

or optionally substituted monocyclic 5- or 6-membered heteroarylene, wherein 1, 2, 3, or 4 atoms in the heteroarylene ring system are independently oxygen, nitrogen, or sulfur;

G is of formula:

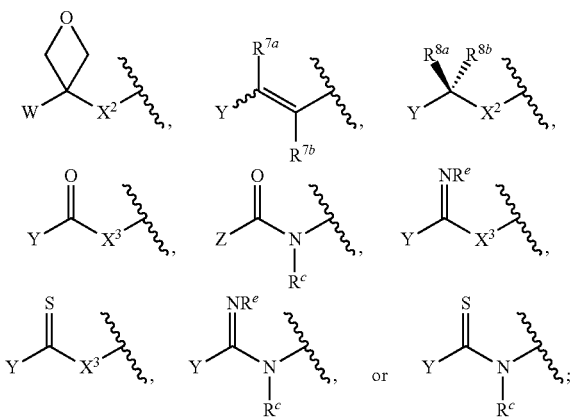

each of W, Y, and Z is independently optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —OR$^e$, —N(R$^e$)$_2$, optionally substituted carbocyclyl, optionally substituted heterocyclyl, optionally substituted aryl, optionally substituted heteroaryl, or of formula:

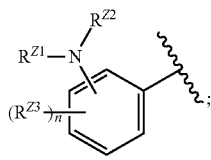

n is 0, 1, 2, 3, or 4;
each of R$^{Z1}$ and R$^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or R$^{Z1}$ and R$^{Z2}$ are joined to form an optionally substituted heterocyclic or optionally substituted heteroaryl ring;
each occurrence of R$^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$, or two R$^{Z3}$ are joined to form an optionally substituted aryl or optionally substituted heteroaryl ring;
X$^1$ is a bond, —O—, —C(R$^d$)$_2$—, —(CH$_2$)$_q$—, —NH—, or —NR$^f$—;
X$^2$ is a bond, —O—, —C(R$^d$)$_2$—, —(CH$_2$)$_t$—, —NH—, or —NR$^f$—;
X$^3$ is a bond, —O—, —C(R$^d$)$_2$—, or —(CH$_2$)$_t$—;
R$^f$ is optionally substituted C$_{1-6}$ alkyl, optionally substituted acyl, or a nitrogen protecting group;
A-B is —(R$^A$)$_2$C—C(R$^B$)$_2$— or —R$^A$C=CR$^B$—, wherein each occurrence of R$^A$ is independently hydrogen, halogen, optionally substituted alkyl, optionally substituted acyl, —OR$^{S1}$, or —N(R$^e$)$_2$, and each occurrence of R$^B$ is independently hydrogen, halogen, optionally substituted alkyl, optionally substituted acyl, —OR$^{S2}$, or —N(R$^e$)$_2$;
X$^5$ is —O—, —S—, —C(R$^d$)$_2$—, or —NR$^c$—;
each of R$^{7a}$ and R$^{7b}$ is independently hydrogen, halogen, optionally substituted C$_{1-6}$ alkyl, —OR$^e$, or —N(R$^e$)$_2$;
each of R$^{8a}$ and R$^{8b}$ is independently hydrogen, halogen, optionally substituted C$_{1-6}$ alkyl, —OR$^e$, or —N(R$^e$)$_2$;
each of R$^{9a}$ and R$^{9b}$ is independently hydrogen, halogen, optionally substituted C$_{1-6}$ alkyl, —OR$^e$, or —N(R$^e$)$_2$;
each of R$^{S1}$ and R$^{S2}$ is independently hydrogen, optionally substituted C$_{1-6}$ alkyl, optionally substituted acyl, or an oxygen protecting group, or R$^{S1}$ and R$^{S2}$ are joined to form an optionally substituted heterocyclic ring;
L$^S$ is a bond, —O—, —NR$^c$—, optionally substituted alkylene, optionally substituted alkenylene, optionally substituted alkynylene, optionally substituted acylene, or optionally substituted arylene;
each of V$^1$, V$^2$, V$^3$, V$^7$, V$^8$, and V$^9$ is independently N or CR$^V$, wherein each R$^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$;
V$^N$ is N, NR$^N$, or CR$^N$;
R$^N$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^{Na}$)$_2$;
each occurrence of R$^{Na}$ independently hydrogen, optionally substituted C$_{1-6}$ alkyl, optionally substituted acyl, or a nitrogen protecting group, or both R$^d$ are joined to form and optionally substituted heterocyclic or optionally substituted heteroaryl ring;
each occurrence of R$^d$ is independently hydrogen, halogen, optionally substituted C$_{1-6}$ alkyl, —OR$^e$, or —N(R$^e$)$_2$;
each occurrence of R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two R$^c$ are joined to form and optionally substituted heterocyclic or optionally substituted heteroaryl ring;
each occurrence of R$^c$ is independently hydrogen, optionally substituted C$_{1-6}$ alkyl, optionally substituted acyl, or a nitrogen protecting group;
each of h, q, and t is independently 1, 2, or 3; and
⌒ indicates that each bond of the ring is a single or double bond.

17. A method of inhibiting HHQ biosynthesis in an infection in a subject or in a microorganism, the method comprising administering to the subject or contacting the microorganism with a compound of Formula (I):

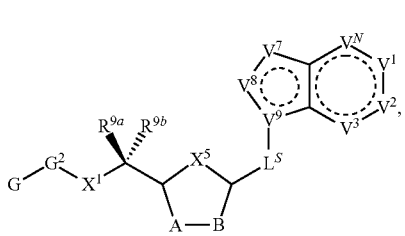
(I)

or a pharmaceutically acceptable salt, stereoisomer, or tautomer thereof, wherein:

$G^2$ is —S(=O)$_2$—, —P(=O)(R$^e$)—, —P(=O)(OR$^e$)—, —P(=O)(N(R$^e$)$_2$)—, —P(=S)(R$^e$)—, —P(=S)(OR$^e$)—, —P(=S)(N(R$^e$)$_2$)—, —Si(OR$^e$)$_2$—, —C(=O)—, —C(=S)—, —C(=NR$^f$)—, —(CH$_2$)$_h$—,

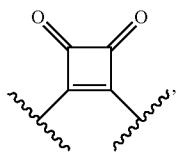

or optionally substituted monocyclic 5- or 6-membered heteroarylene, wherein 1, 2, 3, or 4 atoms in the heteroarylene ring system are independently oxygen, nitrogen, or sulfur;

G is of formula:

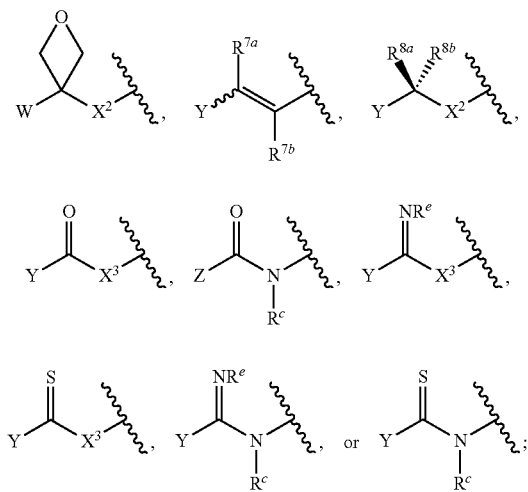

each of W, Y, and Z is independently optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —OR$^e$, —N(R$^e$)$_2$, optionally substituted carbocyclyl, optionally substituted heterocyclyl, optionally substituted aryl, optionally substituted heteroaryl, or of formula:

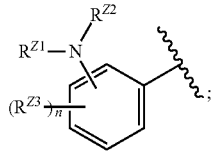

n is 0, 1, 2, 3, or 4;
each of $R^{Z1}$ and $R^{Z2}$ is independently hydrogen, optionally substituted alkyl, optionally substituted carbocyclyl, optionally substituted heterocyclyl, optionally substituted aryl, optionally substituted heteroaryl, optionally substituted acyl, or a nitrogen protecting group, or $R^{Z1}$ and $R^{Z2}$ are joined to form an optionally substituted heterocyclic or optionally substituted heteroaryl ring;
each occurrence of $R^{Z3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$, or two R are joined to form an optionally substituted aryl or optionally substituted heteroaryl ring;
$X^1$ is a bond, —O—, —C(R$^d$)$_2$—, —(CH$_2$)$_q$—, —NH—, or —NR$^f$—;
$X^2$ is a bond, —O—, —C(R$^d$)$_2$—, —(CH$_2$)$_r$—, —NH—, or —NR$^f$—;
$X^3$ is a bond, —O—, —C(R$^d$)$_2$—, or —(CH$_2$)$_t$—;
$R^f$ is optionally substituted C$_{1-6}$ alkyl, optionally substituted acyl, or a nitrogen protecting group;
A-B is —(R$^A$)$_2$C—C(R$^B$)$_2$— or —R$^A$C=CR$^B$—, wherein each occurrence of R$^A$ is independently hydrogen, halogen, optionally substituted alkyl, optionally substituted acyl, —OR$^{S1}$, or —N(R$^e$)$_2$, and each occurrence of R$^B$ is independently hydrogen, halogen, optionally substituted alkyl, optionally substituted acyl, —OR$^{S2}$, or —N(R$^e$)$_2$;
$X^5$ is —O—, —S—, —C(R$^d$)$_2$—, or —NR$^c$—;
each of $R^{7a}$ and $R^{7b}$ is independently hydrogen, halogen, optionally substituted C$_{1-6}$ alkyl, —OR$^e$, or —N(R$^e$)$_2$;
each of $R^{8a}$ and $R^{8b}$ is independently hydrogen, halogen, optionally substituted C$_{1-6}$ alkyl, —OR$^e$, or —N(R$^e$)$_2$;
each of $R^{9a}$ and $R^{9b}$ is independently hydrogen, halogen, optionally substituted C$_{1-6}$ alkyl, —OR$^e$, or —N(R$^e$)$_2$;
each of $R^{S1}$ and $R^{S2}$ is independently hydrogen, optionally substituted C$_{1-6}$ alkyl, optionally substituted acyl, or an oxygen protecting group, or $R^{S1}$ and $R^{S2}$ are joined to form an optionally substituted heterocyclic ring;
$L^S$ is a bond, —O—, —NR$^c$—, optionally substituted alkylene, optionally substituted alkenylene, optionally substituted alkynylene, optionally substituted acylene, or optionally substituted arylene;
each of $V^1$, $V^2$, $V^3$, $V^7$, $V^8$, and $V^9$ is independently N or CR$^V$, wherein each R$^V$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^e$)$_2$;
$V^N$ is N, NR$^N$, or CR$^N$;
$R^N$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —NO$_2$, —CN, —OR$^e$, or —N(R$^{Na}$)$_2$;

each occurrence of R$^{Na}$ independently hydrogen, optionally substituted C$_{1-6}$ alkyl, optionally substituted acyl, or a nitrogen protecting group, or both R$^d$ are joined to form and optionally substituted heterocyclic or optionally substituted heteroaryl ring;

each occurrence of R$^d$ is independently hydrogen, halogen, optionally substituted C$_{1-6}$ alkyl, —OR$^e$, or —N(R$^e$)$_2$;

each occurrence of R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two R$^e$ are joined to form and optionally substituted heterocyclic or optionally substituted heteroaryl ring;

each occurrence of R$^e$ is independently hydrogen, optionally substituted C$_{1-6}$ alkyl, optionally substituted acyl, or a nitrogen protecting group;

each of h, q, and t is independently 1, 2, or 3; and

◯ indicates that each bond of the ring is a single or double bond.

18. A method of inhibiting biosynthesis of a virulence factor in an infection in a subject or in a microorganism, the method comprising administering to the subject or contacting the microorganism with a compound of claim 1, or a pharmaceutically acceptable salt stereoisomer, or tautomer thereof.

19. A method of inhibiting biofilm formation in a subject or on a surface, the method comprising administering to the subject or contacting the surface with a compound of claim 1, or a pharmaceutically acceptable salt, stereoisomer, or tautomer thereof.

20. A method of eradicating a biofilm, the method comprising contacting the biofilm with a compound of claim 1, or a pharmaceutically acceptable salt, stereoisomer, or tautomer thereof.

21. A method of treating an infectious disease in a subject comprising administering to the subject an effective amount of a compound of claim 1, or a pharmaceutically acceptable salt, stereoisomer, or tautomer thereof.

22. The compound of claim 6, wherein the compound is selected from the group consisting of:

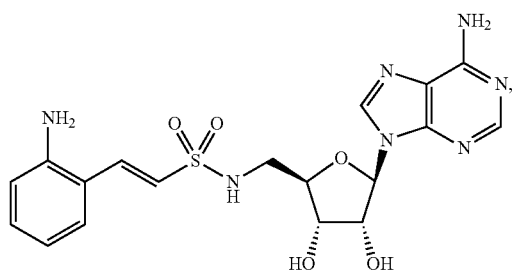

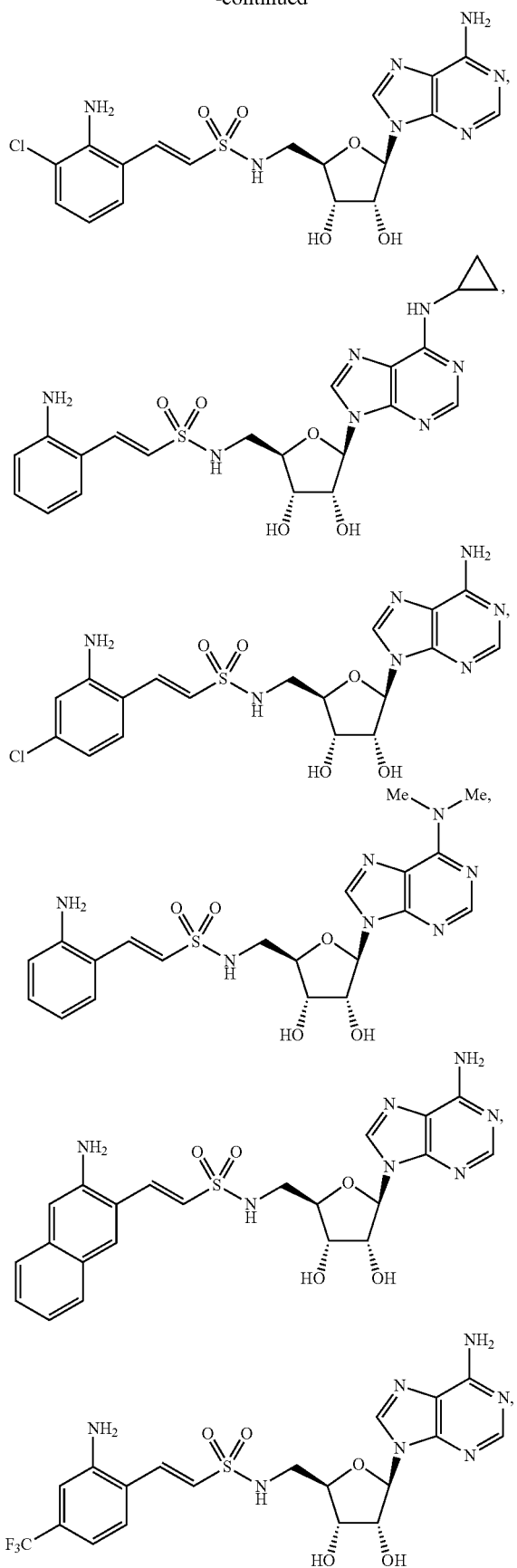

197
-continued
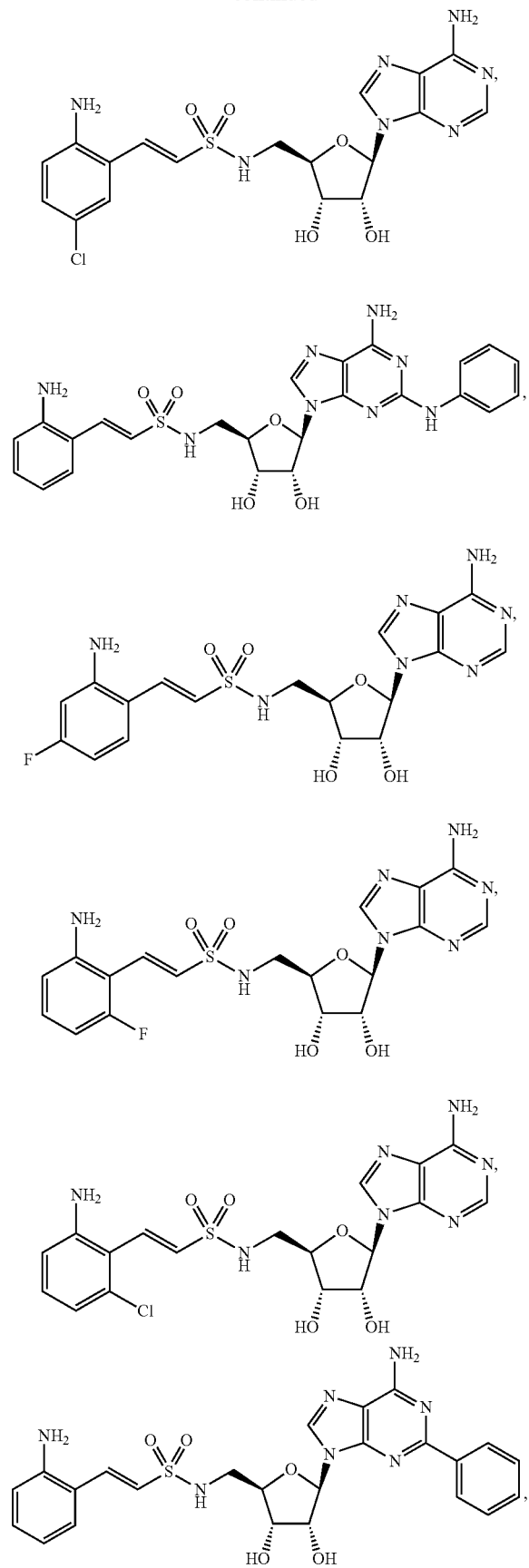
198
-continued
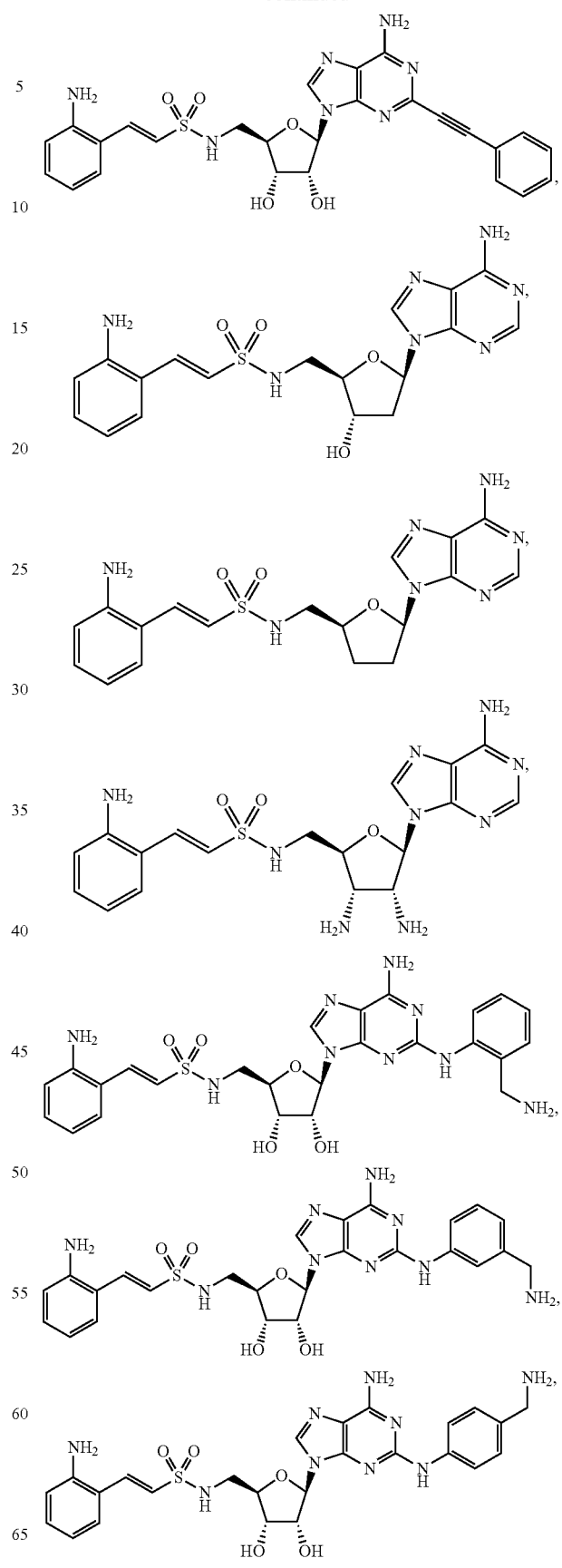

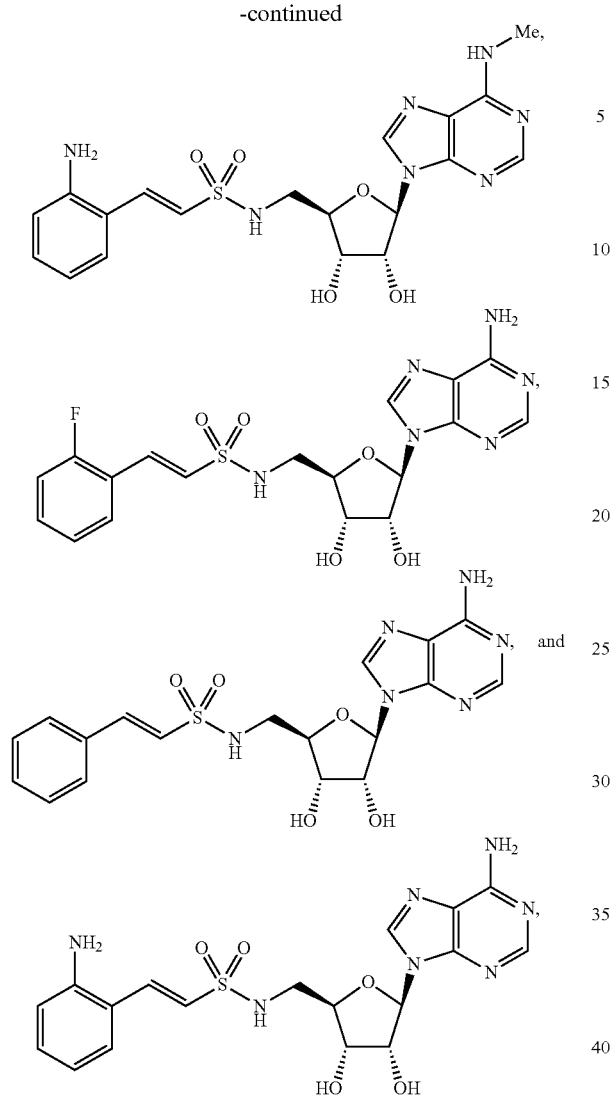

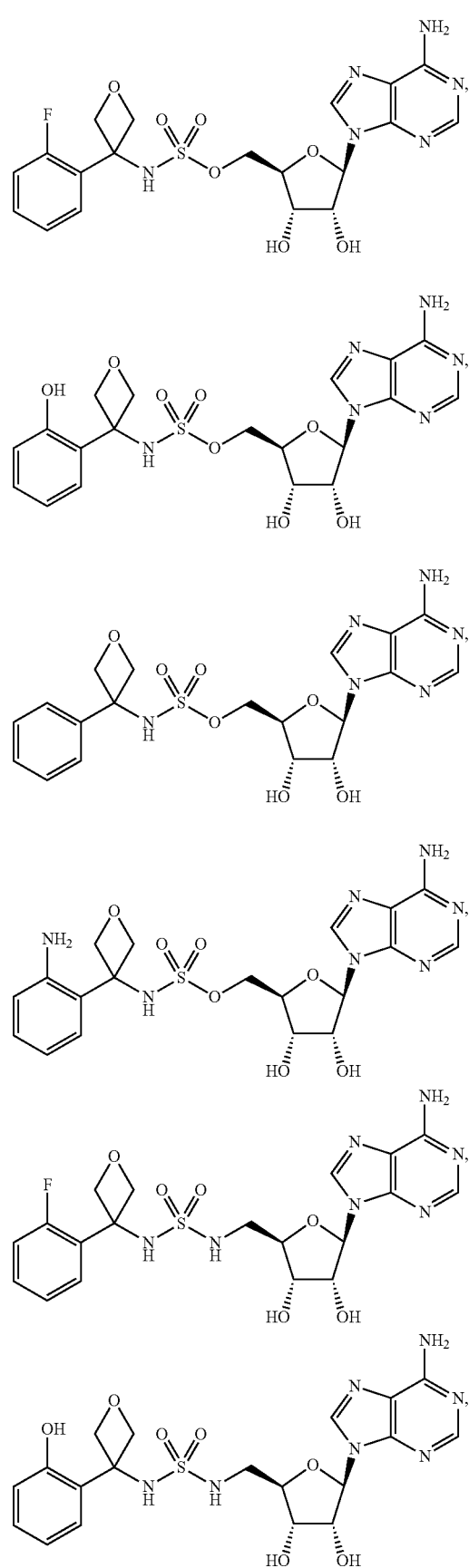

and pharmaceutically acceptable salts, stereoisomers, and tautomers thereof.

23. A pharmaceutical composition comprising a compound of claim 6, or a pharmaceutically acceptable salt, stereoisomer, or tautomer thereof, and a pharmaceutically acceptable excipient.

24. A method of treating an infectious disease in a subject in need thereof comprising administering to the subject an effective amount of a compound of claim 6, or a pharmaceutically acceptable salt, stereoisomer, or tautomer thereof.

25. A method of inhibiting biosynthesis of a virulence factor in an infection in a subject or in a microorganism, the method comprising administering to the subject or contacting the microorganism with a compound of claim 6, or a pharmaceutically acceptable salt, stereoisomer, or tautomer thereof.

26. A method of inhibiting biofilm formation or eradicating a biofilm in a subject or on a surface, the method comprising administering to the subject or contacting the surface with a compound of claim 6, or a pharmaceutically acceptable salt, stereoisomer, or tautomer thereof.

27. The compound of claim 9, wherein the compound is selected from the group consisting of:

-continued

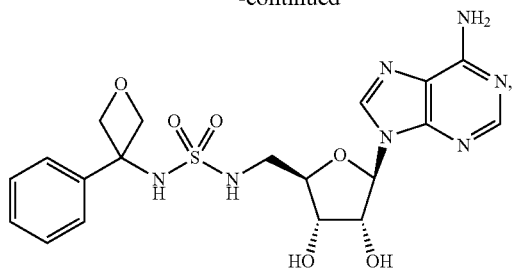

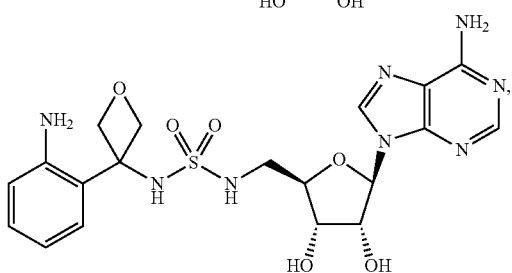

and pharmaceutically acceptable salts, stereoisomers, and tautomers thereof.

28. A pharmaceutical composition comprising a compound of claim 9, or a pharmaceutically acceptable salt, stereoisomer, or tautomer thereof, and a pharmaceutically acceptable excipient.

29. A method of treating an infectious disease in a subject in need thereof comprising administering to the subject an effective amount of a compound of claim 9, or a pharmaceutically acceptable salt, stereoisomer, or tautomer thereof.

30. A method of inhibiting biosynthesis of a virulence factor in an infection in a subject or in a microorganism, the method comprising administering to the subject or contacting the microorganism with a compound of claim 9, or a pharmaceutically acceptable salt, stereoisomer, or tautomer thereof.

31. A method of inhibiting biofilm formation or eradicating a biofilm in a subject or on a surface, the method comprising administering to the subject or contacting the surface with a compound of claim 9, or a pharmaceutically acceptable salt, stereoisomer, or tautomer thereof.

32. The method of claim 15, wherein the compound is of Formula (II):

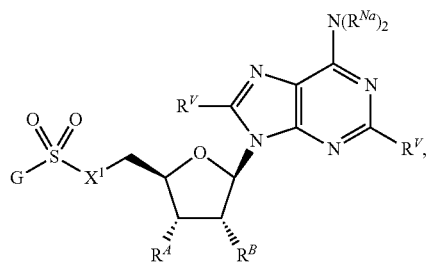

or a pharmaceutically acceptable salt, stereoisomer, or tautomer thereof.

33. The method of claim 15, wherein the compound is of one of the following formulae:

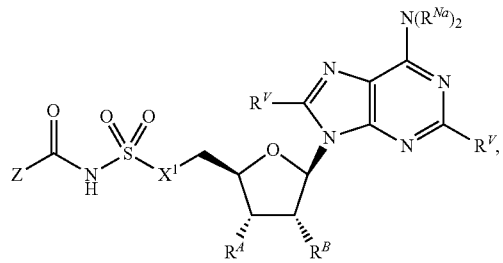

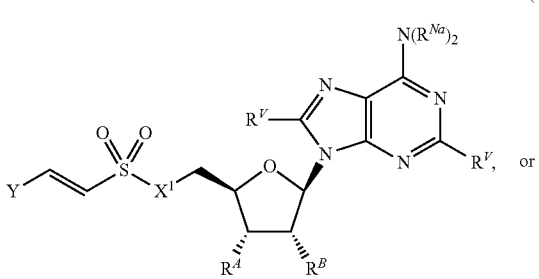

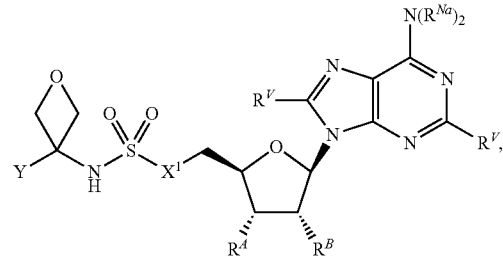

or a pharmaceutically acceptable salt, stereoisomer, or tautomer thereof.

34. The method of claim 15, wherein the compound is of one of the following formulae:

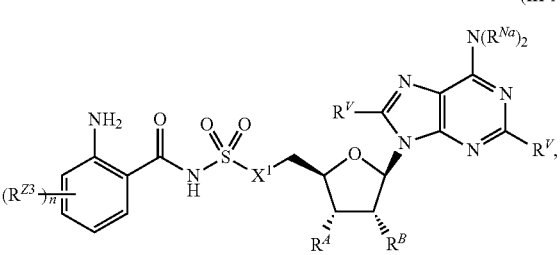

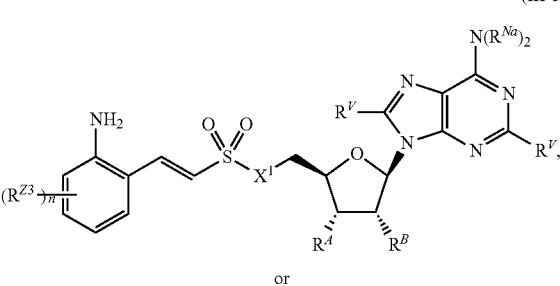

or

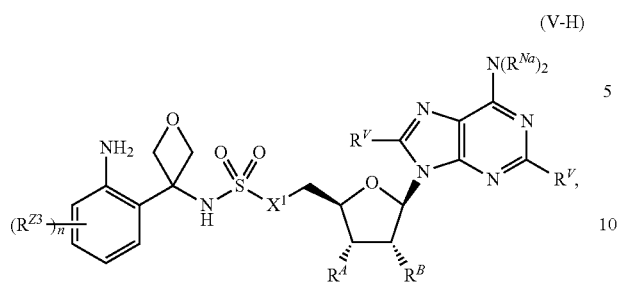
or a pharmaceutically acceptable salt, stereoisomer, or tautomer thereof.
35. The method of claim 15, wherein the compound is selected from the group consisting of:
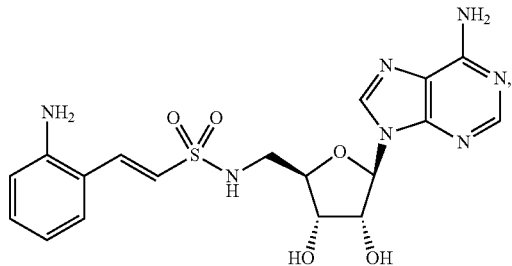
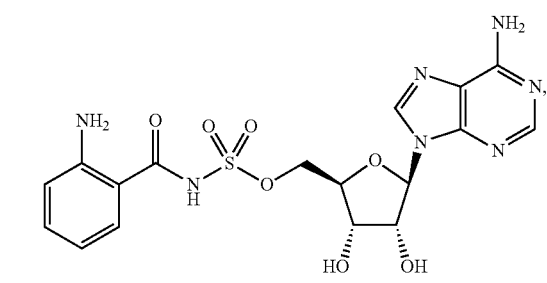
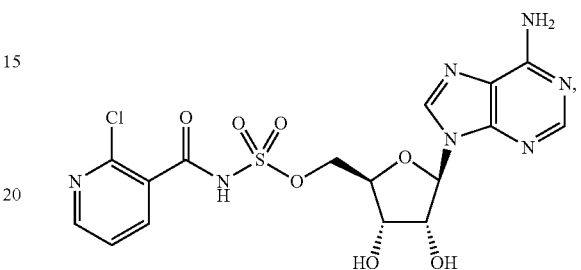
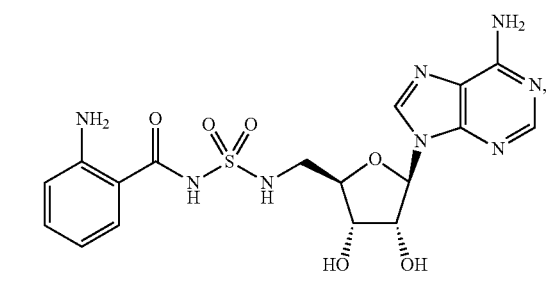
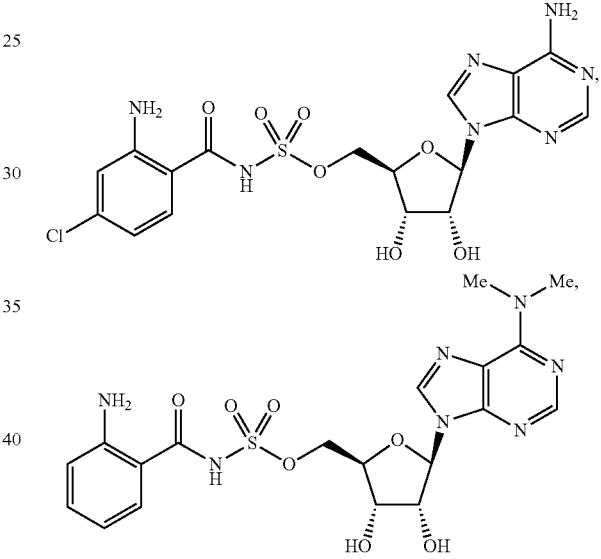
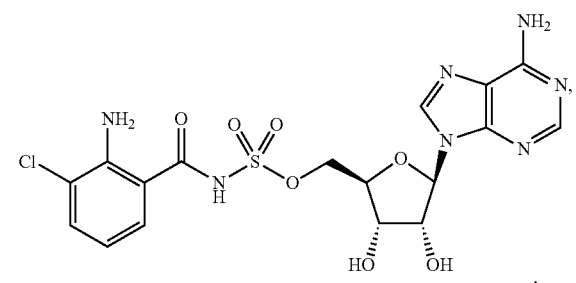
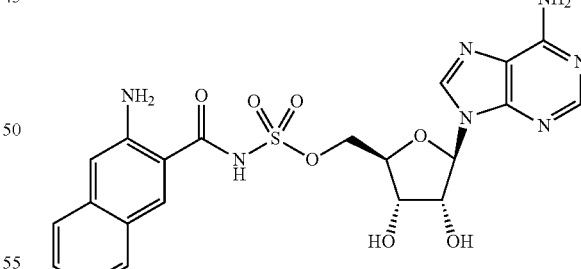
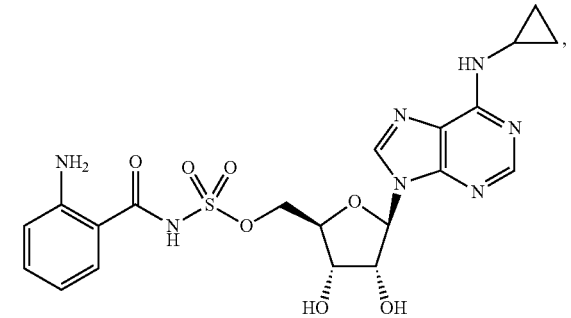
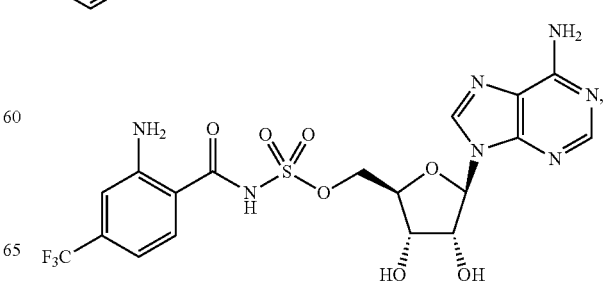

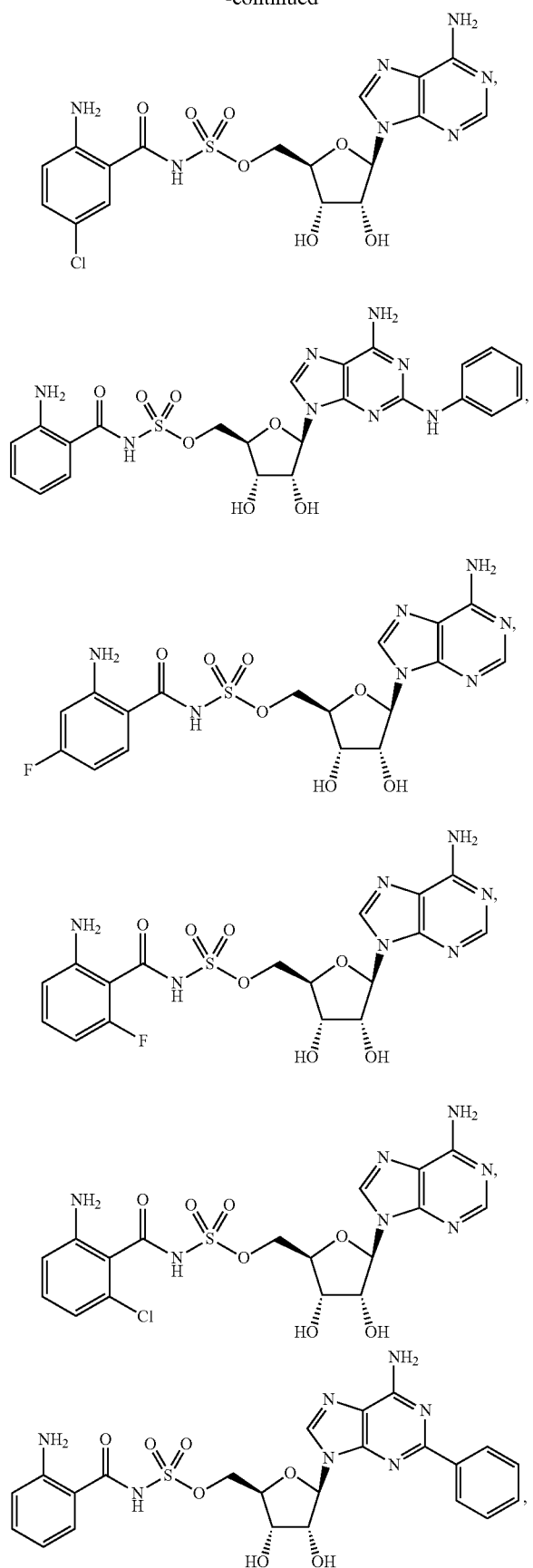
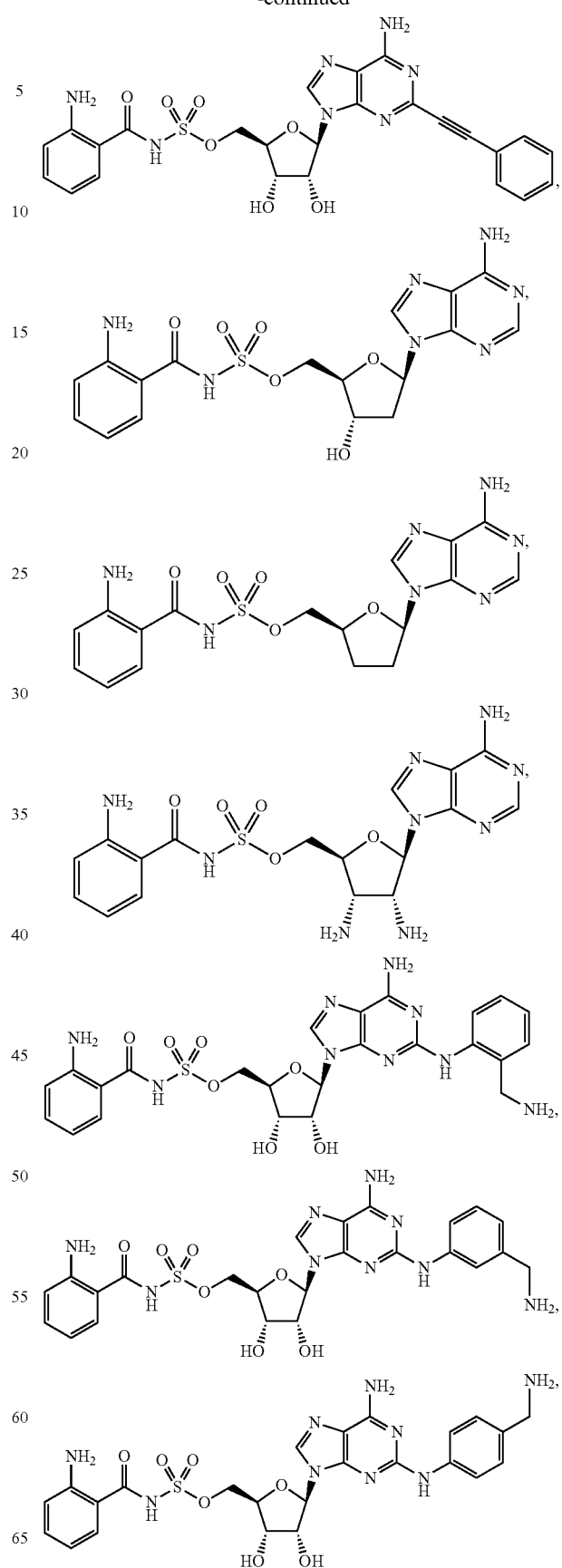

-continued
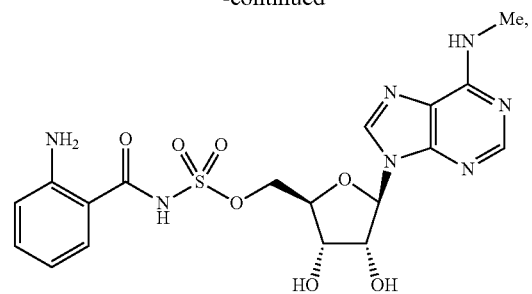
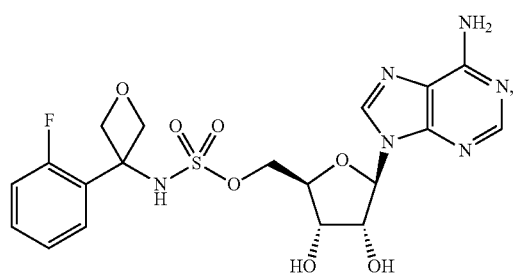
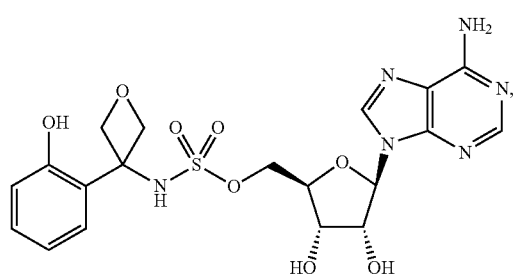
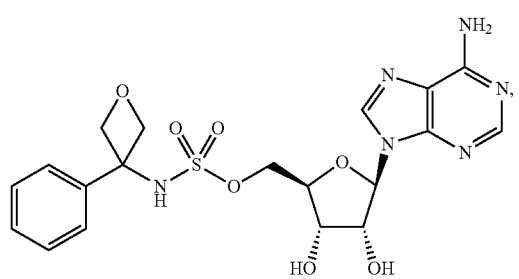
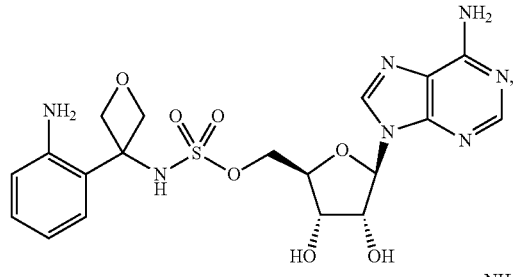
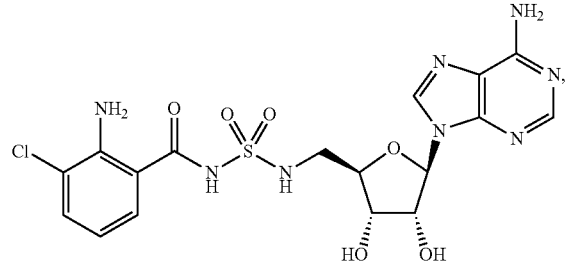
-continued
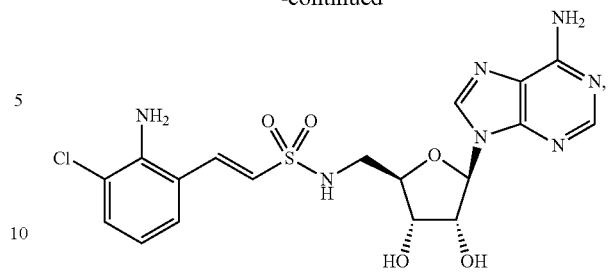
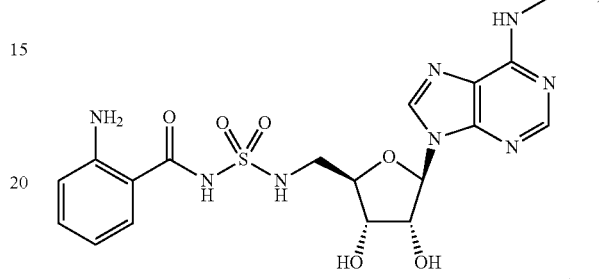
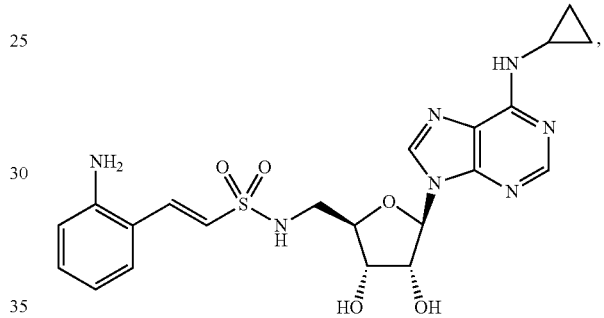
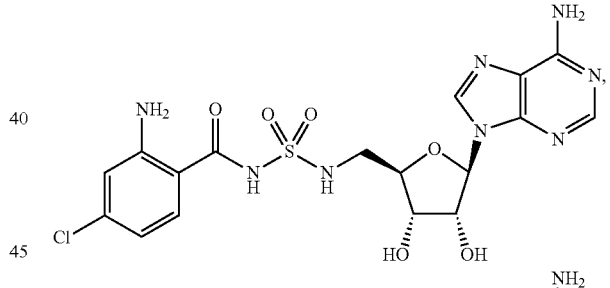
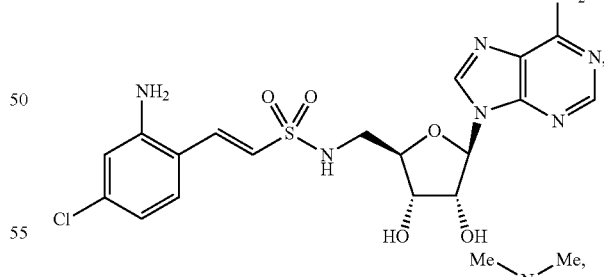
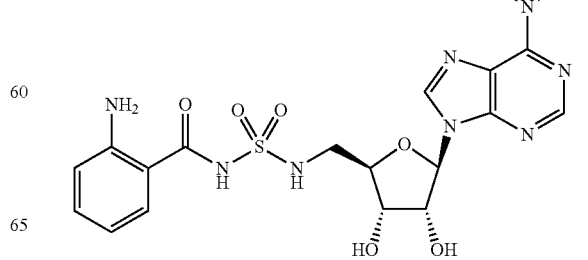

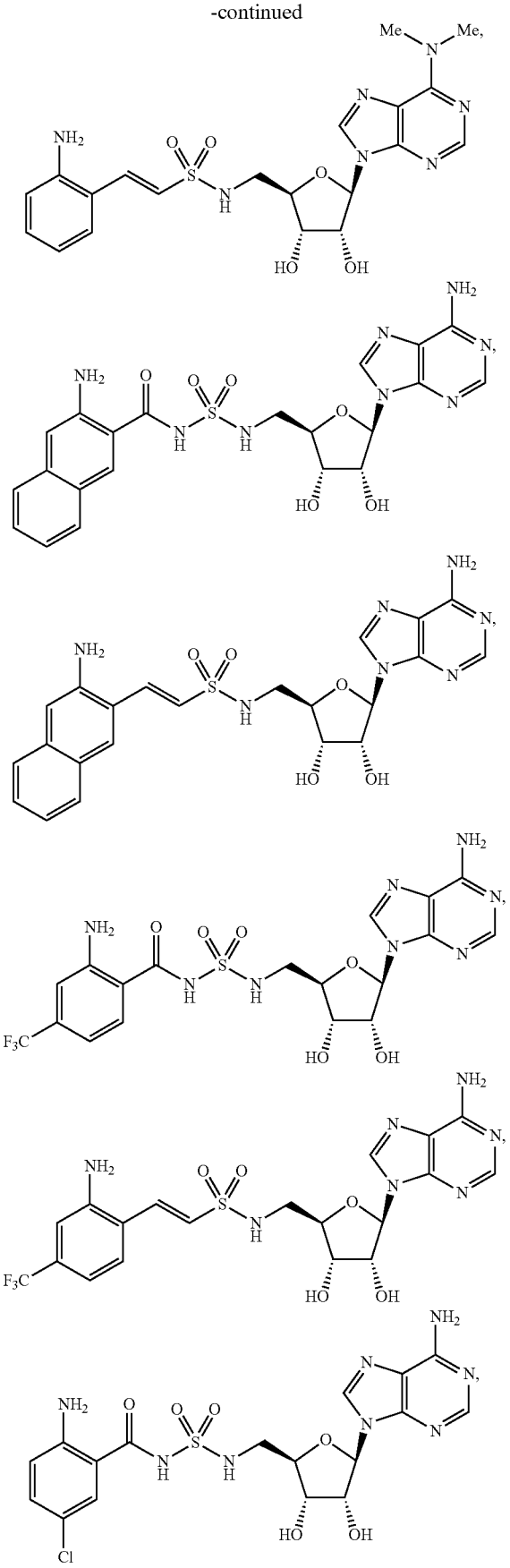
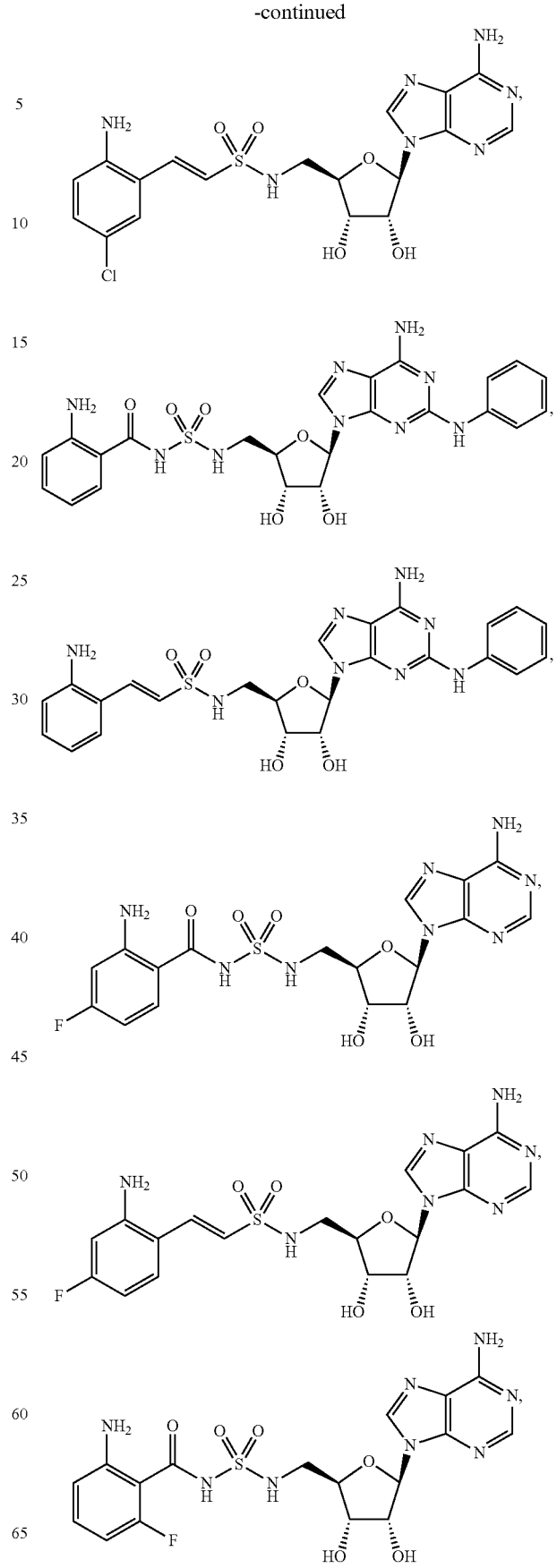

211
-continued
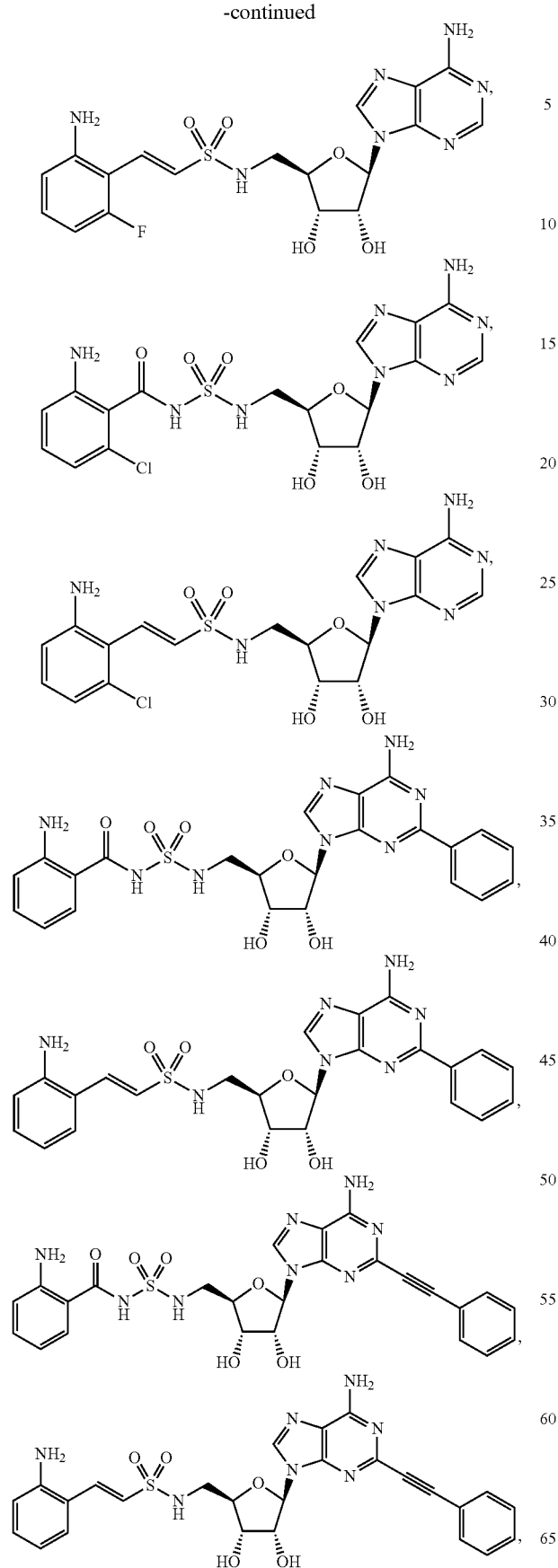
212
-continued
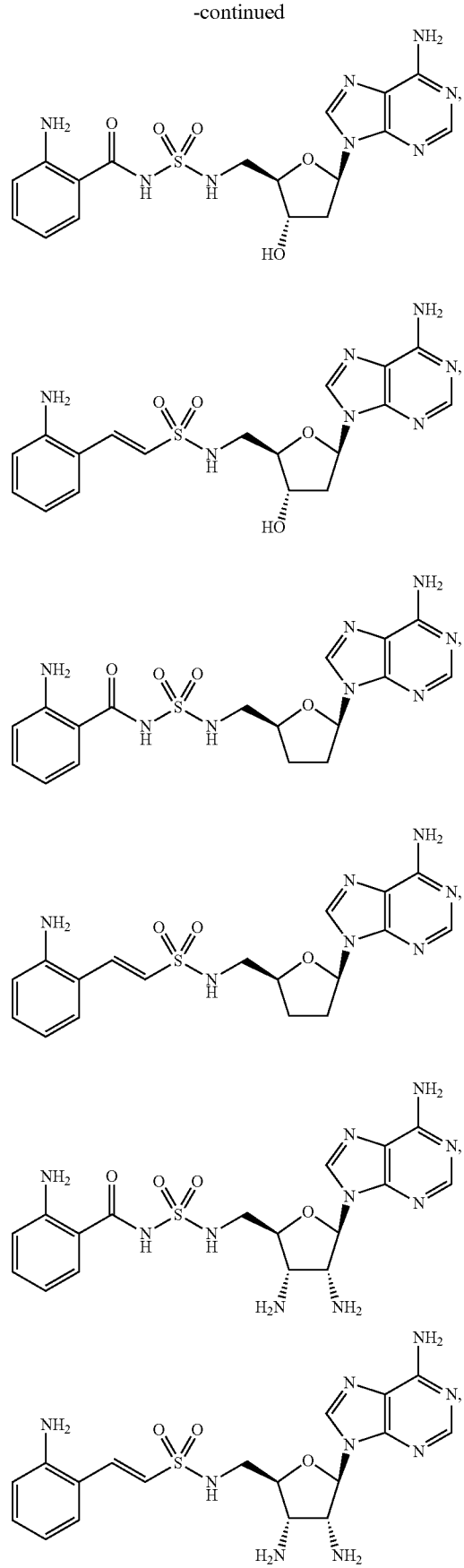

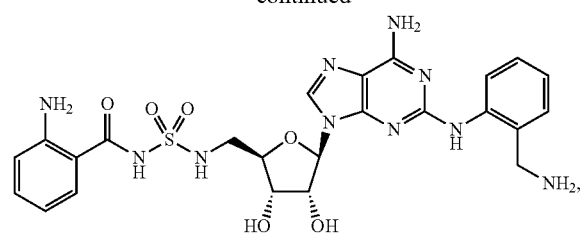
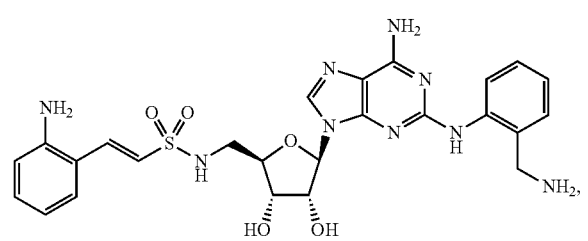
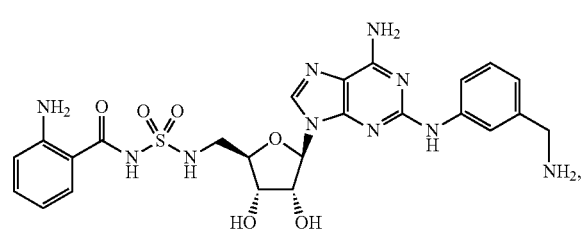
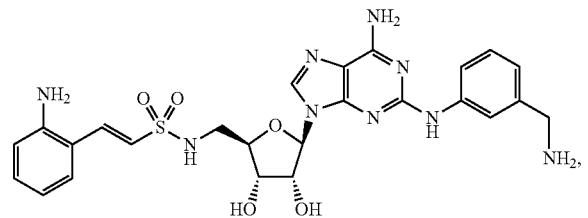
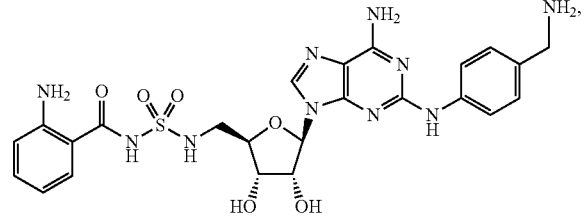
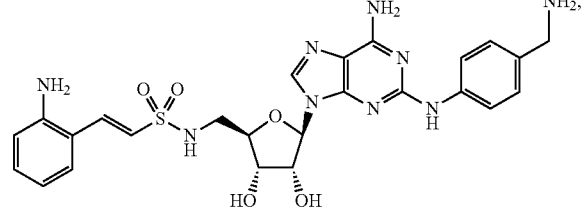
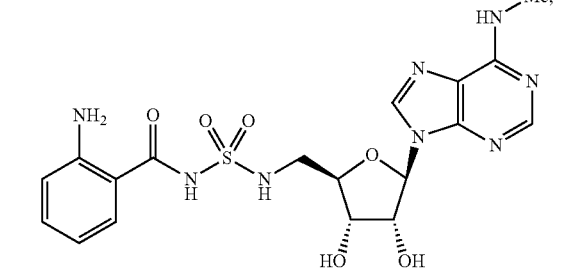
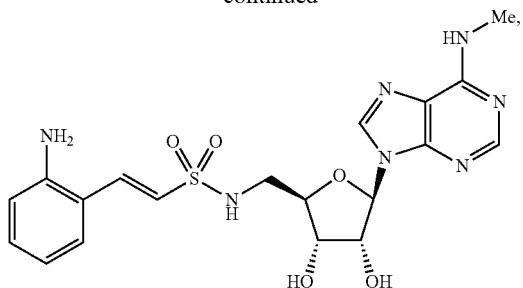
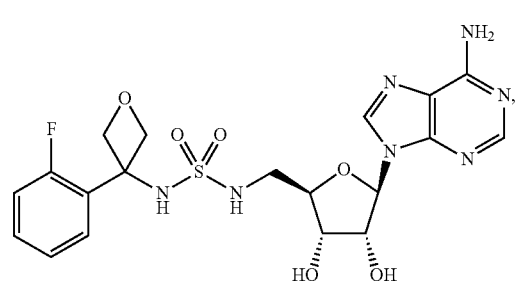
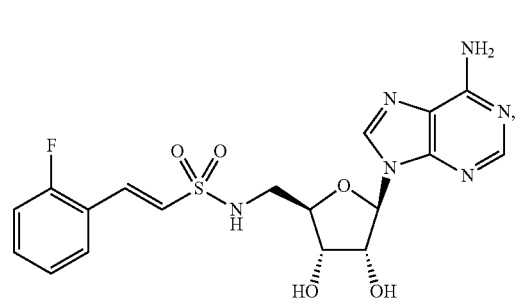 [SMILES: Nc1ccccc1/C=C/S(=O)(=O)NC[C@H]1O[C@@H](n2cnc3c(N)ncnc32)[C@H](O)[C@@H]1O]
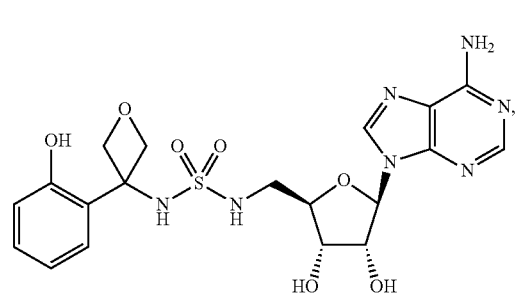
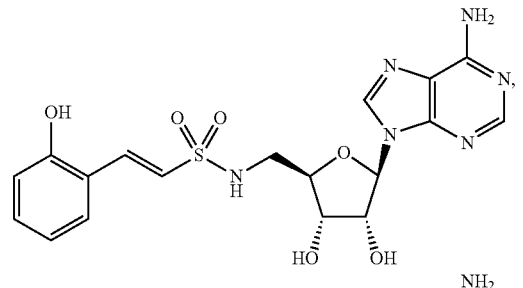
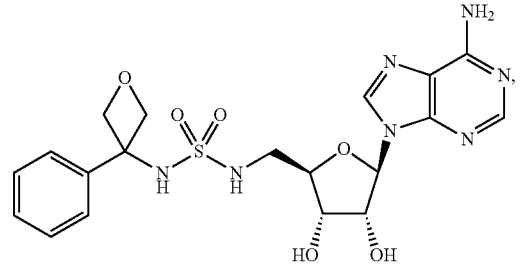

-continued
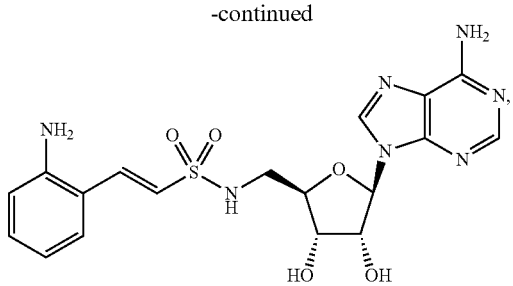
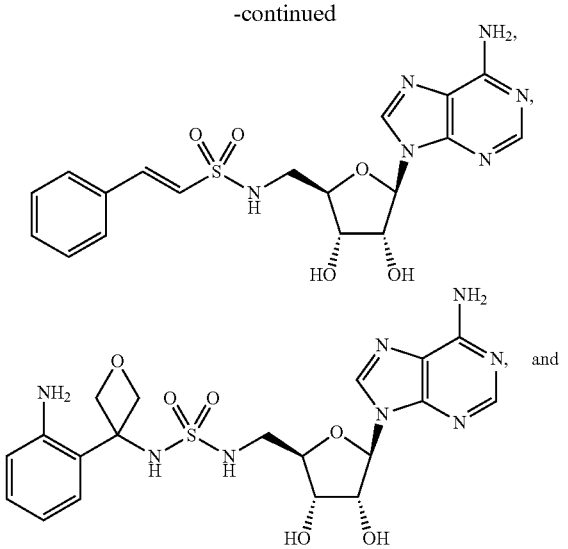
and pharmaceutically acceptable salts, stereoisomers, and tautomers thereof.
36. The method of claim 15, wherein the *Pseudomonas* infection is a *P. aeruginosa* infection.
* * * * *

UNITED STATES PATENT AND TRADEMARK OFFICE
CERTIFICATE OF CORRECTION

PATENT NO. : 10,874,686 B2  
APPLICATION NO. : 15/765004  
DATED : December 29, 2020  
INVENTOR(S) : Derek Shieh Tan et al.

Page 1 of 1

It is certified that error appears in the above-identified patent and that said Letters Patent is hereby corrected as shown below:

In the Claims

In Claim 15, at Column 188, Lines 22-25, the text:
"$-C(=O)-, -C(=S)-, -C(=NR^f)-,$"
Should be replaced with:
-- $-C(=O)-, -C(=S)-, -C(=NR^f)-, -(CH_2)_h-,$ --.

In Claim 16, at Column 190, Lines 53-55, the text:
"$-C(=O)-, -C(=S)-, -C(=NR^f)-,$"
Should be replaced with:
-- $-C(=O)-, -C(=S)-, -C(=NR^f)-, -(CH_2)_h-,$ --.

In Claim 34, at Column 202, Line 55, the text:
"(III-H)"
Should be replaced with:
--(IV-H)--.

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 1

<210> SEQ ID NO 1
<211> LENGTH: 517
<212> TYPE: PRT
<213> ORGANISM: Pseudomonas aeruginosa

<400> SEQUENCE: 1

```
Met Ser Thr Leu Ala Asn Leu Thr Glu Val Leu Phe Arg Leu Asp Phe
1               5                   10                  15

Asp Pro Asp Thr Ala Val Tyr His Tyr Arg Gly Gln Thr Leu Ser Arg
            20                  25                  30

Leu Gln Cys Arg Thr Tyr Ile Leu Ser Gln Ala Ser Gln Leu Ala Arg
        35                  40                  45

Leu Leu Lys Pro Gly Asp Arg Val Val Leu Ala Leu Asn Asp Ser Pro
    50                  55                  60

Ser Leu Ala Cys Leu Phe Leu Ala Cys Ile Ala Val Gly Ala Ile Pro
65                  70                  75                  80

Ala Val Ile Asn Pro Lys Ser Arg Glu Gln Ala Leu Ala Asp Ile Ala
                85                  90                  95

Ala Asp Cys Gln Ala Ser Leu Val Val Arg Glu Ala Asp Ala Pro Ser
            100                 105                 110

Leu Ser Gly Pro Leu Ala Pro Leu Thr Leu Arg Ala Ala Ala Gly Arg
        115                 120                 125

Pro Leu Leu Asp Asp Phe Ser Leu Asp Ala Leu Val Gly Pro Ala Asp
    130                 135                 140

Leu Asp Trp Ser Ala Phe His Arg Gln Asp Pro Ala Ala Ala Cys Phe
145                 150                 155                 160

Leu Gln Tyr Thr Ser Gly Ser Thr Gly Ala Pro Lys Gly Val Met His
                165                 170                 175

Ser Leu Arg Asn Thr Leu Gly Phe Cys Arg Ala Phe Ala Thr Glu Leu
            180                 185                 190

Leu Ala Leu Gln Ala Gly Asp Arg Leu Tyr Ser Ile Pro Lys Met Phe
        195                 200                 205
```

-continued

```
Phe Gly Tyr Gly Met Gly Asn Ser Leu Phe Phe Pro Trp Phe Ser Gly
    210                 215                 220

Ala Ser Ala Leu Leu Asp Asp Thr Trp Pro Ser Pro Glu Arg Val Leu
225                 230                 235                 240

Glu Asn Leu Val Ala Phe Arg Pro Arg Val Leu Phe Gly Val Pro Ala
                245                 250                 255

Ile Tyr Ala Ser Leu Arg Pro Gln Ala Arg Glu Leu Leu Ser Ser Val
                260                 265                 270

Arg Leu Ala Phe Ser Ala Gly Ser Pro Leu Pro Arg Gly Glu Phe Glu
            275                 280                 285

Phe Trp Ala Ala His Gly Leu Glu Ile Cys Asp Gly Ile Gly Ala Thr
            290                 295                 300

Glu Val Gly His Val Phe Leu Ala Asn Arg Pro Gly Gln Ala Arg Ala
305                 310                 315                 320

Asp Ser Thr Gly Leu Pro Leu Pro Gly Tyr Glu Cys Arg Leu Val Asp
                325                 330                 335

Arg Glu Gly His Thr Ile Glu Glu Ala Gly Arg Gln Gly Val Leu Leu
                340                 345                 350

Val Arg Gly Pro Gly Leu Ser Pro Gly Tyr Trp Arg Ala Ser Glu Glu
            355                 360                 365

Gln Gln Ala Arg Phe Ala Gly Gly Trp Tyr Arg Thr Gly Asp Leu Phe
            370                 375                 380

Glu Arg Asp Glu Ser Gly Ala Tyr Arg His Cys Gly Arg Glu Asp Asp
385                 390                 395                 400

Leu Phe Lys Val Asn Gly Arg Trp Val Val Pro Thr Gln Val Glu Gln
                405                 410                 415

Ala Ile Cys Arg His Leu Pro Glu Val Ser Glu Ala Val Leu Val Pro
                420                 425                 430

Thr Cys Arg Leu His Asp Gly Leu Arg Pro Thr Leu Phe Val Thr Leu
            435                 440                 445

Ala Thr Pro Leu Asp Asp Asn Gln Ile Leu Leu Ala Gln Arg Ile Asp
450                 455                 460

Gln His Leu Ala Glu Gln Ile Pro Ser His Met Leu Pro Ser Gln Leu
465                 470                 475                 480

His Val Leu Pro Ala Leu Pro Arg Asn Asp Asn Gly Lys Leu Ala Arg
                485                 490                 495

Ala Glu Leu Arg His Leu Ala Asp Thr Leu Tyr His Asp Asn Leu Pro
                500                 505                 510

Glu Glu Arg Ala Cys
            515
```